(12) United States Patent
Selitrennikoff et al.

(10) Patent No.: US 6,716,625 B1
(45) Date of Patent: Apr. 6, 2004

(54) HISTIDINE KINASES OF ASPERGILLUS AND OTHER FUNGAL SPECIES, RELATED COMPOSITIONS, AND METHODS OF USE

(76) Inventors: Claude Selitrennikoff, 264 Ponderosa Pine, Evergreen, CO (US) 80267; Greg Pott, 10073 Hooker Way, Westminster, CO (US) 80031

( * ) Notice: Subject to any disclaimer, the term of this patent is extended or adjusted under 35 U.S.C. 154(b) by 173 days.

(21) Appl. No.: 09/636,728

(22) Filed: Aug. 9, 2000

Related U.S. Application Data

(63) Continuation-in-part of application No. 09/338,156, filed on Jun. 22, 1999, now abandoned, which is a continuation of application No. 08/843,530, filed on Apr. 16, 1997, now Pat. No. 5,939,306.

(51) Int. Cl.$^7$ .............................. C12N 5/00; C12N 9/12; C07H 21/04
(52) U.S. Cl. ..................... 435/325; 435/194; 435/183; 435/252.1; 435/252.3; 435/320.1; 435/410; 435/536; 435/23.1; 435/23.2; 435/23.7; 435/530; 435/350
(58) Field of Search ................. 435/194, 320.1, 435/252.1, 325, 252.3; 536/23.1, 23.2, 23.7; 530/350

(56) References Cited

U.S. PATENT DOCUMENTS

| | | | |
|---|---|---|---|
| 3,687,808 A | 8/1972 | Merigan, Jr. et al. | 195/28 N |
| 4,683,195 A | 7/1987 | Mullis et al. | 435/6 |
| 4,683,202 A | 7/1987 | Mullis | 435/91 |
| 4,873,196 A | 10/1989 | Selitrennikoff | 435/254 |
| 4,965,188 A | 10/1990 | Mullis et al. | 435/6 |
| 5,034,506 A | 7/1991 | Summerton et al. | 528/391 |
| 5,416,016 A | 5/1995 | Low et al. | 435/240.1 |
| 5,489,677 A | 2/1996 | Sanghvi et al. | 536/22.1 |
| 5,521,291 A | 5/1996 | Curiel et al. | 530/391.7 |
| 5,539,082 A | 7/1996 | Nielsen et al. | 530/300 |
| 5,543,158 A | 8/1996 | Gref et al. | 424/501 |
| 5,587,361 A | 12/1996 | Cook et al. | 514/44 |
| 5,595,756 A | 1/1997 | Bally et al. | 424/450 |
| 5,599,928 A | 2/1997 | Hemmi et al. | 540/474 |
| 5,602,240 A | 2/1997 | De Mesmaeker et al. | 536/22.1 |
| 5,625,050 A | 4/1997 | Beaton et al. | 536/24.1 |
| 5,633,360 A | 5/1997 | Bischofberger et al. | 536/22.1 |
| 5,652,356 A | 7/1997 | Agrawal | 536/245 |
| 5,670,633 A | 9/1997 | Cook et al. | 536/23.1 |
| 5,677,439 A | 10/1997 | Weis et al. | 536/23.1 |
| 5,681,941 A | 10/1997 | Cook et al. | 536/23.1 |
| 5,688,941 A | 11/1997 | Cook et al. | 536/25.3 |
| 5,700,920 A | 12/1997 | Altmann et al. | 536/221 |
| 5,700,922 A | 12/1997 | Cook | 536/23.1 |
| 5,703,044 A | 12/1997 | Roberts et al. | 514/12 |
| 5,705,188 A | 1/1998 | Junichi et al. | 424/450 |
| 5,714,331 A | 2/1998 | Buchardt et al. | 435/6 |
| 5,719,262 A | 2/1998 | Buchardt et al. | 530/300 |
| 5,750,692 A | 5/1998 | Cook et al. | 544/253 |
| 5,912,153 A | 6/1999 | Selitrennikoff et al. | 435/193 |
| 6,001,600 A | 12/1999 | Hodgson et al. | 435/69.3 |

FOREIGN PATENT DOCUMENTS

| | | |
|---|---|---|
| WO | WO 93/24510 | 12/1993 |
| WO | WO 94/26764 | 11/1994 |
| WO | WO 97/30731 | 8/1997 |

OTHER PUBLICATIONS

Agnan et al., "Cloning Heterologous Genes: Problems and Approaches," Fungal Genet. Biol., 21 :292–301 [1997].

Alex et al., "*COS1*, a two–component histidine kinase that is involved in hyphal development in the opportunistic pathogen *Candida albicans*,"Proc. Natl. Acad. Sci. USA 95:7069–7073 [1998].

Alexander and Perfect, "Antifungal resistance trends towards the year 2000. Implication for therapy and new approaches," Drugs 54:657 [1997].

Anderson and Young, Quantiative Filter Hybridisation, in *Nucleic Acid Hybridisation* [1985].

Armstrong et al., "Invasive Aspergillosis: Diagnosis and Treatment," Issues Mycol., 2:1–20 [1997].

Ausubel et al. (eds.), Current Protocols in Molecular Biology, vol. 1–4, Ch. 11: "Immunology," Ch. 18: "Analysis of Protein Phosphorylation," John Wiley & Sons, Inc., New York [1994 ].

Barrett et al., "Antibacterial agents that inhibit two–component signal transduction systems, " Proc. Natl Acad. Sci. USA 95:5317–5322 [1998].

Beck–Sague et al., "Secular trends in the epidemiology of nosocomial fungal infection in the United States, 1980–1990. National Nosocomial Infection Surveillance System," J. Infect. Dis., 167:1247–1251 [1993].

Beever, "Osmotic Sensitivity of Fungal Variants Resistant to Dicarboximide Fungicides," Trans. Br. Mycol. Soc., 80:327–331 [1983].

Borgia et al., "Bidirectional gene transfer between *Aspergillus fumigatus* and *Aspergillus nidulans*, " FEMS Microb. Lett., 122:227–231 [1994].

Boschman et al., "Thirteen–Year Evolution of Azole Resistance in Yeast Isolates and Prevalence of Resistant Strains Carried by Cancer Patients at a Large Medical Center, "Antimicrob. Agents Chemother., 42:734–738 [1998].

Bow, "Invasive fungal infections in patients receiving intensive cytotoxic therapy for cancer," Br. J. Haematol., 101:1–4 [1998].

Brown et al., "Insertional mutagenesis of *Aspergillus fumigatus*," Mol. Gen. Genet., 259:327 [1998].

(List continued on next page.)

Primary Examiner—Richard Hutson
(74) Attorney, Agent, or Firm—Medlen & Carroll LLP

(57) ABSTRACT

The present invention relates to fungal histidine kinases. In particular, the present invention is directed to histidine kinases from Neurospora (e.g., *N. crassa*), Candida (e.g, *C. albicans*), and Aspergillus (e.g., *A. fumigatus*), and related compositions. Furthermore, the present invention provides compositions and methods for the identification of compounds having antifungal activity, as well as compositions and methods for the treatment of fungal infections.

8 Claims, 29 Drawing Sheets-

OTHER PUBLICATIONS

Cairns, "Fungal infections in the acquired immunodeficiency syndrome," J. Electron Microsc. Techn.; 8:115–131 [1988].

Calera et al., "Identification of a putative histidine kinase two–component phosphorelay gene (CaHK1) in *Candida albicans*," Yeast 14:665–674 [1998].

Caricchio et al., "Apoptosis provoked by the oxidative stress inducer menadione (Vitamin $K_3$) is mediated by the Fas/Fas ligand system," Clin. Immunol., 93:65–74 [1999].

Cole et al., "The EBV–Hybridoma Technique and Its Application to Human Lung Cancer," in *Monoclonal Antibodies and Cancer Therapy*, Alan R. Liss, Inc., pp. 77–96 [1985].

Conney and Emerson, Thermophilic Fungi: An Account of Their Biology, Activities and Classification, Freeman and Co., San Francisco [1964].

Coombs, *Dictionary of Biotechnology*, Stockton Press, New York NY [1994] (Title Page Only).

Cotter, "Antisense therapy of hematologic malignancies," Semin. Hematol., 36:9–14 [1999].

de Souza Pereira and Geibel, "Direct observation of oxidative stress on the cell wall of *Saccharomyces cerevisiae* strains with atomic force microscopy," J. Mol. Cell Biochem., 201:17–24 [1999]).

Denning et al., "Pulmonary aspergillosis in the acquired immunodeficiency syndrome," New Eng. J. Med., 324:654–662 [1991].

Deschenes et al., "Antifungal Properties and Target Evaluation of Three Putative Bacterial Histidine Kinase Inhibitors," Antimicrobial Agents and Chemotherapy 43(7):1700–1703 [1999].

Falke et al., "The Two–Component Signaling Pathway of Bacterial Chemotaxis: A Molecular View of Signal Transduction by Receptors, Kinases, and Adaption Enzymes," Ann. Rev. Cell. Dev. Biol., 13:457 [1997].

Fan and Mendelsohn, "Therapeutic application of anti-growth factor receptor antibodies," Curr. Opin. Oncol., 10:67–73 [1998].

Fonzi and Irwin, "Isogenic strain construction and gene mapping in *Candida albicans*," Genetics 134:717–728 [1993].

Galgiani et al., National Committee for Clinical Laboratory Standards (NCCLS), "Reference Method for Broth Dilution Antifungal Susceptibility Testing of Yeasts," Publication M27–t, vol. 15, No.10, pp. 1–29 [1995].

Goodwin et al., "A nationwide survey of clinical laboratory methodologies for fungal infections," J. Med. Vet. Mycol., 30:153–160 '1992'.

Graybill, "The future of antifungal therapy," Clin. INfect. Dis., 22(Suppl.2):S166 [1996].

Hanson et al., "Synergy between cilofungin and amphotericin B in a murine of candidasis,"Antimicrob. Agents Chemother., 35:1334–1337 [1991].

Hanson and Stevens, "Comparison of Antifungal Activity of Amphotericin B Deoxycholate Suspension with That of Amphotericin B Cholesteryl Sulfate Colloidal Dispersion," Antimicrob. Agents Chemother., 36:486–488 [1992].

Harlow and Lane (eds.), *Antibodies: A Laboratory Manual*, Cold spring Harbor Laboratory Press [1988] (Title Page Only).

Harth et al., "Treatment of *Mycobacterium tuberculosis* with antisense oligonucleotides to glutamine synthetase mRNA inhibits glutamine synthetase activity, formation of the poly–L–glutamate/glutamine cell wall structure, and bacterial replication," Proc. Natl. ACad. Sci. USA 97(1):418–423 [2000].

Hess et al., "Phosphorylation assays for proteins of the two–component regulatory system controlling chemotaxis in *Escherichia coli*," Methods Enzymol., 200:188–204 [1991].

Hillard et al., "Multiple Mechanisms of Action for Inhibitors of Histidine Protein Kinases from Bacterial Two–Component Systems," Antimicrobial Agents and Chemotherapy 43:1693–1699 [1999].

Hong et al., "Vitro Antifungal Activity and Cytotoxicity of a Novel Membrane–Active Peptide," Antimicrobial Agents and emotherapy 43(7):1704–1707 [1999].

Hua et al.,"Ethylene Insensitivity Conferred by *Arabidopsis ERS* Gene," Science 269:1712–1714 [1995].

Kennedy and Sigler, *Aspergillus, Fusarium*, and Other Opportunistic Moniliaceous Fungi, Murray et al., (eds), *Manual of Clinical Microbiology*, 6th ed., pp. 765–790, ASM Press, Washington, D.C. [1995].

Keshet and Ben–Sasson, "Anticancer Drug Targets: Approaching Angiogenesis," J. Clin. Invest., 104:1497–1501 [1999].

Köhler and Milstein, "Continuous cultures of fused cells secreting antibody of predefined specificity," Nature 256:495–497 [1975].

Kozbor and Roder, "The production of monoclonal antibodies from human lymphocytes," Immunol. Today 4:72 [1983].

Laurino et al., "Monoclonal Antibodies, Antigens and Molecular Diagnostics: A Practical Overview," Ann. Clin. Lab Sci., 29(3):158–166 [1999].

Leberer et al., "Signal transduction through homologs of the Ste20p and Ste7p protein kinases can trigger hyphal formation in the pathogenic fungus *Candida albicans*," Proc. Natl. Acad. Sci. USA 93:13217–13222 [1996].

Li et al., GenBack Accession No. U77605[1996].

Loomis et al., "Histidine kinases in signal transduction pathways of eukaryotes," J. Cell Sci., 110:1141–1145 [1997].

Lortholary et al., "Invasive Aspergillosis in Patients With Acquired Immunodeficiency Syndrome: Report of 33 Cases," Amer. J. Med., 95:177–187 [1993].

Madden et al., "Cell Polarity and Morphogenesis in Budding Yeast," Ann. Rev. Microbiol., 52:687 [1998].

Madhani and Fink, "The control of filamentous differentiation and virulence in fungi," Trends Cell Biol., 8:348–353 [1998].

Madhani and Fink, "The riddle of MAP kinase signaling specificity," Trends Genet., 14:151–155 [1998].

Meunier et al., "Candidemia in Immunocompromised Patients," Clin. Infect. Dis., 14[suppl. 1]:S120 [1992].

Miller et al., "Pulmonary Aspergillosis in Patients With AIDS," Chest 105:37–44 [1994]).

Mitchell, in *Zinsser Microbiology*, W.K. Joklik, et al. [eds], Appleton, Century–Crofts, Norwalk, CT, pp. 1183–1190 [1984].

Morgan et al., "Two–component signal–transduction systems in budding yeast MAP a different pathway?," Trends Cell. Biol., 5:453–457 [1995].

Nielsen et al., "Peptide nucleic acids (PNAs): Potential anti–sense and anti–gene agents," Anticancer Drug Des., 8:53–63 [1993].

Nielsen et al., "Sequence–Selective Recognition of DNA by Strand Displacement with a Thymine–Substituted Polyamide," Science 254:1497 [1991].

Parkinson and Kofoid, "Communication Modules in Bacterial Signaling Proteins," Ann. Rev. Genet., 26:71–112 [1992].

Piddock, "Antibacterials—mechanisms of action," Curr. Opin. Microbiol., 1(5):502–508 [1998].

Polis et al., "Fungal Infections in Patients with the Acquired Immunodeficiency Syndrome," in DeVita et al. (eds), *AIDS: Biology, Diagnosis, Treatment, and Prevention*, 4th ed., Lippincott–Raven, [1997].

Roychoudhury et al., "High Throughput Autophosphorylation Assay for Bacterial Protein Histidine Kinases," Biol. Screening 2(2):85–90 [2997].

Sachs, "Posttrancscriptional Control of Gene Expression in Filamentous Fungi," Fungal Genet. Biol., 23:117–124 [1998].

Sokal and Rohlf, *Biometry*, $2^{nd}$ Edition, W.H. Freeman, San Francisco [1981].

Tang et al., "An Aspergillus fumigatus alkaline protease mutant constructed by gene disruption is deficient in extracellular elastase activity," Mol. Microbiol., 6:1663–1671 [1992].

Tentler et al., "Inhibition of *Neurospora crassa* Growth by a Glucan Synthase–1 Antisense Construct," curr. Microbiol., 34(5):303–308 [1997].

Trinci et al., "Tip Growth of Fungal Hyphae," J. Gen. Microbiol., 103:243–248 [1977].

Unkles, in *Applied Molecular Genetics of Filamentous Fungi*, Kinghorn and Turner, Eds., pp. 28–52, Chapman and Hall London [1992].

Wang et al., "A Highly Conserved Mechanism of Regulated Ribosome Stalling Mediated by Fungal Arginine Attenuator Petides That Appears Independent of the Charging Status of Arginyl–tRNAs," J. Biol. Chem., 274:37565–37574 [1999].

Warnock, "Fungal infections in neutropenia: current problems and chemotherapeutic control," Antimicrob. Chemother., 41:95 [1998].

Wurgler–Murphy and Saito, "Two–component signal transducers and MAPK cascades," Trends Biol. Sci., 22:172 [1997].

Goueli et al., "A Novel and Simple Method to Assay the Activity of Individual Protein Kinases in a Crude Tissue Extract," Anal. Biochem., 225:10–17 [1995].

Fabret and Hoch, "A Two–Component Signal Transduction System Essential for Growth of *Bacillus subtilis*: Implications for Anti–Infective Therapy," J. Bacteriol., 180:6375–6383 [1998].

Loomis et al., "Two–component signal transduction systems in eukaryotic microorganisms," Curr. Opin. Microbiol., 1:63–648 [1998].

Moellering, "Antibiotic resistance: lessons for the future," Clin. Infect. Dis., 27 Suppl. 1:S135–140, discussion S141–142 [1998].

Srikantha et al., "The two–component hybrid kinase regulato CaNIK1 of Candida albicans," Microbiol., 144:2715–2729 [1998].

Anaissie, "Opportunistic Mycoses in the Immuncompromised Host: Experience at a Cancer Center and Review," Clin. Infect. Dis. 14[Suppl.1]: S43–sS3 [1992].

*Zinsser Microbiology*, Chapter 87, "Opportunisic Mycoses," W.K. Joklik, et al., [eds.], Appleton, Century–Crofts, Norwalk, CT, pp. 1183–1190 [1984].

Walsh and Dixon, "Spectrum of Mycoses," *Medical Microbiology*, 4th ed, Baron (ed.) University of Texas Medical Branch, Galveston, TX, pp. 919–925 [1996].

Chandler, Mycotic Diseases, 8 Candidiasis, *Color Atlas and Text of Histopathology of Mycotic Diseases*, pp. 42–46 [1980].

Meunier et al., "Fungal Infections in Immunocompromised Hosts: Candidemia in Immunocompromised Patients," Clin. Infect. Dis. 14[Suppl. 1]:S120–S125 [1992].

Loose et al., "Distribution of a Corticosteroid–binding Protein inCandida and Other Fungal Genera," J. Gen. Microbiol.129:2379–2385 [1983].

Loose and Feldman, "Characterization of a Unique Corticosterone–binding Protein in *Candida albicans*," J. Biol. Chem. 257:4925–4930 [1982].

Cole, "Basic Biology of Fungi," in *Medical Microbiology*, 4th ed., Baron (ed.), University of Texas Medical Branch, Galveston, TX, pp. 903–911 [1996].

McGinnis and Tyring, "Introduction to Mycology," in *Medical Microbiology*, 4th ed., Baron (ed.), University of Texas Medical Branch, Galveston, TX, pp. 893–902 [1996].

Dixon and Walsh, "Antifungal Agents," in *Medical Microbiology*, 4th ed., Baron (ed.), University of Texas Medical Branch, Galveston, TX, pp. 926–932 [1996].

Gooday, "Chitin metabolism: A target for antifungal and antiparasitic drugs," *Molecular Aspects of Chemotherapy*, E. Borowshi (ed.), Pergamon Press, pp. 175–185 [1990].

Georgopapadakou and Tkacz, "The fungal cell wall as a drug target," Trends Microbiol. 3:98–104 [1995].

Schmatz et al., "Treatment of *Pneumocystis carinii* pneumonia with 1,3–β–glucan synthesis inhibitors," Proc. Natl. Acad. Sci. 87:5950–5954 [1990].

Alex and Simon, "Protein histidine kinases and signal transduction in prokaryotes and eukaryotes," Trends Genet. 10:133–138 '1994'.

Swanson et al., "Histidine and aspartate phosphorylation: two–component systems and the limits of homology," Trends Biochem. Sci. 19:485–490 [1994].

Parkinson et al., "Communication Modules in Bacterial Singaling Proteins,"Ann. Rev. Genet. 26:71–112[1992].

Chang et al., "Arabidopsis Ehylene–Response Gene ETR1: Similarity of Product to Two–Component Regulators," Science 262:539–544 [1993].

Ota and Varshavsky, "A Yeast Protein Similar to Bacterial Two–Component Regulators," Science262:566–569 [1993].

Maeda et al., "A two–component system that regulates an osmosensing MAP kinase cascade in yeast," Nature 369:242–245 [1994].

Schuster et al., "The hybrid histidine kinase DokA is part of the osmotic response system of *Dictyostelium*," EMBO J. 15:3880–3889 [1996].

Wang et al., "A two–component histidine kinase gene that functions in *Dictyostelium* development,"EMBO J. 15:3890–3898 [1996].

Kakimoto, "CK11, a Histidine Kinase Homolog Implicated in Cytokinin Signal Transduction," Science274:982–985 [1996].

Alex et al., "Hyphal development in *Neurospora crassa*: Involvement of a two–component histidine kinase," Proc. Natl. Acad. Sci. 93:3416–3421 [1996].

Morgan et al., "Two–component signal–transduction systems in budding yeast MAP a different pathway?," *Trends Cell Biol.* 5:453–457 [1995].

Posas et al., "Yeast HOG1 MAP Kinase Cascade Is Regulated by a Multistep Phosphorelay Mechanism in the SLN1–YPD1–SSK1 'Two–Component' Osmosensor," *Cell* 86:865–875 [1996].

Appleby et al., "Signal Transduction via the Multi–Step Phosphorelay: Not Necessarily a Road Less Traveled," *Cell*86:845–848 [1996].

Burbulys et al., "Initiation of Sporulation in B. subtilis is Controlled by a Multicomponent Phosphorelay," *Cell* 64:545–552 [1991].

Uhl and Miller, "Integration of multiple domains in a two–component sensor protein: the *Bordetella pertussis* BvgAS phosphorelay," *EMBO J.* 15:1028–1036 [1996].

Brown et al., "Yeast Skn7p functions in a eukaryotic two–component regulatory pathway," *EMBO J.* 13:5186–5194 [1994].

Brown et al., "SKN7, a Yeast Multicopy Suppressor of a Mutation Affecting Cell Wall β–Glucan Assembly, Encodes a Product with Domains Homologous to Prokaryotic Two–Component Regulators and to Heat Shock Transcription Factors," *J. Bacteriol.* 175:6908–6915 [1993].

Krems et al., "The response regulator–like protein Pos9/Skn7 of *Saccharomyces cerevisiae* is involved in oxidative stress resistance," *Curr. Genet.* 29:327–334 [1996].

Page et al., "Identification of ASK10 as a Multicopy Activator of Skn7p–dependent Trasnciption of a HIS3 Reporter Gene," *Yeast* 12:267–272 [1996].

Springer, "Genetic Control of Fungal Differentiation: The Three Sporulation Pathways of *Neurospora crassa*," *BioEssays* 15:365–374 [1993].

Vollmer and Yanofsky, "Efficient cloning of genes of *Neurospora crassa*," *Proc. Natl. Acad. Sci.*83:4869–4873 [1986].

Dieffenbach and Dveksler, *PCR Primer, a Laboratory Manual,* Cold Spring Harbor Press, Plainview NY [1995 ].

Mullis et al., "Specific Enzymatic Ampliification of DNA In Vitro: The Polymerase Chain Reaction," *Cold Spring Harbor Symposia,* vol. LI, pp. 263–273 [1986].

Coombs, *Dictionary of Biotechnology,* Stockton Press, New York NY [1994].

Anderson and Young, "Quantitative Filter Hybridisation, " in *Nucleic Acid Hybridisation*[1985].

Selitrennikoff et al., "Formation and Regeneration of Protoplasts Derived from a Temperature–Sensitive *Osmotic Strain* of *Neurospora crassa*," *Exp. Mycol.* 5:155–161 [1981].

Davis and deSerres, "Genetic and Microbiological Research Techniques for *Neurospora crassa*," *Meth. Enzymol.* 27A:79–143 [1970].

Grindle and Dolderson, "Notes and Brief Articles: Effects of a Modifier Gene on the Phenotype of a Dicarboximide–Resistant Mutant of *Neurospora Crassa*," *Trans. Brit. Mycol. Soc.* 87:457–487 [1986].

Sambrook et al. (eds.), *Molecular Cloning: A Laboratory Manual,* Cold Spring Harbor Laboratory Press, Cold Spring Harbor, NY, [1989].

Volimer and Yanofsky, *Proc. Natl. Acad. Sci.* 83:4869–4873 [1986].

Orbach et al., "Cloning and Characterization of the Gene for β–Tubulin from a Benomyl–Resistant Mutant of *Neurospora crassa* and Its Use as a Dominant Selectable Marker, "*Mol. Cell. Biol.* 6:2452–2461 [1986].

Selitrennikoff and Sachs, "Lipofectin increases the efficiency of DNA–mediated transformation of *Neurospora crassa,*" *Fungal Genet. Newsl.* 38:90–91 [1991].

White and Woodward, "A simple method for making disposable race tubes," *Fungl Genet. Newsl.* 42:79 [1995].

Altschul et al., "Basic Local Alignment Search Tool," *J. Mol. Biol.* 215:403–410 [1990].

Bairoch, "Teh PROSITE dictionary of sites and patterns in proteins, its current status," *Nucl. Acids Res.* 21:3097–3103 [1993].

Bruchez et al., "Regulatory sequences in the transcription of *Neurospora crassa* genes: CAAT box, TATA box, Introns, Poly(A) tail formation sequences,"*Fungal Genet. News.* 40:89–96 [1993].

Nagasawa et al., "A novel sensor–regulator protein that belongs to the homologous family of signal–transduction proteins involved in adaptive responses in *Escherchia coli,*" *Mol. Microbiol.*6:799–807 [1992].

Liao et al., "Molecular Characterization of Two Gene Loci Required for Production of the Key Pathogenicity Factor Pectate Lyase in *Pseudomonas viridiflava, Mol. Plant–Microbe Interact .*"7:391–400 [1994].

Corbell and Loper, "A Global Regulator of Secondary Metabolite Production in *Pseudomonas fluorescens* Pf–5,"*J. Bacteriol.* 177:6230–6236 [1995].

Perego and Hoch, "Protein aspartate phosphatases control the output of two–component signal transduction systems," *Trends Genet.* 12:97–101 [1996].

Stock et al., "Signal transduction in bacteria," *Nature* 344:395–400 [1990].

Perkins et al., "Chromosomal Loci of Neurospora crassa , " Microbiol. Rev. 46:426–570 [1982].

Gierasch, "Signal Sequences," *Biochem.* 28:923–930 [1989].

von Heijne, "A new method for predicting signal sequence cleavage sites," *Nucleic Acids Res.* 14: 4683–4690 [1986].

Larsson et al., "A gene encoding sn–glycerol 3–phosphate dehydrogenase (NAD+) complements an osmosensitive mutant of *Saccharomyces cerevisiae,*" *Mol. Microbiol.* 10:1101–1111 [1993].

Ausubel, *Current Protocols in Molecular Biology*, unit 6.3 Wiley, New York [1994].

Aatsinki et al., "A Coupled One–Step Reverse Transcription PCR Procedure for Generation of Full–Length Open Reading Frames," *BioTechn.* 16:282–288 [1994].

Dale et al., "A Rapid Single–Stranded Cloning Strategy for Producing a Sequential Series of Overlapping Clones for Use in DNA Sequencing: Application to Sequencing the Corn Mitochondrial 18 S rDNA," *Plasmid* 13:31–40 [1985].

Orbach et al., "The *Neurospora crassa arg–2* Locus," *J. Biol. Chem.* 265:10981–10987 [1990].

Okamoto et al., "Nit–3m, the structural gene of nitrate reductase in *Neurospora crassa*: nucleotide sequence and regulation of mRNA synthesis and turnover," Mol. Gen. Genet.227:213–223 [1991].

Bruchez et al., "Regulatory sequences involved in the translation of *Neurospora crassa* mRNA: Kozak sequences and stop codons," *Fungal Genet. Newsl.* 40:85–88 [1993].

Lupas et al,m "Predicting Colied Coils from Protein Sequences," *Science*252:1162–1164 [1992].

Yao and Spudich, "Primary structure of an archaebacterial transducer, a methyl–accepting protein associated with sensory rhodopsin I," *Proc. Natl. Acad. Sci.* 89:11915–11919 [1992].

Reinert et al., "Genetic Regulation of the qaGene Cluster of Neurospora crassa: Induction of qa Messenger Ribonucleic Acid and Dependency on qa–1Function," *Mol. Cell. Biol.* 1:829–835 [1981].

Case et al., "Efficient transformation of *Neurospora crassa* by utlizing hybrid plasmid DNA," *Proc. Natl. Acad. Sci.* 76:5259–5263 [1979].

Metzenberg, "An alternate way of collecting, storing and dissecting Neurospora ," *Fungal Genet. Newsl.* 35:28 [1988].

Selker, "Premeiotic Instability of Repeated Sequences in *Neurospora Crassa*," *Ann. Rev. Genet.* 24:579–613 [1990].

Manning and Mitchell, "Strain Variation and Morphogenesis of Yeast– and Mycelial–Phase *Candida albicans* in Low––Sulfate, Synthetic Medium," *J. Bacteriol.* 142:714–719 [1980].

Scherer and Stevens, "A *Candida albicans* dispersed, repeated gene family and its epidemiologic applications," *Proc. Natl. Acad. Sci.* 85:1452–1456 [1988].

Moreno et al., "Molecular Genetic Analysis of Fission Yeast *Schizosaccharomyces pomb*," *Meth. Enzymol.* 194:795–823 [1991].

Vieia and Messing, "New pUC–derived cloning vectors with different selectable markers and DNA replication origins," *Gene* 100:189–194 [1991].

Hughes, "Histidine kinases hog the limelight," *Nature* 369:187–188 (1994), reports on the conclusions drawn from the analysis of Maeda et al. (Maeda et al.,*Nature* 369:242–245 [1994].

Wingrove and Gober, "Identification of an Asymetrically Localized Sensor Histidine Kinase Responsible for Temporally and Spatially Regulated Transcription," *Science* 274:597–601 (1996) .

Huang et al., "Purification of a Protein Histidine Kinase from the Yeast *Saccharomyces cerevisiae*," *The American Society for Biochemistry and Molecular Biology* 266(14):9023–9031 (1991).

Orth et al., "A Serine (Threonine) Protein Kinase Confers Fungicide Resistance in the Phytopathogenic Fungus *Ustilago maydis*," *Appl.Environ. Microbiol.* 61(6):2341–2345 (1995).

Livingston, "Locus–specific Changes in Cell Wall Composition Characteristic of Osmotic Mutants of *Neurospora crassa*," *J. Bacteriol.* 99(1):85–90 (1969).

Brewster et al., "An Osmosensing Signal Transduction Pathway in Yeast," *Science* 259:1760–1763 (1993).

Koshland, "The Two–Component Pathway Comes to Eukaryotes," *Science* 262:532 (1993).

Tentler et al., "Inhibition of *Neurospora crassa* Growth by a Glucan Synthase–1 Antisense Construct," *Curr. Microbiol.* 34:1–6 (1997).

Simons et al., "Cell wall 1,6–β–glucan synthesis in *Saccharomyces cerevisiae* depends on ER glucosidases I and II, and the molecular chaperone BiP/Kar2p," *EMBO J.* 17:396–405 (1988).

Linden et al., "Blue Light Regulation in *Neurospora crassa*," *Fungal Gen. Biol.* 22:141–150 (1997).

Scott, "Biochemical Genetics of Morphogenesis in Neurospora," *Ann. Rev. Microbiol.* 30:85–104 (1976).

Reynaga–Peña and Bartnicki–Garcia, "Apical Branching in a Temperature Sensitive Mutant of *Aspergillus niger*," *Fungal Gen. Biol.* 22:153–167 (1997).

Kobayashi, "Fungi," *Microbiology*, Fourth Edition, J.B. Lippincott Company, Philadelphia, pp. 737–765 (1990).

Berry, "Candidiasis, " *Diagnostic Atlas of the Major Systemic Fungal Infections*, Pfizer Inc., pp. 41–46 (1994).

Bennett, "Antimicrobial Agnets (Continued): Antifunal Agents," *Goodman & Gilman's The Pharmacological Basis of Therapeutics*, Ninth Edition, (eds. Hardman et al.); McGraw–Hill, New York, pp. 1175–1190 (1996).

Nagashashi et al., "Isolation of CaSLN1 and CaNIK1, the genes for osmosensing histidine kinase homologues, from the pathogenic fungus *Candida albican*," *Microbiology* 144:425–432 (1998).

Schumacher et al., "The Osmotic–1 Locus of *Neurospora crassa* Encodes a Putative Histidine Kinase Similar to Osmosensors of Bacteria and Yeast," *Current Microbiology* 34:340–347 (1997).

```
            • • • • • • • • ▽▽▽▽▽
Oslp    MTDGPTLAAIAALVKSLAVDPATTQTSGLRPSTHVRLPGPYTREKGD
BorA    MTNYSLRAR----------------MMILILAPTVLIGLLLSIFFV
RepA    NRRTDTGCWRKSV----LNKLGIKGRVLLLTILPASLMAAVLGGYF-
ApdA    M---------------LKKLGIKGRVLLLTLLPTSLMALVLGGYF-
Slnlp   MRFGLPSKLELTPPFRIGIRTQLTALVSIVALGSLIILAVTTGVYFT Oslp    VVRIEQLETAAIAASPPAMPDTPNAPTDALFSNGTLSPSSETPDARY
BorA    ----------------------------------------------
RepA    ----------------------------------------------
ApdA    ----------------------------------------------
Slnlp   DRLYIAAQLKSSQIDQTLNYLYYQAYYLASRDALQSSLTSYVAGNKS Oslp    FIDEALEGLREHVDDQSKLLDSQRQELAGVNAQLIEQKQLQEKALAI
BorA    ----------------------------------------------
RepA    ----------------------------------------------
ApdA    ----------------------------------------------
Slnlp   SVIQKFLSSSNLFYVAKVYDSSFNAVLNATNNGTGDLIPEDVLDSLF Oslp    LERELWKHQKANEAFQKALREIGEIVTAVARGDLSKKVRMNSVEMDP
BorA    ----------------------------------------------
RepA    ----------------------------------------------
ApdA    ----------------------------------------------
Slnlp   PSSLETIGILTDPVLNSTDYLMSMSLPIFANPSIILTDSRVYGYITI Oslp    INTMMDQLQVFSSEVSRVAREVGTEGILGGQAQIEGVDGTWKELTDN
BorA    ----------------------------------------------
RepA    ----------------------------------------------
ApdA    ----------------------------------------------
Slnlp   SVFNDTTALEHSTIAIISAVYNSQGKASGYHFVFPPYGSRSDLPQKV Oslp    TDQVREIASVTTAVAHGDLTKKIERPAKGEILQLQQTINTMVDQLRT
BorA    ----------------------------------------------
RepA    ----------------------------------------------
ApdA    ----------------------------------------------
Slnlp   ISSAFRNGKGGSLKQTNILSTRNTALGYSPCSFNLVNWVAIVSQPES Oslp    ARDVGTEGILGGQADVEGVQGMWNELTVNVNAMANNLTTQVRDIIKV
BorA    ----------------------------------------------
RepA    ----------------------------------------------
ApdA    ----------------------------------------------
Slnlp   LAKIITGTVIAIGVFVILLTLPLAHWAVQPIVRLQKATELITEGRGL
```

*FIG. 3A*

```
Oslp  LTQKVQAECRGEIFELKKTINSMVDQLQQFAREVTKIAREVGTEGRL
BarA  ------------------------------------------------
RepA  ------------------------------------------------
ApdA  ------------------------------------------------
Slnlp SRASSFKRGFSSGFAVPSSLLQFNTAEAGSTTSVSGHGGSGHGSGAA Oslp  VQGTWRDLTENVNGMAMNLTTQVREIAKVTTAVAKGDLTKKIGVEVQ
BarA  YNDLQRQLEDAGASIIEPLAVSTEYGMSLQNRESIGQLI-SVLHRRH Oslp  IEARRMVIEEIPYTLRGTVFNALKTLAVKANEKFLDL-TYRVDHSV-
BarA  LEAGKLILESIPFPLRSTLDEVVTLLAHSSHDKGLEL-TLNIKSDV-
RepA  IEAGKLVLDNIPFNLRDLLQDTLTILAPAAHAKQLEL-VSLVYRDT-
ApdA  IEAGKLVLDSIPFNLRDLLQDTLTILAPAAHAKQLEL-VSLVYRDT-
Slnlp NVLQRTKLEKRDFCITDVALQIKSIFGKVAKDQRVRLSISLFPNLIR Oslp  FRLRQIILNLVGNAIKFTEHGEVSLTIQKASSVQCSTEEY--------
BarA  LRLQQIITNLVGNAIKFTENGNIDILVEKRALSNTKV----------
RepA  LRLRQILTNLVSNAIKFTRQGTIVARAMLEDETEEHA----------
ApdA  LRLKQILTNLVSNAIKFTREGTIVARAMLEEEHEDSV----------
Slnlp NRIIQIVMNLVSNALKFTPVDGTVDVRMKLLGEYDKELSEKKQYKEV Oslp  ------------------------------------------------
BarA  ------------------------------------------------
RepA  ------------------------------------------------
ApdA  ------------------------------------------------
Slnlp TENLETTDKYDLPTLSNHRKSVDLESSATSLGSNRDTSTIQEEITKR Oslp  ------------------------------------------------
BarA  ------------------------------------------------
RepA  ------------------------------------------------
APDA  ------------------------------------------------
Slnlp YKKVNDREKASNDDVSSIVSTTTSSYDNAIFNSQFNKAPGSDDEEGG

*****                              ***
Oslp  ----AIEFVVSDTGIGIPADKLDLIFDTFQQADGSMTRKFGGTGLGL
BarA  ----QIEVQIRDTGIGIPERDQSRLFQAFRQADASISRRHGGTGLGL
RepA  ----QLRISVQDTGIGLSSQDVRALFQAFSQADNSISRQPGGTGLGL
ApdA  ----QLRISIQDTGIGLSNQDVRALFQAFSQADNSLSRQPGGTGLGL
Slnlp PKTWVISIEVEDTGPGIDPSLQESVFHPFVQGDQTLSRQYGGTGLGL
```

FIG. 3B

```
Os1p   LMGGDVWVKSEYGKGSKFFFTCVVRLANDDISLIAKQLNPYKSHQVL
BorA   EMGGDISFHSQPNRGSTFWFHINLDL-NPNIIIEGPSTQCLAGKRLA
RepA   QMGGEIGVDSTPGEGSEFWISLNLPKAREDREETANQALEGLRAAVL
ApdA   QMGGEIGVDSTPGEGSEFWISLNLPKTRDDAEDLPGPPLLGRRVAVL
Slnlp  MMHGTMKLESKVGVGSKFTFTLPLNQTKEISFADMEFPFEDEFNPES Os1p   HGPEIAKMLHGLGLVPIVVDSERNPALEKARAAGQAPYD-VIIVDSI
BorA   AQCTL-DILSETPL--EVVYSPTFSALPPAHYDMMLLGIAVTFREPL
RepA   ALEHQLEDCGLQTVVFTNLENLLNGVTAAHETPQAIDLVVLGVTALE
ApdA   ALQHQLEDCGLEVTPFNTLEALTNGITGVHQSEQAIDLAVLGITTND
Slnlp  SVAKSIKSRQSTSSVATPATNRSSLTNDVLPEVRSKGKHETKDVGNP Os1p   S-VDDFKYLPIVLLAPVVHVSLKSCLDLGITSYMTTPCQLIDLGNGM
BorA   KAVSMTDFLMLALPCHAQVNAEKLKQDGIGACLLKPLTPTRLLPALT
RepA   HIWDLENLNCKVMVLCPTTEHALFQMSVHDVYTQLQAKPACNRKLQK
ApdA   HIWDLEHLGCKVLVLCPTTEQTLFHLSVPNPHSQLQAKPACTRKLRR
Slnlp  DNGGLEQLQEKNIKPSICLTGAEVNEQNSLSSKHRSRHEGLGSVNLD Os1p   TPSLA-DNTKSFEILLAE----DNTVNQRLAVKILEKYHHVVTVVGN
BorA   TLLPVTDESKLAMTVMAV---DDNPANLKLIGALLEDMVQHVELCDS
RepA   RAVRTDVALPLSSRAPRVLCVDDNPANLLLVQTLLEDMGAEVVAVDG
ApdA   RRARSEPEETLSSRAPRVLCVDDNPANLLLIQTLLEDMGAKVLAVDN
```

FIG. 3C

```
Cos1    1   ------------------------------------------------------------DLL
OS-1    1   MTDGPTLAAIAALVKSLAVDPATTQTSGLRPSTHVRLPGPYTREKGDLERELSALVVRIE
BAR-A   1   ------------------------------------------------------------
SLN1    1   ----------------------------------------MRFGLPSKLELTPPFRIG

Cos1    4   CWSCVVAIYKAPPYINKKFFLSVVYLEFLPLSPMNPTKKPRLSPMQPSVFEILNDP--EL
OS-1    61  QLETAAIAASPPAMPDTPNAPTDALFSNGTLSPSSETPDARYPAPLPRNGFIDEAL--EG
BAR-A   1   ------------------------------------------------------------
SLN1    19  IRTQLTALVSIVALGSLIILAVTTGVYFTSNYKNLRS-DRLYIAAQLKSSQIDQTLNYLY

Cos1    62  YSQHCHSLRETLLDHFN---------------------HQATLIDTYEHELEKSKNANK
OS-1    119 LREHVDDQSKLLDSQRQELAGVNAQLIEQKQLQEKALAIIEQERVATLERELWKHQKANE
BAR-A   1   ------------------------------------------------------------
SLN1    78  YQAYYLASRDALQSSLTSYVAGN----K-----------SADNWVDSLSVIQKFLSSSNL

Cos1    100 AFQQALS--EIGTVVISVAM--GDLSKKVEIHTVE---NDPEILKVKITINTMMDQLQTF
OS-1    179 AFQKALR--EIGEIVTAVAR--GDLSKKVRMNSVE---MDPEITTFKRTINTMMDQLQVF
BAR-A   1   -------------MTNYSLR--ARMMILILAPTVL---IG-LLLSIFFVVHRYNDLQRQL
SLN1    123 FYVAKVYDSSFNAVLNATNNGTGDLIPEDVLDSLFPLSTDTPLPSSLETIGILTDPVLNS
                                                        .  ..         .    *

Cos1    153 ANEVTKVATEVANG--ELGGQAKNDGSVGIWRSLTDNVNIMALNLTNQVREIADVTRAV-
OS-1    232 SSEVSRVAREVGTEG-ILGGQAQIEGVDGTWKELTDNVNVMAQNLTDQVREIASVTTAV-
BAR-A   42  EDAGASIIEPLAVST-EYGMSLQN------RESIGQLISVLHRRHSDIVRAISVYD----
SLN1    183 TDYLMSMSLPIFANPSIILTDSRVYGYITIIMSAEGLKSVFNDTTALEHSTIAIISAVYN
              .    .                            .      .      *.

Cos1    210 -AKGDLSRKINVHAQGEILQLQRTINTMVDQLRTFAFEVSKVARDVGVLGILGGQALIEN
OS-1    290 -AHGDLTKKIERPAKGEILQLQQTINTMVDQLRTFASEVTRVARDVGTEGILGGQADVEG
BAR-A   91  -ENNRLFVISNFHLDPSSMQLGSNV--------PFPRQLT-VTRD--------GDIMILR
SLN1    243 SQGKASGYHFVFPPYGSRSDLPQKVFSIKN--DTFISSAFRNGKG-GS----LKQTNILS
                             *        *         .

Cos1    269 VEGIWEELTDNVNAMALNLTTQVRNI-ANVTTAVAKGDLSKKVTADCKGEILDLKLTINQ
OS-1    349 VQGMWNELTVNVNAMANNLTTQVRDI-IKVTTAVAKGDLTQKVQAECRGEIFELKKTINS
BAR-A   133 TPIISESYSP-----DESPSSDAKNS-QNMLGYIALELDLKSVRLQQYKEIF--------
SLN1    296 TRNTALGYSP----CSFNLVNWVAIVSQPESVFLSPATKLAKIITGTVIAIGVFVILLTL
                                                    ..   .
                                                            FIG. 6A
```

```
Cos1   328  MVDRLQNFALAVTTLSREVGTLGILGGQAN---VQDVEGAWKQVTENVNLMATNLTNQVR
OS-1   408  MVDQLQQFAREVTKIAREVGTEGRLGGQAT---VHDVQGTWRDLTENVNGMAMNLTTQVR
BAR-A  179  -IS----------SVMMLFCIGIALIFG---------------WR---LMR-----DVTGPIR
SLN1   352  PLAHWAVQPIVRLQKATELITEGRGLRPSTPRTISRASSFKRGFSSGFAVPSSLLQFNTA
                 .          .                   .

Cos1   385  SIATVTTAVAHGDLSQKIDVHAQGEILQLKNTINKMVDSLQLFASEVSKVAQDVGINGKL
OS-1   465  EIAKVTTAVAKGDLTKKIGVEVQGEILDLKNTINTMVDRLGTFAFEVSKVAREVGTDGTL
BAR-A  208  NMVNTVDRIRRGQLDSRVEGFMLGELDMLKNGINSMAMSLAAYH----------------
SLN1   412  EAGSTTSVSGHG-GSGHGSGAAFSANSSMKSAINLGNEKMSPPEEE-NKIPNN-HTDAKI
                .*    .              .*  **     .

Cos1   445  GIQAQVSDVDGLWKEITSNVNTMASNLTSQVR-----------------
OS-1   525  GGQAQVDNVEGKWKDLTENVNTMASNLTSQVRGISTVTQAIANGDMSRKIEVEAKGEILI
BAR-A  252  --------------EEMQHNIDQATSDLRETLE-----------------
SLN1   469  SMDGSLNHDLLGPHSLRHNDTDRSSNRSHILT-----------------
                    *   .*

Cos1   477  --------------------------------------------------
OS-1   585  LKETINMMVDRLSIFCNEVQRVAKDVGVDGIMGGQADVAGLKGRWKEITTDVNTMANNLT
BAR-A  271  --------------------------------------------------
SLN1   501  --------------------------------------------------

Cos1   477  ----AFAQITAAATDGDFTRFITVEALGEMDALKTK---INQMVFNLRESLQRNT----A
OS-1   645  AQVRAFGDITNAATDGDFTKLVEVEASGEMDELKKK---INQMVYNLRDSIQRNT----Q
BAR-A  271  ----Q-MEIQNVELD-------------------------------L
SLN1   501  ----TSANLTEARLP-DYRRLFSDELSDLTETFNTMTDALDQHYALLEERVRARTKQLEA

Cos1   526  AREAAELANSAKSEFLANMSHEIRTPLNGIIGMTQLSLDTELTQYQREMLSIVHNLANSL
OS-1   698  AREAAELANKIKSEFLANMSHEIRTPMNGIIGMTQLTLDTDLTQYQREMLNIVNSLANSL
BAR-A  282  AKKRAQEAARIKSEFLANMSHELRTPLNGVIGFTRLTLKTELTPTQRDHLNTIERSANNL
SLN1   556  AKIEAEAANEAKTVFIANISHELRTPLNGILGMTAISMEETDVNKIRNSLKLIFRSGELL
            *. *. *    *. *.**.***.***.**..*  *  ...   *   *   .     *

Cos1   586  LTIIDDILDISKIEANRMTVEQIDFSLRGTVFGALKTLAVKAIEKNLDLTYQCDSSFPDN
OS-1   758  LTIIDDILDLSKIEARRMVIEEIPYTLRGTVFNALKTLAVKANEKFLDLTYRVDHSVPDH
BAR-A  342  LAIINDVLDFSKLEAGKLILESIPFPLRSTLDEVVTLLAHSSHDKGLELTLNIKSDVPDN
SLN1   616  LHILTELLTFSKNVLQRTKLEKRDPCITDVALQIKSIFGKVAKDQRVRLSISLFPNLIRT
            * *.   .*  **      .*    ..            .... *.
```

FIG. 6B

```
Cos1   646   LI--GDSFRLRQVILNLAGNAIKFTK-EGKVSVSVKKSD-K-MVLDSKLLLEVCVSDTGI
OS-1   818   VV--GDSFRLRQIILNLVGNAIKFTE-HGEVSLTIQKASSV-QCSTEEYAIEFVVSDTGI
BAR-A  402   VI--GDPLRLQQIITNLVGNAIKFTE-NGNIDILVEKRA----LSNTKVQIEVQIRDTGI
SLN1   676   MVLWGDSNRIIQIVMNLVSNALKFTPVDGTVDVRMKLLGEYDKELSEKKQYKEVYIKKGT
             ..  **  *.. *.. **  **.***    *  ...                      *

Cos1   701   GIEK-----DKLGL--IFDTFCQADCSTTRKFGGTGLGLSISKQLIHLMGGEIWVTSEYG
OS-1   874   GIPA-----DKLDL--IFDTFQQADGSMTRKFGGTGLGLSISKRLVNLMGGDVWVKSEYG
BAR-A  455   GIPE-----RDQSR--LFQAFRQADASISRRHGGTGLGLVITQKLVNEMGGDISPHSQPN
SLN1   736   EVTENLETTDKYDLPTLSNHRKSVDLESSATSLGSNRDTSTIQEEITKRN-TVANESIYK
                .        .    *    *..            .   .    .    *

Cos1   754   SGSNFYFTVCVSPS-NIRYTRQTEQLLPFSSHYVLFVSTEHTQEELDVLRDGIIELGLIP
OS-1   927   KGSKFFFTCVVRLA-NDDISLIAKQLNPYKSHQVLFIDKGRTGHGPEIAK-MLHGLGLVP
BAR-A  508   RGSTFWFHINLDLNPNIIIEGPSTQCLAGKRLAYVEPNSAAAQCTLDILSETPLEVVYSP
SLN1   795   KVNDREKASNDDVS-SIVSTTISSYDNAIFNSQFNKAPGSDDEEGGNLGRPIENPKTWVI

Cos1   813   IIVRN-----IEDATLTEPVKYDIIMID-SIEIAKKLRLLSEVKYIPLVLVHHSIPQLNM
OS-1   985   IVVDSERNPALEKARAAGQAPYDVIIVD-SIEDARRLRSVDDFKYLPIVLLAP-VVHVSL
BAR-A  568   TFSALPP---AHYDMMLLGIAVTFREPL-TMQHERLAKAVSMTDFLMLALPCH--AQVNA
SLN1   854   SIEVEDTGP-GIDPSLQESVFHPFVQGDQTLSRQYGGTGLGLSICRQLANMMH--GIMKL
                                         ..              .

Cos1   867   RVCIDLGISSYANTPCSIT---DLASAIIPAL-----ESRSISQN---SDES-VRYKILL
OS-1   1043  KSCLDLGITSYMTTPCQLI---DLGNGMVPAL-----ENRATPSL---ADVT-KSFEILL
BAR-A  622   EKLKQDGIGACLLKPLTPT---RLLPALTEFC-----HHKQNTLLPV-TDESKLAMTVMA
SLN1   911   ESKVGVGSKFTFTLPLNQTKEISFADMEFPFEDEFNPESRKNRRVKFSVAKSIKSRQSTS
                    *        *

Cos1   915   AEDNLVNQR--LAVAILEKQG----HLVEVVEN---G-LE-----AYEAIKRNKYDVVLM
OS-1   1091  AEDNTVNQR--LAVKILEKYH----HVVTVVGN---G-EE-----AVEAVKRKKFDVILM
BAR-A  673   VDDNPANLK--LIGALLEDMV----QHVELCDS---G-HQ-----AVERAKQMPFDLILM
SLN1   971   SVATPATNRSSLTNDVLPEVRSKGKHETKDVGNPNMGREEKNDNGGLEQLQEKNIKPSIC
                . . *  .*     .         *  .     *  .

Cos1   960   DVQMPVMGGFEATEKIRQWEKKSNPIDSLTFRTPIIALTAHAMLGDREKSLAKGMDDYVS
OS-1   1136  DVQMPIMGGFEATAKIREYERSLG---SQ--RTPIIALTAHAMMGDREKCIQAQMDEYLS
BAR-A  718   DIQMPDMDGIRLACELIHQLPHQQ-------QTPVIAVTAHAMAGQKEKLLGAGMSDYLA
SLN1   1031  LTGAEVNEQNSLSSKHRSRHEGLG---SVNLDRPFLQSTGTATSSRNIPTVKDDDKNETS
                ..                              *. *  *
```

FIG. 6C

```
Cos1   1020   KPLKP----KLLMQT--------------------INKCIHNINQLKELSRN---SRGSDF
OS-1   1191   KPLQQ----NHLIQT--------------------ILKCATLGGQLLEKNRERELTRAADA
BAR-A   770   KPIEEERLHNLLLRYKPGSGISSRVVTPEVNEIVVNPNATLDWQLALRQAAGKTDLARDM
SLN1   1088   VKILVVED-NHVNQEVIKRMLN--------LEGIENIELACDGQEAFDKVKELTSKGENY
                    .      . .                                          *

Cos1   1054   AKKMTRN-TPGSTTRQGSDEGS---------VEDMIGDTPRQGS---VEGGGTSSRPVQR
OS-1   1228   VTGGRRD-NGMYSASQAAQHAA---------LRPPLATRGLTAA---DSLVSGLESPSIV
BAR-A   830   LQMLLDF-LPEVRNKVEEQLVGENPEGLVDLIHKLHGSCGYSGVPRMKNLCQLIEQQLRS
SLN1   1139   NMIFMDVQMPKVDGLLSTKMIRRDLG----YTSPIVALTAFADD---SNIKECLESGMNG

Cos1   1101   RSATEGSITTISEQIDR--------------
OS-1   1275   TADKEDPLSRARASLSEPN--IHKAS----
BAR-A   889   GTKEEDLEPELLELLDEMDNVAREASKILG
SLN1   1192   FLSKPIKRPKLKTILTEFCAAYQGKKNNK-
```

*FIG. 6D*

FIG. 10A 8.3 kb DNA sequence of *FOS-1* Genomic DNA 8256 bp

```
GAATTCCATTGGCTGATTGATGGATAAAATCATCTTTGTTGTCTTCGCAAAGTGAAGTCTGC
ATCAAATGAGGGGACTAAAGTCAGGTGATTGCGCTGCCATCGTAAGGCTCGAGACATTGTGA
TTGGTTCTTTCGACCAAGACTACAGTACTCGGAGTATATTGTCAAAGATACCAGATCGAATT
GTTGAGAAGATTCGTCTGTAAAAGGCGCCGGTAGTTTTTATTAAGGAAGGTCAGATCAATGA
TTGGGCTGGGTCGCCAAAGGGATGAAACTATTTTGGCTTTCACAAGTAGTTTAGTGAAACTC
CACAACCCGCAAGACGGCAACAAGACGGCATGGCATTATATGTAGCATGACTCGCAGAGTCA
GAAGAACGTCCCATTCTTTGCAGATCTTAAACTATTGGCTCTAATTTTTAGCCAAAAGTCTT
CGGATAAACGCCGTCTCTAGGGAGGCATGAACATCCCACAGGTCTGTCGGTATGGGCCGCTA
GTTTCTTCCATATTGGTCGGATCATTAAACCTAAGGTGAGTTGACGTGCCTTGCAATGCTTT
GGCTGCAGATTAGTCTTCTTCTAGTCCACTGTACTGATAATAACTATCGTCCTCGACTAGCG
GGTAGAGCCGACAGTCGGACCTGAGCGCTCTCCAATTCCAACACAGATGTCAGGAGCCATTT
TTGCGAGGAGGTTTGTGGCTGGAGGATATAAAGGAATGAGCTGCAATGCATCTGAACGGTGA
TGGGGTCATAGTTTGTGTTTAAAAGGATCAATCTCGGATACAGCAGGTGCTGTCAGCATCGT
CCAAGATCTTCTTCCTTCGGGCGGCTTTGTTGTGTGATTTGTACCCTCATCCTTTCCGTTAA
GAATCTAGCTTTCTTGATATTTGTGGAAGATCTCATCCCAGTAGTCAGTGACAAACGATTCG
AGTCTCAAATCTCAACAGAAGTGCCAGCAAGGTCTCACGCACAAAATGGGGGACTGCGATAA
AAATCTCCAAATGCCTCCTGTACCGTTCTCACAACGTCCAATCATCATTCTAGGCGCAGGGA
TCATTGGGTGCGCTACAGCAAGACAGCTTCTCTTAAATGGCTTTCGCGTTGTGGTTGTTGCC
GAGTTCCTGCCAGGCGATCAAAATATTTTTACGCATCAGCCTGGGCTGGAGCAACATGGCAT
GCTGCTGGCGGGATCAGTTCCGAATATCGATACCTTCAAGCTGTTACGCATCGGCATCTGTT
GAAGATGGCGCAAGAAGGCCCCGAATCCGGAGTTTGTCTTGTGGATGCGCGCGAATATCTCG
AAGAAGCGCCATCTGAGAACTCCTCAATCTGGGGTAAGACTGTGGTCACAAATGTAGGTAAT
GGAGCGGTCCCACTCATGGTGTATGGACATACTGATGAGGTAGTTTCGCGAACTTTGAACCC
GGGCGAAATATCCTTCCTAAACTTCCATTGCGGGTGGTCATACCAAACACTGGTAAACGGAT
CCGACGCGTCACTTGCCCTATCTCCGAGATCAGATAACGGCTCTTGGTGGCCAGTTCATTCG
AAAGCGGGTCGAGTCCCTCCAAGAGCTGTACGCCATGTTTCCCGAGTCAAGTGTCTTCATCA
ATGCCAGCGGGCTCGGAAGCAAAACCCTCACCGACGTTCGGGATGATAAGTGCTTTCCTGAG
CGAGGCCAGAATGTCTTTTATCGTACCGACAAGTGTCGACAGATGTACTTTCGCAATGGAAA
AGAGTACACCTATGTCATCCCCCGTCCTTTATCCGAGGGGGTAGTGTTAGGGGAGTCAAGC
AGCCGAACAACCTGTCAGTGACGTTTCCTGTGCATGCATCTATGACGAAGCTAACATTATAT
AGGTCCCCAGAGGTTGACATAGACGTTGCTCGAGACGAGATCGCGCGCGCTCATCGTTCGCA
CCAGAGATTGTTCCCGCAGACCCCCCGAAGAGTCATTGAGCTATATTATTGGTATTCGACC
ATCAAGGCAAGGTGGGTTTCGCTTGCATTCTGAGCAATTGGGCCAGCGGACAGTCTTATCAG
CTTATGGATTCGGAGGCGGCGGCTATGCGTTTTCGTATGGTATAGCGGAAGCGTTGTTGACG
ATGCTGGAGAAGTGCGAGAGAGAAAATGTCATCATATAATATCTCTATGTTAACCTGGAGCA
CCCTTTAGGAAGAATCCCAGAGCAATATAGGCTTGTTGTTGCTACTGCTTCCACCCTATGCA
TGTAAGCCTATGAAGTGTGCCTCAGGCTGGCCAAGAAGCCTGAAATGGCAAGGCATACCACA
TTAAATTGACGACCTGCTCCATCCTTCCATGCCAGATAAAGTTACCGAGTCCACACAGCAAC
AGCGACAATGACAATGACAAGTCAGCTACCTAAGGTTAGTACAGCTATGGACTCGCAGGAAC
TTAAACTTTCAGCTAAGTTCGACCCCGGCTGGCCACGTTGAATTACGTTGCCAATGCAATTC
```

FIG. 10B

```
CTCGTGAATCTTTGGCGTCAGCGGGTCCTCCCGATCGCAGATCCCTGACACATTTTCAGGCT
CCAAATAATAAAATTTACTCCAACTTGAGTCAGACTCGTCTTGATCCAGCGCTTCCAAGCTT
TGGCTTGTTTCGTTCAGGAGCCTGGATCCATTCCATCACGCACTCAGCCACCCCAGCCAGGC
GCGCGGATGGGGTACACAGACGTTCTTCTACAGTTACTACCCGTTGTTAACTTATCAAAATT
CGAGGCGACCAGCAGTGCTCTCAAGGAGTAAGGTTTCGGCCGAGTCCTTTCTTAGTATGGAA
GGAATGCCACACTCGATATGTCATCATGTCATCGGCTCTCACGATCGGCTGAGCTATGAGCA
TCCGTGTGCCAGCTTCCCGGAGATCGCTGGTAAATATCGCATCTTGCTTTGAAGCGATTAAG
AAACCACCATACAAAGGCGGACTATGGAAAGGAAAAGCACCAATGTCGGATTCGATTGTCGA
ACCCAGCGAGTTCATGATTCATGTCAGATGCAAGGGATCTGTGCGGCTAGGTTGCTTGATCG
GGTTTAGTGGAATTGTCATGTATACTCTCTGCACGGAGCAGAATTTCAAAGCCGACGAGTTG
AGCCAGATGTGATCGTATTCAAGTGATTAAAGTGCAAGGGACACAGTAAGTAGTGCTAGAGA
TCTAGGATTTACTCGCCTCTCCACAGAGGTACACAAACAATCTTCAGCTAAAGAGGTACTCC
GTACAGTGGGCGAAGAAACAACTATTTCTGATTGACTCTTCCCATCAAAGTACTGTTATGTG
GGTCTGCAACTTAACTCTGGTAGGCCATTCACGATTCACACAGAATGACAAAAACAGGTTCA
TGTACCGCCATTCCTTCCCCGCAGCCCACTGGAACTTCTTTCCAACCAGTGGCTGCACAGCA
AAATCGCAAACATGGTGCAAGTGTGTAAGATGAGTAGGGTCTCTCTCGGTGCGCTCTGCGAT
GACGTGGGTGGTAGTAGTCTACTGTGGTTATGCGACTGAATGGAATATTATCCTTATGGGCC
TACTGGCCCGCAGGCCTGCAACTGGTTCTTTTGAATGGTCTTTTAACGAATTTCCAATACAC
AACAAATACGGGTCAAAATTACAATCCTTATTTGCCTCTTGAGTGTCGGAACTGAATAAGTT
AAGAGTATTAACTAGTTAGTTAATTACTAGGTACTAAACTGCATGATTACTTTTATGTGGGG
CCGGCGAGAATCGTCATCTGCAACTGTGTTTCTACTCGGCGTATTTCTCAGTGATACCTTTC
CACATTCCATGTGCATCTACTGATCATCCATCTGTCGTCTTCTGGGTGAGTGAGTGGACTAG
TCCAGAATCCTGCTTGCAATTCTCATCTGTCGCCCACTCGGCCGGTTCTCGGCTTCGGACGT
CCTTGGTTGCGCCACAGGGGAAGACAGGCAAAAGGCAGAGAGCCACAGCACAGACTTGGGAA
ACTGATAAAACAACCACTCTCCTCATGCGTATTTGAAGTAGCGAGTTCTCGGTTGGCTTCT
TTTCTGCTGTTATCTCGCTACCTTTGTTGTGGGGATTCAGCTAGCCTAAATGGCCCTCGAC
AAGGAGCTTCTTCACCTTCATCTCGGGGATGGCCAGCAGCGACCCTACAAGCTTTCCACGGT
CGCTACTCCTCCCGATGAAGAGCAGCTCAATCTTCAACGCAGTGATAAGGATACAGCTGAAC
CGTCTCAAACTCCCCGCTGTGACACTCCGCGAGAGGCCCACACAGAGATCGTACAGAACGAT
ACTTCCTCGCTGAATCGAATTTTCCGCTTCACTCCTGTGCCGACCCTCATCCTCGACTCGTC
CTTGCGCGTGATTGAGGTCTCGGAGAGCCACCTTGCTTTCTGCGGAAAGTCTCGAGACTTTG
TGCTGGGTGCCTCCATCTACGAGCTTCCCCTCGCCACTATACCTGCGCCAGACATTGCGACT
CTGAACGGTGCTTTGCACGTGGCGATTACGACTCGGGCTGTCCAGGTTGTCGAAACTATCCA
CCTTCCCAGAATAAGCTCTTATTTTCACTGAAAATCACCCCCATTTTCCAGGGATCCACTC
TGCTGAACCTAGTTCTGGAAGCGCACAACGTCACAAGGACCCATACCGAGTCACTGCATAAT
GCCTACATCAATGAGACTTACAAGATCCTGGTTGACACGATCCGAGATTACGCTATCTTTAT
GCTGGACGCGCGCGGCAACATTGTAACGTGGAATTCGGGCGCTGCGATTATCAAGGGATATA
AGGCGGATGAGATTATCGGTCGGCATTTCTCGGTCTTCTACGGACCCGAGGATCGGCTGGCA
GACAAGCCTGGGAAGGAGCTCGAATTGTGCCTACGGGACGGAAAGTCGAGGATGAAGGCTG
GCGGTATCGTCAGGATGGTTTACGGTTTTGGGCCAACGTAATGATTACGCCTATCTTCTCAT
TCGGTCGGCACGTTGGTTTCGTCAAAATCACTCGCGACTTGACCGAGCGCAAAGCGGCTGAA
GCGCGGATGGTGGCAGCTTTTGAGGAATCATCCAAGATGAAGAGTGACTTCCTGGCCAACAT
GAGCCACGAGATTCGGACTCCCATGAATGGAATGCACCTGGCATTGACCATGTTGGGGAGCA
```

FIG. 10C

```
CGGAGCTCGACACCCAGCAGCGTGAATACACTTCCATTATCGAGGATTCCATGTCGATTTTG
CTTCAAGTAATCAACGACGTCCTTGATTATTCTAAGTTATCCTCCGGCACCTTCTCTCTGAA
CACAGATGTCTTGAGCGTTGAGAATATTGTGGGAGCAGTGGTACGGAATTGCAAGGCCTTAA
ACCCTGCCGTGGAGATCTCCTGTTCCATGCCTCCGGGCTTCCCAAAACTGCTCCGGGGTGAT
CCGCTTCGCTATCGGCAAGTGATCCAGAACCTCGTGGGAAATGCGATGAAGTTTACCGAGAA
AGGCCATGTCAAGGTCACCCATCGCTTTGCAGTAGAGGAGCACGATGCCAATAGGTACATAA
TCACGACAGAAGTCACTGATACTGGCATCGGGGTGCCCGAAGATGCTATAAACACTCTTTTT
ACCCCATTTACGCGCTTTGCGGATTCAGCCACCAAGCGCTATCAGGGTACAGGACTTGGCTT
GTCCATCTGCAAGAGCTTGGCAGAGCTGATGGATGGCAGTGTTGGTTATAAACCCAACCCAG
AAGGAAAGGGTAGCTGCTTTTGGCTCAACGTGAGAATGCAAGCTGTCGACATTCCAGCGCCT
AGTAAAGACACTCCCGCTGCTACCGCCGAAAATACGTACGAACCCATCGAAGAGGTCAAGGA
GATTGCGCCTCACATGCACATATTGCTGGTGGAAGATAATATGGTGAACCAAATCGTTATGC
TGAAGCTTCTCAAAAGCCTCGGTTTCGAACGTGTCGACACGGCCTGGGACGGCGCAGACGCA
GTCCGACAGGTGAAACAAACACCTCTCTTACAATGTTATTCTTATGGACATCAACATGCC
GGTTATGAATGGACTCGAAGCAACGACCAAGATCCGTGAAGTGAACAGCGAGGTACCCATCA
TAGCACTCACCGGGAATGCGCTCAAGGGAGACGCGGAGACATACCTTGCCAGAGGCATGAAC
GATTACGTCGCCAAACCAGTTCATCGCAAGCGGCTTGTGCAGTTGTTGTGGAAGTGGCTCGG
TTCGTGAGCAACTGTTCCTCTGGCCTCGCTGGCCGGTGGCTCCTCCGTTGGGACAAGACCTG
ATTGTCCTGTTATAACTTAAAGTGGGCTTGGATGCACCTTTGCCCGCACCCTATCTACCAT
AGCTCTCGCCCTCAGTTGAGCGGTGTCTCGCTCATACTAAACGAGGCGCTATCTTTGGTCGG
CTTTGAACTATCCGGCTATGCATCTTTCATAGCCTCATCAATCGCCAAAAGAAATGGCCTTG
ATGGCTATCAGCTTCTCGACAGATTTTCACGTCCGCGTACGTTGGCCATTCACAGTACATAT
TTTTCGCGGACCCTGCATACTCCACCCTTTCATTATTTGCCTCTTCGATCACGGTTCGCCAT
CAATCATCCATCATAATAAAGCGAACCGTCTCCGAAATGGATTCAGTTGCCTGGCTCGGGT
TGTCCGGTTGGGTAACACAGGAGTTTGGCCAAGTTTGCGGATGGTCATGGAGACCTATGGAA
CGAGGCTATACATTCATGAGAGAAATGTACGGCTAGCGAGCAATTGTTCTAGACCAGGATAG
CACTAAGCATCCTGTCCGATCATGTCACGATACTATTGAGTCGTTTGTCTATCAGGCCGCTA
CCCAAGCCGGGTGTATTCATGTAACACGAATTGATTGCATTTAATGGTGGCATGAATTAATG
AGTGTCCTTCTACATCTAGTTCATCCGTTGTACCTCTTCTGTCCTTTTAGTGTATTTGTCGA
GTGTCACACGACCGTGCAACTGTAGCGCCATGTACTTGCTCGGCTCCAACATTTGCACCTGT
TGAGGGTAGCCTGTTCAACAATTCTCACCACAACGGCGACAGCGTCCCGATGAAGTACGATC
CTCCTCCATCCTACATCCTACTCCTTCAAATCAGCGCGTCCATCCCTGCAGTGCTTCAACCG
TCACTCATCAAGTTGATCTTTACCTATTTGCCCGTAAATTCGGGCTAGATCGGCGGTGGGGT
TGGGCCTTAGCTCAATGCGAGAAGGTAGAACCTCCTGAACTACTGAGTTGCTCGCAAAACTT
GTTTACGCTTTGCGCATGCTTCTTCAAGGCTTATCCTGGCGGCGGCTGTATACCGAGGCTAT
GCTTACGAAACGGTCAATGCCGCATATCCCTTCAAGTCGGACAACCTTGTTTACAGACAGTG
TCCTACCTTGTGTCTGTGCGTGAGAGGTGAACCGTGAACCTGATCGCCTGTCTTTTGGCGGT
TGATGATATGAAGATCGTGGTTGTGGATTCTCACGTGTGCTTGGGCAAGTCTTCCCGAGGCA
TGGAAACAGCTCCGCTGGTAACGACTGACTGCATGCATCTTTAATCACAGCCGTGCCTGTTG
TCTCAAAGAATGAAAGGACGGGCTATGATAAGCTTCAGCTAGCCTCCTATGGTCTATCAGAA
CACAAAGATAAAAGGTGCCTAGAACTTCCATTTCTAGTATAGTAGAAGTGATAGTGCATAT
TTCCTCCATCCCCGCTGTGGTACAACGCCATGAACGAGGAGAACCGCGGTGCCACACAACC
GATCCGGGTAGGACGCAATCCGTAATTGATGTCGATCGACATGATAGCAGGGGCTGATCCTC
CATCTTAGCATGTGCACGATTCTAATAGCTCCGCTCTGTACTAGTGCTAAGCCCCACTGCAA
```

FIG. 10D

```
CGTTCCATCATAATAGTCAACATCAGGGTCTAATGCATGATGGGTATGATATGCGAGTCGTG
CGGGGGTCGTTGATGTCGATCAGGAGAGATGGGTCCAAACATTTATATGAAGCGGTTCCCCA
GGCCGTCTTGCTAGGTACACACAAGCTATTCTTGCGCTGAATAATGCGACTTTCACACGTAC
TCCTAGAACTGCAGCTGCAGCTGGCGTTCTGGCTATCCCACCCGAACGACTATGTCGTGCAT
GAACGTCGTGCTGTCCTCCTCGCTCCTGGACGGGGAGAAAAGACTTGATAAGGCCTCTATC
CTGCCTATGAGGATTGGTCTCACTCAGTCTAACCTAAATTGCGTCATGACTTGTTGATGAGA
TGTTGTACTT
```

FIG. 11A

FOS-1 cDNA 3168 bp

```
ATGCGACTGAATGGAATATTATCCTTATGGGCCTACTGGCCCGCAGGCCTGCAACTGGTTCT
TTTGAATGGTCTTTTAACGAATTTCCAATACACAACAAATACGGGTCAAAATTACAATCCTT
ATTTGCCTCTTGAGTGTCGGAACTGAATAAGTTAAGAGTATTAACTAGTTAGTTAATTACTA
GGTACTAAACTGCATGATTACTTTTATGTGGGGCCGGCGAGAATCGTCATCTGCAACTGTGT
TTCTACTCGGCGTATTTCTCAGTGATACCTTTCCACATTCCATGTGCATCTACTGATCATCC
ATCTGTCGTCTTCTGGGTGAGTGAGTGGACTAGTCCAGAATCCTGCTTGCAATTCTCATCTG
TCGCCCACTCGGCCGGTTCTCGGCTTCGACGTCCTTGGTTGCGCCACAGGGGAAGACAGGC
AAAAGGCAGAGAGCCACAGCACAGACTTGGGAAACTGATAAAACAACCACTCTCCTCATGCG
TATTTTGAAGTAGCGAGTTCTCGGTTGGCTTCTTTTCTGCTGTTATCTCGCTACCTTTGTTG
TGGGGGATTCAGCTAGCCTAAATGGCCCTCGACAAGGAGCTTCTTCACCTTCATCTCGGGGA
TGGCCAGCAGCGACCCTACAAGCTTTCCACGGTCGCTACTCCTCCCGATGAAGAGCAGCTCA
ATCTTCAACGCAGTGATAAGGATACAGCTGAACCGTCTCAAACTCCCCGCTGTGACACTCCG
CGAGAGGCCCACACAGAGATCGTACAGAACGATACTTCCTCGCTGAATCGAATTTTCCGCTT
CACTCCTGTGCCGACCCTCATCCTCGACTCGTCCTTGCGCGTGATTGAGGTCTCGGAGAGCC
ACCTTGCTTTCTGCGGAAAGTCTCGAGACTTTGTGCTGGGTGCCTCCATCTACGAGCTTCCC
CTCGCCACTATACCTGCGCCAGACATTGCGACTCTGAACGGTGCTTTGCACGTGGCGATTAC
GACTCGGGCTGTCCAGGTTGTCGAAACTATCCACCTTCCCAGAATAAGCTCTTATTTTTCAC
TGAAAATCACCCCCATTTTCCAGGGATCCACTCTGCTGAACCTAGTTCTGGAAGCGCACAAC
GTCACAAGGACCCATACCGAGTCACTGCATAATGCCTACATCAATGAGACTTACAAGATCCT
GGTTGACACGATCCGAGATTACGCTATCTTTATGCTGGACGCGCGCGGCAACATTGTAACGT
GGAATTCGGGCGCTGCGATTATCAAGGGATATAAGGCGGATGAGATTATCGGTCGGCATTTC
TCGGTCTTCTACGGACCCGAGGATCGGCTGGCAGACAAGCCTGGGAAGGAGCTCGAATTGTG
CCTACGGGACGGAAAAGTCGAGGATGAAGGCTGGCGGTATCGTCAGGATGGTTTACGGTTTT
GGGCCAACGTAATGATTACGCCTATCTTCTCATTCGGTCGGCACGTTGGTTTCGTCAAAATC
ACTCGCGACTTGACCGAGCGCAAAGCGGCTGAAGCGCGGATGGTGGCAGCTTTTGAGGAATC
ATCCAAGATGAAGAGTGACTTCCTGGCCAACATGAGCCACGAGATTCGGACTCCATGAATG
GAATGCACCTGGCATTGACCATGTTGGGGAGCACGGAGCTCGACACCCAGCAGCGTGAATAC
ACTTCCATTATCGAGGATTCCATGTCGATTTGCTTCAAGTAATCAACGACGTCCTTGATTA
TTCTAAGTTATCCTCCGGCACCTTCTCTCTGAACACAGATGTCTTGAGCGTTGAGAATATTG
TGGGAGCAGTGGTACGGAATTGCAAGGCCTTAAACCCTGCCGTGGAGATCTCCTGTTCCATG
CCTCCGGGCTTCCCAAAACTGCTCCGGGGTGATCCGCTTCGCTATCGGCAAGTGATCCAGAA
CCTCGTGGGAAATGCGATGAAGTTTACCGAGAAAGGCCATGTCAAGGTCACCCATCGCTTTG
CAGTAGAGGAGCACGATGCCAATAGGTACATAATCACGACAGAAGTCACTGATACTGGCATC
GGGGTGCCCGAAGATGCTATAAACACTCTTTTTACCCCATTTACGCGCTTTGCGGATTCAGC
CACCAAGCGCTATCAGGGTACAGGACTTGGCTTGTCCATCTGCAAGAGCTTGGCAGAGCTGA
TGGATGGCAGTGTTGGTTATAAACCCAACCCAGAAGGAAAGGGTAGCTGCTTTTGGCTCAAC
GTGAGAATGCAAGCTGTCGACATTCCAGCGCCTAGTAAAGACACTCCCGCTGCTACCGCCGA
AAATACGTACGAACCCATCGAAGAGGTCAAGGAGATTGCGCCTCACATGCACATATTGCTGG
TGGAAGATAATATGGTGAACCAAATCGTTATGCTGAAGCTTCTCAAAAGCCTCGGTTTCGAA
CGTGTCGACACGGCCTGGGACGGCGCAGACGCAGTCCGACAGGTGAAACAAACACCTCTCTC
```

FIG. 11B

```
TTACAATGTTATTCTTATGGACATCAACATGCCGGTTATGAATGGACTCGAAGCAACGACCA
AGATCCGTGAAGTGAACAGCGAGGTACCCATCATAGCACTCACCGGGAATGCGCTCAAGGGA
GACGCGGAGACATACCTTGCCAGAGGCATGAACGATTACGTCGCCAAACCAGTTCATCGCAA
GCGGCTTGTGCAGTTGTTGTGGAAGTGGCTCGGTTCGTGAGCAACTGTTCCTCTGGCCTCGC
TGGCCGGTGGCTCCTCCGTTGGGACAAGACCTGATTGTCCTGTTATAACTTAAAGTGGGCTT
GGATGCTCCATCCTTTGCCCGCACCCTATCTACCATAGCTCTCGCCCTCAGTTGAGCGGTG
TCTCGCTCATACTAAACGAGGCGCTATCTTTGGTCGGCTTTGAACTATCCGGCTATGCATCT
TTCATAGCCTCATCAATCGCCAAAAGAAATGGCCTTGATGGCTATCAGCTTCTCGACAGATT
TTCACGTCCGCGTACGTTGGCCATTCACAGTACATATTTTTCGCGGACCCTGCATACTCCAC
CCTTTCATTATTTGCCTCTTCGATCACGGTTCGCCATCAATCATCCATCATAATAAAGCGA
ACCGTCTCCGAAATGGATTCAGTTGCCTGGCTCGGGTTGTCCGGTGGGTAACACAGGAGTT
TGGCCA
```

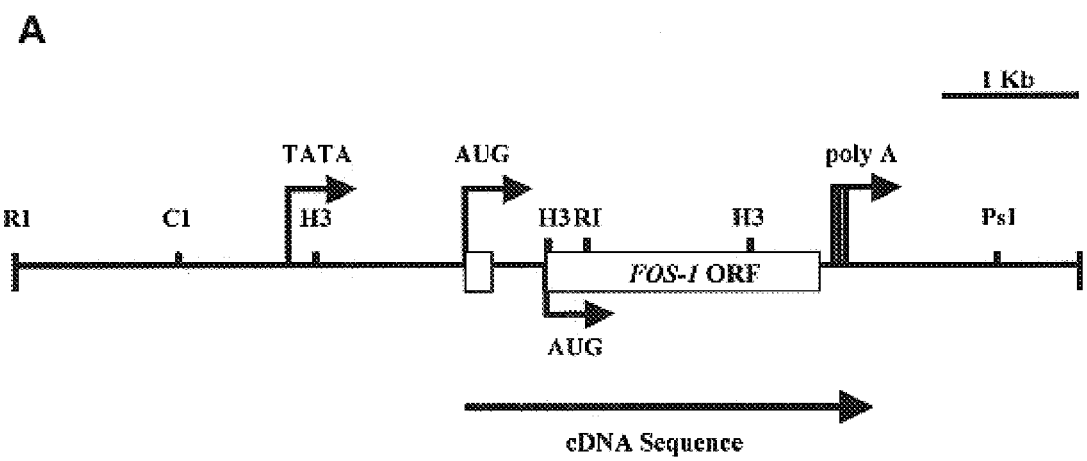
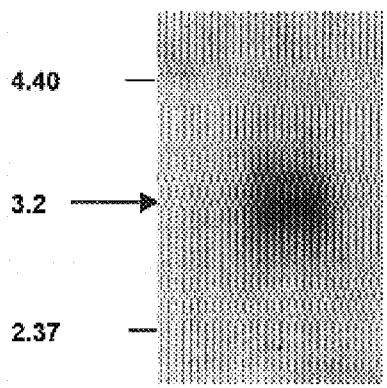
FIG. 12

FIGURE 13

FOS-1 cDNA OPEN READING FRAME TRANSLATIONS

A) Fos-1p (708 amino acids)

```
MALDKELLHLHLGDGQQRPYKLSTVATPPDEEQLNLQRSDKDTAEPSQTPRCDTPREAHT
EIVQNDTSSLNRIFRFTPVPTLILDSSLRVIEVSESHLAFCGKSRDFVLGASIYELPLAT
IPAPDIATLNGALHVAITTRAVQVVETIHLPRISSYFSLKITPIFQGSTLLNLVLEAHNV
TRTHTESLHNAYINETYKILVDTIRDYAIFMLDARGNIVTWNSGAAIIKGYKADEIIGRH
FSVFYGPEDRLADKPGKELELCLRDGKVEDEGWRYRQDGLRFWANVMITPIFSFGRHVGF
VKITRDLTERKAAEARMVAAFEESSKMKSDFLANMSHEIRTPMNGMHLALTMLGSTELDT
QQREYTSIIEDSMSILLQVINDVLDYSKLSSGTFSLNTDVLSVENIVGAVVRNCKALNPA
VEISCSMPPGFPKLLRGDPLRYRQVIQNLVGNAMKFTEKGHVKVTHRFAVEEHDANRYII
TTEVTDTGIGVPEDAINTLFTPFTRFADSATKRYQGTGLGLSICKSLAELMDGSVGYKPN
PEGKGSCFWLNVRMQAVDIPAPSKDTPAATAENTYEPIEEVKEIAPHMHILLVEDNMVNQ
IVMLKLLKSLGFERVDTAWDGADAVRQVKQTPLSYNVILMDINMPVMNGLEATTKIREVN
SEVPIIALTGNALKGDAETYLARGMNDYVAKPVHRKRLVQLLWKWLGS
```

B) mini-FOS-1 uORF polypeptide (49 amino acids)

```
MRLNGILSLWAYWPAGLQLVLLNGLLTNFQYTTNTGQNYNPYLPLECRN
```

FIG. 15A

```
cos-1    ------------------------------------------------------------
os-1     MTDGPTLAAIAALVKSLAVDPATTQTSGLRPSTHVRLPGPYTREKGDLERELSALVVRIE
fos-1    ------------------------------------------------------------ cos-1    --------MNPTKKPR-------------LSPMQPSVFEILNDPELYSQHCHSLRETLL
os-1     QLETAAIAASPPAMPDTPNAPTDALFSNGTLSPSSETPDARYPAPLPRNGFIDEALEGLR
fos-1    ------------------------------------------------------------ cos-1    DHFNHQATLID-----------------------------TYEHELEKSKNANKAS
os-1     EHVDDQSKLLDSQRQELAGVNAQLIEQKQLQEKALAIIEQERVATLERELWKHQKANEAF
fos-1    ------------------------------------------------------------ cos-1    QQALSEIGTVVISVAMGDLSKKVEIHTVENDPEILKVKITINTMMDQLQTFANEVTKVAT
os-1     QKALREIGEIVTAVARGDLSKKVRMNSVEMDPEITTFKRTINTMMDQLQVFSSEVSRVAR
fos-1    ------------------------------------------------------------ cos-1    EVAN-GELGGQAKNDGSVGIWRSLTDNVNIMALNLTNQVREIADVTRAVAKGDLSRKINV
os-1     EVGTEGILGGQAQIEGVDGTWKELTDNVNVMAQNLTDQVREIASVTTAVAHGDLTKKIER
fos-1    -------------------MALDKELLHLHLGDGQQRPYKLSTVATPPDE------
                                *                             * cos-1    HAQGEILQLQRTINTMVDQLRTFAFEVSKVARDVGVLGILGGQALIENVEGIWEELTDNV
os-1     PAKGEILQLQQTINTMVDQLRTFASEVTRVARDVGTEGILGGQADVEGVQGMWNELTVNV
fos-1    ----EQLNLQRSDKDTAEPSQTPRCDTPREA-HTE---------IVQNDTSSLNRIFRFT
             *   * **          *           * cos-1    NAMALNLTTQVRNIANVTTAVAKGDLSKKVTADCKGEILDLKLTINQMVDRLQNFALAVT
os-1     NAMANNLTTQVRDIIKVTTAVAKGDLTQKVQAECRGEIFELKKTINSMVDQLQQFAREVT
fos-1    PVPTLILDSSLRVIEVSESHLAFCGKSRDFVLGASIYELPLATIPAPDIATLN-----G-
             *     * *       *                        *           * cos-1    TLSREVGTLGILGGQANVQDVEGAWKQVTENVNLMATNLTNQVRSIATVTTAVAHGDLSQ
os-1     KIAREVGTEGRLGGQATVHDVQGTWRDLTENVNGMAMNLTTQVREIAKVTTAVAKGDLTK
fos-1    ALHVAITTRAVQVVETIHLPRISSYFSLKITPIFQGSTLLNLVLEAHNVTRTHTESLHNA
                *                                 *    *    ** cos-1    KIDGHPKGEILQLKNTINKMVDSLQLFASEVSKVAQDVGINGKLGIQAQVSDVDGLWKEI
os-1     KIGVEVQGEILDLKNTINTMVDRLGTFAFEVSKVAREVGTDGTLGGQAQVDNVEGKWKDL
fos-1    YINETYKILVDTIRDYAIFMLDARGNIVTWNSGAAIIKGYKADEIIGRHFSVFYGPEDRL
             *             * *      * *   *                        * cos-1    TSNVNTMASNLTSQVR-------------------------------------
os-1     TENVNTMASNLTSQVRGISTVTQAIANGDMSRKIEVEAKGEILILKETINNMVDRLSIFC
fos-1    ADKPGKELELCLRDGK------------------------------------- cos-1    -----------------------------------AFAQITAAATDG
os-1     NEVQRVAKDVGVDGIMGGQADVAGLKGRWKEITTDVNTMANNLTAQVRAFGDITNAATDG
fos-1    -----------------------------VEDEGWRYRQDG
                                                        **
```

FIG. 15B

```
cos-1    DFTRFITVEASGEMDALKTKINQMVFNLRESLQRNTAAREAAELANSAKHEFLANMSHEI
os-1     DFTKLVEVEASGEMDELKKKINQMVYNLRDSIQRNTQAREAAELANKTKHEFLANMSHEI
fos-1    LRFWANVMITPIFSPGRHVGFVKITRDLTERKAAEARMVAAFEESSKMKSDFLANMSHEI
                  *           *  *      ******** cos-1    RTPLNGIIGMTQLSLDTELTQYQREMLSIVHNLANSLLTIIDDILDISKIEANRMTVEQI
os-1     RTPMNGIIGMTQLTLDTDLTQYQREMLNIVNSLANSLLTIIDDILDLSKIEARRMVIEEI
fos-1    RTPMNGMHLALTMLGSTELDTQQREYTSIIEDSMSILLQVINDVLDYSKLSSGTFSLNTD
         *        *  *   ***   *     **   *  * cos-1    DFSLRGTVFGALKTLAVKAIEKNLDLTYQCDSSPPDNLIGDSPRLRQVILNLAGNAIKFT
os-1     PYTLRGTVFNALKTLAVKANEKFLDLTYRVDHSVPDHVVGDSPRLRQIILNLVGNAIKFT
fos-1    VLSVENIVGAVVR--NCKALNPAVEISCSMPPGPPKLLRGDPLRYRQVIQNLVGNAMKFT
            *     **              *        **  *  **  *   * *** cos-1    KECKVSVSVKK-SDKMVLDSKLLLEVCVSDTGIGIEKDKLGLIFDTFCQADGSTIRKFGG
os-1     EHGEVSLTIQKASSVQCSTEEYAIEFVVSDTGIGIPADKLDLIFDTFQQADGSMIRKFGG
fos-1    EKGHVKVTHRF-AVEEHDANRYIITTEVTDTGIGVPEDAINTLFTPFTRFADSAIKRYQG
         *  *                      *  *****     *     *  *    *  * cos-1    TGLGLSISKQLIHLMGGEIWVTS-EYGSGSNFYPTVCVSPSNIRYTRQTEQLLPFSSHYV
os-1     TGLGLSISKRLVNLMGGDVWVKS-EYGKGSKFFFTCVVRLANDDISLIAKQLNPYKSHQV
fos-1    TGLGLSICKSLAELMDGSVGYKPNPEGKGSCFWLNVRMQ---------AVD-IPAPSKDT
         ******* *  *  ** *       *  **  *  *  **  *                *  * cos-1    LFVSTEHTQEELDVLRDGIIELGLIPIIV---RN--IEDATLTEPVKYDIIMIDSIEIAK
os-1     LFIDKGRTGHGPEIAK-NLHGLGLVPIVVDSERNPALEKARAAGQAPYDVIIVDSIEDAR
fos-1    PAATAENTYEPIEEVK----EIAPHMHIL-------------------------------
                 * cos-1    KLRLLSEVKYIPLVLVHHSIPQLNMRVCIDLGISSYANTPCSITDLASAIIPALESRSIS
os-1     RLRSVDDFKYLPIVLLAP-VVHVSLKSCLDLGITSYMTTPCQLIDLGNGMVPALENRATP
fos-1    ----------------------------------------------LV------------ cos-1    QNSDESVRYKILLAEDNLVNQKLAVRILEKQ-GHSVEVVENGLEAYEAIKRN--KYDVVL
os-1     SLADNTKSFEILLAEDNTVNQRLAVKILEKY-HHVVTVVGNGEEAVEAVKRK--KFDVIL
fos-1    ---------------EDNMVNQIVMLKLLKSLGFERVDTAWDGADAVRQVKQTPLSYNVIL
                        * *        *      *      *    *    *    *  * cos-1    MDVQMPVMGGFEATEKIRQWEKKSNPIDSLTFRTPIIALTAHAMLGDREKSLAKGMDDYV
os-1     MDVQMPIMGGFEATAKIREYERSLG-----SQRTPIIALTAHAMMGDREKCIQAQMDEYL
fos-1    MDINMPVMNGLEATTKIREVNSEVP---------IIALTGNALKGDAETYLARGMNDYV
            * *   * *   *              ***  *   **  *      * cos-1    SKPLKPKLLMQTINKCIHNINQLKELSRN---SRGSDFAKKMTRNTPGSTTRQGSDEGSV
os-1     SKPLQQNHLIQTILKCATLGGQLLEKNRERELTRAADAVTGGRRDNGMYSASQAAQHAAL
fos-1    AKPVHRKRLVQLLWKWLGS-----------------------------------------
            **        *   * cos-1    KDMIGDTPRQGSVEGGGTSSRPVQRRSAREGSITTISEQIDR-------
os-1     RPPLATRGLTAADSLVSGLESPSIVTADKEDPLSRARASLSEPNIHKAS
fos-1    ------------------------------------------------
```

A
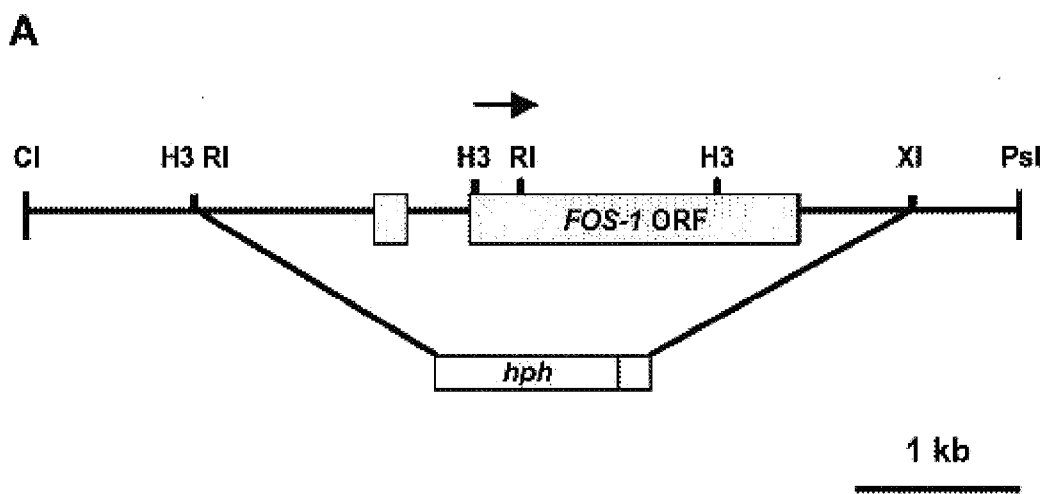
B
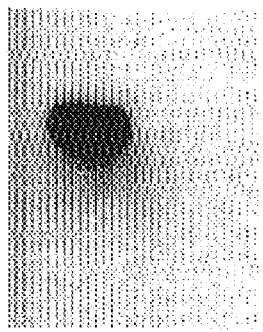
wild type  ΔFOS-1
FIG. 16

FIGURE 19
Partial FOS-2 and FOS-3 nucleotide and amino acid sequences

Ambiguous positions in the nucleotide sequence are indicated by "N"
Corresponding ambiguous positions in the amino acid sequence are indicated by "X"

A) *FOS-2* (241 bp)

TTGAACGCATGNGGGATTTGAATCCCGTTTNAAGAACCGATTACGCCTATCTTAAAATT
CCGTCGGCACGTTGGTTTCGTCAAAATCACTCGCGACTTGACCGATTTTAAAGCGGCTG
AAGCGCGGATGGTGGCAGGTTTTGAGGAATNATCCAAGATGAAGAGTGATTTTCTGGCC
AACATGAGCCACGAGATTCGGACTTCAATGAATGGAATGCACATGGCATTTGACCATAA
AATCC

B) Fos-2p (80 aa)

LNAXGIXIPFEEPITPIFSFGRHVGFVKITRDLTERKAAEARMVAGFEEXSKMKSDFLA
NMSHEIRTSMNGMHMAFDHKI

C) *FOS-3* (196 bp)

TGGAAACCCCTTCAAAGCTTCCCAAGAAGCTNATGGATGGCAGTGTTAGGTTATAAACC
CAACCCANAAGGAAAGGGTCACTGCTTTTGGCTCAACGTGAGAATGCAAGCTGTCGGCA
TTCCAGCGCCTAGCTTAAAGACACTCCCGCTGTTACCCGCCGAAAATCTTACCNAACCC
ATTCAATATAGGTTAAGGC

D) Fos-3p (66 aa)

WKPLQSFPRSXWMAVLGYKPNPXGKGHCFWLNVRMQAVGIPAPSLKTLPLLPAENLTXP
IQYRLR

HISTIDINE KINASES OF ASPERGILLUS AND OTHER FUNGAL SPECIES, RELATED COMPOSITIONS, AND METHODS OF USE

This application is a Continuation-in-Part of U.S. patent application Ser. No. 09/338,156, filed Jun. 22, 1999, now abandoned, which is a Continuation of U.S. patent application Ser. No. 08/843,530, filed Apr. 16, 1997, now U.S. Pat. No. 5,939,306.

This invention was made during the course of work supported by the United States Government, under the National Institutes of Health Grant Number R01-AI33354-03. As such, the United States Government may have certain rights to this invention.

FIELD OF THE INVENTION

The present invention relates to fungal histidine kinases. In particular, the present invention is directed to histidine kinases from Neurospora (e.g., *N. crassa*), Candida (e.g, *C. albicans*), and Aspergillus (e.g., *A. fumigatus*), and related compositions. Furthermore, the present invention provides compositions and methods for the identification of compounds having antifungal activity, as well as compositions and methods for the treatment of fungal infections.

BACKGROUND

Fungal organisms have become increasingly significant pathogens in immunocompromised patients, especially those who because of cancer, organ transplantation, chemotherapy, pregnancy, age, diabetes, complications following extensive surgery, and various immune system dysfunctions, are at risk of experiencing life-threatening diseases caused by organisms which do not ordinarily pose a threat to normal, immunocompetent people. Indeed, immunocompromised patients perhaps provide the greatest challenge to modern health care delivery. For example, fungal infections have become one of the leading factors contributing to morbidity and mortality in cancer patients, and fungi account for 4–12% of nosocomial (hospital-acquired) pathogens in leukemia patients (E. Anaissie, Clin. Infect. Dis., 14[Suppl.1]:S43 [1992]). The incidence of nosocomial bloodstream infections with fungi such as Candida ("candidemia") has increased in recent years and now accounts for 5.6% of all primary bloodstream infections (Id.). There are an estimated 200,000 patients/year who acquire nosocomial fungal infections, with bloodstream infections having a mean mortality rate of 55% (See e.g., Beck-Sague et al., J. Infect. Dis., 167:1247 [1993]; and the Centers for Disease Control website at www.cdc.gov/ncidod/publications/brochures/hip.html). Fungi infections may also be life-threatening in other settings, such as in the case of intravenous drug abusers who use non-sterile substances to dilute drugs prior to injection.

Deep-seated mycoses are being increasingly observed in patients undergoing organ transplants and aggressive chemotherapy. For solid organ transplantation, the incidence of fungal infections ranges from 5% in kidney recipients, 15–25% in lung and heart recipients, and up to 40% in liver recipients (Alexander et al., Drugs 54:657 [1997]). The most common fungal pathogens are the opportunistic yeast, *C. albicans* and the filamentous mold, *A. fumigatus* (See, Bow, Br. J. Haematol., 101:1 [1998]; and Warnock, J. Antimicrob. Chemother., 41:95 [1998]).

AIDS patients are also at great risk for fungal infections. An estimated 80% of AIDS patients acquire fungal infections and suffer a mortality rate of 10–20% as a result of these infections (See, Cairns, J. Electron Microsc. Techn. 8:115 [1988]).

Candida

Of the over 100 Candida species, approximately seven are isolated with great frequency from human specimens (T. Mitchell, in *Zinsser Microbiology*, W. K. Joklik, et al., [eds], Appleton, Century-Crofts, Norwalk, Conn., pp. 1183–1190 [1984]). A brief taxonomic chart of Candida is shown in Table 1. Some Candida species are related to organisms, such as Saccharomyces in the subclass Hemiascomycetidae, class Ascomycetes, subdivision Ascomycotina, division Ascomycota. Also, some mycologists consider *C. stellatoidea* to be a variant of *C. albicans*.

TABLE 1

TAXONOMY OF THE GENUS CANDIDA

| | |
|---|---|
| Kingdom: | Mycetae (Fungi) |
| Division: | Deuteromycota |
| Subdivision: | Deuteromycotina |
| Form Class: | Deuteromyces |
| Form Subclass: | Blastomycetidae |
| Genus: | Candida |
| Species: | albicans |
| | glabrata |
| | guilliermondi |
| | krusei |
| | lipolytica |
| | lusitaniae |
| | parapsilosis |
| | pseudotropicalis |
| | rugosa |
| | stellatoidea |
| | tropicalis |

The first exposure to fungi experienced by many humans occurs during the birth process, when *C. albicans* present in the mother's vaginal canal colonizes the buccal cavity, and portions of the upper and lower gastrointestinal tract of the newborn. This colonization usually results in the establishment of *C. albicans* as a commensal organism in these areas, for the life of the individual. However, *C. albicans* is also the most common fungal pathogen of humans, worldwide, with other Candida species becoming increasingly important in fungal disease in humans and other animals.

As a commensal, *C. albicans* exists as a unicellular yeast; during invasive disease, the organism has a filamentous morphology. The implication of *C. albicans* in disease may indicate that the patient has a co-existing immune, endocrine or other debilitating disorder that must also be addressed in order to effectively manage the fungal disease. The principal risk factors that predispose individuals to deeply invasive candidiasis include protracted course of broad spectrum antimicrobials, cytotoxic chemotherapy, corticosteroids, and vascular catheters.

Candida Infection and Diagnosis

Because clinical Candida infections and disease may be acute or chronic, superficial or disseminated, the disease syndromes are many and varied. While *C. albicans* is most commonly implicated, various other Candida species can and do invade most organ systems of the body. For example, *C. tropicalis*, *C. parapsilosis*, *C. guilliermondi*, *C. krusei*, and *C. lusitaniae* have emerged as important pathogens in cancer patients (E. Anaissie, supra). Candidiasis due to *C. albicans*, as well as other Candida species, is the most common opportunistic fungal infection observed (See, Walsh and Dixon, "Spectrum of Mycoses," in Baron (ed.), *Medical Microbiology*, 4th ed, University of Texas Medical Branch, Galveston, Tex. [1996], pp. 919–925). Superficial candidiasis may involve the epidermal and mucosal surfaces (e.g., the oral cavity, pharynx, esophagus, intestines, urinary bladder, and vagina). In deep candidiasis, the gastrointestinal tract and intravascular catheters are the two major portals of entry, with the kidneys, liver, spleen, brain, eyes, heart, and other tissues being the major sites involved.

The major difficulties in treating Candida infections are encountered in cases of systemic disease. Chronic mucocutaneous, pulmonary candidiasis, endocarditis, and fungemia must be diagnosed early and treated promptly with an appropriate antifungal regimen, in order to avoid fatality (W. Chandler, *Color Atlas and Text of Histopathology of Mycotic Diseases*, p. 44 [1980]). The incidence of candidiasis in certain patient populations is striking. Up to 30% of leukemia patients acquire systemic candidiasis (E. Anaissie, supra). This is of great significance, as some reports indicate that the fatality rate for disseminated candidiasis in cancer patients is 80% (F. Meunier, et al., Clin. Infect. Dis., 14[Suppl. 1]:S120 [1992]). Also, fatalities in most organ transplant patients who succumb to infection are most often due to opportunistic organisms, of which Candida is the leading mycotic agent (T. Mitchell, supra).

The probability of postoperative systemic candidiasis is related to the length of operation and may involve contamination with organisms during the surgery or contamination through such diverse postoperative procedures as indwelling catheters or the use of prophylactic antibacterial compounds (Id.). Prosthetic devices, including artificial heart valves or intravenous lines can be colonized and introduce Candida into the patient's bloodstream (Id.).

Significantly, many patients who develop systemic candidiasis were given corticosteroids prior to development of their Candida infection. Corticosteroids are known to depress the immune system and are often used to prevent transplant rejection. Corticosteroids and antibacterials predispose to candidiasis by depressing phagocytic activity and cell-mediated immunity, reducing the bacterial flora and indirectly increasing the Candida population (Id.). Perhaps also importantly, corticosteroids have been hypothesized to directly act on fungi and may contribute to disease progression in patients with systemic candidiasis (See e.g., D. S. Loose et al., J. Gen. Microbiol., 129:2379 [1983]; D. S. Loose and D. Feldman, J. Biol. Chem., 257:4925 [1982]).

Because of the delays necessary in making a definitive diagnosis, physicians usually treat patients empirically. For superficial infections, topical antifungals are often used; the prognosis for most types of these infections is usually quite good. For systemic disease, highly toxic antifungals must often be used. Administration of these compounds requires careful patient monitoring (patients are usually admitted) because of their serious side effects (e.g., the nephrotoxicity, hypokalemia, anemia, fever and other toxic effects associated with the use of amphotericin B).

Aspergillus

Aspergillus species, as well as various other opportunistic hyaline molds have long been associated with infection and disease in humans and other animals. Indeed, in patients with positive fungal cultures, Aspergillus species are the second most common isolate, after Candida species (See, Kennedy and Sigler, "*Aspergillus, Fusarium*, and Other Opportunistic Moniliaceous Fungi, in Murray et al., (eds), *Manual of Clinical Microbiology*, 6th ed., ASM Press, Washington, D.C. [1995], pp. 765–790); and Goodwin et al., J. Med. Vet. Mycol., 30:153 [1992]). There are multiple members of the genus Aspergillus, including the *A. fumigatus* group, *A. niger*, *A. flavus*, and many others (e.g., *A. candidus*, *A. carneus*, *A. clavatus*, *A. deflectus*, the *A. fischeri* group, *A. flavipes*, the *A.glaucus* group, the *A. nidulans* group, *A. ochraceus*, *A. oryzae*, *A. parasiticus*, *A. restrictus*, *A. sydowii*, *A. terreus*, *A. ustus*, and *A. versicolor*). In addition to these organism names, telomorphic stages of the Aspergillus species are also included in the Eurotium, Emericella, and Neosartorya species.

*A. fumigatus* is the most frequently observed fungus in airborne spore surveys (Armstrong et al., Issues Mycol., 2:1–20 [1997]). The organism is essentially ubiquitous, as it is capable of growing in a variety of environments, including air ducts, houseplant soil, compost piles, etc. In addition, the organism is capable of growing over a wide temperature range, from −12° C. to 50–55° C. (See e.g., Conney and Emerson, Thermophilic Fungi: An Account of Their Biology, Activities and Classification, Freeman and Co., San Francisco [1964]). Of the members of the genus Aspergillus, *A. fumigatus* is the most common human pathogen. Three main types of disease have been associated with *A. fumigatus*, namely allergic asthma, aspergilloma, and invasive aspergillosis (See e.g., Lortholary et al., Amer. J. Med., 95:177–187 [1993]). Allergic pulmonary asthma due to *A. fumigatus* exposure affects an estimated 50,000 individuals in the U.S. Most cases are successfully treated with anti-asthma medication and their episodes are self-limiting. Aspergillomas are formed when fungal spores germinate in situ in tissue such as the lungs and form fungus balls. Aspergilloma patients often cough up hyphal plugs. There is no invasion of underlying tissues and in most cases, treatment involves the simple surgical removal of the aspergilloma. Invasive aspergillosis involves the invasion of host tissues, and is most commonly observed in patients with predisposing conditions (e.g., immunosuppressive drugs, neutropenia, chemotherapy, AIDS). Transplant (e.g., bone marrow or organ) and chemotherapy patients are at the greatest risk for this form of aspergillosis (See e.g., Denning et al., New Eng. J. Med., 324:654–662 [1992]; and Miller et al., Chest 105:37–44 [1994]). Aspergillosis is presumptively diagnosed when there is an unexplained pulmonary infiltrate, a patient is unresponsive to antibacterials and/or there is a fever of unknown origin. The prognosis for patients with invasive disease is particularly grave, with mortality rates >50% (See e.g., Polis et al., "Fungal Infections in Patients with the Acquired Immunodeficiency Syndrome," in DeVita et al. (eds), *AIDS: Biology, Diagnosis, Treatment, and Prevention*, 4th ed., Lippincott-Raven, [1997]), due to the lack of a rapid diagnostic method to confirm *A. fumigatus* infection, and the lack of safe antifungal drugs.

Fungal Physiology and Treatment of Fungal Diseases

The development of effective antifungal agents has lagged behind that of antibacterial agents. As bacteria are prokaryotic and offer numerous structural and metabolic targets that differ from humans, we have been more successful in identifying and developing antibacterial agents. In contrast, like humans, fungi are eukaryotic.

Thus, most agents toxic to fungi are also toxic to humans. In addition, because fungi generally grow more slowly and in multi-cellular forms in vitro, they are more difficult to quantify than bacteria, complicating experiments designed to evaluate the in vitro and/or in vivo properties of potential antifungals.

Four general groups of antifungals have been developed, including the polyenes (e.g., amphotericin, nystatin, and pimaricin), azoles (e.g., fluconazole, itraconazole, and ketoconazole), allylamines and morpholines (e.g., naftifine and terbinafine), and antimetabolites (e.g., 5-flurocytosine). The site of action for most antifungals is the ergosterol present in the fungal cell membrane, or its biosynthetic pathway. However, other antifungals act at other sites, such as the fungal cell wall.

Fungal Cell Wall

The fungal cell wall is a rigid, stratified structure that consists of chitinous microfibrils encased in a matrix of small polysaccharides, proteins, lipids, inorganic salts, and pigments, that provides support and shape to the cell. The chitin within fungal cell walls is a ($\beta$1-4)-linked polymer of N-acetyl glucosamine, polymerized by chitin synthase at the plasma membrane.

The major polysaccharides of the cell wall matrix consist of non-cellulosic glucans, including glycogen-like compounds, mannans (mannose polymers), chitosan (glucosamine polymers), and galactans (galactose polymers). Fucose, rhamnose, xylose, and uronic acids may also be present in small amounts. The term "glucan" is used in reference to a large group of D-glucose polymers with glycosidic bonds. Of these, the most common glucans present in the fungal cell wall are in the $\beta$-configuration. Polymers with ($\beta$1-3)- and ($\beta$1-6)-linked glucosyl units with various proportions of 1-3 and 1-6 linkages are common cell wall components. Many fungi, and yeasts in particular, have soluble peptidomannans within a matrix of $\alpha$- and $\beta$-glucans, as part of the outer portion of their cell wall. The fungal cell wall is essential for the viability of the organism, as it prevents osmotic lysis of the cell. Even a small lesion within the cell wall can lead to the extrusion of cytoplasm due to the internal pressure within the cell (See, Cole, "Basic Biology of Fungi, in Baron (ed.), *Medical Microbiology*, 4th ed., University of Texas Medical Branch, Galveston, Tex. [1996], pp. 903–911). Indeed, creation of such lesions is the mechanism of action of many antifungal compounds.

As *C. albicans* may be in the form of budding yeast cells, pseudohyphae, germ tubes, true hyphae, and chlamydospores, differences between these forms are of interest in the development of antifungals. In the yeast form, the *C. albicans* cell wall contains approximately 30–60% glucan, 25–50% mannan (mannoprotein), 1–2% chitin, 2–14% lipid, and 5–15% protein (McGinnis and Tyring, "Introduction to Mycology," in Baron (ed.), *Medical Microbiology*, 4th ed., University of Texas Medical Branch, Galveston, Tex. [1996], pp. 893–902). Glucans with ($\beta$1-3) and ($\beta$1-6)-linked groups comprise a high percentage of the yeast cell wall. These glucans may impede the access of amphotericin B to the plasma membrane (See, McGinnis and Tyring, supra, at p. 896).

For filamentous fungi (e.g., Aspergillus) cell wall synthesis and assembly occur only at each hyphal apex, while for yeasts, extension occurs at the bud tip, followed by intercalary growth (Madden et al., Ann. Rev. Microbiol., 52:687 [1998]; and Trinci et al., J. Gen. Microbiol., 103:243–248 [1977]). Chitin and other carbohydrate polymers, with the exception of (1,6)$\beta$-glucan, are synthesized de novo at the hyphal tips. Although it is incompletely understood, the assembly of fungal cell walls can be simplistically divided into five steps, including cell wall precursor synthesis, cell wall polymer synthesis, cell wall polymer assembly, morphogenesis, and regulation.

Fungal Cell Membrane

The fungal plasma (i.e., cell) membrane is similar to mammalian plasma membranes, with the exception being that fungal plasma membranes contain ergosterol, rather than cholesterol as the principal sterol. The plasma membrane is selectively permeable, and apparently regulates the passage of materials into and out of the cell. Sterols present in the membrane provide structure, modulate membrane fluidity, and may control other physiologic events.

Polyene antifungals (e.g., amphotericin B, nystatin, and pimaricin) bind ergosterol, to form complexes that allow the rapid leakage of cellular potassium, other ions, and small molecules out of affected fungal cells. This results in the inhibition of fungal glycolysis and respiration. Other antifungals such as the azoles (e.g., fluconazole, imidazole, ketoconazole, and itraconazole), and allylamines and morpholines interfere with the ergosterol biosynthesis. Inhibition of ergosterol formation may result in permeability changes in the plasma membrane, growth inhibition, and may lead to excessive chitin production and abnormal fungal growth.

Fungal Microtubules

Fungi also possess microtubules composed of tubulin. These structures are involved in the movement of organelles, chromosomes, nuclei, and Golgi vesicles. Microtubules are the principal components of the spindle fibers that aid movement of the chromosomes during mitosis and meiosis. Exposure to some antifungal agents disrupts the movement of the nuclei, mitochondria, vacuoles, and apical vesicles. In addition, destruction of cytoplasmic microtubules interferes with transport of secretory materials, and may inhibit cell wall synthesis. Griseofulvin, a compound commonly used to treat dermatophytic infections binds with microtubule-associated proteins involved in tubulin assembly, and acts by stopping mitosis at metaphase.

Antifungal Compounds

Despite the identification of cell membrane, cell wall, and microtubule targets for antifungal action, antifungal development has been slow. Amphotericin B remains the treatment mainstay for life-threatening and other mycoses. Discovered in 1956, amphotericin B remains the drug of choice for candidiasis, cryptococcosis, aspergillosis, zygomycosis, coccidioidomycosis, histoplasmosis, blastomycosis, and paracoccidioidomycosis. Amphotericin B must be administered intravenously and is associated with numerous, often serious side effects, including phlebitis at the infusion site, fever, chills, hypokalemia, anemia, and nephrotoxicity). Importantly, fungal resistance to amphotericin B has been reported for various opportunistic fungi, including *Pseudallescheria boydii*, Fusarium, Trichosporon, and some *C. lusitaniae* and *C. guilliermondii* isolates (See, Dixon and Walsh, "Antifungal Agents," in Baron (ed.), *Medical Microbiology*, 4th ed., University of Texas Medical Branch, Galveston, Tex. [1996], pp. 926–932).

Nystatin is another broad-spectrum polyene antifungal. However, its toxicity to humans prevents its widespread use. Currently, it is limited to topical applications, where it is effective against yeasts, including *C. albicans*. Pimaricin (natamycin) is a topical polyene active against yeasts and molds; this compound is used to treat superficial mycotic eye infections.

Ketoconazole was the first antifungal developed that was suitable for oral administration, although it may also be used topically. In non-immunocompromised patients, it may be used to treat histoplasmosis and blastomycosis. It is also used against mucosal candidiasis and various cutaneous mycoses (e.g., dermatophyte infections, pityriasis versicolor, and cutaneous candidiasis). However, it is not useful for treatment of aspergillosis or systemic yeast infections. The triazoles (e.g., fluconazole and itraconazole) have found use in systemic mycoses. Fluconazole is now often used to treat candidemia in non-neutropenic patients, and may be used in cryptococcosis and some cases of coccidioidomycosis. Itraconazole is often effective against histoplasmosis, blastomycosis, sporotrichosis, coccidioidomycosis, and some cases of cryptococcosis and aspergillosis.

Side effects are not as common with the azoles as with amphotericin B, although life-threatening hepatic toxicity may result from long-term use. Other side effects include nausea, vomiting, and drug interactions with such compounds as cyclosporin, antihistamines, anticoagulants, anti-seizure and oral hypoglycemic medications, as well as other compounds, are of potential concern. In addition, the emergence of clinically-resistant strains has raised additional concerns with these compounds (Boschman et al., Antimicrob. Agents Chemother., 42:734 [1998]; and Graybill, Clin. Infect. Dis., 22(Suppl.2):S166 [1996]).

Unlike antibacterials, few antimetabolite compounds are useful as antifungals. The most commonly used antifungal is 5-fluorocytosine, a fluorinated analog of cytosine. However, like other antimetabolites, the emergence of drug resistance has become a problem. Thus, it is seldom used alone. Nonetheless, in combination with amphotericin B, it remains the treatment of choice for cryptococcal meningitis, and is effective against some diseases caused by dematiaceous fungi.

Other antifungals include griseofulvin, an antimicrobial produced by *Penicillium griseofulvin*, that is active against most dermatophytes. Potassium iodide is another compound that is used as an antifungal to enhance transepidermal elimination of fungal organisms in cases of cutaneous and lymphocutaneous sporotrichosis, although it is not effective against *Sporothrix schenckii* in vitro.

Antifungal susceptibility testing is generally not standardized, and the results of in vitro tests do not always correspond to the in vivo results. Thus, preliminary antifungal selection is often made on the basis of the specific organism identified as being involved in the patient's disease. While this approach may be useful in avoiding selection of an antifungal to treat fungi known to exhibit primary resistance to an agent, it is less useful in the selection of antifungals to treat fungi known to develop secondary (i.e., drug-induced) resistance.

Primary, as well as secondary, antifungal resistance has become an increasing problem. For example, with most polyenes, the resistance is almost always primary (i.e., the susceptibility profiles for the species are characteristic, inherent, and rarely change in response to drug exposure). Primary and secondary resistance to azoles has been reported for most medically important yeasts. In view of the development of resistance, as well as the relative lack of variety available in the selection of antifungals, there remains a need for the development of compounds useful for treatment of fungal diseases.

SUMMARY OF THE INVENTION

The present invention relates to osmosensing histidine kinases and methods for their use in screening antifungal compounds for their activity against fungal organisms, as well as for the development of antifungal compounds.

In one embodiment, the present invention provides a purified and isolated nucleic acid sequence encoding at least a portion of an osmosensing histidine kinase, wherein the sequence is selected from the group consisting of SEQ ID NO: 1, 3, 4 and 16, and their complementary sequences. In one preferred embodiment, the nucleic acid sequence is from Neurospora. In alternative embodiments, the present invention provides compositions comprising the nucleic acid sequences selected from the group consisting of SEQ ID NO: 1, 3, 4 and 16, and their complementary sequences.

The present invention also provides polynucleotide sequences that hybridize under stringent conditions to the nucleic acid sequence selected from the group consisting of SEQ ID NOS: 3 and 16.

The present invention further provides substantially purified proteins comprising the amino acid sequences selected from the group consisting of SEQ ID NOS: 2, 5, 10, 11 and 17.

The present invention also provides expression vectors that contain nucleic acid sequences selected from the group consisting of SEQ ID NOS: 1, 3, 4 and 16, and their complementary sequences. It is contemplated that these sequences may be encoded by one or more expression vectors. It is also contemplated that the expression vectors of the present invention be present within host cells. In one embodiment, the host cell is prokaryotic, while in preferred embodiments, the host cell is eukaryotic. In particularly preferred embodiments, the host cell is a fungal cell. In alternate preferred embodiments the host cell is selected from the group consisting of Neurospora, Candida, Aspergillus, and Saccharomyces. In yet another particularly preferred embodiment, the host cell comprises *Candida albicans*.

The present invention also provides host cells comprising at least one DNA sequence selected from the group consisting of SEQ ID NOS: 1, 3, 4 and 16, or a portion thereof, such that the host cell expresses a fungal histidine kinase or a portion thereof. In one preferred embodiment, the fungal histidine kinase is a Neurospora crassa histidine kinase. In another preferred embodiment, the host cell expresses *Candida albicans* histidine kinase. In an alternative preferred embodiment, the host cell expresses Saccharomyces histidine kinase.

The present invention provides compositions and methods related to osmosensing fungal histidine kinases. In particular, the present invention provides amino acid and nucleic acid sequences of fungal histidine kinases from organisms such as Candida (e.g., *C. albicans*) and Neurospora (e.g., *N. crassa*). The present invention further provides compositions and methods for the development of antifungal compounds.

The present invention relates to fungal histidine kinases and methods for their use in screening compounds for antifungal activity, as well as for the development of antifungal compounds. Furthermore, the present invention provides compositions and methods for the treatment of fungal infections.

In one embodiment, the present invention provides a histidine kinase polypeptide from the fungal species *Aspergillus fumigatus*, named Fos-1p (SEQ ID NO: 35). The present invention also provides a second polypeptide encoded on the FOS-1 transcription unit, named mini-FOS-1 uORF (SEQ ID NO: 48). In related embodiments, the present invention provides compositions comprising the amino acid sequences selected from the group consisting of SEQ ID NOS: 35 and 48. In another related embodiment, the present invention provides nucleotide sequences encoding the polypeptides of SEQ ID NOS: 35 and 48. In another related embodiment, the present invention provides compositions comprising the nucleotide sequences encoding the polypeptides of SEQ ID NOS: 35 and 48.

In another embodiment, the present invention provides nucleotide sequences corresponding to genomic and cDNA nucleotide sequence from the *A. fumigatus* FOS-1 locus (SEQ ID NOS: 34 and 36, respectively), the Fos-1p open reading frame (SEQ ID NO: 59) and the mini FOS-1 uORF (SEQ ID NO: 47), and their complementary sequences. In a related embodiment, the present invention provides compositions comprising these genomic and cDNA nucleotide sequences. In another related embodiment, the present invention provides vectors comprising these nucleotide sequences. In an alternative embodiment, it is contemplated that these vectors are expression vectors. In a related embodiment, the vectors of the present invention are contained within a host cell. In one embodiment, the host cell is prokaryotic, while in another embodiment, the host cell is eukaryotic.

In another embodiment, the present invention provides a pure, isogenic strain of the fungal species *Candida albicans* having homozygous deletion of the endogenous loci encoding the amino acid sequence of Cos-1p (SEQ ID NO:17). Similarly, the present invention also provides a pure, isogenic strain of the fungal species *Aspergillus fumigatus* having homozygous deletion of the endogenous loci encoding the amino acid sequences of Fos-1p and mini-FOS-1 uORF polypeptide (SEQ ID NOS: 35 and 48, respectively).

The present invention provides antibodies directed against the *C. albicans* histidine kinase Cos-1p (SEQ ID NO: 17), the *A. fumigatus* histidine kinase Fos-1p (SEQ ID NO: 35), and the *A. fumigatus* mini-FOS-1 uORF polypeptide (SEQ ID NO: 48). The antibody of the present invention is selected from the group consisting of monoclonal antibodies and polyclonal antibodies.

The present invention also provides polynucleotide sequences that hybridize under stringent conditions to the nucleotide sequence of *C. albicans* COS-1 (SEQ ID NO: 16) and *A. fumigatus* FOS-1 cDNA (SEQ ID NO: 36).

In other embodiments, the present invention provides methods for identifying compounds which are candidates for development as antifungal drugs. In one embodiment, a method is provided to identify compounds which are antifungal drug candidates comprising the testing of a compound for the ability to inhibit in vitro histidine and/or aspartate kinase activities of a purified fungal histidine kinase protein. In an alternative embodiment of this method, the amino acid sequence of the fungal histidine kinase protein is selected from SEQ ID NOS: 2, 5, 17 and 35.

In an alternative embodiment, another method is provided to identify compounds which are antifungal drug candidates comprising the testing of a compound for the ability to inhibit in vitro histidine and/or aspartate kinase activities of a fungal histidine kinase protein and the ability of that same compound to inhibit or prevent fungal growth in culture. In another related embodiment, an alternative method is provided to identify compounds which are antifungal drug candidates comprising testing the ability of a compound to inhibit in vitro histidine and/or aspartate kinase activities of a fungal histidine kinase protein, testing the ability of that same compound to inhibit or prevent fungal growth in culture, and testing the ability of the compound to suppress or prevent in vivo candidosis/candidemia in a non-human animal. In a related method, the in vivo candidosis/candidemia is in a mouse.

In another embodiment, the method to identify compounds which are antifungal drug candidates uses a fungal strain that is selected from the *Neurospora crassa, Candida albicans* and *Aspergillus fumigatus*. In still another embodiment, the method to identify compounds which are antifungal drug candidates uses a fungal strain selected from a wild-type *Neurospora crassa* strain, a wild-type *Candida albicans* strain, a wild-type *Aspergillus fumigatus* strain, a pure, isogenic strain of *Neurospora crassa* having homozygous deletion of the endogenous loci encoding the amino acid sequence set forth in SEQ ID NO: 2, a pure, isogenic strain of *Candida albicans* having homozygous deletion of the endogenous loci encoding the amino acid sequence set forth in SEQ ID NO: 17, and a pure, isogenic strain of *Aspergillus fumigatus* having homozygous deletion of the endogenous loci encoding the amino acid sequences set forth in SEQ ID NOS: 35 and 48.

In related embodiments, the present invention also provides compounds which are antifungal drug candidates, wherein said compound (i) inhibits in vitro kinase activity of a histidine kinase protein; or (2) inhibits in vitro kinase activity of a histidine kinase protein and inhibits fungal growth in culture; or (3) inhibits in vitro kinase activity of a histidine kinase protein, inhibits fungal growth in culture and inhibits in vivo candidosis/candidemia in a mouse.

In another embodiment, the present invention provides synthetic polypeptides which encompass the phosphorylation sites of a fungal histidine kinase, where the phosphorylation site is a histidine phosphorylation site or an aspartate phosphorylation site. In a related embodiment, the synthetic peptides comprise the phosphorylation sites provided in SEQ ID NOS: 41 and 42.

In another embodiment, the present invention provides purified, synthetic oligonucleotides consisting of between 12 and 200 nucleotides having antisense complementarity to the nucleotide sequence of a fungal histidine kinase gene. In a related embodiment, the invention provides oligonucleotides having antisense complementarity to the nucleotide sequence selected from the group consisting of SEQ ID NOS: 16, 34 and 36.

In another embodiment, the present invention provides a method for treating a subject for the purpose of eradicating, mitigating or preventing a fungal infection. This method provides a subject, an antifungal agent selected from the group consisting of (i) a monoclonal or polyclonal antibody directed against a fungal histidine kinase protein, (ii) a compound which is an antifungal drug candidate selected from the group consisting of a compound which inhibits the in vitro kinase activity of a histidine kinase protein, a compound which inhibits the in vitro kinase activity of a histidine kinase protein and inhibits fungal growth in culture, and a compound which inhibits the in vitro kinase activity of a histidine kinase protein, inhibits fungal growth in culture, and inhibits in vivo candidosis/candidemia in a mouse, (iii) an isolated, synthetic peptide, wherein said peptide comprises the amino acid sequences of a histidine phosphorylation site or an aspartate phosphorylation site, and (iv) a synthetic antisense oligonucleotide having complementarity to the nucleotide sequence of a fungal histidine kinase, and finally, a means of delivery of said antifungal agent to the subject. In various embodiments of this method, the subject may be displaying pathology resulting from a fungal infection, may be suspected of displaying pathology resulting from a fungal infection, or be at risk of displaying pathology resulting from a fungal infection. In still other embodiments of this method, the delivery of the antifungal agent may be systemic, localized or topical.

In summary, the present invention provides compositions and methods related to fungal histidine kinases. In particular, the present invention provides amino acid and nucleotide sequences of fungal histidine kinases from organisms such as Candida (e.g., *C. albicans*), Neurospora (e.g., *N. crassa*), and Aspergillus (e.g., *A. fumigatus*). The present invention further provides compositions and methods for the identification and development of antifungal compounds, as well as the treatment of subjects to eradicate, mitigate or prevent fungal infections.

DESCRIPTION OF THE DRAWINGS

FIG. 3A–C is an amino acid sequence alignment of the proteins Os1p (SEQ ID NO:25), BarA (SEQ ID NO:26), RepA (SEQ ID NO:27), ApdA (SEQ ID NO:28), and Sln1p (SEQ ID NO:29).

FIG. 6A–D is an amino acid sequence alignment of the proteins Cos-1p (SEQ ID NO:30), Os-1p (SEQ ID NO:2), BarA (SEQ ID NO:31), and Sln1 (SEQ ID NO:32).

FIG. 7A depicts the COS-1 knock-out targeting vector used to make the ΔCOS-1 strain. The black bar above the COS-1 gene indicates the approximate location of the probe used in Southern blot analysis of potential ΔCOS-1 strains. FIG. 7B shows a Southern blot using genomic DNA isolated from potential ΔCOS-1 strains and the probe indicated in FIG. 7A.

FIG. 10A–D shows the 8256 base pair nucleotide sequence of the wild-type Aspergillus fumigatus FOS-1 genomic region, set forth as SEQ ID NO:34.

FIG. 11A–B shows the 3168 base pair sequence of the wild-type A. fumigatus FOS-1 cDNA set forth as SEQ ID NO:36.

FIG. 12A shows a schematic representation of the FOS-1 genomic locus. The Fos-1p and mini-Fos-1 upstream open reading frames are indicated as open rectangles. A putative transcription start site (TATA), two putative translational start sites (AUG), polyadenylation signal sequences (polyA) and restriction sites are indicated. Also shown is the relative position of the isolated FOS-1 cDNA. FIG. 12B shows a Northern blot of A. fumigatus polyA RNA using a radiolabelled probe derived from the isolated FOS-1 cDNA.

FIG. 13A shows the predicted 708 amino acid sequence of wild-type A. fumigatus histidine kinase Fos-1p protein, set forth as SEQ ID NO:35. FIG. 13B shows the predicted 49 amino acid sequence of the wild-type A. fumigatus FOS-1 upstream mini-open reading frame (mini FOS-1 uORF), set forth as SEQ ID NO:48.

FIG. 15A–B shows a sequence alignment for the histidine kinase proteins Os-1p (SEQ ID NO:2), Cos-1p (SEQ ID NO:17) and Fos-1p (SEQ ID NO:35), from fungal species N. crassa, C. albicans, and A. fumigatus, respectively. In this Figure, the H box, ATP binding motif, D box, and N, G1 and G2 boxes are shaded, while the amino acid positions showing identity between all three species are indicated with an asterisk, and the putative histidine and aspartate phosphorylation targets are indicated with an arrow.

FIG. 16A depicts the A. fumigatus FOS-1 knock-out targeting vector pFOSKO2 used to make the ΔFOS-1 strain. The bar with arrow above the FOS-1 gene indicates the approximate position of a radiolabeled probe used in Southern blotting to identify ΔFOS-1 strains. FIG. 16B provides a Southern blot probing A. fumigatus genomic DNA cut with EcoRI derived from a wild-type strain and a FOS-1 knock-out strain using a probe derived from the FOS-1 ORF indicated in FIG. 16A by an arrow.

FIGS. 19A and 19C show the nucleotide sequences of the A. fumigatus histidine kinase PCR products FOS-2 (SEQ ID NO:37) and FOS-3 (SEQ ID NO:38) respectively. FIGS. 19B and 19D show the corresponding amino acid translations of the A. fumigatus histidine kinase proteins Fos-2p (SEQ ID NO:39 and Fos-3p (SEQ ID NO:40), respectively.

DESCRIPTION OF THE INVENTION

Figure 1:
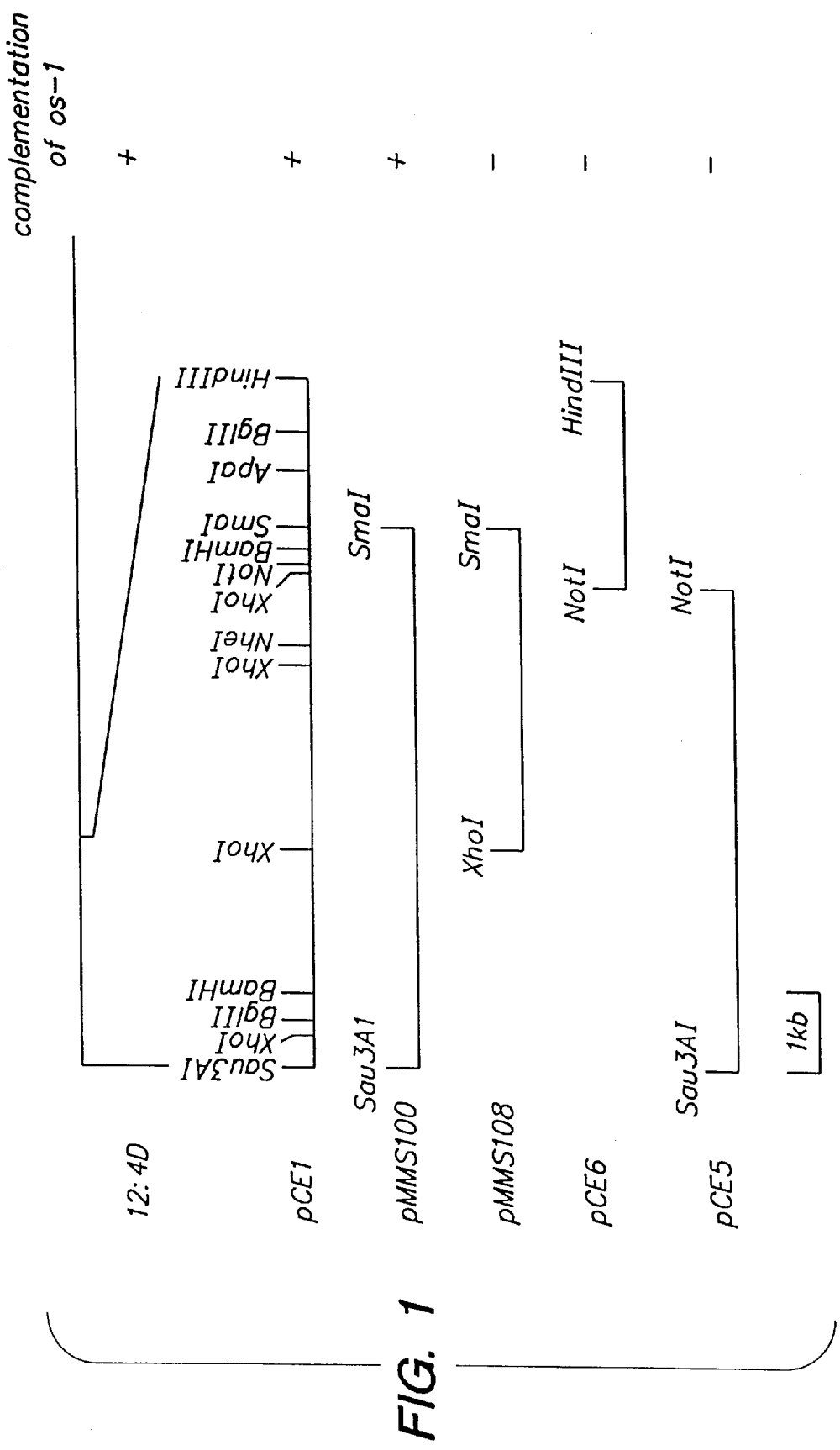
FIG. 1 shows a map of the 12:4D cosmid and its restriction sites, in comparison with pCE1, PMMS100, pMMS108, pCE6, and pCE5.

The present invention relates to fungal histidine kinases genes and proteins, related compositions, and methods for their use in identifying compounds for antifungal activity. In particular, the present invention provides new targets for antifungal compounds, namely novel histidine kinase proteins. Importantly for development of antifungals with minimal toxicity, the present invention provides targets that are widespread among diverse fungal species, but are absent from humans and other mammals.

Histidine kinases may be involved in fungal cell wall biosynthesis, assembly or integrity. The lack of chitin, (1-6)β-glucan and (1-3)β-glucan in mammalian cells makes their biosynthesis pathways attractive targets for antifungal compounds. For example, chitin synthase and (1-3)β-glucan synthase have been considered as targets for antifungal development (See e.g., G. W. Gooday, "Chitin metabolism: A target for antifungal and antiparasitic drugs," in E. Borowski (ed.), Molecular Aspects of Chemotherapy, Pergamon Press [1993] pp. 175–185; N. Georgopapadalou and J. Tkacz, "The fungal cell wall as a drug target," Trends Microbiol., 3:98–104 [1995]). Indeed, Pneumocystis carinii pneumonia has been successfully treated with (1-3)β-glucan synthase inhibitors (D. Schmatz et al., Proc. Natl. Acad. Sci., 87:5950–5954 [1982]).

The present invention provides compositions and methods suitable for developing antifungal drugs which target histidine kinase genes and proteins. Importantly, the present invention demonstrates that a histidine kinase gene contributes to fungal virulence. Furthermore, disruption of the histidine kinase gene results in alteration of normal cell wall composition or structure. The present invention provides advantages over antifungal compounds that target chitin biosynthesis, as the present invention provides antifungal agents which likely have the ability to disrupt not only chitin biosynthesis, but other cellular processes as well.

Histidine Kinase Function and Activity

Two-component signal transduction pathways appear to be the main mechanisms by which bacteria, fungi and plants respond to environmental signals (Falke et al., Ann. Rev. Cell. Dev. Biol., 13:457 [1997]; Loomis et al., J. Cell Sci., 110:1141 [1997]; Wurgler-Murphy and Saito, Trends Biol. Sci., 22:172 [1997]; Madhani et al., Trends Cell Biol., 8:348 [1998]; Brewster et al., Scinece 259:1760 [1993]; and Madhani et al., Trends Genet., 14:151 [1998]). Although an understanding of the mechanism is not necessary in order to use the present invention, the pathways are briefly described below. Often, the initial protein in the pathway is a transmembrane histidine kinase that dimerizes in response to an external signal. One partner of the dimer phosphorylates a specific histidine residue of the other partner and the phosphoryl group is subsequently transferred to an aspartyl residue of a response-regulator protein. This results in the activation of a pathway leading to the up-regulation of specific genes. In bacteria, the histidine kinase sensor and the response regulator are separate proteins. In fungi and other lower eukaryotes, both the histidine kinase and the response proteins are the same protein. Two-component histidine kinases have not been found in humans and thus, represent useful targets for the development of antifungal drugs.

The fungal histidine kinase system is a two-component signal transduction system. In bacterial systems, one variety of this two-component signalling pathway conveys a signal generated by an environmental stimulus into the interior of the cell through a series of reversible protein phosphorylation reactions (See e.g., L. A. Alex and M. I. Simon, Trends Genet., 10:133–138 [1994]). Both prokaryotes and eukaryotes have been found to have these two-component systems (See e.g., L. A. Alex and M. I. Simon, supra; R. V. Swanson et al., Trends Biochem. Sci., 19:485–490 [1994]; J. S. Parkinson et al., Ann. Rev. Genet., 26:71–112 [1992]); C. Chang et al., Science 262:539–544 [1993]; J. Hua et al., Science 262:539–544 [1995]; I. M. Ota and A. Varshavsky, Science 262:566–569 [1993]; T. Maeda et al., Nature 369:242–245 [1994]; Schuster et al., EMBO J., 5:3880–3889 [1996]; Wang et al., EMBO J., 5:3890–3898 [1996]; Kakimoto, Science 274:982–985 [1996]; and L. A. Alex et al., Proc. Natl. Acad. Sci., 93:3416–3421 [1996]). However, prior to the development of the present invention, the histidine kinase systems of *N. crassa* and the medically important fungi *C. albicans* and *A. fumigatus* were not known.

In the most simple form of the histidine kinase system, the first component is an autophosphorylating histidine kinase, the activity of which is modulated in response to a specific stimulus; the second component is a response regulator. This response regulator serves as a substrate for the histidine kinase. An aspartate residue of the regulator becomes phosphorylated after phosphoryl transfer from the histidine residue of the kinase. It is the phosphorylation of the response regulator that controls its function. The kinase domain is comprised of a module of approximately 250 amino acids with five sequence blocks that are conserved (H, F, G1, G2, and N). The H box is the site of histidine autophosphorylation, while the F, G1 and G2 boxes are believed to be involved in nucleotide binding; the function of the N box is unknown. The response regulator domain ("response regulator," "D box," or "receiver domain") may be identified from the number and spacing of a module of conserved aspartate, lysine, and hydrophobic residues in a module of approximately 120 amino acids. These signaling modules (i.e., the histidine kinase and response regulator) may be found in various contexts within other signaling proteins found in bacteria, slime molds and plants, but are absent from humans.

Fungal Histidine Kinases

As determined to date for all eukaryotes that contain histidine kinase proteins (with the exception of plants), the histidine kinase and response regulator activities reside in the same protein. Fungal two-component systems have been identified that are sensitive to extracellular osmolarity fluctuations (i.e., the Os-1p in *Neurospora crassa*). Under appropriate osmolarity conditions, an enzymatic cascade is activated and cell wall biosynthesis is stimulated in *N. crassa*. This response is critical, as fungal cells that are incapable of adjusting to changes in extracellular osmolarity are nonviable (See, L. Alex and M. Simon, Trends Genet., supra; and B. Morgan et al., J. Cell Biol., 5:453–457 [1995]). Fungal pathogens must be able to quickly respond (i.e., via glycerol synthesis and cell wall biosynthesis) to changes in osmolarity found in various tissues.

Although an understanding of the mechanism(s) are not necessary in order to use the present invention, the pathways are briefly described below. In *S. cerevisiae*, the Sln1p/Ypd1p/Ssk1p proteins comprise a two-component signal transduction pathway that regulates the Hog1 MAPK cascade (F. Posas et al., Cell 86:865–875 [1996]). The HOG1 pathway is responsible for the control of genes necessary for adaptation to high external osmolarity. The Sln1p/Ypd1p/Ssk1p pathway is actually a special form of the two-component system known as a phosphorelay system (See, Appleby et al., Cell 86:845–848 [1996], for review). Examples of these systems are found in bacteria where they mediate sporulation in *Bacillus subtilis* (D. Burbulys et al., Cell, 64:545–552 [1991]) and transcription of virulence factors in *Bordetella pertussis* (M. Uhl and J. Miller, EMBO J., 15:1028–1036 [1996]). The phosphorelay system involves a set of multiple phosphotransfer reactions alternating between histidine and aspartate. For example, autophosphorylation of the histidine kinase occurs (e.g., at the "H1" site) and there is subsequent transfer to an aspartate residue ("D1"). This aspartate can lie in the same protein as the kinase (as in the case of BvgS in *B. pertussis*) or it can be a separate protein (as in the case of SpoOF in *B. subtilis*). There is then transfer from the aspartate (D1) to a second histidine residue ("H2"). The H2 site can be within the same protein as the first site (e.g., BvgS) or in a separate protein (e.g., SpoOB). Finally there is transfer from the histidine at H2 to another aspartate residue ("D2"). Generally, D2 is in a separate response regulator that is the protein with some function (e.g., DNA binding).

In the *S. cerevisiae* pathway, the Sln1p is an osmosensing transmembrane histidine kinase. Under conditions of low osmolarity, Sln1p first autophosphorylates a histidine residue (H1) and this phosphate is transferred to an internal aspartate residue (D1). Phosphate is then transferred from the D1 site of Sln1p to a histidine (H2) on a small protein called Ypd1p. Finally, the phosphoryl group is transferred to yet another protein, the response regulator Ssk1p (D2). Phosphorylation of Ssk1p results in a protein that cannot activate the HOG1 pathway (i.e., Sln1p is a negative regulator of the HOG1 pathway). Under conditions of high osmolarity, Sln1p is inhibited, resulting in dephosphorylation of Ssk1p which can now activate the HOG1 cascade to allow activation of multiple osmolarity responses (See, B. Morgan et al., J. Cell. Biol., 5:453–457 [1995]; and F. Posas et al., Cell 86:865–875 [1996]). Mutants with sln1 and HOG-1 deletions are non-viable under conditions of high osmolarity, while constitutive HOG-1 mutants are non-viable under conditions of low osmolarity.

The Skn7p is another response regulator found in *S. cerevisiae*. So far, the cognate histidine kinase for Skn7p has not been found. (Although it is known from the completed genome project of *S. cerevisiae* that Sln1p is the only two-component histidine kinase in this organism.) The SKN7 gene was isolated as a suppressor of KRE9, a mutant defective in (1-6)β-glucan synthesis (See, J. L. Brown et al., EMBO 13:5186–5194 [1994]; and J. L. Brown et al., J. Bacteriol., 175:6908–6915 [1993]). This gene is also known as "POS9" and was identified as a gene important for the adaptation of yeast to oxidative stress (See e.g., B. Krems et al., Curr. Genet., 29:327–334 [1996]). It has also been linked to a potential transcription factor Ask10p (See, Page et al., Yeast 12:267–272). The SKN7 protein (Skn7p) has been shown to share homology to DNA-binding motifs, Sln1p, and a putative receiver domain (See, J. Morgan et al., J. Cell. Biol., 5:453–457 [1995]; J. L. Brown et al., EMBO, supra; and J. L. Brown et al., J. Bacteriol., supra).

In addition, Skn7p has been shown to be phosphorylated in vivo, an observation that is consistent with the inclusion of a receiver domain. The role of SKN7, HOG1, and the histidine kinases that activate them make them attractive targets for antifungal compounds. However, prior to the development of the present invention, insufficient information was available regarding the distribution and function of histidine kinases in fungi of medical significance (e.g., *C. albicans* and *A. fumigatus*) for such use.

An alternative osmosensor of the HOG1 pathway has also been identified. The gene SHO1 (synthetic high osmolarity sensitive) encodes a protein of 367 amino acids with homology to SH3-containing signal transduction proteins (e.g., GRB2, c-scr, and PLCγ). Sho1p is believed to be localized in the plasma membrane, and activates the MAPKK (MAP kinase kinase) Pbs2p, by phosphorylation of Pbs2p at $Ser^{514}$ and $Thr^{518}$. However, Sho1p appears to have a minor role in the regulation of the HOG1 pathways, as Sho1p is not able to compensate for Sln1p mutations.

*N. crassa, C. albicans* and *A. fumigatus* Histidine Kinase Systems

In a preferred embodiment of the present invention, the osmotic-1 (COS-1) gene encoding the histidine kinase of *C. albicans* is provided. In alternative embodiments of the present invention, the OS-1 gene encoding the histidine kinase of *N. crassa* is provided. In still other embodiments, the FOS-1 gene of *A. fumigatus* is provided. However, it is contemplated that other histidine kinase genes and proteins from these and other fungal species having homology to the *C. albicans, N. crassa* and *A. fumigatus* histidine kinase genes and proteins of the present invention will be identified using the sequence information and methods provided herein.

In preliminary experiments during the development of the present invention, *N. crassa* was used, as it is particularly well-suited to the study of fungal cell wall assembly. This organism has been "domesticated" and methods have been developed to manipulate the organism in the laboratory. *N. crassa* exhibits both an asexual vegetative and a sexual phase in its life cycle (See e.g., M. L. Springer, BioEssays 15:365–374 [1993]). During vegetative growth, *N. crassa* forms a branched multicellular network of hyphae (i.e., a mycelium). Hyphae extend from the apical tip and form branches at regular intervals, often fusing with other hyphae. Upon conditions of nutrient deprivation and desiccation, the mycelium sends up aerial hyphae, which then differentiate into conidiophores that, in turn, ultimately produce conidia, which can also function as male gametes during the sexual cycle. *N. crassa* forms microconidia, as well as macroconidia. The microconidia are uninucleate and may be crossed in such a manner that only monokaryons are involved. The macroconidia are multinucleate, with an average of three nuclei per macroconidium. When placed in a suitable environment, populations of macroconidia proceed synchronously through germination, including the de novo synthesis of cell wall material.

In order to address the suitability of using the fungal histidine kinase pathway as a target for development of antifungals, experiments were conducted to analyze the osmotic sensitivity and other characteristics of *N. crassa* strains deficient at this genetic locus. Osmotically-sensitive mutants of *N. crassa* were found to be unable to grow in liquid media supplemented with 4% NaCl. During the development of the present invention, four osmotic genes within *N. crassa* were identified (designated as OS-1, OS-2, OS-4, and OS-5). The OS-1 strains have altered cell wall compositions containing decreased amounts of alkali-soluble glucose, are morphologically abnormal, and produce few macroconidia.

In addition, *N. crassa* strains with a temperature-sensitive allele of OS-1 form protoplasts (i.e., cells lacking cell walls), when grown in specialized media at non-permissive temperature (e.g., 37° C.). In these cultures, both (1-3)β-glucan and chitin biosyntheses occurred, but the polymers were excreted into the medium, rather than being assembled into cell wall material. Thus, OS-1 mutants are not defective in (1-3)β-glucan or chitin synthases. When the growth temperature is shifted to 25° C. (i.e., a permissive temperature for OS-1 function), the cell wall-less (i.e., protoplast) populations regenerate cell walls, and grow in the form of hyphae. Each of the identified OS mutants was tested; it was determined that only OS-1 strains can form protoplasts that grow and divide. These results indicated that OS-1 has a fundamental and essential role in fungal cell wall assembly.

Next, the OS-1 gene was localized to a member of the ordered Vollmer-Yanofsky cosmid library (S. Vollmer and C. Yanofsky, Proc. Natl. Acad. Sci., 83:4861 [1986]). The original cosmid clone containing the OS-1 gene was then isolated, cloned and sequenced. A single open reading frame (ORF) of approximately 4.3 kb interrupted by four introns was identified. The ORF was found to encode a predicted protein of 1298 amino acids (Alex et al., Proc. Natl. Acad. Sci., 93:3416–3421 [1996]). Gene replacement experiments were used to confirm that the ORF encodes the Os-1p protein. In subsequent experiments, the predicted OS-1 protein was shown to have significant homology to bacterial and yeast signal transduction two-component histidine kinases (See, FIG. 6). The sequence analysis identified three areas of significant homology corresponding to the H-Box, ATP-binding site, and D-Box.

The present invention also provides a histidine kinase gene from the medically important fungal species *C. albicans* (COS-1). The COS-1 gene was identified using a degenerate PCR strategy based on consensus domains among other known histidine kinase proteins (e.g., OS-1 and SLN1). *C. albicans* genomic DNA was prepared and used as a template in PCR, as described in Example 8. The complete gene sequence was obtained by screening a *C. albicans* genomic library using the previously obtained PCR product as a probe, as described in Examples 9 and 10. The Cos-1p protein shows 60% identity and 70% similarity with *N. crassa* Os-1p. Indeed, the H-Box sequence is identical between these proteins.

In order to study the potential of using the COS-1 gene or protein as a target for antifungal drug development, the phenotypes of COS-1 hemizygous and homozygous knockout strains were studied. These knockouts were made using techniques common in the art, as described in Example 11.

The phenotypic analyses of these *C. albicans* COS-1 knockout strains are described in Example 12. These analyses included analysis of cell viability under low and high osmolarity, hyphal formation, growth rates, and sensitivity to antifungal compounds. Slight differences from the wild-type strain were noted in the timing of hyphal formation and altered colony morphology. However, these mutant strains did not demonstrate any remarkable phenotypes as compared to the wild-type C. albicans strain.

These results are in sharp contrast to OS-1 deletion strains of N. crassa that were found to have very distinct phenotypic differences from wild-type, are highly resistant to vinclozolin, and hypersensitive to NaCl. The dramatic differences are present despite the significant amino acid and protein structure similarities shared between Os-1p and Cos-1p.

However, comparison of the virulence of the wild-type and COS-1 knockout C. albicans strains indicated significant differences between the two strains. An in vivo mouse model of candidosis/candidemia was used to assay the relative virulence these C. albicans strains (Example 13). In this assay, mice were inoculated with known concentrations of C. albicans strains, and the subsequent mouse mortality was scored. Briefly, the homozygous COS-1 knockout strain showed significantly reduced virulence compared to the virulence of the wild-type strain tested in parallel. An hemizygous COS-1 knockout strain showed virulence that was intermediate between that of the wild-type and homozygous knockout strains. Furthermore, no differences in the distribution of the two strains in the organs was found, suggesting that the differences in virulence are not due to altered clearance and avoidance from the key target organ, the kidneys.

These results are significant, in that they demonstrate that deletion of the Cos-1p gene product renders the fungal species less virulent. Thus, it is contemplated that compounds which inactivate the Cos-1p gene product will find use as antifungal compounds. Furthermore, it is contemplated that this example provides an easily adapted protocol for the in vivo evaluation of a compound for antifungal activity.

In the present invention, a histidine kinase gene from Aspergillus fumigatus was also identified and characterized. As discussed previously, A. fumigatus is a medically significant fungal species. Using strategies similar to those used to isolate C. albicans COS-1, an A. fumigatus histidine kinase genomic sequence and cDNA were isolated (SEQ ID NOS: 34 and 36, See Examples 14 and 16), and the gene was named FOS-1. The present invention also provides an A. fumigatus FOS-1 knockout strain, as described in Example 18. Phenotypic characterization of this mutant strain is provided in Example 19.

Phenotypic characterization of the A. fumigatus FOS-1 knockout strain included analyses of morphology, growth rates, conidial germination rates, resistance to novozym 234, osmotic stress, oxidative stress compounds, and sensitivity to antifungal drugs. Some phenotypic differences were observed between the wild-type and mutant FOS-1 strains. Briefly, the wild-type and ΔFOS-1 A. fumigatus strains grew at similar rates on a variety of solid media, and both strains formed identical hyphal masses in liquid media. No differences were detected between the morphologies of wild-type and ΔFOS-1 strains grown using a number of liquid and solid media with respect to hyphal, conidiophore and conidial morphology. However, only ~30% of ΔFOS-1 hyphal tips developed into conidiophores, while 80–90% of wild-type hyphal tips developed into conidiophores. No significant differences were observed in the number of germinating conidia from wild-type and ΔFOS-1 strains.

With regard to sensitivity to oxidative stress-inducing compounds, no differences in hyphal growth/extension rates were seen comparing the wild-type and ΔFOS-1 strains when tested using either diamide or menadione-containing solid media.

However, the wild-type and ΔFOS-1 A. fumigatus strains showed unexpected differences in their sensitivities to a cell wall degrading enzyme. The hyphae of the ΔFOS-1 strain showed more resistance to novozym 234 digestion than the wild-type strain, suggesting that the cell-wall compositions and/or structure of wild-type and ΔFOS-1 strains are not identical.

The wild-type and ΔFOS-1 strains were also tested for osmo-sensitivity. Surprisingly, it was observed that the ΔFOS-1 mutant strain grew at rates slightly greater than the wild-type strain in media containing 5% or 10% NaCl.

With regard to sensitivity to antifungal compounds, no differences in minimum inhibitor drug concentration were observed when using the wild-type or ΔFOS-1 strains were found. The antifungal compounds tested included amphotericin B, nikkomycin Z, benomyl, miconazole, ketoconazole, fluconazole, cilofungin, 5-fluorocytosine and calcofluor white M2R new.

The resistance of wild-type and ΔFOS-1 strains to dicarboximide antifungals vinclozolin, iprodione and procymidone was also compared. No differences in the extent of conidiation or in hyphal and conidiophore morphologies between wild-type and ΔFOS-1 strains was observed during these experiments. However, significant differences were observed in the hyphal extension rates of the wild type and ΔFOS-1 strains when grown on media containing the various dicarboximide drugs. In this experiment, the ΔFOS-1 strain grew at significantly greater rates than the wild-type strain on media containing the various dicarboximides.

In summary, these results demonstrate that although wild type and ΔFOS-1 A. fumigatus strains behave similarly in some conditions, there are also some significant differences in their physiologies. It is contemplated that the physiological properties inherent to the ΔFOS-1 A. fumigatus strain will find use in the development of antifungal compounds that inactivate the FOS-1 gene product, Fos-1p. It is further believed that the physiological traits associated with loss of activity of Fos-1p reduce the virulence of affected A. fumigatus cells.

Furthermore, the present invention also provides partial nucleotide and amino acid sequences for at least one additional histidine kinase gene from A. fumigatus in addition to FOS-1. These partial nucleotide sequences have been given the names FOS-2 and FOS-3, which are described in Example 20. These sequences were identified using the same protocol that identified the FOS-1 gene (See, Example 14).

Utility of Fungal Histidine Kinase Systems

The results obtained during the development of the present invention indicated that fungal histidine kinase systems (e.g., COS-1 and FOS-1) are suitable, useful and desirable targets for antifungal development. The present invention provides nucleotide and amino acid sequences for a family of fungal histidine kinase genes and proteins. The present invention also provides compositions related to these histidine kinase sequences, including vectors comprising these nucleotide sequences, antibodies specific to histidine kinase proteins, antisense oligonucleotides specific to histidine kinase transcripts, and histidine kinase synthetic peptides. The present invention also provides methods for the identification of compounds which have antifungal activity, and methods for treating patients having fungal infections. However, it is not intended that the assay systems provided by the present invention be limited to any particular histidine kinase gene or any particular fungal species.

The present invention finds use in the identification of compounds (i.e., drugs) that have therapeutic value by eliminating, mitigating or preventing pathogenic fungal infections. Examples of conditions, diseases and disorders which can be treated using compositions and methods of the present invention are listed, but not limited to, those below.

| | |
|---|---|
| adiaspiromycosis | mycotic keratitis |
| aspergillosis | mycotic keratosis |
| dermatophytoses | onychomycosis |
| blastomycosis | oomycosis |
| candidemia | otomycosis |
| cercosporamycosis | paracoccidiomycosis |
| systemic and superficial candidiasis | penicillosis |
| (i.e., candidosis) | phaeohyphomycosis |
| chromoblastomycosis | phaeomycotic cyst |
| chromomycosis | piedras (black piedra, white piedra) |
| coccidioidomycosis | pityriasis nigra |
| cryptococcosis | pityriasis versicolor |
| cryptomycosis | (i.e., tinea versicolor) |
| dermatomycosis | pneumonia |
| entomophthoramycosis | protothecosis |
| favus (tinea favosa) | rhinosporidiosis |
| fusariosis | ringworm |
| geotrichosis | sporotrichosis |
| histoplasmosis | systemic mycoses |
| hyalohyphomycosis | tinea |
| lobomycosis | torulopsosis |
| maduramycosis (Madura foot) | trichomycosis axillaris |
| mycetoma | zygomycosis |
| mucormycosis | |

However, it is not intended that the present invention be limited to treating only those conditions, diseases and disorders listed above, as it is contemplated that the present invention finds use in the treatment of other diseases, disorders or conditions caused by pathogenic fungal infections. Similarly, it is not intended that use of the present invention be limited to the treatment of a disease, disorder or condition caused by any particular fungal species.

Screening Method to Identify Compounds Having Antifungal Activity

Compositions and methods provided by the present invention find use in the identification of antifungal drugs. Embodiments of some of the methods of the present invention incorporate a biochemical assay to identify compounds capable of inhibiting histidyl and/or aspartyl kinase activities associated with the proteins of the present invention. It is contemplated that compounds which inhibit the kinase activity or activities of the proteins of the present invention will find use in drug development. In preferred embodiments of these methods of the invention, the in vitro analysis of candidate compounds is followed by at least one additional step of testing. These additional steps of testing are a fungal growth assay in culture, and a candidosis/candidemia mouse model.

Thus, in particularly preferred embodiments of the invention, the identification of candidate antifungal therapeutic drugs is conducted in three consecutive steps. A drug candidate advances to the next step of screening if it satisfies criteria of the previous step. This sequential screening provided by the particularly preferred methods of the present invention include the following steps.

1) Identification of Compounds Which Inhibit In Vitro Histidine Kinase Autophosphorylation Activity The first screening step provided by the present invention comprises an in vitro kinase assay to identify compounds which inhibit histidyl and/or aspartyl kinase activity of a histidine kinase protein in vitro. In some preferred embodiments, this assay is automated and permits rapid, high throughput screening of large numbers of candidate compounds. Equipment used in the automation of screening is known in the art (e.g., robotic technology, such as the Biomek 2000 from Beckman Instruments, Inc.).

Briefly, in order to conduct the assay, a recombinant fungal histidine kinase protein (e.g., Cos-1p or Fos-1p) is first produced and purified. The kinase activity of this purified protein is then assayed in the presence and absence of a test compound by incubation with a radiolabelled ATP substrate, and measuring radiolabel incorporation into the histidine kinase protein (i.e., autophosphorylation), or phosphorylation of another peptide or protein substrate present in the reaction. Suitable protocols to assess or measure kinase activity in vitro are known in the art (Ausubel et al., Current Protocols in Molecular Biology, Ch. 18 "Analysis of Protein Phosphorylation," John Wiley & Sons, Inc. (eds), New York [1994]). Furthermore, protocols suitable for measurement of kinase activities associated with proteins of the two-component histidine kinase signal transduction systems are also known (See, e.g., Deschenes et al., Antimicrobial Agents and Chemotherapy 43(7):1700–1703 [1999]; Hilliard et al., Antimicrobial Agents and Chemotherapy 43:1693–1699 [1999]; Barrett et al., Proc. Natl. Acad. Sci. USA 95:5317–5322 [1998]; Roychoudhury et al., J. Biomolec. Screening 2(2):85–90 [1997]; Hess et al., Methods Enzymol., 200:188–204 [1991]; Huang et al., J. Biol. Chem., 266(14):9023–9031 [1991]). Indeed, it is not intended that the present invention be limited to any particular kinase assay protocol, as other kinase assays also find use with the invention.

It is also intended that any suitable technique for the production and purification of a purified, recombinant histidine kinase protein will find use with the present invention. For example, the Fos-1p protein may be produced and isolated using a glutathione S-transferase (GST) fusion protein protocol, as described in Example 21. The use of GST fusion proteins to produce purified polypeptides is common in the art. However, it is not intended that the present invention be limited to any particular method for histidine kinase protein expression and purification.

As those of skill in the art recognize, numerous protocols for the purification of proteins are available. Thus, any suitable method for protein purification will find use in the purification of histidine kinase proteins used in the present invention. These alternative protocols include, but are not limited to, the use of maltose binding protein (MBP) fusion proteins, polyhistidine (i.e., 6xHis) tagged fusion proteins, or thioredoxin tagged fusion proteins (i.e., to facilitate purification). Furthermore, histidine kinase proteins without any fused tag may also be purified using techniques common in the art.

In an alternative embodiment of the present invention, the histidine kinase protein is artificially overproduced in an overexpression cellular host system (or harvested from its native source in fungal cells). The protein is extracted by disrupting (by any suitable method) the microorganisms (or cells if the protein is produced within the host). The resultant crude extract is then subjected to conventional biochemical techniques used for protein purification. As known in the art, numerous techniques for protein purification exist (e.g., ammonium sulfate precipitation, gel chromatography, HPLC, ion exchange chromatography, and affinity chromatography). It is contemplated that any suitable method for purification will find use in the present invention. Furthermore, these techniques may be used in an appropriate combination.

Further still, it is not intended that the present invention be limited to using a full length histidine kinase protein in these kinase assay methods. Either full length or truncated histidine kinase proteins can be used in these in vitro assays. Where truncated histidine kinase proteins are used, these portions contains at least one active kinase domain.

In preferred embodiments, the purified histidine kinase protein is then used in a kinase reaction in the presence of a radiolabelled ATP substrate, under conditions such that the histidine kinase displays histidyl or aspartyl phosphorylation activity. In addition, an identical reaction is run in which a compound being tested for kinase- inhibition activity is included. It is contemplated that this kinase assay be conducted in such a manner as to maximize throughput, and may use 96, 256 or 1024-multiwell plates, or any other type of apparatus that permits the simultaneous, automated and/or robotic analysis of multiple samples. It is not intended that the present invention be limited to any particular kinase reaction conditions or apparatus. Indeed, it is contemplated that any suitable kinase reaction conditions, apparatus or equipment will find use in the present invention.

In particularly preferred embodiments, radiolabelling of the protein is then measured by either scintillation counting, or by visualization following gel electrophoresis. Relative counts between reaction wells (or lanes) with and without the test compound indicate whether or not the test compound inhibited the kinase activity of the histidine kinase protein. It is contemplated that the kinase assay and scintillation counting protocols explicitly provided by the present invention may be automated by using robotics designed for use in high throughput screening. However, it is not intended that the present invention be limited to any particular scintillation counting protocol, either manual or automated. Indeed, it is contemplated that any suitable scintillation counting protocol, reagents or apparatus will find use with the present invention.

2) Identification of Compounds Which Inhibit the Growth of Fungi in Culture

In some preferred embodiments of the invention, compounds with the ability to inhibit histidine kinase activity are then tested for antifungal activity using fungal culture assays. Methods to test the antifungal activity of any given compound are common in the art, and include microtiter broth assays, agar diffusion assays, and agar-dilution assays (See, e.g., National Committee for Clinical Laboratory Standards [NCCLS], "Reference Method for Broth Dilution Antifungal Susceptibility Testing of Yeasts," Vol. 15, No. 10, Publication M27-T [1995]). It is contemplated that such methods may be easily adapted to provide for high throughput screening of large numbers of compounds.

In addition, some embodiments of the present invention provide dose-analysis growth inhibition assays for determining antifungal activity of test compounds. Briefly, various amounts of a test compound and a fungus (e.g., *C. albicans, A. fumigatus*) are coincubated. The growth rates of the fungus in the absence and presence of the candidate drug are determined and compared.

However, it is not intended that the invention be limited to the use of any one particular fungal growth assay. Indeed, it is contemplated that numerous other growth inhibition assays find use with the invention. Similarly, although *C. albicans* and *A. fumigatus* are equally suitable for use in this assay, it is not intended that the invention be limited to the use of these two species.

3) Identification of Compounds Which Inhibit or Eliminate Fungal Infection in an In Vivo Mouse Model System.

In addition, in some particularly preferred embodiments of the present invention, compounds which demonstrate an ability to inhibit the kinase activity of a histidine kinase protein in vitro and have antifungal properties in culture are tested in an in vivo mouse model of candidosis/candidemia (e.g., as described in Example 13).

Briefly, five-week-old female CD-1 mice (Charles River Laboratories) are infected intravenously with a wild-type *C. albicans* strain. Concurrently, a second set of mice are coinjected with a test compound. Mouse mortality is scored through 14 days post-infection.

Alternatively, mice can be injected with the test compound after an interval of time following the original inoculation with *C. albicans*. This alternative protocol allows the determination of whether a compound can eliminate infection (i.e., as opposed to preventing the infection).

However, it is not intended that the invention be limited to the use of any one particular in vivo infection assay. It is contemplated that other in vivo infection assays will find use with the present invention. Indeed, it is contemplated that any method suitable to determine the in vivo effectiveness of an antifungal compound or combination of compounds will find use in the present invention. Similarly, although *C. albicans* is used in this assay, it is not intended that the invention be limited to the use of this one species.

Use of Mimetic Peptides as Antifungal Therapeutics

During the development of the present invention, it was determined that histidine kinase proteins show domains of highly conserved amino acids (See, FIGS. 3, 6, 14 and 15). In particular, the "H-Box" domain (which contains a histidine residue that receives the phosphoryl group) and the "D-Box" domain (i.e., the "receiver domain" which contains an aspartate residue, to which is transferred the phosphoryl group from the donor histidine residue) are highly conserved. These domains do not appear in any known human proteins.

It is contemplated that peptides (or other molecules) which interfere with the normal functioning of these domains will find utility as antifungal agents. It is further contemplated that synthetic peptides which mimic the primary amino acid sequence of the H-Box or D-Box of fungal histidine kinases will cause disruption of histidine kinase H-Box and D-Box function, resulting in disruption of the function of the endogenous histidine kinase protein.

Two synthetic peptides, corresponding to the consensus amino acid sequences of the "H-box" and "D-box", which find use with the present invention, are:

H-box KS(D/E)FLANMSHEIRTP(M/L)NG(M/I) (SEQ ID NO:41), and
D-box V(I/V)LMD(I/V)(N/Q)MPVM (SEQ ID NO:42)

It is contemplated that synthetic peptides, such as those provided in SEQ ID NOS: 41 and 42 be tested for their ability to suppress the kinase activity of fungal histidine kinase proteins (i.e., to identify them as candidate drugs for development as antifungal agents, using the present invention. However, it is not intended that mimetic peptides be limited to the peptides provided in SEQ ID NOS: 41 and 42. Indeed, it is contemplated that other peptides corresponding to domains within the histidine kinase proteins but which have no homology to human sequences will also be identified as candidates for development as antifungal drugs. Methods for the production, testing and use of mimetic peptides as antifungal agents is known in the art (See, e.g., Hong et al., Antimicrobial Agents and Chemotherapy 43(7):1704–1707 [1999]).

Uses of Anti-histidine Kinase Antibodies as Therapeutics

The present invention provides *C. albicans* strains which contain deletion of the COS-1 gene locus. These *C. albicans* strains demonstrate reduced virulence in an in vivo mouse candidosis/candidemia model. Thus, it is contemplated that inactivation of the gene or gene product by any other mechanism will also reduce the virulence of C. albicans. Thus, it is contemplated that antibodies directed against fungal histidine kinases which disrupt normal histidine kinase function will find use as antifungal agents.

The present invention describes the production of polyclonal and monoclonal antibodies directed against a fungal histidine kinase protein. These antibodies find use in therapeutic applications in the treatment of fungal infections. Furthermore, the anti-histidine kinase antibodies of the present invention also find other uses, including but not limited to Western blotting, enzyme-linked immunosorbence assays (ELISAs), immunoprecipitation, and immunohistochemistry, using methods common in the art.

Numerous methods for the production and purification of antibodies are well known in the art, and can be found in various sources (See e.g., Sambrook et al. (eds.), Molecular Cloning, Cold Spring Harbor Laboratory Press [1989]; Harlow and Lane (eds.), Antibodies: A Laboratory Manual, Cold Spring Harbor Laboratory Press [1988]; Ausubel et al. (eds.), Current Protocols in Molecular Biology, Ch. 11, John Wiley & Sons, Inc., New York [1994]).

Polyclonal Antisera Production: Briefly, a fungal histidine kinase protein, any portion thereof, either native or synthetically produced, is used to raise polyclonal antisera in an animal (e.g., rabbit, rat, mouse, etc.). Using standard techniques, the mammalian host, typically a rabbit, is immunized with the histidine kinase antigen. The histidine kinase antigen may or may not be conjugated to additional protein sequences. The antigen may be mixed with an adjuvant (e.g., Freund's incomplete or complete adjuvant) prior to immunization. The dosage of the antigen administered per animal is typically between 0.1 and 10 mg when no adjuvant is used, and between 1.0 and 100 µg when an adjuvant is used, and is typically injected via intravenous, subcutaneous or intraperitoneal routes. The animals typically receive antigenic boosts at regular intervals; it is not intended that the interval of immunization be particularly limited. In preferred embodiments, immunization is carried out one to 10 times, preferably 2 to 5 times, at intervals of several days to several weeks, preferably at intervals of 2 to 5 weeks. Bleeds are obtained at regular intervals for analysis of antigen-specific immunoreactivity, using techniques common in the art (e.g., Western immunoblots).

Monoclonal Antibody Production: For preparation of monoclonal antibodies directed toward a fungal histidine kinase protein, or any portion thereof, any technique that provides for the production of antibody molecules by continuous cell lines in culture may be used. These methods include but are not limited to the hybridoma technique originally developed by Kohler and Milstein (Kohler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in Monoclonal Antibodies and Cancer Therapy, Alan R. Liss, Inc., pp. 77–96 [1985]).

For example, to produce a monoclonal antibody specific for a fungal histidine kinase protein of the present invention, the following protocol may be used. It is not intended that the present invention be limited to the use of this or any other protocol, as numerous protocols for generating antibody-producing cells are known, and find use in the present invention.

Inoculation and Recovery of Antibody-producing Cells

A mammalian animal host is immunized according to the protocol described above to produce polyclonal antisera. Subsequently, at 1 to 10 days, preferably 3 days, after the final immunization, antibody-producing cells will be collected. As antibody-producing cells, spleen cells, lymph node cells, peripheral blood cells, etc. may be enumerated. Among them, spleen cells and local lymph node cells are preferable.

Cell Fusion and Formation of Hybridoma Cell Lines

In order to obtain hybridomas which produce the monoclonal antibody, cell fusion between the antibody-producing cells described above and myeloma cells will be performed. As the myeloma cells to be fused to the antibody-producing cells, a commonly available cell strain of an animal such as mouse may be used. Preferably, a cell strain to be used for this purpose is one which has drug selectivity, cannot survive in HAT selective medium (i.e., containing hypoxanthine, aminopterin and thymidine) when infused, and can survive there only when fused to antibody-producing cells. Mouse myeloma cell strains including but not limited to, P3X63Ag.8.U1(P3U1), Sp2/0, NS-1 may be used as myeloma cells.

Subsequently, the myeloma cells and the antibody-producing cells described above will be subjected to cell fusion. For example, $1 \times 10^9$ cells/ml of the antibody-producing cells and $1 \times 10^8$ cells/ml of the myeloma cells will be mixed together in equal volumes in an animal cell culture medium such as serum-free DMEM or RPMI-1640, and reacted in the presence of a cell fusion promoting agent. In some embodiments, polyethylene glycol with an average molecular weight of 1,500 Da may be used as the cell fusion promoting agent. Alternatively, the antibody-producing cells and the myeloma cells may be fused in a commercial cell fusion apparatus utilizing electric stimulation (e.g., electroporation).

Selection and Cloning of Hybridoma Lines

Following the cell fusion, hybridomas will be selected from the cell culture. As a method for this selection, the resultant cell suspension will be appropriately diluted with fetal bovine serum containing RPMI-1640 medium or the like, and then plated on microtiter plates at a density of about $2 \times 10^5$ cells/well. A selective medium will be added to each well, and cultured in that selective medium. As a result, about 14 days after the start of cultivation in the selective medium, the growing cells will be obtained as hybridomas.

Subsequently, screening will be performed as to determine the presence of the antibody of interest in the culture supernatant of the grown hybridomas. The screening of hybridomas may be performed by any of conventional methods. For example, a part of the culture supernatant of a well in which a hybridoma is grown will be collected and subjected to enzyme immunoassay or radioimmunoassay.

Cloning of the fused cell is performed by the limiting dilution method or the like. Finally, the hybridoma of interest which is a monoclonal antibody-producing cell will be established.

Production of the Monoclonal Antibody

In some embodiments of the present invention, conventional cell culture methods or the abdominal dropsy formation method may be employed for recovering the monoclonal antibody from the hybridoma of interest (i.e., a monoclonal antibody-producing cell).

In the cell culture method, the hybridoma will be cultured in an animal cell culture medium such as 10% fetal bovine serum-containing RPMI-1640 medium, MEM medium or a serum-free medium under conventional culture conditions (e.g., at 37° C. under 5% $CO_2$) for 2 to 10 days. Then, the monoclonal antibody will be recovered from the culture supernatant.

In the abdominal dropsy formation method, about $1 \times 10^7$ cells of the hybridoma will be administered into the abdominal cavity of an animal syngeneic to the mammal from which the myeloma cells were derived, to thereby propagate the hybridoma greatly. One to two weeks thereafter, the abdominal dropsy or serum will be collected.

Antibody Purification: Following the production of polyclonal or monoclonal antibodies, the antibodies are purified using any suitable method known in the art, including but not limited to Protein A/Protein G affinity, ammonium sulfate salting out, ion exchange chromatography, gel filtration, affinity chromatography, or using these methods in combination. For descriptions of these methods, see, e.g., Sambrook et al. (eds.), Molecular Cloning, Cold Spring Harbor Laboratory Press (1989); Harlow and Lane (eds.), *Antibodies: A Laboratory Manual*, Cold Spring Harbor Laboratory Press (1988); Ausubel et al. (eds.), *Current Protocols in Molecular Biology*, Ch. 11, John Wiley & Sons, Inc., New York (1994).

The antibodies produced by the present invention find use in numerous applications in addition to therapeutic applications, including Western immunoblotting, enzyme linked immunosorbence assays (ELISAs), immunoprecipitation, immunoaffinity purification, immunohistochemistry, and clinical diagnostic applications using methods known in the art (See e.g., Harlow and Lane (eds.), *Antibodies: A Laboratory Manual*, Cold Spring Harbor Laboratory Press [1988]; Ausubel et al. (eds.), *Current Protocols in Molecular Biology*, Vol. 1–4, John Wiley & Sons, Inc., New York [1994]; and Laurino et al., *Ann. Clin. Lab Sci.*, 29(3):158–166 [1999] for general descriptions of these methods).

In view of numerous alternative protocols known in the art for the production of polyclonal and monoclonal antibodies, it is not intended that the present invention be limited to any particular method. For example, any fungal histidine kinase protein or fragment thereof, may potentially be used as the immunogen, and the immunogen may be either synthetic or from a biological source, recombinant or native. It is also not intended that the present invention be limited to any particular fungal histidine kinase immunogen, immunization methods, immunization schedule, animal species, test protocol for determining antibody production or antibody purification method.

Uses of Antisense Oligonucleotides to Histidine Kinase Genes as Antifungal Therapy As discussed above, the present invention provides *C. albicans* strains which contain a deletion of the COS-1 gene locus. These *C. albicans* strains demonstrate reduced virulence in an in vivo mouse candidosis/candidemia model. Thus, it is contemplated that inactivation of the histidine kinase gene by any mechanism in a pathogenic fungal species will reduce the pathogenicity of that species.

Antisense nucleic acid technology allows the selective downregulation of gene expression in vivo. The specific hybridization of an antisense oligomeric nucleic acid with its target nucleic acid results in the downregulation of production of functional gene product, through a still poorly understood mechanism. Nonetheless, an understanding of the mechanism is not necessary to use the present invention. Antisense targeting may disrupt such functions as DNA replication, transcription, mRNA translation, translocation of the RNA to the site of protein translation, translation of protein from RNA, splicing of RNA to yield one or more mRNA species, and catalytic activity that may be engaged in or facilitated by the RNA. The use of antisense technology in the development of antimicrobial therapies is known in the art (Harth et al., Proc. Natl. Acad. Sci. USA 97(1):418–423 [2000]; Piddock, Curr. Opin. Microbiol., 1(5):502–508 [1998]). It has previously been shown that the presence of antisense transcripts of a target fungal gene was effective in downregulating activity of that gene product, and growth of the fungal strain (Tentler et al., Curr. Microbiol., 34(5):303–308 [1997]).

The present invention provides antisense synthetic oligonucleotides between 12 and 200 nucleotides in length having antisense complementarity to the nucleotide sequences of SEQ ID NOS: 16, 34 or 36 for use in the development of antifungal agents. Thus, antisense oligonucleotides directed against a gene or transcript encoding a fungal histidine kinase are useful as antifungals. It is not intended that the antisense oligonucleotides of the present invention be limited to complementarity with the nucleotide sequences of SEQ ID NOS: 16, 34 or 36. Indeed, it is contemplated that antisense oligonucleotides having complementarity to other histidine kinase genes in addition to the histidine kinase genes provided by the present invention also find use with the invention. Other histidine kinase genes may be from the same species as those provided in the present invention (e.g., FOS-2 and FOS-3) and histidine kinase genes from other pathogenic fungal species.

It is contemplated that such antisense oligonucleotides will contact and be translocated within fungal cells in a subject having either systemic or localized fungal infection, or these antisense oligonucleotides will find use as prophylactic agents. This treatment results in the fungal cells containing these histidine kinase antisense oligonucleotides to be growth inhibited or display reduced virulence. It is contemplated that this method will also find use in controlling bacterial infections, as bacteria also contain histidine kinase genes not found in humans.

In preferred embodiments of the invention, specific nucleotide sequences within a gene or transcript are targeted for antisense disruption. A generally preferred target site is the region encompassing the translation initiation or termination codon of the open reading frame (ORF) of the gene. Eukaryotic and prokaryotic genes may have two or more alternative start codons, any one of which may be preferentially utilized for translation initiation under a particular set of conditions. In the present invention, any start codon and region surrounding the start codon may be used as a target for antisense disruption. Similarly, a translation termination codon (or "stop codon") and surrounding region of a gene may also be effectively targeted for antisense disruption. The terms "start codon region" and "stop codon region" refer to a portion of an mRNA or gene that encompasses from about 25 to about 50 contiguous nucleotides in either direction (i.e., 5' or 3') from a translation initiation or stop codon.

The ORF of a gene or gene transcript is also a region that may be effectively targeted. Other target regions include the 5' untranslated region (5' UTR; i.e., the portion of an mRNA in the 5' direction from the translation initiation codon, and thus including nucleotides between the 5' cap site and the translation initiation codon of an mRNA or corresponding nucleotides on the gene), and the 3' untranslated region (3' UTR; i.e., the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. It is contemplated that the cap region and mRNA splice sites (i.e., intron-exon junctions) will also find use as preferred target regions.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

It is understood that the sequence of an anti sense molecule need not be 100% complementary to that of its target nucleic acid to be specifically hybridizable. However, a sufficient degree of complementarity is desired in order to avoid non-specific binding of the antisense molecule to non-target nucleotide sequences under the conditions in which specific binding is required (i.e., under physiological conditions in the case of in vivo therapeutic treatment).

The specificity of gene inactivation associated with antisense oligonucleotides makes them ideal candidates for drug development as therapeutic agents, as is known in the art. For example, antisense oligonucleotides have been employed as therapeutic moieties in the treatment of disease states. Antisense oligonucleotides have been safely and effectively administered to humans and numerous clinical trials are presently underway. It is thus established that oligonucleotides are useful therapeutic modalities that can be configured for use in treatment regimes, including regimes to treat fungal infections.

While antisense oligonucleotides are a preferred form of antisense compound, the present invention provides other oligomeric antisense compounds, including but not limited to oligonucleotide mimetics, described in more detail below. The antisense molecules in accordance with this invention preferably comprise from about 8 to about 30 nucleobases (i.e., from about 8 to about 30 linked bases), although it is contemplated that both longer and shorter sequences will find use in the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined herein, oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides.

Preferred modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Examples of the preparation of the above phosphorus-containing linkages are described in U.S. Pat. Nos.: 5,587,361 and 5,625,050, both of which are herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Examples of such oligonucleosides are included in U.S. Pat. Nos.: 5,633,360 and 5,677,439, both of which are herein incorporated by reference.

In other preferred oligonucleotide mimetics, both the sugar and the internucleoside linkage (i.e., the backbone) of the nucleotide units are replaced by novel groups. The base units are maintained in order to facilitate hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Examples of PNA compounds are described in various references, including U.S. Pat. Nos.: 5,539,082; 5,714,331; and 5,719,262, both of which are herein incorporated by reference, and Nielsen et al., Science 254:1497 (1991).

The most preferred embodiments of the invention include oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—]. Examples of the use of phosphorothioate backbones, oligonucleosides with heteroatom backbones, and morpholino backbone structures are included in various references, including U.S. Pat. Nos.: 5,489,677, 5,602,240 and 5,034,506, each of which is herein incorporated by reference.

The modified oligonucleotides of some embodiments of the present invention also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, 0-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta 78:486 [1995]) (i.e., an alkoxyalkoxy 5 group). A further preferred modification includes 2'-dimethylaminooxyethoxy (i.e., a O(CH$_2$)$_2$ON(CH$_3$)$_2$ group), also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other preferred modifications include 2'-methoxy(2'-O—CH$_3$), 2'-aminopropoxy(2'-OCH$_2$CH$_2$CH$_2$NH$_2$) and 2'-fluoro (2'-F). In other embodiments, similar modifications are made at other positions on the oligonucleotide, particularly the 3' position of the sugar on the 3' terminal nucleotide or in 2'-5' linked oligonucleotides and the 5' position of 5' terminal nucleotide. In other embodiments, the oligonucleotides have sugar mimetics such as cyclobutyl moieties in place of the pentofuranosyl sugar. Descriptions of such modified sugar structures include, but are not limited to, U.S. Pat. Nos.: 5,670,633 and 5,700,920, both of which are herein incorporated by reference.

In still other embodiments of the invention, the oligonucleotides also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, herein incorporated by reference.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. and are presently preferred base substitutions, even more particularly when combined with 2'-O-methoxyethyl sugar modifications. Various references describe modified nucleobases including, but not limited to, U.S. Pat. Nos.: 5,681,941 and 5,750,692, both of which are herein incorporated by reference.

Another modification of the oligonucleotides of the present invention involves chemically linking one or more moieties or conjugates to the oligonucleotide. This linkage enhances the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety. Examples of such oligonucleotide conjugates include, but are not limited to, those described in U.S. Pat. Nos.: 5,599,928 and 5,688,941, both of which are herein incorporated by reference.

It is not necessary for all positions in a given molecule to be uniformly modified, and in fact, in some embodiments of the invention, more than one of the aforementioned modifications is incorporated in a single compound or even at a single nucleoside within an oligonucleotide. The present invention also includes antisense compounds which are chimeric compounds. As used herein, "chimeric" antisense compounds or "chimeras," are antisense compounds, particularly oligonucleotides, which contain two or more chemically distinct regions, each made up of at least one monomer unit (i.e., a nucleotide in the case of an oligonucleotide compound). These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. As an example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art are used.

In some embodiments of the invention, chimeric antisense compounds of the present invention are produced as composite structures of two or more oligonucleotides, modified oligonucleotides, oligonucleosides and/or oligonucleotide mimetics as described above. The preparation of such hybrid structures are described in various references, including U.S. Pat. Nos.: 5,652,356 and 5,700,922, both of which are herein incorporated by reference in their entirety.

Methods for Treating a Subject

The present invention provides methods for treating a subject for eradicating, alleviating or preventing a fungal infection in or on the subject. In various embodiments, the methods use compositions provided by the present invention, including an antibody against a fungal histidine kinase protein, a candidate antifungal drug, a synthetic, antisense oligonucleotide specific for a fungal histidine kinase transcript, and a histidine kinase mimetic peptide. In addition, these antiflugal agent compositions find use alone or in combination.

It is contemplated that these compositions be delivered to a subject using a wide variety of means, including systemic, localized or topical delivery. Antibodies, antisense oligonucleotides, and mimetic peptides, in general, have been shown to have therapeutic value in the treatment of human subjects (e.g., Cotter, Semin. Hematol., 36:9–14

[1999]; Keshet and Ben-Sasson, J. Clin. Invest., 104:1497–1501 [1999]; Fan and Mendelsohn, Curr. Opin. Oncol., 10:67–73 [1998]).

The antifungal agents of the present invention can be utilized as therapeutic agents, or in a prophylactic manner. A subject, preferably a human, suspected of having a fungal infection, or at risk of contracting a fungal infection, is treated by administering an antifungal agent. The antifungal agents of the present invention are utilized in pharmaceutical compositions by adding an effective amount of the antifungal agent to a suitable pharmaceutically acceptable diluent or carrier.

In some embodiments of the invention, the antifungal compositions are admixed, encapsulated, conjugated or otherwise associated with other molecules, molecule structures or mixtures of compounds (e.g., liposomes, receptor targeted molecules, oral, rectal, topical or other formulations) for assisting in uptake, distribution and/or absorption (See, e.g., U.S. Pat. Nos.: 5,416,016; 5,521,291; 5,543,158; and 5,595,756, all of which are herein incorporated by reference).

The antisense molecules of the treatment method of the present invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the present invention also includes prodrugs and pharmaceutically acceptable salts of the compounds of the invention, as well as pharmaceutically acceptable salts of such prodrugs, and other bioequivalents.

As used herein, the term "prodrug" refers to a therapeutic agent prepared in an inactive form that is converted to an active form (i.e., drug) within the body or cells due to the action of endogenous enzymes or other chemicals and/or conditions. In particular, prodrug versions of the oligonucleotides of the present invention, for example, are prepared as SATE [(S-acetyl-2-thioethyl)phosphate] derivatives according to the methods disclosed in WO 93/24510 in WO94/26764, herein incorporated by reference.

As used herein, the term "pharmaceutically acceptable salts" refers to physiologically and pharmaceutically acceptable salts of the compounds of the invention (i.e., salts that retain the desired biological activity of the parent compound and do not impart undesired toxicological effects thereto). Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine. The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise, the salts are equivalent to their respective free acid for purposes of the present invention.

As used herein, a "pharmaceutical addition salt" includes a pharmaceutically acceptable salt of an acid form of one of the components of the compositions of the invention. These include organic or inorganic acid salts of the amines. Preferred acid salts include the hydrochlorides, acetates, salicylates, nitrates and phosphates. Other suitable pharmaceutically acceptable salts are well known to those skilled in the art and include basic salts of a variety of inorganic and organic acids. For example, hydrochloric acid, hydrobromic acid, sulfuric acid or phosphoric acid; carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations include, but are not limited to, alkaline, alkaline earth, ammonium and quaternary ammonium cations. Carbonates or hydrogen carbonates are also contemplated.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids (e.g., hydrochloric acid, hydrobromic acid, sulfuric acid, phosphoric acid, nitric acid and the like); (c) salts formed with organic acids (e.g., acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like); and (d) salts formed from elemental anions (e.g., chlorine, bromine, and iodine).

The present invention also provides pharmaceutical compositions and formulations that include the antifungal agents of the present invention. It is contemplated that the compositions of the invention will be administered using any suitable route depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; intracranial; intrathecal or intraventricular. Oligonucleotides with at least one 2'-O-methoxyethyl modification are believed to be particularly useful for oral administration.

Pharmaceutical compositions and formulations for topical administration may include, but are not limited to, transdermal patches, ointments, lotions, creams, gels, drops, suppositories, sprays, liquids and powders. In some embodiments, conventional pharmaceutical carriers, aqueous, powder or oily bases, thickeners, etc., are necessary or desirable.

Compositions and formulations for oral administration include, but are not limited to, powders or granules, suspensions or solutions in water or non-aqueous media, capsules, sachets or tablets. In some embodiments, other constituents, such as thickeners, flavoring agents, diluents, emulsifiers, dispersing aids or binders are also included.

In some embodiments, compositions and formulations for parenteral, intrathecal or intraventricular administration include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. It is contemplated that these compositions will be generated from a variety of components that include, but are not limited to, preformed liquids, self-emulsifying solids and self-emulsifying semi-solids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

It is contemplated that compositions of the present invention will be formulated into any of many possible dosage forms such as, but not limited to, tablets, capsules, liquid syrups, soft gels, suppositories, and enemas. In some embodiments, the compositions of the present invention are formulated as suspensions in aqueous, non-aqueous or mixed media. In still further embodiments, aqueous suspensions further contain substances that increase the viscosity of the suspension including, for example, sodium carboxymethylcellulose, sorbitol and/or dextran. In yet other embodiments, the suspension also contains stabilizers.

In one embodiment of the present invention the pharmaceutical compositions are formulated and used as foams. Pharmaceutical foams include formulations such as, but not limited to, emulsions, microemulsions, creams, jellies and liposomes. While basically similar in nature these formulations vary in the components and the consistency of the final product.

In some embodiments, agents that enhance uptake of the antifungal agent by the fungal cell are also be added to the pharmaceutical and other compositions of the present invention. For example, cationic lipids, such as lipofectin (U.S. Pat. No. 5,705,188, herein incorporated by reference), cationic glycerol derivatives, and polycationic molecules, such as polylysine (WO 97/30731), also enhance the cellular uptake of oligonucleotides.

In still other embodiments, the compositions of the present invention additionally contain other adjunct components conventionally found in pharmaceutical compositions. Thus, for example, some compositions contain additional, compatible, pharmaceutically-active materials such as, for example, antipruritics, astringents, local anesthetics or anti-inflammatory agents, or additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) which do not deleteriously interact with the antifungal agent of the formulation.

Certain embodiments of the invention provide pharmaceutical compositions containing (a) an antibody or antisense oligonucleotide antifungal agent, and (b) one or more other antifungal chemotherapeutic agents covalently or non-covalently attached to the antibody or oligonucleotide. Such embodiments have the value of delivering an additional antifungal activity specifically to the fungal cells in addition to the antibody or oligonucleotide of the method. Alternatively, it is contemplated that an antifungal agent used in the present invention is targeted specifically to fungal cells by delivering the antifungal agent within liposomes which display on their external surface antibodies specific for fungal cell-wall components.

In another related embodiment, more than one antisense oligonucleotide of different specificities is used to treat a subject for the purpose of eliminating a fungal infection. For example, one antisense oligonucleotide targeted to a first nucleic acid site (e.g., the start codon region of a fungal histidine kinase transcript) is delivered to a subject, followed by one or more additional antisense oligonucleotides targeted to a second nucleic acid site (e.g., the stop codon region of a fungal histidine kinase transcript). In some embodiments, two or more combined antisense oligonucleotides are used together (i.e., concurrently) or sequentially.

Dosing is dependent on severity and responsiveness of the disease state to be treated, with the course of treatment lasting from several days to several months, or until a cure is effected or a diminution of the fungal infection is achieved. In some embodiments of the invention, optimal dosing schedules are calculated from measurements of drug accumulation in the body of the patient. The administering physician determines optimum dosages, dosing methodologies and repetition rates for each patient, as needed. Optimum dosages may vary depending on the relative potency of individual antifungal agents, and can generally be estimated based on $EC_{50}$s found to be effective in in vitro and in vivo animal models. In general, dosage is from 0.01 µg to 100 g per kg of body weight, and is given at least once, at least once on a daily, weekly, monthly or yearly basis, or by any other schedule. The treating physician estimates repetition rates for dosing based on measured residence times and concentrations of the drug in bodily fluids or tissues. In some embodiments, following successful treatment, the subject undergoes maintenance therapy to prevent the recurrence of the fungal infection, wherein the antifungal agent is administered in maintenance doses. These maintenance doses are determined by the physician. In some cases, the maintenance dose is the same as the therapeutically effective dose, while in other cases, the maintenance dose is different from the therapeutically effective dose.

From the previous discussion it is apparent that the present invention solves a need in the art for compositions and methods for the development of antifungal therapeutics as well as methods for identifying compounds which have antifungal drug activity against various pathogenic and opportunistic fungi and bacteria.

DEFINITIONS

To facilitate understanding of the invention, a number of terms are defined below.

The term "sample" as used herein is used in its broadest sense. The term "sample" as used herein refers to any type of material obtained from humans or other animals (e.g., any bodily fluid or tissue), cell or tissue cultures, cell lines, or a culture of microorganisms. "Sample" also encompasses food and feed (whether solid or liquid), media (whether solid or liquid) for the growth and maintenance of microorganisms and cell cultures, equipment and its components (e.g., dialysis, intravenous, and nasogastric tubing), disposable, as well as reusable patient care items (including catheters), environmental surfaces, soil, water and other fluids, and reagents (e.g., buffers). A biological sample suspected of containing nucleic acid encoding a histidine kinase may comprise a cell or cells, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "eukaryote" refers to organisms distinguishable from "prokaryotes." It is intended that the term encompass all organisms with cells that exhibit the usual characteristics of eukaryotes such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "antimicrobial" is used in reference to any compound which inhibits the growth of, or kills microorganisms, including eukaryotes such as fungi (i.e., it includes antifungals). It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

As used herein, the term "antimetabolite" refers to any substance with a close structural resemblance to another, essential substance (i.e., metabolite) that is required for normal physiologic function. Typically, antimetabolites exert their effects by interfering with the utilization of the essential metabolite.

As used herein, the term "polyploid" refers to cells or organisms which contain more than two sets of chromosomes per nucleus.

The terms "nucleic acid sequence," "nucleotide sequence," "oligonucleotide" or "nucleic acid molecule" as used herein refer to an oligonucleotide or polynucleotide, and fragments or portions thereof, and to DNA or RNA of genomic or synthetic origin which may be single- or double-stranded, and represent the sense or antisense strand. Similarly, "amino acid sequence" as used herein refers to a peptide or protein sequence. "Peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al., Anticancer Drug Des., 8:53–63 [1993]).

The term "nucleotide" as used herein refers to any nucleotide that comprises any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The terms "peptide," "polypeptide" and "protein" all refer to a primary sequence of amino acids that are joined by covalent "peptide linkages." In general, a peptide consists of a few amino acids, typically from 2–25 amino acids, and is shorter than a protein. Polypeptides may encompass either peptides or proteins. As used herein, a recited "amino acid sequence" may refer to an amino acid sequence of a naturally occurring protein molecule, a protein produced by recombinant molecular genetic techniques, or a synthetic or naturally occurring peptide, and may refer to a portion of a larger "peptide," "polypeptide" or "protein," and is not meant to limit the amino acid sequence to the complete, native amino acid sequence associated with the recited protein molecule.

A "deletion" is defined as a change in either nucleotide or amino acid sequence in which one or more nucleotides or amino acid residues, respectively, are absent. The deletion of an entire gene locus is frequently designated by the symbol "Δ" followed by the gene name. For example, an *A. fumigatus* fungal strain having a knockout of its two FOS-1 gene loci is referred to as "ΔFOS-1." As used herein, the term "isogenic strain" refers to a strain (e.g., a yeast strain) that carries one allele at a given gene locus (i.e., every individual in the population is homozygous at that given locus). For example, an *A. fumigatus* fungal strain, where every cell of that population contains a knockout of its two FOS-1 gene loci is isogenic for that deletion.

As used herein, the term "purified" or "to purify" refers to the removal of contaminants from a sample. As used herein, the term "substantially purified" refers to molecules, either nucleic or amino acid sequences, that are removed from their natural environment, "isolated" or "separated," and are at least 60% free, preferably 75% free, and most preferably 90% free from other components with which they are naturally associated. An "isolated polynucleotide" is therefore a substantially purified polynucleotide.

As used herein, the term "probe" refers to an oligonucleotide (i.e., a sequence of nucleotides), whether occurring naturally as in a purified restriction digest or produced synthetically, which is capable of hybridizing to another oligonucleotide or polynucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

"Amplification" is defined as the production of additional copies of a nucleic acid sequence and is generally carried out using polymerase chain reaction (PCR) or other technologies well known in the art (e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the method of K. B. Mullis (U.S. Pat. Nos. 4,683,195, 4,683,202 and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the term "polymerase" refers to any polymerase suitable for use in the amplification of nucleic acids of interest. It is intended that the term encompass such DNA polymerases as Taq DNA polymerase obtained from *Thermus aquaticus*, although other polymerases, both thermostable and thermolabile are also encompassed by this definition.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for insertion into recombinant vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR. (See, K. B. Mullis, et al., Cold Spring Harbor Symposia, Vol. LI, pp. 263–273 [1986]). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. As used herein, the term "amplification reagents" refers to those reagents (deoxyribonucleoside triphosphates, buffer, etc.), needed for amplification except for primers, nucleic acid template and the amplification enzyme.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

As used herein, the terms "complementary" or "complementarity" are used in reference to antiparallel polynucleotides (i.e., a sequence of nucleotides) related by the base-pairing rules. For example, the sequence 5'-AGTTC-3' is complementary to the sequence 3'-TCAAG-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid, and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding, the probe will not hybridize to the second non-complementary target.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" (Coombs, *Dictionary of Biotechnology*, Stockton Press, New York N.Y. [1994]. Conditions which constitute high or low stringency are common to one familiar with the art, and are described in numerous sources (e.g., Anderson and Young, Quantitative Filter Hybridisation, in *Nucleic Acid Hybridisation* [1985] and Ausubel et al. (eds.), *Current Protocols in Molecular Biology*, Vol. 1–4, John Wiley & Sons, Inc., New York [1994]).

"Stringency" typically occurs in a range from about $T_m$–5° C. (i.e., 5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridisation, in *Nucleic Acid Hybridisation* [1985]). Other references include more sophisticated computations which take structural as well as sequence characteristics into account for the calculation of $T_m$.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

As used herein, the term "antisense" is used in reference to any nucleic acid which is antiparallel to and complementary to another nucleic acid. Antisense DNA or RNA may be produced by any method. For example, a cDNA or a portion of a cDNA may be subcloned into an expression vector containing a promoter which permits transcription either in vitro or in vivo. The cDNA or a portion of the cDNA is subcloned in such a way that it is in the reverse orientation relative to the direction of transcription of the cDNA in its native chromosome. Transcription of this antisense cDNA produces an RNA transcript that is complementary and antiparallel to the native mRNA. Alternatively, an antisense nucleic acid may be a synthetically-produced oligonucleotide. The mechanism by which an antisense nucleic acid produces effects in a biological system is unclear, however, likely involves the formation of a duplex with its complementary nucleic acid within either the nucleus or cytoplasm of a cell. These duplexes are theorized to block transcription of the native mRNA or prevent its translation. Using antisense techniques, an "artificial knockout" mutant may be reproduced in an animal or animal cell line. The term "antisense strand" is used in reference to a nucleic acid strand that is complementary to the "sense" strand. The designation (−) (i.e., "negative") is sometimes used in reference to the antisense strand, with the designation (+) (i.e., "positive") sometimes used in reference to the sense strand.

As used herein the term "portion" when in reference to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO: 17," encompasses the full-length *Candida albicans* histidine kinase protein and fragments thereof. As used herein, a "truncated" protein is a portion of a protein that retains a biochemical activity. For example, in an in vitro kinase assay that measures histidyl or aspartyl kinase activity of a histidine kinase protein, either a full length or a truncated histidine kinase protein can be used. Where a truncated histidine kinase protein is used, the truncated protein retains at least one active kinase activity (i.e., a portion of the histidine kinase protein that is able to phosphorylate a histidine substrate or an aspartate substrate, or both).

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. Thus, it is contemplated that this definition will encompass variants of histidine kinase. Such variants can be tested in functional assays, such as growth inhibition assays.

The term "derivative" as used herein refers to the chemical modification of a nucleic acid encoding histidine kinase structures. Illustrative of such modifications would be replacement of hydrogen by an alkyl, acyl, or amino group. A nucleic acid derivative would encode a polypeptide which retains essential biological characteristics of naturally-occurring histidine kinase.

As used herein, the term "host cell" refers to any cell capable of harboring an exogenous nucleic acid or gene product. The host cell may also transcribe and/or translate and express a gene contained on the exogenous nucleic acid. The exogenous nucleic acid may come from any source, and may be synthetic or produced by another cell or organism. The exogenous nucleic acid may or may not be subject to replication. For example, the bacterium *Escherichia coli* strain DH5α may act as a host cell for a bacterial expression vector encoding a *C. albicans* histidine kinase.

As used herein, the term "antifungal" or "antifungal agent" or "antifungal chemotherapeutic" or "antifungal drug" refers to any compound, substance or agent used in the treatment of fungal disease, infection or colonization. It includes fungicidal as well as fungistatic compounds which act on fungi in vitro, as well as in vivo.

As used herein, the term "histidine kinase" refers to an enzyme that acts as a signal transduction histidine kinase, where specific histidine and aspartate amino acid residues are subject to phosphorylation and dephosphorylation regulatory mechanisms. In particular, the term refers to histidine kinases that are components in two-component signal transduction systems. It is contemplated that histidine kinase proteins are involved in various cell functions. A single histidine kinase protein may be involved in the regulation of only one cell process, or may have multiple regulatory functions, including but not limited to osmolarity responses, and cell-wall assembly. Histidine kinase proteins may have functions not yet identified.

As used herein, a "drug" can be any molecule of any composition, including protein, peptide, nucleic acid, organic molecule, inorganic molecule, or combinations of molecules, biological or non-biological, which are capable of producing a physiological response. As used herein, a "drug" provides at least one beneficial response in the cure, mitigation, treatment or prevention of a disease, condition or disorder (e.g., to treat a fungal infection). A compound is considered a "drug candidate" if it is not yet known if that compound will provide at least one beneficial response in the cure, mitigation, treatment or prevention of a disease, disorder or condition.

The following definitions are the commonly accepted definitions of the terms "identity," "similarity" and "homology." Percent identity is a measure of strict amino acid conservation. Percent similarity is a measure of amino acid conservation which incorporates both strictly conserved amino acids, as well as "conservative" amino acid substitutions, where one amino acid is substituted for a different amino acid having similar chemical properties (i.e. a "conservative" substitution). The term "homology" can pertain to either proteins or nucleic acids. Two proteins can be described as "homologous" or "non-homologous," but the degree of amino acid conservation is quantitated by percent identity and percent similarity. Nucleic acid conservation is measured by the strict conservation of the bases adenine, thymine, guanine and cytosine in the primary nucleotide sequence. When describing nucleic acid conservation, conservation of the nucleic acid primary sequence is sometimes expressed as percent homology. In the same nucleic acid, one region may show a high percentage of nucleotide sequence conservation, while a different region can show no or poor conservation. Nucleotide sequence conservation can not be inferred from an amino acid similarity score. Two proteins may show domains that in one region are homologous, while other regions of the same protein are clearly non-homologous.

As used herein, the term "in vitro" refers to an artificial environment and to processes or reactions that occur within an artificial environment. The term "in vivo" refers to the natural environment (e.g., in an animal or in a cell) and to processes or reactions that occur within a natural environment. The definition of an in vitro versus in vivo system is particular for the system under study. For example, as used herein, studies of histidine kinase phosphorylation using purified proteins and reagents is an in vitro system. Conversely, the study of *C. albicans* virulence within a mouse is an in vivo experimental system. The study of fungal growth inhibition in a laboratory broth culture has aspects of both an in vitro and in vivo environment.

As used herein, the term "subject" refers to any animal being examined, studied or treated. It is not intended that the present invention be limited to any particular type of subject. It is contemplated that multiple organisms will find use in the present invention as subjects. In some embodiments, humans are the preferred subject.

As used herein, a subject displaying pathology resulting from a fungal infection, disease, disorder or condition refers to a subject who displays signs or symptoms typically observed for a particular fungal disease. However, the term also encompasses subjects presenting with few, atypical or ambiguous signs or symptoms which may be indicative of a fungal infection (i.e., the subject is suspected of displaying pathology resulting from a fungal infection). A subject at risk of displaying pathology resulting from a fungal infection includes subjects that have compromised immune systems (e.g., subjects with disease that impairs the immune system, or subjects that have received immunosuppressive drugs). Signs or symptoms of a fungal infection include, but are not limited to, inflammation, fever, redness, soreness, skin discoloration, elevated immune system activity and immune system cell counts, a fungal cell mass and/or allergic response.

A fungal infection may be "localized," (i.e., the infection is confined to a relatively small area or a single tissue, such as the skin), or may be "systemic," (i.e., the infection has spread to multiple sites, tissues or organs in a subject, typically via the circulatory or lymphatic systems). Similarly, delivery of an antifungal agent can be topical (e.g., where delivery is by a cream or lotion on the surface of the skin), localized, or systemic (e.g., where delivery is by the circulatory system via an intravenous injection, or by gastrointestinal absorption if taken by mouth).

As used herein, the term "inhibit" refers to the act of diminishing, suppressing, alleviating, preventing, reducing or eliminating. For example, a compound which inhibits fungal growth may completely cure (eradicate all fungal cells from a subject), prevent fungal growth, kill all fungal cells present (fungicidal), stop or slow further fungal growth (fungistatic) or reduce the rate of fungal growth compared to the rate of growth of an untreated experimental control sample. The term "inhibit" encompasses both in vitro as well as in vivo fungal growth.

EXPERIMENTAL

As used herein, the gene names OS-1 and NIK-1 are synonymous, and refer to the same genetic locus and gene product. Similarly, the gene names CaNik1, CHIK1, CNIK1 and COS-1 are synonymous, and refer to the same genetic locus and gene product. Furthermore, variations in these written names using capital or lowercase letters, italicized or non-italicized fonts, with or without hyphens, also refer to the same gene and gene product. The designation of a wild-type or non-wild-type gene may also vary.

The following examples are provided in order to demonstrate and further illustrate certain preferred embodiments and aspects of the present invention and are not to be construed as limiting the scope thereof.

As used herein, the following scientific abbreviations/notations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); MW (molecular weight); ° C. (degrees Centigrade); OD (optical density); EDTA (ethylenediamine-tetracetic acid); EGTA (ethyleneglycol-bis-($\beta$-aminoethyl ether)); SDS (sodium dodecyl sulfate); PAGE (polyacrylamide gel electrophoresis); UV (ultraviolet); bp (base pair); kb, kbp or Kb (kilobase pairs); YPD (yeast extract, Bacto-peptone and dextrose medium); PTC (40% polyethylene glycol 3300 [Sigma], 50 mM Tris-HCl pH 8.0, and 50 mM $CaCl_2$); 0.05 M Pipes, pH 6.5 (0.05 mM sodium phosphate, 0.001 M EDTA, 0.1 M NaCl, 5% NaCl; IETGN buffer (20 mM imidazole-HCl pH 6.8, 1 mM EDTA, 1 mM EGTA, 12 mM monothioglycerol, 20% glycerol, 100 mM sodium chloride); KTED (0.3 M KCl, 0.01 M Tris-HCl, pH 7.4, 0.001 M EDTA, 0.001 M dithiothreitol); $\mu$g/ml (microgram per milliliter); mm (millimeter); xg (times gravity); HPLC (high pressure liquid chromatography)l; DDT (dithiothreitol); PMSF (phenylmethylsulfonyl fluoride); KGlu (potassium glutamate); SSC (salt and sodium citrate buffer); SDS (sodium dodecyl sulfate); PAGE (polyacrylamide gel electrophoresis), s and sec (seconds), m and min (minutes), h and hr (hours), w/v (weight to volume measure), v/v (volume to volume measure).

Restriction enzymes, other common molecular biology enzymes and reagents used in these experiments are widely available from numerous sources, including NEB, Promega, Fisher and Stratagene. Fungal and bacterial media, such as Sabouraud's dextrose broth or LB, and agar-containing formulations of these media, are available from suppliers such as Difco.

As used herein, the following abbreviations apply: Ambion (Ambion, Inc., Austin, Tex.); Amersham or Amersham-Pharmacia (Amersham-Pharmacia Biotech, Inc., Piscataway, N.J.); Applied Biosystems and Perkin Elmer (Perkin Elmer/Applied Biosystems, Foster City, Calif.); BASF (BASF Wyandotte Corp., Fairfield, N.J.); Beckman Instruments, Inc. (Beckman Instruments, Inc., Fullerton, Calif.); Bellco (Bellco Glass, Inc., Vineland, N.J.); Bio-Rad (Bio-Rad Laboratories, Hercules, Calif.); BRL or Gibco-BRL or Life Technologies (GIBCO BRL Life Technologies, Gaithersburg, Md.); Calbiochem (Calbiochem-Novabiochem, San Diego, Calif.); Charles River Laboratories (Charles River Laboratories, Inc., Wilmington, Mass.); Clonetech (Clonetech, Palo Alto Calif.); Cornell (Cornell University, Ithaca, N.Y.); DIFCO or Difco (Difco Laboratories, Detroit, Mich.); Dupont (Dupont, Wilmington, Del.); Dynamic Microsystems (Dynamic Microsystems, Silver Spring, Md.); Eastman Kodak (Eastman Kodak, Rochester, N.Y.); Eppendorf (Eppendorf/Brinkmann Instruments, Westbury, N.Y.); FGSC (Fungal Genetics Stock Center, University of Kansas Medical Center, Kansas City, Kans.); Fisher (Fisher Scientific, Pittsburgh, Pa.); Gene Codes (Gene Codes, Ann Arbor, Mich.); GENSET (Geneset, San Diego, Calif.); ICN (ICN Biochemicals, Inc., Costa Mesa, Calif.); Idaho Technology (Idaho Technology, Salt Lake City, Utah); Intelligenetics (Intelligenetics, Campbell, Calif.); Klett (Klett Manufacturing Co., New York, N.Y.); Kodak (Eastman Kodak, Rochester, N.Y.); Millipore (Millipore Corporation, Bedford, Mass.); Molecular Dynamics (Molecular Dynamics, Sunnyvale, Calif.); NEB (New England Biolabs, Beverly, Mass.); Packard Instrument Co. (Packard Instrument Co., Meriden, Conn.); Perkin Elmer (Perkin Elmer/Cetus, Foster City, Calif.); Promega (Promega Corp., Madison, Wis.); Qiagen (Qiagen, Inc., Chatsworth, Calif.); Stratagene (Stratagene, La Jolla, Calif.); USB (United States Biochemical, Cleveland, Ohio); Waters (Waters Corp., Milford, Mass.); and Wisconsin Genetics Computer Group or GCG (Wisconsin Genetics Computer Group, University of Liverpool, U.K.).

EXAMPLE 1

Experimental Reagents

In this Example, experimental reagents used in the development of the present invention are described, including microorganism strains, media and nucleic acids.

A. Fungal and Bacterial Strains

Various *N. crassa* strains were obtained from FGSC, including wild-type (74-OR8-1a), OS-1 (B135), OS-1 (P3282), OS-1 (UCLA-80), OS-4 (NM2010), OS-5 (NM2160), and CUT (LLMI). In addition, an OS-1 (NM233t) NIC-1 strain was constructed by crossing a temperature-sensitive osmotic mutant OS-1 (NM233t) with NIC-1 (S1413a) (See, Selitrennikoff et al., Exp. Mycol., 5:155–161 [1981]). In order to isolate an OS-1-containing fragment smaller than 9.3 kb, several DNA fragments were subcloned and assayed for complementation of OS-1 (NM233t) NIC-1.

The stock strains were grown at 25° C., on solidified Vogel's medium N (See e.g., Davis and deSerres, Meth. Enzymol., 27A:79–143 [1970]), containing sucrose (1.5% w/v) ("VMS" medium). Strains that required nicotinamide were grown on media supplemented with nicotinamide (10 $\mu$g/ml)("VMSN" medium). Benomyl (Dupont) was added to cooled (i.e., 45° C.) VMSN medium, to a final concentration of 1 $\mu$g/ml. Osmotic mutants of *N. crassa* grown on slants of agar-solidified VMS had altered morphologies, appearing as dense, cropped mycelia, as compared with wild-type. The altered morphology was particularly apparent with the CUT mutant. In addition, bright orange spots appearing as pockets of "liquid exudate" (i.e., as described by Grindle and Dolderson, Trans. Brit. Mycol. Soc., 87:457–487 [1986]) were observed with osmotic mutants.

In liquid VMSN, hyphae from each of the os mutants was similar to wild-type. However, when grown in VMSN medium supplemented with 4% (w/v) NaCl, the osmotic mutants had irregularly shaped hyphae compared to wild-type, and some hyphae resembled pseudoconidia. These observations indicated that the osmotic genes are important in the maintenance of normal cell morphology of *N. crassa* grown in media with high osmolarity levels.

E. coli strains XL-1 Blue and TB-1 (Stratagene) used in these experiments were maintained on LB medium (See e.g., Sambrook et al.,(eds.) *Molecular Cloning: A Laboratory Manual*, Cold Spring Harbor Laboratory Press, Cold Spring Harbor, N.Y., [1989]).

B. Plasmids

Plasmid (pMO63), containing an allele of TUB-2 that confers benomyl resistance as a 3.1 kb HindIII DNA fragment in pUC118 was used. pCE1 was constructed by self-ligation of a 13 kb HindIII DNA fragment of cosmid 12:4 D (Vollmer-Yanofsky genomic library; See, Vollmer and Yanofsky, Proc. Natl. Acad. Sci. USA 83:4869–4873 [1989]). The 12:4D cosmid contained approximately 35 kb of DNA that functionally complemented an OS-1 mutant, as shown in FIG. 1. This cosmid was digested with a variety of restriction enzymes and the digests were used to transform competent OS-1 (NM233t) NIC-1 cells.

Figure 4:
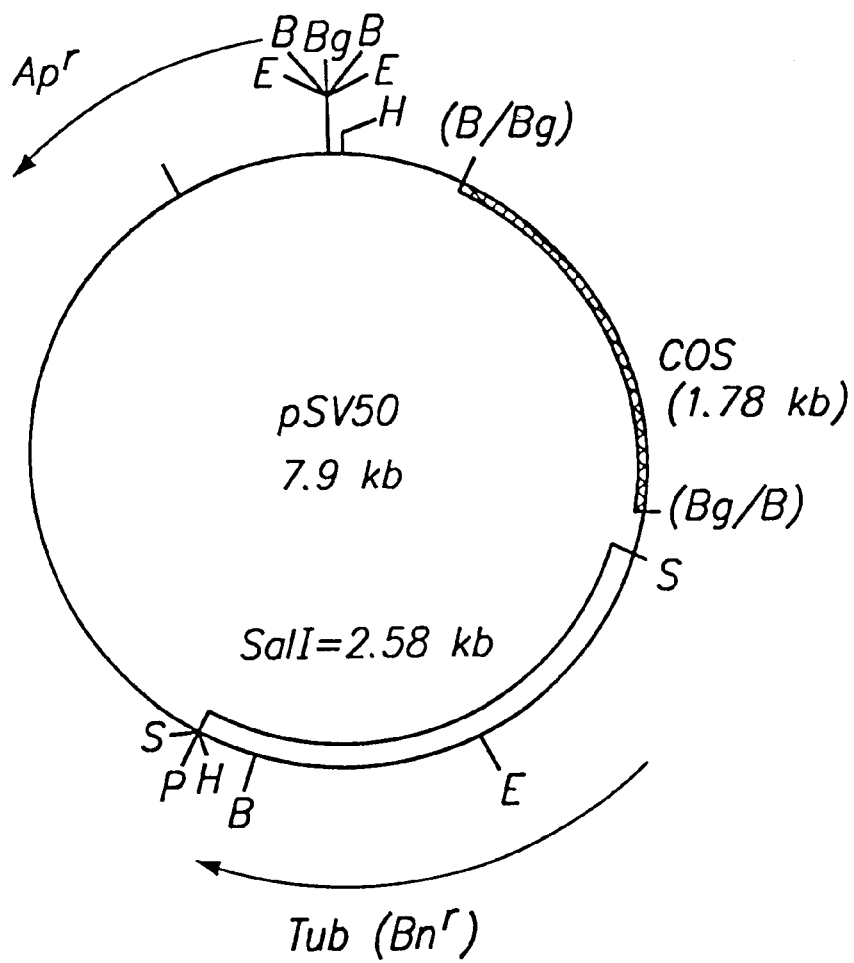
FIG. 4 is a map of the plasmid pSV50.

A cosmid vector, pSV50, that confers benomyl resistance was used to construct the *N. crassa* genomic DNA library (See, FIG. 4; Orbach et al., Mol. Cell. Biol., 6:2452–2461 [1986]; and Vollmer and Yanofsky, supra). pCE1 contained an ampicillin resistance gene, the origin of replication from pSV50 (originally derived from pBR322), and 9.3 kb of genomic *N. crassa* DNA sequence. A NotI/HindIII deletion of pCE1 ("pCE5") containing a 6.5 kb EcoRI/NotI (the EcoRI site is in the polylinker of pCE1 adjacent to a Sau3AI site) DNA fragment of pCE1 inserted into a pBluescript SK⁻ (Stratagene), was created, as well as the plasmid "pCE6." The pCE6 plasmid contained a 2.8 kb NotI/HindIII DNA fragment subcloned from pCE1. Two additional plasmids were also created. The plasmid "pMMS100" contained a 7.0 kb EcoRI/SmaI DNA fragment subcloned from pCE1 into pBluescript SK⁻, while the plasmid "pMMS108" is a partial XhoI deletion of pMMS100 that contained a 4.6 kb XhoI/SmaI DNA insert in pBluescript SK⁻.

EXAMPLE 2

Isolation of *Neurospora crassa* OS-1 Genomic Sequence by Functional Complementation In this Example, competent *N. crassa* spheroplasts were created from the strains and DNA described in Example 1. First, the OS-1 gene was isolated from the Vollmer-Yanofsky *N. crassa* genomic library by a chromosome walk (Vollmer and Yanofsky, supra). Cosmid "12:4D" containing approximately 35 kb of DNA functionally complementing an OS-1 mutant was identified. Cosmid 12:4D DNA was digested with various restriction enzymes, and these digests were used to transform competent OS-1(NM233t) NIC-1 cells.

DNA-mediated transformations were accomplished using the method of Selitrennikoff and Sachs (Selitrennikoff and Sachs, Fungal Genet. Newsl., 38:92 [1991]). In this experiment, competent OS-1 (NM233t), NIC-1, and OS-1 (B135) cells were transformed with the cosmid 12:4D, or co-transformed with subclones of 12:4D and pSV50 or pM063 at a molar ratio of approximately 5:1, respectively. As direct selection of transformants was not possible on 4% (w/v) NaCl medium (VMSN containing 1.5% sucrose) transformant colonies were initially selected for benomyl resistance.

Briefly, the DNA was premixed with 25 µl of a 5 mg/ml heparin solution (125 µg total heparin), to which 100 µl of a spheroplast preparation (approximately $5\times10^7$ cells) were added, and the mixtures were incubated on ice for 30 minutes. Lipofectin (Gibco) was added to a final concentration of 3.5 µg/ml, and incubation continued for 15 minutes at room temperature. Then, 1 ml of PTC was added, gently mixed, and the suspensions were incubated 20 minutes at room temperature. The suspensions were added to VMSN media containing benomyl, incubated for 2–3 days, and then transferred to solid VMSN slants containing 4% (w/v) NaCl, and grown for 2–3 days. Control VMSN slants that did not contain NaCl were also inoculated and incubated. Complementation of the OS-1 mutant salt-sensitive phenotype was then scored. Transformants of the temperature-sensitive OS-1 mutants were grown at 37° C., while transformants of the non-temperature sensitive OS-1 mutant were grown at 26° C.

Introduction of a HindIII digest of 12:4D DNA into OS-1 (NM233t) NIC cells resulted in the production of several transformants that grew in a manner similar to wild-type on NaCl-supplemented media at 37° C., suggesting that HindIII did not cut within the functional OS-1 gene. Subsequently, a HindIII fragment of 12:4D was subcloned as "pCE1" (described in Example 1). pCE1 contained a 9.3 kb genomic DNA fragment that complemented the OS-1 mutant (See, FIG. 1). FIG. 1 illustrates the subcloning of OS-1 by functional complementation. In this Figure, subclones are indicated as an expanded region of the cosmid 12:4D. FIG. 1 also shows that pCE1 was able to complement OS-1. In addition, a NotI/HindIII DNA deletion of pCE1 (pCE5) was not able to complement OS-1. Furthermore, the pCE6 clone (i.e., a cloned NotI/HindIII DNA fragment) did not complement the OS-1 mutant, suggesting that the NotI site is within a functional part of the OS-1 gene. However, a SmaI/HindIII deletion of pCE1 (i.e., "pMMS100") complemented OS-1 (NM233t) nic-1, whereas a partial XhoI deletion of pMMS100 ("pMMS108") did not complement, suggesting that the OS-1 gene is contained within the 7.0 kb Sau3A/SmaI genornic DNA fragment of pMMS100. In addition, transfomrmation of a non-temperature sensitive mutant OS-1 (B135) with pMMS100 resulted in complementation of the salt-sensitive phenotype.

The results of these experiments indicated that a functional OS-1 gene was encoded on the genomic fragment contained in pMMS100. In order to provide additional data to support this conclusion, the growth (i.e., the linear growth rate) of pMMS100 transformants, OS-1 mutants, and wild-type were quantitated on agar-solidified medium with and without 4% (w/v) NaCl in race tubes (See, Davis and deSerres, Meth. Enzymol., 27A:79–143 [1970]), containing agar-solidified VMSN medium supplemented with 4% (w/v) NaCl as needed. The race tubes were constructed from 25 ml disposable pipets (e.g., Fisher) according to the method of White and Woodward (White and Woodward, Fungal Genet. Newsl., 42:79 [1995]). Growth distances were measured relative to the origin of inoculation after 16, 24, 40, 48, and 64.5 hours of incubation at 37° C. Plots of the linear growth distance showed that the growth rates of wild-type, OS-1 mutants, and pMMS100-transformed OS-1 mutants were essentially identical on media without NaCl. However, on media supplemented with 4% (w/v) NaCl, pMMS100-transformed OS-1 mutants showed a restored osmotolerant phenotype, as evidenced by 18- to 26-fold differences between the growth rates of the recipient strains, OS-1 (NM233t) NIC-1 and OS-1 (B135), and the pMMS100-transformed strains (MMS100t-16 and MMS100b-2). These results indicated that a functional OS-1 gene was located on the 7 kb genomic fragment of pMMS100.

EXAMPLE 3

Figure 2:
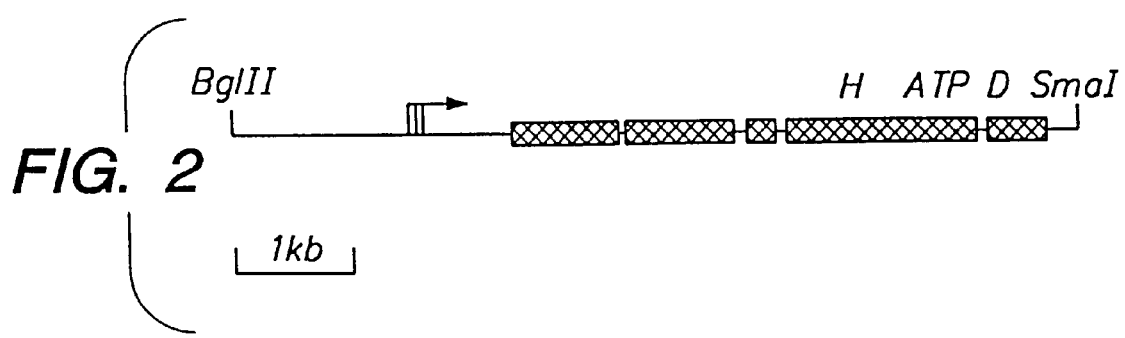
FIG. 2 is a schematic of the *N. crassa* OS-1 gene open reading frame.

Molecular Analysis of the *N. crassa* OS-1 Genomic Sequence In this Example, the DNA sequence of the *N.* crassa OS-1 gene was determined and analyzed. Both strands spanning approximately 6.5 kb of the 7.0 kb DNA fragment of pMMS100 were sequenced from restriction sites BglII to SmaI, as shown in FIG. 2. DNA sequencing and primer syntheses were done by DNA Services (Cornell). Sequence analyses were performed using MacVector™ (Kodak), the basic local alignment search tools, BLAST (S. F. Altschul et al., J. Mol. Biol., 215:403–410 [1990]; PROSITE (A. Bairoch, Nucl. Acids Res., 21:3097–3103 [1993]); and P/C Gene (Intelligenetics). The OS-1 genomic DNA and deduced Os-1p amino acid sequences derived by the protocol provided in this Example were deposited with GenBank (Accession number: U53189; SEQ ID NOS:1 and 2, respectively).

Nucleotide sequence analysis indicated a predicted open reading frame (ORF) of approximately 4.1 kb, interrupted by four introns as shown in FIG. 2. The OS-1 start of translation was identified by sequence similarity to an N. crassa-specific start of translation consensus sequence (i.e., Kozak sequence). Similarly, introns were identified by searching for N. crassa-specific intron consensus sequences (See e.g., J. J. P. Bruchez et al., Fungal Genet. Newsl., 40:89–96 [1993]). The introns ranged in size from 53–66 base pairs. Three sets of sequences that were similar to the N. crassa-specific start of transcription consensus sequence were identified 714–881 base pairs upstream of the predicted start of translation, as indicated by the arrow in FIG. 2. Also in FIG. 2, predicted exons are indicated as hatched rectangles, while introns are indicated as gaps between the rectangles. The H-box, D-box, and ATP-binding motif are also indicated.

Translation of the ORF predicted a 1298 amino acid protein (Os-1p), with a molecular weight of approximately 142 kDa, and a calculated pI of 5.3. A BLAST comparison of Os-1p with protein sequences in several databases indicated similarity with sensor histidine kinases of bacteria and yeast (described in Example 4, below).

FIG. 3 shows an amino acid sequence alignment of Os1p with BarA (bacterial adaptive response) of E. coli (See, Nagasawa et al., Mol. Microbiol., 6:799–807 [1992]), RepA (required from production of extracellular enzymes) of Pseudomonas viridflava (C.-H. Liao et al., Mol. Plant-Microbe Interact., 7:391–400 [1994]), ApdA (antibiotic production) of Pseudomonas fluorescens (N. Corbell and J. E. Loper, J. Bacteriol., 177:6230–6236 [1995]), and Sln1p of Saccharomyces cerevisiae (I. M. Ota and A. Varshavsky, Science 262:566–569 [1993]). In this Figure, the sequence alignments are shown based on data obtained with BLAST, MacVector, and PC/Gene analysis tools. Shaded areas indicate sequence identities; while diamonds (♦) at Os-1p $His^{718}$ and $Asp^{1136}$ indicate the presence of putative phosphoryl group acceptors; underlined sequences indicate hydrophobic regions in Os-1p, BarA, -ApdA, and Sln1p, filled circles (●) and open triangles (◊) indicate Os-1p h- and c-regions, respectively, of a potential signal sequence. The arrow indicates a potential signal peptidase cleavage site.

As shown, sequence similarity was noted between Os-1p and BarA. The overall sequence identity of Os-1p with BarA, RepA, and ApdA was found to be approximately 11%, whereas Sln1p shares approximately 7% identity. The following Table provides a comparison of the D-box receiver domains of Skn1p, Os-1p, Sln1p, and BarA.

TABLE 2

COMPARISON OF D-BOX RECEIVER DOMAINS

| D-Box Receiver Domain | Sequence | SEQ ID NO: |
|---|---|---|
| Skn7p | RYDLVLMDIVMPNLD | SEQ ID NO:21 |
| Os-1p | KFDVILMDVQMPIMG | SEQ ID NO:22 |
| Sln1p | NYNMFIMDVQMPKVD | SEQ ID NO:23 |
| BarA | PFDLILMDIQMPDMD | SEQ ID NO:24 |

Table 3 below shows the regions of homology between the amino acid sequences of Os-1p, BarA, RepA, ApdA, and Sln1p.

TABLE 3

REGIONS OF PROTEIN SEQUENCE HOMOLOGY

| Protein | H-Box | D-Box | ATP-Binding Domain |
|---|---|---|---|
| Os-1p | 698–843 | 1093–1203 | 870–931 |
| BarA | 282–427 | 674–782 | 451–512 |
| RepA | 253–398 | 652–763 | 422–483 |
| ApdA | 274–419 | 673–784 | 443–504 |
| Sln1p | 556–703 | 1081–1207 | 859–920 |

For the Os-1p regions 698–843, 870–931, and 1093–1203, shared amino acid sequence identity with BarA, RepA, and ApdA was found to be 40%, 45%, and 34% respectively. The Sln1p sequence identity with Os-1p in these regions were 27%, 40%, and 22%, respectively. These three domains are characteristic of histidine kinases and aspartate response regulator modules of signal-transduction proteins that couple environmental signals to adaptive responses (See e.g., B. Morgan et al., Trends Cell. Biol., 5:453–457 [1995]; M. Perego and J. Hoch, Trends Genet., 12:97–101 [1996]; and J. B. Stock et al., Nature 344:395–400 [1990]).

Os-1p contains amino acid residues that are conserved among histidine kinases, including the presumed phosphoryl group acceptors $His^{718}$ and $Asp^{1136}$ (See, FIG. 3). As indicated in Table 3, the Os-1p region 698 to 843 comprises the H-box domain and the 1093 to 1203 region comprises the D-box domain. Os-1p also has a conserved ATP-binding motif that is identical to the motif defined for bacterial and yeast response regulator modules (See, Ota and Varshavsky, supra; Parkinson et al., Ann. Rev. Genet., 26:71–112 [1992]; and Perkins et al., Microbiol. Rev., 46:426–570 [1982]).

Sln1p, BarA, RepA, and ApdA each have two hydrophobic regions located near the amino terminus that are potential membrane-spanning domains (See, N. Corbell and J. E. Loper, J. Bacteriol., 177:6230–6236 [1995]; C.-H. Liao et al., Mol. Plant-Microbe Interact. 7:391–400 [1994]; S. Nagasawa et al., Mol. Microbiol., 6:799–807 [1992]; and I. M. Ota and A. Varshavsky, Science 262:566–569 [1993]). Os-1p differs from these regions by having a hydrophobic region at the amino terminus (See, FIG. 3) characteristic of a signal sequence for selective intracellular distribution to the endoplasmic reticulum or the mitochondrial inner membrane (R. H. Davis and F. J. DeSerres, Meth. Enzymol., 27A:79–143 [1970]; and L. M. Gierasch, Biochem., 28:92 [1989]). In addition, Os-1p amino acid residues 4–19 contain the hallmarks of a signal sequence (See, L. M. Gierasch, supra), including a central hydrophobic region ("h-region") and a more polar c-terminal region ("c-region"). Furthermore, between Os-1p amino acid residues $A^{18}$ and $V^{19}$, there is a potential signal peptidase cleavage site (See, FIG. 3), that conforms to the -3,-1 rule (See, Davis and DeSerres, supra; G. von Heijne, Nucleic Acids Res., 14: 4683–4690 [1986]; and K. Larsson et al., Mol. Microbiol. 10:1101–1111 [1993]). These observations suggest that the Os-1p amino terminal domain (i.e., residues 4–19) is a signal sequence that may initiate intracellular distribution of Os-1p.

Additional protein sequence analysis indicated the potential presence of eight potential N-glycosylation sites, one potential tyrosine kinase phosphorylation site ($Tyr^{1028}$), one potential amidation site ($Gly^{1230}$), and one potential cell attachment sequence ($Arg^{196}$-$Gly^{197}$-$Asp^{198}$). Other sites identified include 18 potential protein kinase C phosphorylation sites, 20 potential casein kinase II phosphorylation sites, and 17 potential myristylation sites.

EXAMPLE 4

Isolation of *N. crassa* OS-1 Genomic Sequence by Homology Screening

In this Example, an alternative method for identification of the *N. crassa* histidine kinase gene was developed. This technique used degenerate PCR primers derived from histidine kinase family conserved sequences.

In these experiments, the *N. crassa* strain 74-OR23-1VA (mating type A) obtained from the FGSC (Catalog Number 2489) was used as the source for purification of genomic DNA and mRNA unless otherwise noted. Genomic DNA for PCR was prepared from isolated *N. crassa* nuclei. The *N. crassa* strain used for electroporation is known as "Stadler" (mating type a; characterized as pdx-1;his-2Δ;mtr) obtained from D. Stadler (University of Washington). Handling techniques and growth media for *N. crassa* as used herein are described by Davis and deSerres (R. H. Davis and F. J. deSerres, Meth. Enzymol., 17:79–143 [1970]).

In these experiments, all common molecular biological manipulations were carried out according to standard methods (See, e.g., F. M. Ausubel et al., Current Protocols in Molecular Biology, Wiley, New York [1994]). Reverse transcriptase coupled (RT)-PCR was performed as described by J. T. Aatsinki et al., (J. T. Aatsinki et al., BioTechn., 16:282–288 [1994]), except that the primer concentrations were increased to 1.5 μM. Sequencing of DNA templates was done with Sequence (USB), or by Taq cycle sequencing using dye primer or dye terminator chemistry on an automated sequencer (Applied Biosystems model 373) according to the manufacturer's instructions.

Alignment of histidine kinase members was accomplished using the PILEUP program from the Wisconsin Genetics Computer Group (GCG) package. The following primers were made:

H box forward PCR primer (H1A):
  CA(T/C)GAI(A/T/C)TI(C/A)GIACICICC (SEQ ID NO:6)

The reverse primers were synthesized to code for the N box:
  N1A: GT(A/G)AA(T/C)TTIAIIGC(A/G)TT (SEQ ID NO:7)
  N2A: GC(A/G)TTIC(T/C)IACIA(G/A)(G/A)TT (SEQ ID NO:8)

In these sequences, "I" is deoxyinosine. All primers were purified by electrophoresis through an acrylamide gel (20%/7 M urea) followed by purification over a Sep-Pak $C_{18}$ column. PCR mixtures contained 2.5 μM each primer, 1.4 μg of genomic DNA, 2.5 mM each dATP, dGTP, dCTP, and dTTP in 10 mM Tris-HCl pH 8.3/50 mM KCl/0.001% gelatin/0.5 unit of AmpliTaq (Perkin-Elmer/Cetus) in a total volume of 100 μl. Primers, buffer, and DNA templates were mixed and heated (95° C. for 10 min) in a Perkin-Elmer/Cetus thermocycler and then cooled to 4° C. Nucleotides and polymerase were added and reactions mixtures were cycled 25–30 times at 94° C. (1 min), 40° C. (1 min), and 72° C. (1 min) followed by a 10-min extension at 70° C. Amplification products were purified by electrophoresis through a 1.5% agarose gel, cloned into a T-vector (Promega), and subsequently sequenced. Sequence analysis was performed using Sequencher (version 2.1, Gene Codes) and the GCG package. Homology searches and sequence comparisons were performed using the BLASTX and BESTFIT programs of the GCG package.

Genomic and cDNA Cloning of OS-1

Approximately 150,000 clones from a λJ1 genomic library (FGSC) were screened with a randomly primed OS-1 PCR product (Prime-a-gene, Promega) obtained by amplification of *N. crassa* genomic DNA with the H1A and N2A primers. Positive clones were isolated, digested with BamHI and grouped by common hybridization patterns. A 5.5-kb BamHI fragment was cloned into BamHI-digested pUC18 to yield pHK1. This clone contained the kinase domain as verified by sequence analysis. pHK1 served as a template for the genomic sequencing of OS-1, which was accomplished by a combination of primer walking, sequencing small subclones, and sequencing deletion subclones in M13 (R. M. Dale et al., Plasmid 13:31–41 [1985]). The genomic sequence of OS-1 and predicted amino acid sequence of Os-1p derived by this protocol are shown in SEQ ID NOS:4 and 5, respectively (See also, GenBank Accession number U50264).

Approximately $10^6$ clones from the Orbach and Sachs *N. crassa* cDNA library (Orbach et al., J. Biol. Chem., 265:10981–10987 [1990]; obtained through FGSC) were screened with the OS-1 kinase domain PCR product. Two sets of clones were obtained and designated "M1" and "M10," which started at nucleotides 3285 and 3760 of the genomic sequence, respectively. Both strands of these clones were entirely sequenced. RT-PCR was used to walk upstream of the 5' end of M1 and subsequently clone the entire cDNA coding for OS-1. All RT-PCR products were cloned into a T-vector (Promega) and sequenced. Primer extension with the oligonucleotide NK45 (GAGAGCTGGCTGATCTGTTG) (SEQ ID NO:9), revealed the transcription start site 969 bases upstream of the initiator AUG in the OS-1 mRNA. The cDNA and predicted amino acid sequences of OS-1 derived by this protocol are shown in SEQ ID NOS:3 and 2, respectively, and GenBank Accession number U50263.

Analysis of the alignment of several members of the histidine kinase family indicated that there is a subclass of kinases that contain both a kinase domain and a response regulator domain, termed "hybrid kinases" (See e.g. L. A. Alex and M. I. Simon, Trends Genet., 10:133–138; R. V. Swanson et al., Trends Biochem. Sci., 19:485–490 [1994]; and J. S. Parkinson and E. C. Kofoid, Ann. Rev. Genet., 26:71–112 [1992]). Two eukaryotic kinases, "ETR1" and "SLN1," are members of this subclass.

Degenerate primers with the following translations corresponding to the H and N box domain consensus amino acid sequences were prepared:
  H box: H(E/D)(M/I/L/F)RTP (SEQ ID NO:10)
  N box: NLV(S/G)NA(I/V)KFT (SEQ ID NO: 11)

These primers were used to amplify genomic DNA from *N. crassa*. Two PCR products (designated "NIK-1" and "NIK-2") were obtained. Upon sequencing, these products were found to encode domains homologous to two-component histidine kinases. Southern blot analysis of genomic DNA from *N. crassa* with each PCR product showed that each product corresponded to a unique gene. The gene corresponding to the OS-1 PCR product was cloned and its function in *N. crassa* determined.

The OS-1 PCR product was used as a probe to screen *N. crassa* genomic and cDNA libraries in order to clone the OS-1 gene (See, FIG. 1). The 5' untranslated region is rich in structure and includes an intron of 100 bp. Also, this region is rich in repetitive nucleotide elements, the first of which is the sequence $(AGTC)_6 \ldots (GATC)_6$ (SEQ ID NO:12), which has the possibility of forming a stem-loop structure. Next, the repeat "TACC" is present in tandem 10 times followed shortly by two more repeats. This repeat has also been noticed in the 5' untranslated region of the NIT-3 gene in *N. crassa*, although its significance remains unknown (See, P. M. Okamoto et al., Mol. Gen. Genet., 227:213–223 [1991]). The TACC repeat is followed by a purine-rich segment. The four introns found in OS-1 have consensus splice sites that agree with those found in other genes from *N. crassa* (J. J. P. Bruchez et al., Fungal Genet. Newsl., 40:89–96 [1993]).

Analysis of the predicted amino acid sequence showed that Os-1p is a member of the hybrid class of histidine kinases that contain both a kinase and response regulator domain. The starting AUG is contained within the sequence (GCCCACAATCATGAC) (SEQ ID NO:13) consistent with other genes in *N. crassa* (Bruchez et al., Fungal Genet. Newsl., 40:85–88 [1993]). Os-1p is most similar to the kinase and regulator regions (57%) of the BarA protein from *Escherichia coli* (S. Nagasawa et al., Mol. Microbiol., 6:799–807 [1992]). The function of BarA is not known, but it can apparently act as a multicopy suppressor in a strain that lacks the osmosensor EnvZ (See, S. Nagasawa et al, supra).

The Os-1p protein is novel in that the N-terminal end of the polypeptide contains a unique 90-amino acid motif, which is repeated 5 times, followed by a short sixth truncated repeat. The N-terminal repeat region has a high probability of forming a coiled-coil structure when analyzed with the algorithm of Lupas and Stock (A. Lupas et al., Science 252:1162–1164 [1992]). A computer search using the BLAST program revealed that the N-terminal end of Os-1p shares homology [P(N), $1.2 \times 10^{-6}$] with bacterial sensory transducers, most notably Htr1 which functions to couple sensory rhodopsin to a soluble histidine kinase, and thus regulate phototaxis in *Halobacterium salinarium* (V. J. Yao and J. L. Spudich, Proc. Natl. Acad. Sci., 89:11915–11919 [1992]). Analysis of the distribution of polar and hydrophobic residues in the amino acid sequence of Os-1p suggested that the protein is soluble.

EXAMPLE 5

Analysis of *N. crassa* OS-1 Gene Expression

In this Example, the expression of the OS-1 gene during the vegetative and sexual phases of the *N. crassa* life cycle was examined.

Total RNA was prepared from *N. crassa* at various stages of development as described by Reinert et al., (W. R. Reinert et al., Mol. Cell. Biol., 1:829–835 [1981]). For mycelial RNA, cultures were harvested after 8–16 hours of growth in Vogel's 1×liquid medium at 30° C., as described by Davis and deSerres (Davis and deSerres [1970], supra). For germlings, conidia (10 cells per ml) were grown (3 hours at 30° C.) in Vogel's 1×liquid medium. Protoperithecia were prepared by inoculation with a drop of conidial suspension onto a cellophane paper placed on the surface of a Westergaard's plate (See e.g., Davis and deSerres [1970], supra) and growth was allowed to proceed in the light at 25° C., until protoperithecia were visible (approximately 8 days). Cells were scraped from the cellophane and RNA was prepared as described above. All mRNA fractions were purified using Oligotex resin (Qiagen).

Expression of OS-1 was found to be stage specific as the transcript (5.5 kb by Northern analysis) could be detected by RT-PCR of mRNA only during the vegetative phase of *N. crassa* life cycle and not after differentiation into the sexual phase.

EXAMPLE 6

Construction and Characterization of a *N. crassa* OS-1 Deletion Mutant

In this Example, the role of OS-1 in development of *N. crassa* was investigated by making a *N. crassa* OS-1-deficient strain. This strain was then characterized.

Figure 5:
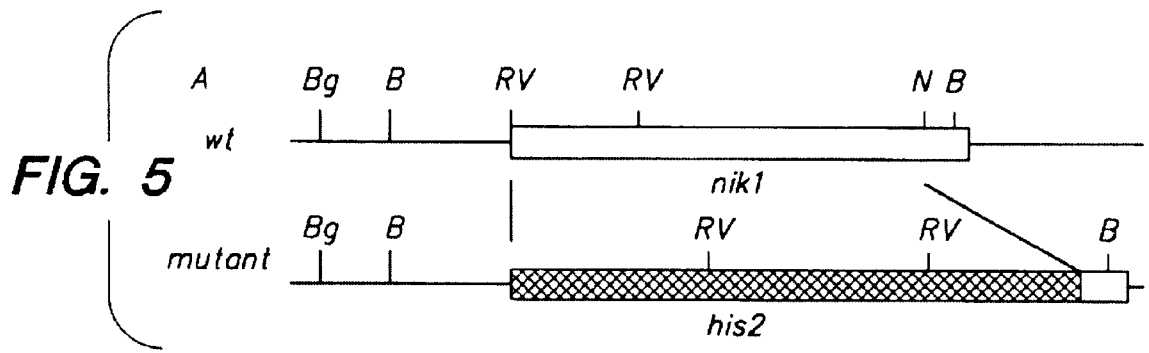
FIG. 5 is a schematic showing construction of the ΔOS-1 mutant by gene replacement using HIS2 gene sequences.

Construction of ΔOS-1 strain: To determine whether OS-1 is important for fungal development, a deletion mutant was created by replacing OS-1 with the HIS-2+ gene as illustrated in FIG. 5. FIG. 5 is a schematic representation of the genomic DNA structure of wild-type and ΔOS-1 strains. In this Figure, the restriction sites are indicated as follows: Bg, BglII; B, BamHI; RV, EcoRV; and N, NheI.

In this experiment, the plasmid pKB49 was used. pKB49 contains the HIS-2 gene on a 5-kb HindIII fragment subcloned from a cosmid provided by Dorsey Stuart (University of Hawaii). The HIS-2 marker was isolated as a 5-kb HindIII fragment from pKB49 and the ends were made blunt with Klenow fragment. The fragment of pHK1 from the EcoRV site upstream of the OS-1 translational start site to the NheI site was removed and the NheI ends were made blunt with Klenow fragment. The blunt-ended HIS-2 fragment was ligated into the modified pHK1 to yield "pHK1Δnik-1::his-2". The BamHI fragment of pHK1ΔOS-1::his-2 containing the his-2 insertion was used to electroporate conidia from the Stadler strain (pdx-1his-2Δmtr) of *N. crassa* obtained from David Stadler (University of Washington). Transformants were selected for histidine auxotrophy on minimal sorbose plates with regeneration agar (See e.g., Case et al., Proc. Natl. Acad. Sci. USA 76:5259–5263 [1979]) containing pyridoxine hydrochloride (pdx) (10 μg/ml). Approximately 50 transformants were picked from plates onto 1×Vogel's minimal medium slants containing pdx ("VMpdx").

Genomic DNA was isolated from each of these 50 strains (See, R. L. Metzenberg and J. N. Stevens, Neurospora Newsl., 35:28 [1982]), digested with BglII and EcoRV, and transferred onto nylon. Blots were probed with a PCR product to the upstream region of OS-1 (i.e., nucleotides 325–615). Clones containing the desired bands were then subjected to three or four rounds of plating to isolate homokaryons, which were identified by Southern blot analysis (not shown) as well as PCR of genomic DNA. This PCR analysis used the following OS-1-specific primers:

NK7: GTCCTCCAAGTACCCTG (SEQ ID NO:14)

NK16: GATCAGCTACGGACTTTC (SEQ ID NO:15).

The plasmid pKB49 was electroporated into Stadler and clones were subsequently purified in the same manner to yield clone "49-9-5," which served as the wild-type control. DNA from the mutant and wild-type strains were probed with the HIS-2 gene to ensure that multiple copies of the gene were not integrated in the genome.

Phenotypic analysis of ΔOS-1: It was apparent that there were morphological phenotypes associated with the deletion mutant during the vegetative phase. The hyphal structures of ΔOS-1 mutant and wild-type cultures were observed microscopically. In the mutant, many of the aerial hyphae became swollen and misshapen and appeared to lyse. Macroscopically, aerial hyphae of the mutant had the appearance of cotton candy, growing as a mass that filled the culture tube, with large areas of lysis visible. Conidia could be formed by the mutant, but they were adherent and not readily dispersed, in comparison to wild-type conidia. Finally, upon exposure to light, the mutant turned a deep orange or flame color when grown on small agar slants, whereas the wild type was normally peach colored. Therefore, loss of OS-1 function apparently impaired normal vegetative development in *N. crassa*.

The sexual phase of the growth cycle was examined by placing the mutant on Westergaard's medium in slants. Protoperithecia became visible and these could differentiate into perithecia upon fertilization with conidia from a wild-type strain, 74A. Spores could be obtained from this cross but at reduced numbers, which may be due to inactivation of the HIS-2 marker by the process of repeat induced point mutation in *N. crassa* (E. U. Selker, Ann. Rev. Genet., 24:579–613 [1990]). The ability of ΔOS-1 mutants to be fertilized is consistent with the expression pattern of the gene during development.

EXAMPLE 7

Analysis of Osmosensitivity and Hyphal Growth of a *N. crassa* ΔOS-1 Mutant Strain In this Example, the osmosensitivity and hyphal growth characteristics of OS-1 mutants were investigated. The characteristics of the ΔOS-1 mutant resembled those of osmosensitive *N. crassa* mutants whose morphologies are drastically affected by humidity (See e.g., D. D. Perkins et al., Microbiol. Rev., 46:426–570 [1982]). The morphology of the ΔOS-1 mutant appeared to be more similar to that of wild-type when cultures were grown in large flasks or slants as opposed to small slants. Thus, the tolerance of the ΔOS-1 mutant to different osmolytes was tested. Growth of the mutant and wild type cultures were the same on Vogel's minimal medium plates. However, growth on 1 M sorbitol/0.7 M NaCl, (or 1 M KCl) resulted in restricted colonial growth. In addition, the hyphae were excessively branched and bumpy, and aerial hyphae were nonexistent, resulting in a subsequent abrogation of conidia formation. Therefore, it was apparent that the OS-1 deletion manifested itself dramatically under conditions of high osmostress.

The growth response of the mutant in shaking liquid culture was also monitored. Normally, *N. crassa* can grow as a mycelium in submerged shaking liquid culture although it does not conidiate (M. L. Springer, supra). While wild-type cultures grow as a mycelium with the addition of 1 M sorbitol, NaCl, or KCl to the medium, the growth of the mutant was significantly impaired; it tended to form small clumps of irregular-shaped hyphae that were hyper-branched and swollen. These results indicated that the mutant is unable to form a well-defined mycelium under conditions of high osmotic stress.

EXAMPLE 8

Generation of a *Candida albicans* Histidine Kinase Gene PCR Product

In this Example, genomic sequence of a *C. albicans* histidine kinase gene was amplified by PCR and sequenced.

Genomic DNA isolation: In order to isolate the genomic DNA used in the PCR amplification, wild-type *C. albicans* (ATCC strain #36801) was grown as described below. Briefly, cells were grown overnight at 30° C. with shaking in YPD (1% yeast extract, 2% peptone, 2% glucose). The culture was harvested and resuspended in 5 ml lysis buffer (50 mM citrate/phosphate, pH 5.6, 40 mM EDTA and 1.2 M sorbitol). Zymolyase was added (15 mg) and the suspension incubated at 37° C. for 60 minutes. After centrifugation (3000 rpm for 5 minutes) the pellet was resuspended in 5×TE (15 ml). To the resuspended pellet, 1.5 ml of SDS (10%) was added and incubation continued for 5 minutes at 65° C. Then, the mixture was incubated on ice (30 min) following the addition of 5 ml potassium acetate (5 M). The mixture was then centrifuged (5000 rpm for 15 min) and the supernatant filtered through cheesecloth. The clarified supernatant was then precipitated with isopropanol, resuspended in 5×TE, and incubated with RNase. Then, the DNA was phenol extracted, EtOH precipitated, and resuspended in water, as described by Moreno et al. (Moreno et al., Meth. Enzymol., 194:795–823 [1991]).

Generation of a histidine kinase gene PCR product: PCR was then conducted using this isolated genomic DNA as a template. The same degenerate PCR primers used to isolated *N. crassa* histidine kinase genomic sequence were used in this Example to isolate *C. albicans* histidine kinase genomic sequence. These primers were:

H box forward PCR primer (H1A):
   CA(T/C)GAI(A/T/C)TI(C/A)GIACICICC (SEQ ID NO:6)

The reverse primers were synthesized to code for the N box:
   N1A: GT(A/G)AA(T/C)TTIAIIGC(A/G)TT (SEQ ID NO:7)
   N2A: GC(A/G)TTIC(T/C)IACIA(G/A)(G/A)TT (SEQ ID NO:8)

In these sequences, "I" is deoxyinosine. All primers were purified by electrophoresis through an acrylamide gel (20%/7 M urea) followed by purification over a Sep-Pak C18 column (Waters).

PCR mixtures contained 2.5 mM of each primer, 1.4 μg of genomic *C. albicans* DNA, 2.5 mM each dATP, dGTP, dCTP and dTTP, 10 mM Tris HCl pH 8.3, 50 mM KCl, 0.001% gelatin, and 0.5 unit of AmpliTaq (Perkin-Elmer/Cetus) in a total volume of 100 μl. Primers, buffer, and DNA templates were mixed and heated (95° C. for 10 min) in a thermocycler (Perkin-Elmer/Cetus), and then cooled to 4° C. Nucleotides and polymerase were added and reactions mixtures were cycled 25–30 times at 94° C. (1 min), 40° C. (1 min) and 72° C. (1 min), followed by a 10 minute incubation at 70° C. The samples were then electrophoresed in a 1.5% agarose gel, and nucleic acid produced in the PCR reaction was cloned into a T-vector (Promega). This plasmid was called pC1-3.

The PCR product insert of pC1-3 was sequenced, and this sequence is provided in SEQ ID NO:18. The predicted open reading frame amino acid sequence translated from this DNA is shown in SEQ ID NO:19. This PCR product was used as a probe to screen a *C. albicans* genomic library in order to isolate a full length histidine kinase gene sequence, as described in Example 10.

EXAMPLE 9

Isolation of *Candida albicans* Genomic DNA for Use in Genomic Library Construction In this Example, *C. albicans* was grown and used as the source for genomic DNA to prepare a pUC-based genomic library. This library was screened to identify the COS-1 locus (See Example 10) using a probe made from the PCR product described in Example 8.

Candida albicans strain 366 (ATCC 56884) was grown in PYG. An aliquot of actively growing culture was added to Manning and Mitchell's basic salts medium (0.5% w/v $(NH_4)_2SO_4$, 0.02% w/v $MgSO_4.7H_2O$, 1.4% $K_2HPO_4$, 0.6% W/V $KH_2PO_4$, 0.5% w/v NaCl, 1.25% w/v glucose, and $1\times10^{-4}$% w/v biotin), mixed, and incubated with shaking (180 rpm), at 37° C. for approximately 30 hours to mid-log phase, as described by Manning et al. (Manning and Mitchell, J. Bacteriol., 142:714–719 [1980]).

C. albicans DNA was prepared using the method of Scherer and Stevens (Scherer and Stevens, Proc. Natl. Acad. Sci. USA 85:1452–1456 [1988]). Briefly, exponentially growing cells were washed with 1 M sorbitol. Protoplasts were prepared by resuspending the cells 10-fold concentrated in 1 M sorbitol/50 mM potassium phosphate, pH 7.4, 14 mM 2-mercaptoethanol, and 100 μg zymolyase 100T (ICN) per ml, and incubated for 30 minutes at 30° C. The protoplasts were pelleted and resuspended in 50 mM $Na_3EDTA$, 0.2% SDS ($NaDodSO_4$), with 100 μg of proteinase-K per ml. This was incubated for 3 hours, at 50° C. The DNA was then extracted three times with phenol:chloroform (1:1), and precipitated with 2 volumes of ethanol. The DNA was resuspended in 10 mM Tris HCl, pH 7.5, 1 mM $Na_3EDTA$ (TE buffer) with 10 μg RNase A per ml. After overnight (i.e., approximately 18–24 hours), at 4° C., the DNA was precipitated with 2 volumes of 2-propanol, and resuspended in TE buffer.

EXAMPLE 10

Isolation of the C. albicans COS-1 Genomic Sequence

In this Example, a genomic library was constructed and screened in order to isolate a C. albicans histidine kinase gene, called COS-1. The library was screened with a probe made from the PCR product described in Example 8.

A genomic DNA pUC-based library of C. albicans was constructed by digesting total genomic C. albicans DNA (isolated as described in Example 9) with HindIII (NEB). The DNA was size-fractionated on a 0.8% (w/v) agarose gel, fragments between 8 and 10 kb were eluted and ligated with a HindIII-digested calf intestinal alkaline phosphatase-treated pUC21 (GenBank Accession No. M74307; See, Vierra and Messing, Gene 100:189–194 [1991]; SEQ ID NO:20) for 20 h at 12° C. The ligation mixture was used to transform competent DH5α E. coli cells (BRL).

In order to isolate genomic sequence corresponding to the complete COS-1 gene, 9,000 bacterial transformants were screened using the COS-1 PCR product as a probe using standard techniques. One positive clone designated "pMC1" was identified and its 9.0 kb HindIII insert was sequenced using methods known in the art. Briefly, the 9.0 kb HindIII fragment was sequenced by the DNA services at the University of Colorado Health Sciences Center and the California Institute of Technology by primer walking. Primers were synthesized by GENSET, and the California Institute of Technology. The DNA sequences were analyzed using MacVector™ (Eastman Kodak), the basic local alignment search tool (BLAST) and PC/Gene analysis tools.

The COS-1 DNA nucleotide and deduced amino acid sequences are shown in SEQ ID NOS:16 and 17, respectively, and were deposited in GenBank with Accession Number U69886. In SEQ ID NO:16, the predicted coding region begins at nucleotide 433 (i.e., the first nucleotide in the ATG start codon). The coding region of SEQ ID NO:16 ends at nucleotide 3776 (i.e., the first nucleotide in the stop codon).

Alignments of the Cos-1p amino acid sequence with Os-1p, as well as other histidine kinase family members BarA and SLN1 are shown in FIG. 6. This alignment was accomplished using the PILEUP program from the Wisconsin Genetics Computer Group (GCG).

EXAMPLE 11

Construction of ΔCOS-1 Strains

Figure 7:
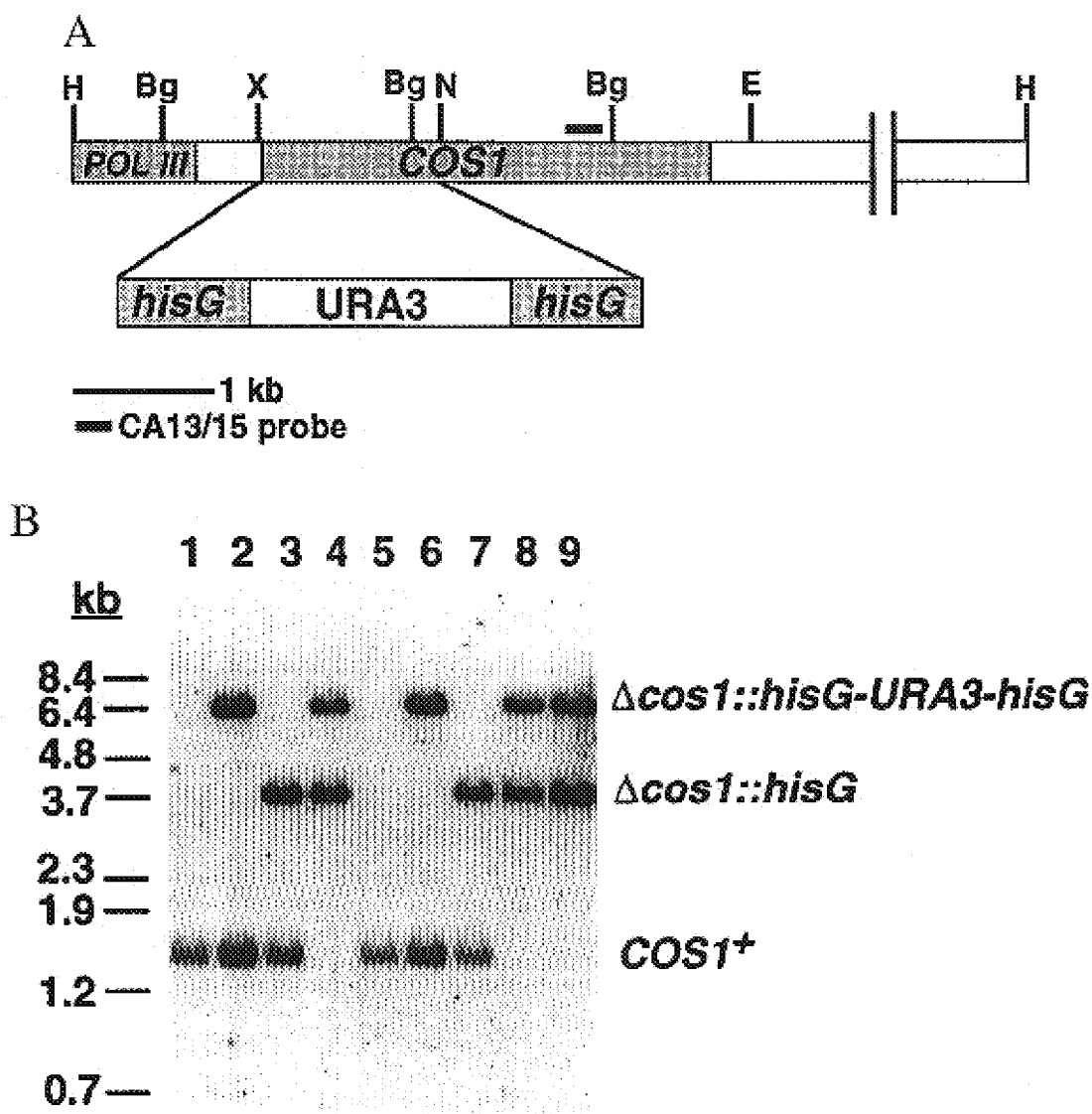
FIGS. 7A and 7B illustrate construction of the C. albicans knockout strain (ΔCOS-1).

In this Example, homozygous and hemizygous COS-1 deletion strains of C. albicans were made. The phenotypes of these stains are discussed in Example 12. A schematic drawing of the gene replacement strategy and a Southern blot demonstrating the disruption of the COS-1 gene locus are shown in FIGS. 7A and 7B, respectively.

Construction of ΔCOS-1 deletion mutant: Both alleles of COS-1 were deleted from a C. albicans isolate using the "URA Blaster" technique of Fonzi and Irwin (Fonzi and Irwin, Genetics 134:717–728 [1993]). The first step in this technique was to construct a targeting knock-out vector specific for the C. albicans COS-1 gene (depicted in FIG. 7A). To accomplish this, a 1.3-kb XhoI/NcoI COS-1 fragment was removed from a plasmid containing the COS-1 genomic sequence, and the NcoI overhang remaining on the cut plasmid blunt-ended by treatment with Klenow fragment. To this plasmid backbone, a 3.6-kb SalI/BglII fragment (where the BglII site had been blunt-ended by treatment with Klenow fragment) containing a hisG-URA3-hisG cassette (B. Cormack, Stanford University) was ligated. The resulting plasmid, called "pKOCOS-1," served as the knock-out targeting vector and permitted the selection of C. albicans cells which had stably integrated the vector. Restriction sites shown in FIG. 7A are H (HindIII), Bg (BglII), X (XhoI), N (NcoI) and E (EcoRI).

Spheroplasts of a C. albicans (ura⁻) strain were transformed with the pKOCOS-1 targeting vector which had been linearized with HindIII. Following transformation, ura⁺ transformants were selected on SD plates containing 1 M sorbitol. Genomic DNA was isolated from several transformants and digested with BglII. DNA fragments were resolved by electrophoresis through an 0.8% (wt/vol) agarose gel and transferred to a nylon membrane. Blots were probed with a PCR fragment corresponding to nucleotides 3528–3996 of the COS-1 genomic sequence. The PCR product was generated using the following primers:

CA13: TGGTACAGGTTTAGGGTTGTC (SEQ ID NO:43)

CA15: AACATGGCGTATTTGCATAGG (SEQ ID NO:44).

In FIG. 7A, the location of this PCR product relative to the COS-1 genomic locus is indicated by a solid bar above the gene structure. Recombinants containing one wild-type allele and one disrupted allele were identified by the presence of the desired bands on the Southern blot. One hisG repeat and the URA3 marker were removed by selection of transformed ura⁺ cells on media containing 5-fluoroorotic acid and where uridine was substituted for uracil. Selection for the loss of hisG-URA3 was followed by Southern blotting with both the CA13/CA15 PCR product and the URA3 gene as probes. This Southern blotting identified ΔCOS-1::hisG/COS-1 clones. These cells then were subjected to a second round of transformation and analysis as described above for replacement of the second COS-1 allele to give ΔCOS-1::hisG/ΔCOS-1::hisG-URA3-hisG, and finally the homozygous COS-1 knockout ΔCOS-1::hisG/ ΔCOS-1::hisG. FIG. 7B shows a Southern blot revealing the status of the COS-1 loci in C. albicans isolates. As above, each strain was grown, harvested and genomic DNA extracted. This DNA was digested with BglII, electrophoresed and blotted. These blots were then probed with a radiolabelled PCR product produced by the CA13/CA15 PCR primers. Nucleic acid size markers are indicated to the left. Lanes 1 and 4 do not show any COS-1 gene recombination (parental wild-type), lanes 2 and 6 show recombination in one allele, lanes 3 and 7 show recombination and excision of the URA3 coding sequence from only one COS-1 locus, lanes 4, 8 and 9 show disruption of both COS-1 alleles, but with the URA3 coding sequence remaining intact in one of the COS-1 chromosomal loci.

Further selection pressure yielded the homozygous deletion strain devoid of URA3 sequences. In subsequent discussion, the homozygous COS-1 knock-out ΔCOS-1::hisG/ΔCOS-1::hisG is written "ΔCOS-1/ΔCOS-1." It is important to note that the strategy used to disrupt both alleles of COS-1 resulted in the replacement of the 5' portion of the gene such that no truncated Cos-1p protein could be synthesized.

Complementation of ΔCOS-1 Deletion Mutant: The homozygous ΔCOS-1 deletion mutant (i.e., ΔCOS-1/ΔCOS-1) was complemented by homologous reintegration of the COS-1 gene. To make the targeting vector for the reintegration, a 9.0-kb HindIII fragment was removed from the COS-1 genomic sequence with HindIII and cloned into the HindIII site of pBluescript SK+ to give pBSCOS-1. A 1.3-kb fragment containing URA3 was generated by PCR amplification of pBC19 using the following primers:

U3BF: TGGATCCAGTACTAATAGGAATTGATTTGG (SEQ ID NO:45)
U3BR: TGGATCCTCTAGAAGGACCACCTTTGATTG (SEQ ID NO:46)

The resulting PCR product was cloned into a T-vector (Promega). This vector was digested with BamHI, the URA3 containing fragment isolated and blunt-ended by treatment with Klenow fragment, then ligated into the EheI site downstream from COS-1 in pBSCOS-1 to yield pBSCOS-1/URA3. The relevant insert from pBSCOS-1/ URA3 was isolated after HindIII digestion and used to transform the homozygous A. fumigatus COS-1 knockout strain ΔCOS-1/ΔCOS-1. Following transformation, cells were selected on SD containing 1 M sorbitol. Genomic DNA was isolated from ura+ selected clones, digested with BglII, and blotted to nylon. The PCR product generated using the CA13/CA15 primers (SEQ ID NOS:43 and 44, respectively) was used to probe for the reappearance of the desired COS-1-containing band, and those corresponding strains were isolated.

Alternatively, the ΔCOS-1/ΔCOS-1 strain was complemented with COS-1 by transforming with a 2 μ-based plasmid carrying COS-1. The plasmid, called pYPBCOS-1+, was made by digesting pYPB-ADHpt (described by Leberer et al., Proc. Natl. Acad. Sci. USA 93:13217–13222 [1996]) with NotI and SalI to remove the ADH promoter and ligating to this a COS-1 restriction fragment spanning nucleotides 1060–4865 of the genomic sequence. Following transformation with this plasmid, ura+ transformants were selected on SD plates containing 1 M sorbitol.

EXAMPLE 12

Phenotypic Analysis of C. albicans ΔCOS-1 Strain

In this Example, the phenotypes of wild-type, homozygous deletion (ΔCOS-1/ΔCOS-1), hemizygous (COS-1/ ΔCOS-1), and reconstituted ΔCOS-1 deletion strains of C. albicans (i.e., ΔCOS-1/ΔCOS-1 containing a 2 μ-plasmid carrying the COS-1 gene) were analyzed and compared. In these experiments, viability in low and high osmolarity conditions, hyphal formation, growth rates under a number of different conditions, and sensitivity to a number of antifungal compounds were investigated. The construction of these strains is described in Example 11.

For determination of viability and growth, each strain tested was grown from −80° C. stocks overnight at 37° C. in 50 ml of Sabouraud dextrose broth (30 g/L) (Difco, Catalog Number 0382-17-9) in 250 ml flasks with shaking at 180 rpm. Three hundred milliliter Nephelo flasks (Bellco) containing 60 ml medium were inoculated with 1×10$^6$ cells/ml (final concentration) from the starter culture and incubated at 37° C. with orbital shaking at 180 rpm. The optical density of each culture was determined periodically using a Klett-Summerson Photoelectric Colorimeter (Klett). For cell viability determination, overnight cultures were diluted and known numbers (as determined by hemacytometer counts) were plated onto agar-solidified SD medium and the numbers of resulting colonies determined. The sensitivity of each strain to a number of antifungal drugs in liquid medium was performed essentially as described in the National Committee for Clinical Laboratory Standards (NCCLS) 27T-protocol (Galgiani et al., NCCLS, 15:1–29 [1995]).

The following phenotypes were observed. Upon deletion of only one copy of the COS-1 gene (COS-1+/ΔCOS-1), the hemizygous mutants could not make hyphae as well as the wild-type strain when grown at 37° C. on solid agar plates, either under conditions of nutrient deprivation or in response to serum. This phenotype was more exaggerated in the ΔCOS-1/ΔCOS-1 mutants. Thus, like the N. crassa OS-1 gene as described in Example 7, C. albicans COS-1 is involved in hyphal development. The defect in hyphal formation was partially complemented by the introduction of a wild-type copy of COS-1 into ΔCOS-1/ΔCOS-1 strains either by homologous recombination into the genome or by expressing COS-1 from a 2 μ-plasmid. In addition, colony morphology of the ΔCOS-1/ΔCOS-1 strain was altered from that of the wild-type parental strain when grown on Spider media (1% (w/v) nutrient broth, 1% (w/v) mannitol, 0.2% (w/v) K$_2$HPO$_4$, 7.5% (w/v) sorbitol, 1.35% (w/v) agar).

The wild-type, COS-1+/ΔCOS-1 and ΔCOS-1/ΔCOS-1 strains were all viable under both low and high osmolarity conditions. All three strains grew at identical rates at 30° C. in yeast nitrogen broth with and without 6% (w/v) NaCl or 10% (v/v) fetal bovine serum (FBS), Saubouraud's medium (Difco) supplemented with either 6% (w/v) NaCl or 10% (v/v) FBS, and minimal medium (Manning and Mitchell, J. Bacteriol., 142:714–719 [1980]) with and without 6% (w/v) NaCl or 10% (v/v) FBS showing that none of the strains had detectable growth defects. In addition, the plating efficiencies of each strain were identical.

Lastly, the wild-type, ΔCOS-1/ΔCOS-1 strain and the hemizygous and reconstituted strains were equally sensitive to fluconazole, amphotericin B, cilofungin, nikkomycin Z, 5-fluorocytosine, ketoconazole, miconazole, vinclozolin, and benomyl in liquid RPMI medium (National Committee for Clinical Laboratory Standards [NCCLS] Protocol, "Reference Method for Broth Dilution Antifungal Susceptibility Testing of Yeasts," Vol. 15, No. 10, Publication M27-T [1995]).

One significant difference between the behavior of OS-1 and COS-1 mutant strains is that the C. albicans COS-1 strains, when grown as yeasts, did not exhibit the osmosensitivity that *N. crassa* OS-1 mutant strains demonstrated. Increased osmolyte concentration was found to also inhibit hyphal development in the wild-type *C. albicans*, such that differences between the wild-type and COS-1 mutant were difficult to assess.

Taken together, these results indicated that the COS-1 mutant strains were not significantly different from the parental strain with respect to a number of growth properties, with the exception of time of hyphal formation and colony morphology.

EXAMPLE 13

Virulence of Wild-type and ΔCOS-1 *C. albicans* Strains

In this Example, the role of the COS-1 gene in *C. albicans* virulence was determined. Virulence of wild-type, homozygous deletion, and hemizygous COS-1 strains of *C. albicans* was assayed and compared using an in vivo murine model of candidosis/candidemia.

Mouse Virulence Assay: A mouse fungal virulence model was used to assay the relative virulence of the *C. albicans* strains. The protocol used in these experiments is similar to that described by Hanson et al. (Hanson et al., Antimicrob. Agents Chemother., 35:1334–1337 [1991]). In brief, mice were infected intravenously with one of the three fungal strains listed above. An innoculum of $6 \times 10^4$ cells was used in each innoculation for each fungal strain. The survival time of each mouse following the innoculation was recorded.

At a fixed time point following inoculation, the pathogen organ burdens were also determined. For determination of organ burdens, mice were euthanized and the number of colony forming units (CFU) in the brain, spleen, liver, kidneys, and lungs determined by quantitative plating of organ homogenates.

Statistical analyses in this Example were performed using standard techniques (Sokal and Rohlf, *Biometry*, $2^{nd}$ Edition, W.H. Freeman, San Francisco [1981]). Differences in mouse survival rates following *C. albicans* infection were determined by comparing the day of death using the Wilcoxon rank sums test. CFU organ burdens were compared using a Mann-Whitney U test. Statistical analyses were done using GB-STAT, version 6.0 (Dynamic Microsystems).

Post-infection genetic analysis of reisolated C. albicans: In order to confirm the genotypes of those individual *C. albicans* colonies cultured following harvesting from necropsied mice, the presence or absence of the COS-1 gene was confirmed by PCR analysis of genomic DNA obtained from the *C. albicans* colonies. To prepare the DNA from the isolated *C. albicans* colonies, 5 ml volumes of SDB were inoculated with each isolate and incubated at 37° C. with shaking at 180 rpm for 18 hours. Cultures were centrifuged (16,000×g), cell pellets were frozen on dry ice and thawed. Individual pellets were resuspended in 50 μl of reverse transcriptase buffer (Life Technologies) containing 10 mM DTT and incubated for 15 minutes at 95° C. Lysates were cooled on ice, centrifuged (16,000×g) to remove cell debris and the supernatants containing DNA were used for PCR.

The PCR reactions were conducted in 10 μl volumes containing 0.5 μM primers, 600 μM dNTPs, 3 mM $MgCl_2$, 10% (v/v) Ficoll (Idaho Technology), and 1.25 units of Taq DNA Polymerase (Fisher Scientific). Amplifications were performed using a Rapidcycler (Idaho Technology) with an initial cycle at 94° C. for 30 s, 30 cycles at 94° C. for 0 s, 55° C. for 0 s, and 72° C. for 15 s, and a final cycle for 30 s, and the resulting mixtures separated by agarose gel electrophoresis.

Virulence of *C. albicans* wild-type and COS-1 deletion strains: To determine whether COS-1 is required for or involved in in vivo virulence, the parental wild-type *C. albicans* strain, the ΔCOS-1/ΔCOS-1 strain, and the hemizygous COS-1⁺/ΔCOS-1 strain were alternately tested in the mouse in vivo virulence assay. In this assay, five-week-old female CD-1 mice (Charles River Laboratories) were infected intravenously with one of the three fungal strains. The inocula were prepared by overnight incubation of each strain in modified synthetic amino acid medium-fungal broth (Hanson and Stevens, Antimicrob. Agents Chemother., 36:486–488 [1992]) at 37° C. with shaking at 140 rpm. Cells were harvested and washed twice with sterile saline followed by centrifugation. The cell pellets were resuspended in sterile saline and the number of cells determined by hemacytometer count. Cells were further diluted in sterile saline to obtain the desired inoculum of $6 \times 10^4$ cells in a total volume of 0.25 ml. Ten mice were used in each experiment to test the virulence of each fungal strain.

Figure 8:
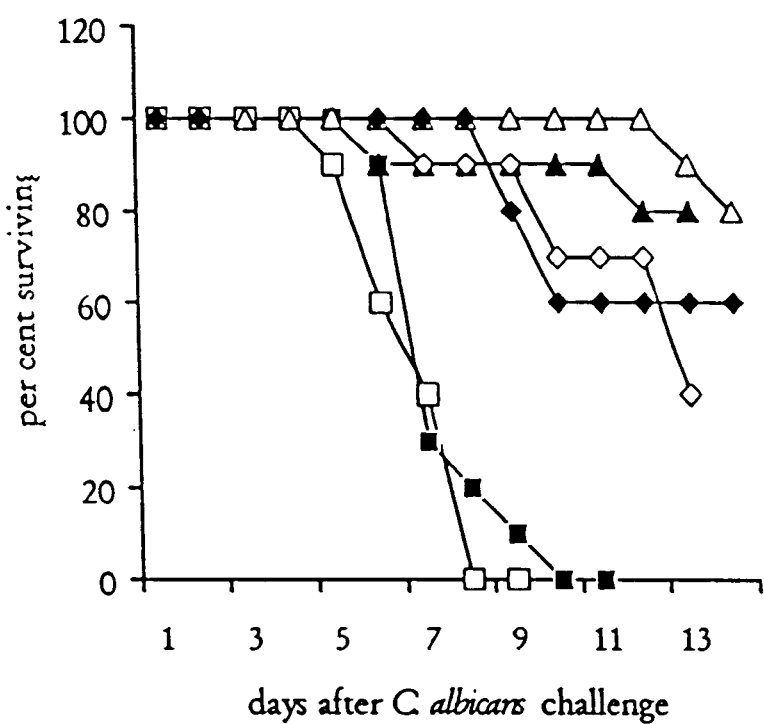
FIG. 8 shows a graph depicting mouse survival following infection with various C. albicans strains (i.e., wild-type, ΔCOS-1, and ΔCOS-1 reconstituted with COS-1 activity from a 2 μ-expression vector). Results from two separate experiments are shown, one using solid characters, the second using empty characters. Squares indicate the wild-type C. albicans strain. Triangles indicates the results using the C. albicans ΔCOS-1 strain. Diamonds indicates the results using the C albicans ΔCOS-1 strain reconstituted with COS-1 activity from a 2 μ-expression vector.

The experiment was performed twice, with the results depicted in FIG. 8. In this Figure, the closed symbols indicate one experiment, while the open symbols indicate the second experiment. The squares (■ and □) represent mouse survival following inoculation with the wild-type parental *C. albicans* strain, the triangles (▼ and Δ) represent mouse survival following inoculation with the ΔCOS-1/ΔCOS-1 deletion strain, and the diamonds (◊ and ♦) represent mouse survival following inoculation with the hemizygous COS-1⁺/ΔCOS-1 strain. Mortality was scored through 14 days of infection. As shown in the Figure, none of mice infected with the wild-type *C. albicans* stain survived through the time course of the experiment. The ΔCOS-1/ΔCOS-1 strain was significantly less virulent than the parental wild-type strain (P<0.01), while the COS-1/ΔCOS-1 strain was intermediate in virulence between the parental and the ΔCOS-1/ΔCOS-1 strain. For example, in one experiment (FIG. 8, open symbols) more animals (6 of 11) infected with the COS-1⁺/ΔCOS-1 strain died due to the fungal infection than did those given the ΔCOS-1/ΔCOS-1 strain (2 of 10).

In addition to scoring mouse survival, five mice from each group were euthanized three hours post-infection to compare the organ tropism of the *C. albicans* strains and determine whether differences in mortality could be attributed to differences in the distribution of the yeast in the organs after the initiation of infection. Brain, spleen, liver, kidney and lung tissue were examined for fungal organ burden. Only in the lungs was there a statistically significant difference in comparative fungal burden comparing the wild-type and the ΔCOS-1/ΔCOS-1 strains. In this case, a greater number of organisms was recovered from the lungs of mice inoculated with ΔCOS-1/ΔCOS-1 *C. albicans*, as compared to the wild-type parental strain (P 0.047); no other differences were found.

At the conclusion of this experiment, all surviving mice were euthanized and the number of *C. albicans* cells in the kidneys was determined using the method described above. The mean burden of fungal cells in the kidneys of surviving mice was not statistically greater in the mice infected with COS-1⁺/ΔCOS-1 than in the ΔCOS-1/ΔCOS-1-infected mice. Likewise, the CFU burdens in the kidneys of COS-1⁺/ΔCOS-1-infected mice were not significantly different from the wild-type-infected mice. However, the CFU burden in ΔCOS-1/ΔCOS-1-infected mouse kidney were statistically different (smaller) from the CFU burden in kidneys of mice infected with the wild-type strain. Thus, in both time to deaths and in organ infectious burdens, the COS-1⁺/

ΔCOS-1 strain was intermediate between the wild-type parental strain and ΔCOS-1/ΔCOS-1 strain.

In addition, a small number of isolates grown from the kidneys from each experimental group were subject to genetic analysis by PCR, as described above. In each case, the C. albicans organism isolated was confirmed to be of the identical genotype as the initial infecting strain.

These data show that the COS-1 homozygous disruption strain had significantly reduced virulence in a murine model of candidosis/candidemia. Thus, COS-1 function contributes significantly to in vivo virulence. This, it is contemplated that COS-1 activity will find use as a novel target for the development of antifungal drugs. Indeed, since two-component histidine kinases have not been found in humans or other mammals, these genes and their respective gene products represent a particularly attractive target for the development of antifungal drugs.

EXAMPLE 14

Isolation of an Aspergillus fumigatus Histidine Kinase Genomic Clone

In this Example, an A. fumigatus high density genomic library was generated and screened using a PCR strategy for the purpose of identifying, isolating and analyzing a histidine kinase gene ("FOS-1") from this fungal species.

In these and subsequent experiments, A. fumigatus (ATCC 16424), originally isolated from lung tissue of an aspergillosis patient was used. A. fumigatus stock cultures were routinely grown at 37° C. on MPG medium (2% w/v malt extract, 2% (w/v) glucose, 0.1% (w/v) peptone, and 2% w/v agar) for conidial growth, or in YG medium (1% w/v yeast extract, and 1% glucose). E. coli strain DH5α (Gibco-BRL) stocks were grown and maintained on LB medium, and supplemented with 100 μg/ml ampicillin where appropriate using techniques common in the art (See e.g., Sambrook et al., [1989], supra).

An A. fumigatus cosmid genomic library from Dr. Tom Adams (Texas A & M, College Station, Tex.) was obtained. This library was constructed by digesting A. fumigatus genomic DNA with MboI, partially filled with dCTP and dTTP using Klenow polymerase, and ligating 20–30 kb DNA fragments into pCosAX which had been linearized with XhoI and partially filled with Klenow polymerase (Borgia et al., FEMS Microb. Lett., 122:227–231 [1994]). The resulting library contained approximately seven genomic equivalents.

This genomic A. fumigatus cosmid library was used to transform DH5α cells, which were then plated on LB-ampicillin plates. The resulting transformed DH5α colonies were used to inoculate individual wells of 64 microtiter plates (96-well plates) containing LB-ampicillin. The cells were grown overnight at 37° C. A BioMek 2000 robot (Beckman) was then used to transfer the cells to Hybond-N+ nylon membrane filters (Amersham) saturated with LB-ampicillin selective medium. The cells were grown for several hours, lysed, dried and cross-linked by baking the blots for 1–2 hours at 80° C. The filters were then ready for pre-hybridization and hybridization treatment.

A probe suitable for screening the A. fumigatus genomic DNA blots for the A. fumigatus histidine kinase was made using a degenerate PCR strategy. The two PCR primers used to isolated the COS-1 gene from C. albicans, H1A and N2A (shown in SEQ ID NOS:6 and 8, respectively), were similarly used to amplify the region containing the H box and the ATP-binding motif, a region found to be highly homologous among members of the histidine kinase family (i.e., the primers included the region between the H box and the ATP-binding motif, See FIG. 6). Using genomic DNA derived from A. fumigatus as a template, a 352 bp PCR fragment was generated (SEQ ID NO:33) and cloned into a TA cloning vector (Invitrogen) to create "pFLA20." This 352 bp DNA fragment was subsequently used to probe the genomic DNA blots using methods known in the art (See, e.g., Agnan et al., Fungal Genet. Biol., 21:292–301 [1997]). Several hybridization signals were observed and the corresponding cosmid clones were isolated. The H1A and N2A primers were again used to verify these cosmid clones, and one cosmid, E4-64, demonstrated a positive PCR product.

Figure 9:
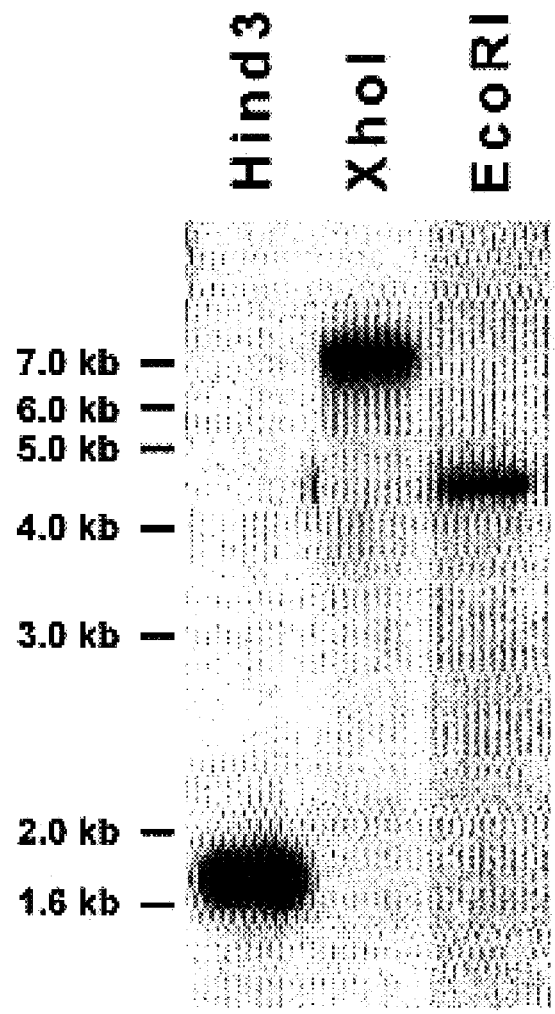
FIG. 9 shows a Southern blot in which the cosmid E4-64 (containing the Aspergillus fumigatus FOS-1 genomic DNA region) was probed. Lane 1 shows digested E4-64 DNA probed with the pFLA20 352 basepair probe. Lanes 2 and 3 shows the E4-64 DNA probed with a 3' probe (afos3'—XhoI product) and a 5' probe (afos5'—EcoRI product), respectively, derived from the positive band in lane 1.

To subclone a smaller DNA fragment containing the entire FOS-1 coding sequence, the E4-64 cosmid was digested with HindIII, electrophoresed on an agarose gel, transferred to nitrocellulose (Zeta Probe, Bio-Rad), and subjected to Southern analysis as described by Agnan et al. (supra). The Southern blot was probed with the 352 bp fragment from pFLA20, and a single 1.7 kb DNA fragment was visualized (as shown in FIG. 9, lane 1). This fragment was gel purified using the Qiaquick Gel Extraction kit (Qiagen) according to the manufacturer's instructions, ligated into pUC18 (Gibco-BRL) and sequenced. Based on computer analysis, this sequence did not contain the entire coding region of FOS-1.

To obtain additional subfragments of FOS-1 DNA sequences, the cosmid E4-64 was digested with several additional restriction enzymes. Two probes were generated from the positive HindIII fragment by digestion with EcoRI and HindIII. This digestion resulted in a 0.6 kb fragment (afos5', corresponding to nucleotides 4141–4742 in the nucleotide sequence of FIG. 10 and SEQ ID NO:34), as well as an 1.1 kb fragment (afos3', corresponding to nucleotides 4742–5899 in the nucleotide sequence of FIG. 10 and SEQ ID NO:34). These DNA fragments were used to probe the Southern blot of the digested E4-64 cosmid clone. The afos5' probe identified a 4.5 kb EcoRI fragment and the afos3' probe identified a 7.5 kb XhoI fragment, also shown in FIG. 9, lanes 3 and 2, respectively. These fragments were subsequently gel-purified as described above, and sequentially ligated into pBluescript II KS– (Stratagene), using methods known in the art. This plasmid was named "pFOS-1C." The entire insert was approximately 12 kb in length, of which approximately 8.1 kb were sequenced by the University of Colorado Cancer Center DNA Sequencing and Analysis Core Facility, using primer walking on both strands. The complete 8256 nucleotide FOS-1 genomic DNA sequence is provided in SEQ ID NO:34 and shown in FIG. 10. This genomic sequence was submitted to GenBank and assigned Accession number U95919.

EXAMPLE 15

FOS-1 Northern Blot Analysis

In this Example, poly(A) RNA (i.e., mRNA) collected from A. fumigatus was isolated and analyzed for the presence of an mRNA transcript corresponding to the FOS-1 gene identified in Example 14.

Total RNA was isolated from A. fumigatus cultures grown for 18 hours in liquid YG medium at 37° C. with orbital shaking (250 rpm) using the RNeasy Plant Mini Kit (Qiagen), according to the manufacturer's instructions. Poly (A) RNA was isolated using the mRNA Purification Kit (Amersham Pharmacia Biotech) and 3 μg was used for Northern analysis. mRNA was denatured for 15 min at 55°

C. before being separated on a formaldehyde gel containing 1.5% (w/v) agarose. The mRNA was transferred to

```
3502-start
            5'-ATGCGACTGAATGGAATATTATCCTTATGG-3'  (SEQ ID NO: 60)
JAPR2       5'-AGATGCACATGGAATGTGGAAAGG-3'       (SEQ ID NO: 61)
3701-start  5'-ATGATTACTTTTATGTGGGG-3'           (SEQ ID NO: 62)
TMR4
            5'-ATCACTGCGTTGAAGATTGAGCTGCTCTTC-3' (SEQ ID NO: 63)
TMF1        5'-TGATCATCCATCTGTCGTCTTCTGGG-3'     (SEQ ID NO: 64)
FHKR2       5'-GCGCTTCCAGAACTAGGTTCAGC-3'        (SEQ ID NO: 65)
FHKLE2      5'-GAGGCCCACACAGAGATCGT-3'           (SEQ ID NO: 66)
H-box 3'rev 5'-TTGATTACTTGAAGCAAAATC-3'          (SEQ ID NO: 67)
H-box 5'    5'-AGCGCGGATGGTGGCAGCTTT-3'          (SEQ ID NO: 68)
GPR3        5'-GCCAAGTCCTGTACCC-3'               (SEQ ID NO: 69)
FHKLE1      5'-GAGATCTCCTGTTCCATGCCT-3'          (SEQ ID NO: 70)
D-box 5'rev 5'-TTTCACCTGTCGGACTGCGTCTGCGCC-3'    (SEQ ID NO: 71)
Os11        5'-CCCGCTGCTACCGCCGAAAATAC-3'        (SEQ ID NO: 72)
TMR1        5'-CTCGTTCCATAGGTCTCCATGACC-3'       (SEQ ID NO: 73)
```

Hybond-N nylon membrane (Amersham Pharmacia) by gravity and immobilized at 80° C. under vacuum for 2 hours. A 630 bp PCR fragment (SEQ ID NO: 49) was generated at the 5' terminus of the FOS-1 ORF using the following primers:

5' primer: 5'-CCTTGCGCGTGATTGAGGTCTCGG-3' (SEQ ID NO: 50)

3' primer: 5'-GCCGACCGAATGAGAAGATAGGCG-3' (SEQ ID NO: 51)

The PCR fragment was labeled with $^{32}$P-dCTP using the DECAprime II Kit (Ambion) and was used to probe the membrane overnight at 42° C. in 50% (v/v) formamide, 10% (w/v) dextran sulfate (MW ~500 kDa), 0.2% (w/v) bovine serum albumin, 0.2% (w/v) polyvinylpyrrolidone (MW 40 kDa), 0.2% (w/v) Ficoll (MW ~400 kDa), 50 mM Tris-HCl, pH 7.5, 1% (w/v) sodium pyrophosphate, 1% (w/v) SDS, 1 M NaCl, 10 mg/ml sheared, denatured salmon sperm DNA. The membrane was washed twice with 0.1×SSPE/1% (w/v) SDS before being exposed to film overnight.

As shown in FIG. 12B, this Northern blot analysis revealed a single species of mRNA of ~3.2 kb.

EXAMPLE 16

Isolation of the FOS-1 cDNA

In this Example, an *A. fumigatus* cDNA library was constructed and screened in order to isolate the FOS-1 cDNA. The SMART cDNA Library Construction Kit (Clonetech) was used.

Briefly, total RNA was isolated from *A. fumigatus* grown in shaking cultures for 18 hours in YG medium at 37° C., and 250 rpm using the RNeasy Plant Minikit (Qiagen) and the manufacturer's instructions. Poly(A) RNA was then isolated using the Oligodex Purification System (Qiagen). Then, 0.6 μg of this poly(A) RNA was used for first strand cDNA synthesis using the reagents provided with a Perkin-Elmer Geneamp 2400 thermocycler, following the manufacturer's instructions. Second strand synthesis and cDNA amplification were then performed, also according to manufacturer's instructions.

The cDNA pool created by this protocol was used as template for a PCR reaction to amplify FOS-1 specific cDNA sequences. A series of PCR primers specific to the FOS-1 genomic sequence were used to amplify fragments from the cDNA in 10 μl reactions containing 0.5 μM primers, 600 μM dNTPs, 3 mM MgCl$_2$, 10% (v/v) Ficoll Loading Dye (Idaho Technology) and 1.25 U Taq DNA Polymerase (Fisher Scientific). The primers used in these reactions were:

PCR was performed using The Rapidcycler (Idaho Technology) using the following conditions: an initial cycle at 94° C. for 30 sec, 30 cycles at 94° C. for 0 sec, 55° C. for sec, and 72° C. for 15 sec, and a final extension at 72° C. for 30 sec.

A single predominant PCR product was observed following each PCR reaction. Both strands of the cDNAs generated by the FOS-1-specific PCR reactions were sequenced at the University of Colorado Cancer Center DNA Sequencing and Analysis Core Facility. The complete sequence of the FOS-1 cDNA derived from these clones was found to be 3168 nucleotides in length, and is provided in FIG. 11 and SEQ ID NO:36.

EXAMPLE 17

Characterization of FOS-1 Gene and Protein Sequences

The FOS-1 gene structure determined using the GeneMark program (http://genemark.biology.gatech.edu/GeneMark/). Translation of the FOS-1 cDNA was performed using the DNA Strider 1.2 program, and sequence comparisons were performed by BLAST analysis, at:

http://www.ncbi.nlm.nih.gov/cgi-bin/BLAST/ and by the Boxshade 3.21 program at:

http://www.ch.embnet.org/software/BOX_form.html

These analyses reveal two open reading frames (ORFs) within the FOS-1 transcription unit. The nucleotide sequence of the smaller of these two ORFs is shown in SEQ ID NO:47. This 147 nucleotide ORF extends from nucleotides 3502 to 3648 of the genomic sequence shown in FIG. 10 and SEQ ID NO:34, and corresponds to nucleotides 1 to 147 of the cDNA sequence shown in FIG. 11 and SEQ ID NO:36.

The nucleotide sequence of the larger of the two ORFs is provided in SEQ ID NO:59. This 2124 nucleotide ORF extends from nucleotide positions 4081 to 6204 of the genomic sequence shown in FIG. 10 and SEQ ID NO:34, and corresponds to nucleotides 580 to 2703 of the cDNA sequence shown in FIG. 11 and SEQ ID NO:36.

A putative TATA box was identified at nucleotides 2141–2147 in the genomic sequence (See FIGS. 10 and 12, and SEQ ID NO:34). No introns were detected either by computer analysis using predicted Aspergillus splices sites (Unkles, In *Applied Molecular Genetics of Filamentous Fungi*, Kinghorn and Turner, Eds., pp. 28–52, Chapman and Hall London [1992]) or by direct sequence analysis of the cDNA. Three putative polyadenylation signal sequences were found at nucleotides 6364, 6439 and 6592 in the genomic sequence (See, FIG. 10 and SEQ ID NO:34), corresponding to positions 2863, 2938 and 3091 in the cDNA sequence (See, FIG. 11 and SEQ ID NO:36).

The small 147 nucleotide ORF predicts a 49 amino acid peptide with a predicted molecular weight of 5,655 Daltons. This gene and peptide are called the mini-FOS upstream ORF (uORF). The amino acid sequence of this 49 amino acid peptide is shown in FIG. 13B, and also provided in SEQ ID NO:48. The amino acid sequence of this peptide shows no homology to any known sequences in the NCBI databases using the NCBI Blast homology search program. Similar small upstream ORFs are known to exist in other yeast and fungal transcription units, and are theorized to play a regulatory role in gene expression (Sachs, Fungal Genet. Biol., 23:117–124 [1998]; and Wang et al., J. Biol. Chem., 274:37565–37574 [1999]).

Figure 14:
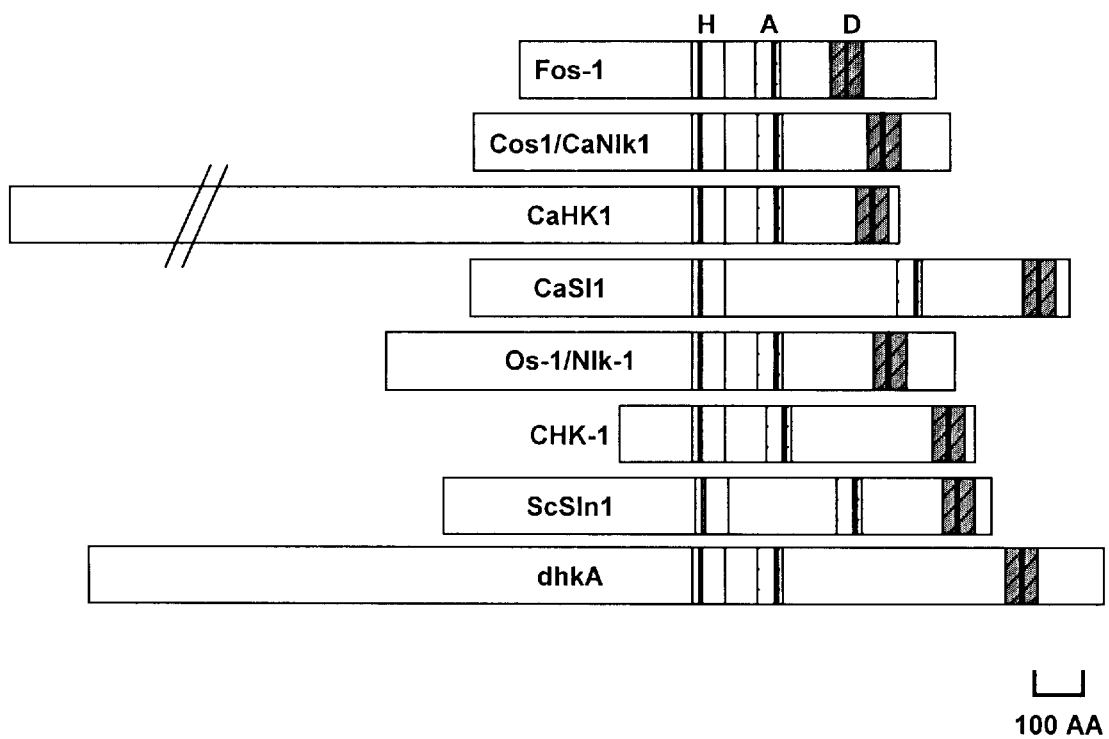
FIG. 14 shows a domain alignment of the histidine kinase proteins from various eukaryotic species. In this Figure, the H box, ATP binding motif, and D box domains are indicated.

The larger ORF is predicted to encode a 708 amino acid protein with a predicted molecular weight of 78.9 kDa (shown in FIG. 13A, and SEQ ID NO:35) showing strong homology to known histidine kinase proteins (See, FIGS. 14 and 15). This gene was called FOS-1, and the gene product was called Fos-1p. From these comparative analyses, Fos-1p was predicted to contain a putative histidine phosphoryl group acceptor at position $His^{337}$ and a putative aspartate phosphoryl group acceptor at position $Asp^{641}$. The predicted protein showed strongest homology to other fungal histidine kinases, particularly to the fungal histidine kinases of *N. crassa* and *C. albicans*, as shown in FIG. 15. Fos-1p showed 28% identity and 43% similarity to Os-1p, and 27% identity and 43% similarity to Cos-1p. By comparison, Os-1p and Cos-1p share 60% identity and 70% similarity.

The organization and spacing of the key domains of Fos-1p, including the H box, ATP-binding motif and the D box are conserved with respect to other eukaryotic histidine kinases (See, FIG. 14). In addition to Fos-1p of the present invention, other histidine kinase proteins have been identified. These proteins are included in FIG. 14 and listed in the Table below.

TABLE 4

EUKARYOTIC HISTIDINE KINASE PROTEINS

| Histidine Kinase Protein | Species | Reference |
|---|---|---|
| Cos1/ CaNik1 | Candida albicans | U.S. Pat. No. 5,939,306; Alex et al., Proc. Natl. Acad. Sci. USA 95:7069–7073 (1998) |
| CaHK1 | C. albicans | Calera et al., Yeast 14:665–674 (1998) |
| CaSln1 | C. albicans | Nagahashi et al., Microbiol., 144:425–432 (1998) |
| Os-1/Nik-1 | Neurospora crassa | U.S. Pat. No. 5,939,306; Schumacher et al., Curr Microbiol., 134:340–347 (1997) |
| CHK-1 | Glomerella cingulata | Li et al., GenBank Accession Number U77605 (1996) |
| ScSln1 | Saccharomyces cerevisiae | Maeda et al., Science 369:242–245 (1994); Ota and Varschavsky, Science 262:566–569 (1993) |
| dhkA | Dictyostelium discoideum | Wang et al., EMBO J., 15:3890–3898 (1996) |

The amino-terminus of Fos-1p showed no similarity to any other known histidine kinases and did not contain the 90 amino acid tandem repeats found in Cos-1p and Os-1p (Alex et al., Proc. Natl. Acad. Sci. USA 93:3416–3421 [1996]; Schumacher et al., Curr Microbiol., 134:340–347 [1997]; and Alex et al., Proc. Natl. Acad. Sci. USA 95:7069–7073 [1998]). Significant divergence was also observed at the carboxyl-terminus. Fos-1p contained no predicted membrane-spanning or secretory domains; computer analysis using the PSORT program indicated that Fos-1p is a cytosolic protein.

EXAMPLE 18

Construction of ΔFOS-1 Strain

In this Example, a FOS-1 knockout targeting vector was constructed and used to knock out the endogenous FOS-1 loci in order to examine the function of Fos-1p in *A. fumigatus*. The FOS-1 allele was deleted from haploid *A. fumigatus* cells by replacement of the FOS-1 genomic sequence with a hygromycin resistance cassette, using homologous recombination.

Construction/transformation of FOS-1 knock-out targeting vector: To make a FOS-1 knockout construct, a 5.9 ClaI/PstI FOS-1 genomic DNA fragment (encompassing the entire FOS-1 coding sequence, 2.6 kb 5' untranslated region (UTR), and 1.1 kb 3' UTR), was subcloned into pBluescript II KS–, and the resulting construct was called "pFOS-1A." Approximately 4.1 kb of this sequence, encompassing the entire FOS-1 coding sequence, was deleted by digesting pFOS-1A with HindIII and XbaI. pID620, a plasmid construct containing an *E. coli* hygromycin resistance gene (hph) fused to the *A. nidulans* TrpC promoter (Brown et al., Mol. Gen. Genet., 259:327 [1998]), was digested with HindIII and ClaI, to produce a 1.4 kb hygromycin cassette, which was then ligated to the identical restriction sites of the digested pFOS-1A construct, to produce pFOSKO2. The final construct contained the hgh coding region flanked by 2.6 kb FOS-1 5' UTR and 0.4 kb FOS-1 3' UTR. The pFOSKO2 plasmid is shown in FIG. 16A.

Transformation of *A. fumigatus* protoplasts was performed as previously described (Tang et al., Mol. Microbiol., 6:1663–1671 [1992]), with some modifications. Briefly, $2 \times 10^8$ conidia were used to inoculate 250 ml YG medium, and grown in shaking cultures overnight at 37° C. and 180 rpm. Mycelia were harvested by filtration over Whatman #2 filter paper and washed. Protoplasts were produced by incubation with Novozym 234 (Novo Industries, 100 mg/ml), at 30° C., for 3–4 hours, purified by filtering over glass wool, concentrated by centrifugation, and resuspended in 15% polyethylene (PEG) 4000, in Buffer 2 (25 mM Tris, pH 7.5, 25 mM $CaCl_2$, 1 M sorbitol) to a final concentration of $1 \times 10^8$ protoplasts/ml.

The pFOSKO2 plasmid (5 μg) was combined with 120 μl of *A. fumigatus* protoplast suspension in 1.5 ml Eppendorf tubes and incubated on ice for 30 minutes. Then, 1 ml of 15% PEG 4000/Buffer 2 was added to the mixture and incubated at room temperature for 10 minutes. The mixture was then added to 20 ml molten MPG agar containing 7.5% (w/v) sorbitol and 150 μg/ml hygromycin B (Calbiochem) and overlaid on 40 ml solidified MPG agar also containing 7.5% (w/v) sorbitol and 150 μg/ml hygromycin B (Calbiochem) in 150 mm x15 mm petri plates. The plates were incubated at 37° C. for 3–5 days and resistant colonies were isolated.

DNA isolation from hygromycin-resistant strains: Genomic DNA was isolated from hygromycin-resistant strains grown for 18 hours in liquid YG medium at 37° C. with orbital shaking (250 rpm) using the following procedure. Hyphae were harvested by vacuum filtration and frozen on dry ice. Hyphae were ground to a fine powder under liquid nitrogen and resuspended in an equal volume of lysis buffer (50 mM Tris, pH 8.0, 50 mM EDTA, pH 8.0, 2%

[w/v] SDS, 1% [v/v] β-mercaptoethanol). The lysates were incubated for 60 min at 37° C. after the addition of 10 μl RNase Plus (Eppendorf-5 Prime) and for an additional 60 min at 65° C. after the addition of Proteinase K (100 μg/ml final concentration). The lysates were extracted twice with phenol:chloroform:isoamyl alcohol (25:24:1), once with chloroform:isoamyl alcohol (24:1), and finally, ethanol precipitated.

Analysis of genomic DNA: Genomic DNA isolated from several hygromycin-resistant transformants was screened for the replacement of the FOS-1 gene by PCR analysis. To test for the absence of the FOS-1 gene, several sets of primers along the FOS-1 coding region were used. One such set of primers used was:

5' primer: 5'-AGCGCGGATGGTGGCAGCTTT-3' (SEQ ID NO: 52)

3' primer: 5'-TTGATTACTTGAAGCAAAATCG-3' (SEQ ID NO: 53)

Once it was confirmed by PCR that the transformants lacked the FOS-1 gene, they were screened for the presence of the hygromycin cassette using PCR on this same genomic DNA template. The PCR was done using the following hph-specific primers:

5' primer: 5'-GACGTCTGTCGAGAAGTTTCTGATCG-3' (SEQ ID NO: 54)

3' primer: 5'-GTATTGGGAATCCCCGAACATCGCCTC-3' (SEQ ID NO: 55)

All 10 μl PCR reactions contained 0.5 μM primers, 600 μM dNTPs, 3 mM MgCl$_2$, 10% (v/v) Ficoll (Idaho Technologies) and 1.25 U Taq DNA Polymerase (Fisher Scientific). PCR was performed using The Rapidcycler (Idaho Technology) using the following conditions: an initial cycle at 94° C. for 30 sec, 30 cycles at 94° C. for 0 sec, 55° C. for 0 sec, and 72° C. for 15 sec, and a final extension at 72° C. for 30 sec.

Those transformants lacking the FOS-1 gene and containing the hygromycin gene (as judged by PCR) were further screened by Southern analyses for the absence of the FOS-1 gene by probing 5 μg of EcoRI-digested genomic DNA with a HindIII/EcoRI DNA fragment (nucleotides 4141 to 4743). The relative position of this probe is indicated with an arrow in FIG. 16A. In brief, 5 μg of genomic DNA from several transformants were digested overnight with EcoRI and the digests separated by agarose-gel electrophoresis. The DNA was transferred to Zeta-Probe GT nitrocellulose membrane (BioRad) by gravity and immobilized at 80° C. under vacuum for 2 hours. The DNA probes were labeled with $^{32}$P-dCTP using the DECAprime II Kit (Ambion) and were used to probe membranes overnight at 65° C. in 0.5 M NaH$_2$PO$_4$, pH 7.2 containing 5% (w/v) SDS. Each membrane was washed twice, once with 40 mM Na$_2$HPO$_4$ containing 5% (w/v) SDS and once with 40 mM Na$_2$HPO$_4$ containing 1% (w/v) SDS before being exposed to film overnight. The result of one such Southern blot is shown in FIG. 16B. This Southern blot shows the presence of a FOS-1 positive band in wild-type genomic DNA, while genomic DNA isolated from a FOS-1 targeted knock-out candidate strain showed no FOS-1 positive band.

Identification of single integration events: Transformants lacking the FOS-1 gene as determined by PCR and Southern analyses were tested by Southern analysis to ensure that ΔFOS-1 strains were derived from a single integration of pFOSKO2 DNA. A 658 bp PCR fragment (SEQ ID NO:56) was generated from the hygromycin gene using the following primers:

5' primer: 5'-GACGTCTGTCGAGAAGTTTCTGATCG-3' (SEQ ID NO:57)

3' primer: 5'-GTATTGGGAATCCCCGAACATCGCCTC-3' (SEQ ID NO:58)

The PCR fragment was labeled with $^{32}$P-dCTP as above and used to probe a Southern blot containing genomic DNA (obtained as described above) digested with SacI/KpnIA. A transformant lacking the resident FOS-1 gene and containing only one copy of the hph gene was identified and named "ΔFOS-1."

EXAMPLE 19

Analysis of the ΔFOS-1 Phenotype

In this Example, the phenotype of the A. fumigatus ΔFOS-1 mutant strain was determined. Specifically, wild-type and ΔFOS-1 mutant strains were compared with respect to morphology, growth rates, conidial germination rates, resistance to novozym 234, osmotic stress, oxidative stress compounds, and sensitivity to antifungal drugs including dicarboximides.

Wild-type and ΔFOS-1 strains were grown using the following media, either in broth or solidified with 1.5% (w/v) agar: YG, MPG, 1xRPMI and Spider (1% [w/v] nutrient broth, 1% [w/v] mannitol, 7.5% [w/v] sorbitol and 0.2% [w/v] K$_2$PO$_4$).

Morphology: Using light microscopy, no differences were detected between the wild-type and ΔFOS-1 strains grown using a number of liquid and solid media with respect to hyphal, conidiophore and conidial morphology.

Conidiation: Wild-type and ΔFOS-1 strains were grown in 50 ml YG medium with 0, 1, 5 and 10% (w/v) NaCl, at 37° C. with orbital shaking (250 rpm) with an inoculum of 1×10$^6$ conidia/ml. The extent of conidiation was determined by direct counting of conidiophores and hyphae by phase contrast microscopy at 400×magnification after various times of incubation.

Using liquid YG medium to culture wild-type and ΔFOS-1 strains, it was observed that after 48 hours of incubation, 80–90% of wild-type hyphal tips had developed into conidiophores while only ~30% of ΔFOS-1 tips had developed into conidiophores.

Conidial germination: To determine the extent of germination of conidia of wild-type and ΔFOS-1 strains, conidia from each strain were placed on MPG plates and the number of colonies resulting after 48 hrs of incubation at 37° C. was determined. To determine if the deletion of FOS-1 had an effect on the extent of conidial germination, equal numbers of conidia were harvested and plated from both the wild-type and ΔFOS-1 strains. After 48 hours incubation at 30° C., the number of colony forming units (CFU) was determined. No significant differences were observed in the number of CFU for the wild-type and ΔFOS-1 strains.

Growth rates: The wild-type and ΔFOS-1 strains grew at similar rates on a variety of solid media, including YG, MPG, RPMI, and Spider. In liquid YG medium both strains formed identical hyphal masses. These results indicate that ΔFOS-1 strains did not exhibit a growth defect.

Resistance to Novozym 234: To determine whether ΔFOS-1 is involved in cell-wall biosynthesis/assembly, the effect of a cell-wall degrading enzyme preparation on wild-type and ΔFOS-1 hyphae was tested. The effect of the cell-wall degrading enzyme novozym 234 (Calbiochem) on protoplast release from the wild-type and ΔFOS-1 strains was determined by incubating hyphae with the enzyme and determining the numbers of protoplasts released at various times (Tang et al., Molec. Biol., 6:1663–1671 [1992]). Briefly, YG medium was inoculated with 1×10⁶ conidia/ml of each strain and incubated overnight at 37° C. with shaking (250 rpm). Resulting hyphae were harvested by filtration over Whatman #2 filter paper and washed with 10 ml of 10 mM Na$_2$HPO$_4$, pH 6.0, 0.8% (w/v) NaCl. Hyphae were incubated at 30° C. in 8 ml 50 mM sodium citrate, pH 5.8, 1 M sorbitol containing 100 mg/ml novozym 234 for 4 hours. The numbers of protoplasts released were counted at various times with a haemocytometer and a Zeiss phase contrast light microscope at 400×.

Figure 17:
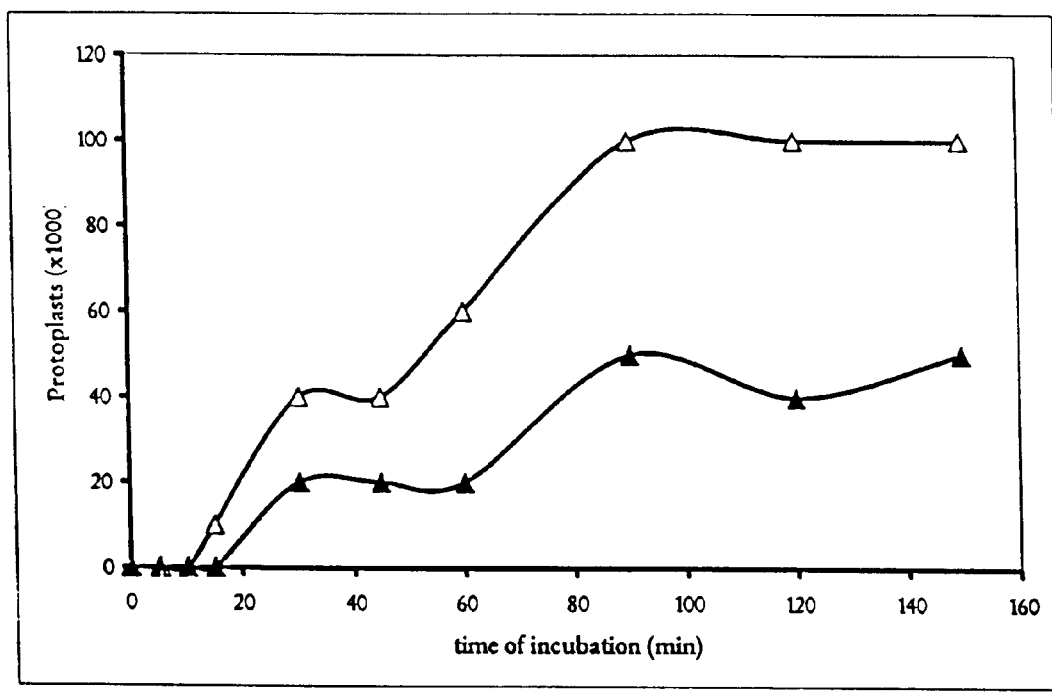
FIG. 17 shows the results of a protoplast growth assay using wild-type and ΔFOS-1 A. fumigatus strains, following a time course of hyphal treatment with novozym 234.

The results of this experiment are presented in FIG. 17. In this Figure, open triangles represent the number of wild-type protoplasts released, and closed triangles represent the number of ΔFOS-1 protoplasts released. As seen in the Figure, the ΔFOS-1 strain was more resistant to novozym 234 than the wild-type strain, suggesting that the cell-wall compositions and/or structure of wild-type and ΔFOS-1 strains are not identical.

Effect of oxidative stress compounds: To determine the effect of various oxidative stress-inducing compounds on hyphal growth in the wild-type and ΔFOS-1 strains, 2 μl water containing 1×10³ conidia were placed as single spots onto 150 mm×15 mm petri plates containing 30 ml agar-solidified MPG medium. In addition, these agar plates contained either diamide (0–2 mM; Sigma) (an SH residue oxidant that attacks surface proteins; de Souza Pereira and Geibel, J. Mol. Cell Biochem., 201:17–24 [1999]), or menadione (0–0.06 mM; Sigma Aldrich) (a superoxide generator; Caricchio et al., Clin. Immunol., 93:65–74 [1999]). These plates were incubated at 37° C. for 3 days. Hyphal growth/extension rates were determined by recording the distance traveled by hyphal fronts after various times of incubation.

No differences in hyphal growth/extension rates were seen comparing the wild-type and ΔFOS-1 strains when tested using either diamide or menadione-containing solid media.

Osmo-Sensitivity: To determine whether Fos-1p was involved in osmo-regulation, similar to Os-1p and Sln-1p, the effect of NaCl on the growth of wild-type and ΔFOS-1 strains was tested. Growth was measured by dry weight measurements taken by harvesting 72-hour cultures, filtering the hyphae over Whatman #2 filter paper, and drying the hyphal masses under vacuum at 80° C. overnight.

Figure 18:
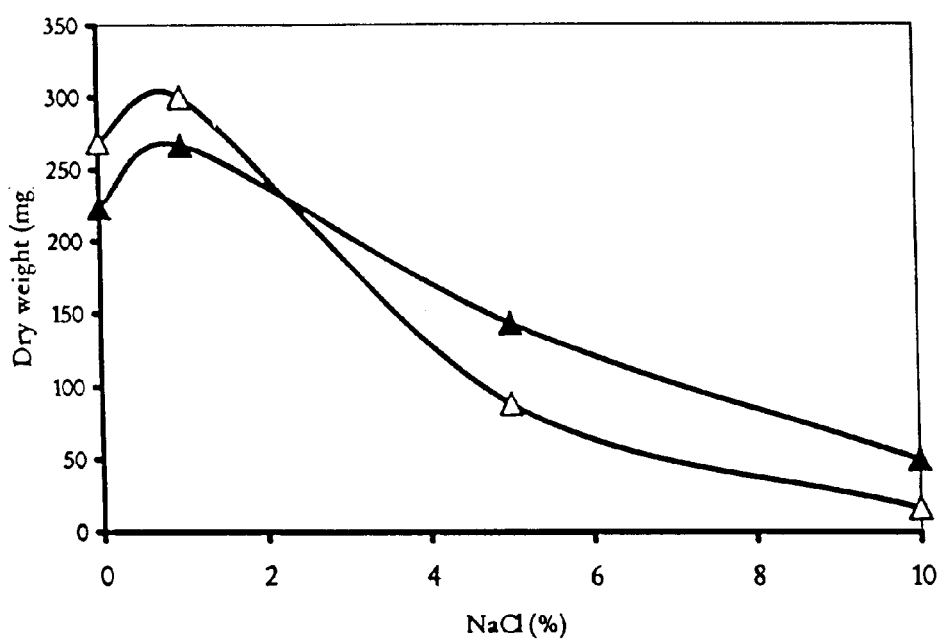
FIG. 18 shows the results of a dry weight growth assay using wild-type and ΔFOS-1 A. fumigatus strains as a function of varying salt concentrations.

The results of this experiment are shown in FIG. 18. Surprisingly, the ΔFOS-1 mutant strain (closed triangles) grew at rates slightly greater than the wild-type strain (open triangles) in medium containing 5% and 10% NaCl. As previously mentioned for medium lacking NaCl, a delay in conidiation of ΔFOS-1 mutant cultures in liquid medium containing NaCl was observed.

Sensitivity to antifungals: To assess the differential sensitivities of the wild-type and ΔFOS-1 strains to a number of antifungal compounds, the minimum inhibitor concentration of amphotericin B, nikkomycin Z, benomyl, miconazole, ketoconazole, fluconazole, cilofungin, 5-fluorocytosine and calcofluor white M2R new against the wild-type and ΔFOS-1 strains was determined. This fungal sensitivity was determined using a variation of the National Committee for Clinical Laboratory Standards (NCCLS) M27T-protocol (Galgiani et al., NCCLS, 15:1–29 [1995]). Briefly, serial dilutions of the anti-fungal drugs were made in 100 μl 1×RPMI medium (Life Technologies) and an additional 100 μl 1×RPMI medium containing 2×10⁴ conidia/ml of each strain was added to each well of 96-well microtiter plates. Plates were incubated for 48 hours with gentle shaking at 37° C. The amount of growth in each well was estimated using a inverted phase microscope. No differences in minimum inhibitor concentration between the wild-type and ΔFOS-1 strains to any of these antifungal compounds were found.

Although an understanding of the mechanism is not necessary in order to use the present invention, resistance to dicarboximide antifungals by a number of fungi appears to involve a histidine kinase mutation. For example, OS-1 mutant strains of N. crassa are highly resistant to vinclozolin and other dicarboximides (Beever, Trans. Br. Mycol. Soc., 80:327–331 [1983]). To test if the ΔFOS-1 strain was also resistant to vinclozolin, iprodione and procymidone, the growth of wild-type and ΔFOS-1 strains on medium containing each drug was examined. Briefly, wild-type and ΔFOS-1 conidia (1×10³ in 2 μl) were inoculated onto agar-solidified MPG medium containing 10 μg/ml vinclozolin or iprodione, or 12 μg/ml procymidone. Hyphal extension rates in mm/hr were recorded, and a mean determined based on at least 12 individual data points. These results of examining the hyphal extension rates in response to these antifungal drugs is summarized in Table 5 below. Results are shown±standard deviation. P values were calculated using the Students t test (http://nimitz.mcs.kent.edu/~blewis/stat/tTest.html).

TABLE 5

DICARBOXIMIDE DRUG SENSITIVITY OF A. fumigatus strains

| | A. fumigatus strain | | |
|---|---|---|---|
| Drug | wild-type | ΔFOS-1 | P value |
| no drug | 0.69 ± 0.08 | 0.65 ± 0.10 | >0.14 |
| vinclozolin | 0.34 ± 0.11 | 0.50 ± 0.05 | <0.0001 |
| iprodione | 0.29 ± 0.11 | 0.52 ± 0.03 | <0.0001 |
| procymidone | 0.21 ± 0.13 | 0.48 ± 0.08 | <0.0001 |

Under these growth conditions, no differences in the extent of conidiation or in hyphal and conidiophore morphologies between wild-type and the ΔFOS-1 strains were observed. However, as seen in the Table above, significant differences in the hyphal extension rates of wild type and ΔFOS-1 strains on medium containing each drug were observed. Note that the hyphal extension rates of wild-type and ΔFOS-1 strains are nearly identical on control medium. In sharp contrast, the ΔFOS-1 strain grew at significantly greater rates than the wild-type strain (P<0.0001) on medium containing each of the various dicarboximides.

EXAMPLE 20

Identification of Additional A. fumigatus FOS Genes

In this Example, additional FOS genes in A. fumigatus were identified. These genes were identified in the same screening protocol that isolated FOS-1, as described in Example 14.

As described in Example 13, the pFLA20 insert (SEQ ID NO:35) was used to probe the high-density genomic A. fumigatus library, which identified the cosmid E4-64, containing the FOS-1 gene. This screen also identified an additional 22 cosmids having the ability to hybridize to the pFLA20 probe. DNA isolated from each of these 22 cosmids was used as a template for PCR, using primers homologous to a portion of the H box and the D box regions (SEQ ID NOS:6 and 8, respectively). The resulting PCR products were separated on agarose gels, the prominent bands gel-purified, a 200 bp region of this nucleic acid sequenced, and the predicted amino acid sequences from these cosmids determined. Two of these cosmids contained sequences homologous to but distinct from the previously identified FOS-1 histidine kinase gene, and were given the names "FOS-2," and "FOS-3," as they were the second and third *A. fumigatus* histidine kinase nucleotide sequences identified. These sequences may be either from the same histidine kinase gene, or represent sequences from two different genes. The DNA sequence of the PCR product generated from the FOS-2 containing cosmid is shown in FIG. 19A and SEQ ID NO: 37, and the FOS-3 nucleotide sequence is shown in FIG. 19C and SEQ ID NO: 38. Similarly, the predicted amino acid sequence of Fos-2p (derived from the nucleotide sequence of the PCR product) are shown in FIG. 19B and SEQ ID NO: 39, while the predicted Fos-3p amino acid sequence is shown in FIG. 19D and SEQ ID NO: 40.

The partial Fos-2p amino acid sequence shows strongest homology to Fos-1p amino acids 288–349, while Fos-3p shows strongest conservation to Fos-1p amino acids 535–579. These preliminary results indicate that *A. fumigatus* has a minimum of two, and possibly three, histidine kinase genes.

EXAMPLE 21

Methods to Identify Compounds Which are Antifungal Drug Candidates

In this Example, methods to identify compounds which are potential therapeutics for treating fungal infections are provided. The preferred method incorporates a biochemical assay to identify compounds which are able to inhibit the activity of histidine kinase proteins in vitro. Compounds which inhibit histidine kinase proteins represent candidates for drug development. In some preferred embodiments, candidate compounds then advance to at least one additional step in screening for potential as antifungal drugs. In particularly preferred embodiments, the identification of candidate antifungal therapeutic compounds is conducted in three steps. These are:

1) Identification of compounds which inhibit histidine kinase protein activity in vitro.
2) Identification of compounds which inhibit the growth of fungi in culture.
3) Identification of compounds which inhibit or eliminate fungal infection in an in vivo mouse model system.

1) Identification of Compounds Which Inhibit Histidine Kinase Protein Activity In Vitro The identification of compounds which inhibit histidine kinase activity in vitro involves a rapid, high throughput assay capable of screening large numbers of candidate compounds. This assay may be automated (e.g., using robotic technology known in the art). Briefly, this assay entails the production and purification of a recombinant fungal histidine kinase protein (e.g., Cos-1p or Fos-1p), the incubation of this purified protein with a radiolabelled ATP substrate in the presence or absence of a test compound, and measuring radiolabel incorporation into the same protein (i.e., autophosphorylation) or another in vitro substrate. Kinase assays in general (See, e.g., Ausubel et al., *Current Protocols in Molecular Biology*, Ch. 18 "Analysis of Protein Phosphorylation," John Wiley & Sons, Inc. (eds), New York [1994]), and in particular kinase assays for the analysis of two-component signal transduction histidine kinase systems (See, e.g., Deschenes et al., Antimicrobial Agents and Chemotherapy 43(7):1700–1703 [1999]; Hilliard et al., Antimicrobial Agents and Chemotherapy 43:1693–1699 [1999]; Barrett et al., Proc. Natl. Acad. Sci. USA 95:5317–5322 [1998]; Roychoudhury et al., J. Biomolec. Screening 2(2):85–90 [1997]; Hess et al., Methods Enzymol., 200:188–204 [1991]; Huang et al., J. Biol. Chem., 266(14):9023–9031 [1991]) are known in the art. These kinase assays measure histidyl kinase activity, or measure the histidyl to aspartyl phosphotransferase activity of a histidine kinase protein. Either full length or truncated histidine kinase proteins can be used in these in vitro assays. Where truncated histidine kinase proteins are used, these proteins retain at least one active kinase activity (i.e., a portion of the histidine kinase protein that is able to phosphorylate a histidine substrate or an aspartate substrate, or both). One protein synthesis and kinase assay protocol which finds use with the present invention is provided below. It is not intended that the present invention be limited to use of this one protocol, as it is contemplated that any suitable protein synthesis and kinase assay will also find use with the present invention.

Production and Purification of a Recombinant Fungal Histidine Kinase Protein

Numerous techniques for the production and purification of a recombinant histidine kinase protein may be used. Either full length or truncated histidine kinase proteins may be used in this assay. For example, the Fos-1p protein may be produced and isolated using a glutathione S-transferase (GST) fusion protein protocol. In this protocol, the nucleotide sequence encoding Fos-1p is subcloned in-frame into a pGEX plasmid, as found in the Bulk GST Purification Module Kit (Amersham/Pharmacia) and used to transform a BL21 *E. coli* host strain. This subcloning results in the transcription and translation of a fusion protein consisting of GST and Fos-1p. Colonies expressing GST-Fos-1p fusion protein are selected by Western blotting utilizing an anti-GST antibody (Amersham/Pharmacia). Positive clones are grown at room temperature, stimulated with 0.6 mM isopropyl β-D-thiogalactoside (IPTG) and subsequently lysed by sonication. The soluble GST-Fos-1p fusion protein is purified utilizing a Glutathione Sepharose 4B affinity column (Amersham/Pharmacia) and eluted with reduced glutathione buffer according to the manufacturer's instructions.

To assess the purity of the eluted recombinant fusion protein, samples are subjected to SDS-PAGE and stained with Coomassie brilliant blue. Alternatively, purity of the GST fusion protein is assessed in a Western blot using anti-GST antibody (Amersham/Pharmacia).

Kinase Reaction Using Purified Protein and a Radiolabelled ATP Substrate

The purified histidine kinase protein described above is then incubated in the presence of a radiolabelled ATP substrate, under conditions such that the histidine kinase displays histidyl-kinase or aspartyl-kinase activity, or the histidine kinase protein mediates the phosphorylation of some other peptide or protein substrate. In addition, an identical reaction is run containing a compound being tested for kinase- inhibition activity. In one variation of this protocol, the kinase assay is performed in a multi-well format (e.g., a 96 or 1024 well plate) in order to maximize throughput. The plates may be either Millipore DEAE or nitrocellulose filter plates with 0.65 and 0.2 μm pore size, respectively. These plates contain a sealed microporous membrane underneath the filter at the bottom of each well such that following an incubation, the reaction mixtures are vacuum-filtered. During filtration, the proteins in the reaction are trapped by the filters. The GST-Fos-1p kinase reaction is initiated in each well in a volume of 75 µl reaction buffer (50 mM Tris-HCl, pH 7.5, 50 mM KCl and 5 mM $MgCl_2$, 10 µM unlabelled ATP supplemented with 1–5 µCi (equivalent to 0.1–0.5 µM) [γ-$^{32}$P]ATP or [γ-$^{33}$P]ATP, and 20 µg/ml of GST-Fos-1p protein). The reaction is incubated for 30 minutes at room temperature, and terminated by the addition of 25 µl EDTA to a final concentration of 25 mM. Next, to each well is added 150 µl of 50 mM Tris-HCl, pH 7.5 buffer containing 5% $Na_2HPO_4$ if using DEAE filters, or 500 mM NaCl if using nitrocellulose filters. The filter plate is then subjected to filtration under vacuum to remove the reaction mixtures from the wells using a Millipore Manifold vacuum device. Next, each well is washed with 900 µl of DEAE or nitrocellulose wash buffer (as described above), which is removed from the wells by filtration under vacuum. These washing steps are required to removed free radiolabelled ATP from the wells and filters. Finally, each well is washed with 400 µl of water to remove salts. The filter plate is dried at 37° C. for 2 hours.

Measurement of Kinase Activity by Scintillation Counting

After drying, radioactivity associated with each well is quantitated by adding 200 µl of a suitable scintillation fluid (e.g., MicroScint 20, Packard Instrument Co.) and scintillation counting using a suitable scintillation counter (e.g., Packard TopCount MicroPlate Scintillation Counter, Packard Instrument Co.). Relative counts between reaction wells with or without the test compound indicate whether or not the test compound inhibited histidine kinase protein activity.

This kinase assay and scintillation counting protocol may be automated by using robotics for high throughput screening (e.g., the Biomek 2000 robot from Beckman Instruments, Inc.)

Measurement of Kinase Activity by Visualization following PAGE

As an alternative to scintillation counting, phosphorylation of the histidine kinase protein, or phosphorylation of another peptide or protein target may be determined by direct visualization by resolving the proteins on polyacrylamide gel electrophoresis followed by autoradiography or radioimaging analysis.

When using such techniques, the following protocol may be used. The kinase reaction is run identically to that described above. However, the reaction is terminated by the addition of 4:1 volumes of SDS-PAGE stop solution containing 125 mM Tris-HCl, pH 6.8, 4% SDS, 10% β-mercaptoethanol, 20% glycerol, and 0.1% bromophenol blue. The samples are then subjected to SDS-PAGE followed by autoradiography or radioimaging analysis and quantitation (e.g., using a PhosphorImager, Molecular Dynamics, Sunnyvale, Calif.). The images obtained with such an imager can be used to quantitate the relative level of radioactivity associated with a protein band corresponding to the histidine kinase protein or other kinase substrate.

2) Identification of Compounds Which Inhibit the Growth of Fungi in Culture

As a second step in the identification of candidate drugs that have antifungal activity in humans, the antifungal activity of a candidate compound in culture may be assessed. Methods to test the antifungal activity of a compound in culture are known in the art, and are provided in many sources. For example, such protocols can be found in the National Committee for Clinical Laboratory Standards (NCCLS) Protocol book (Galgiani et al., NCCLS, 15:1–29 [1995]).

One such protocol which finds use with the present invention is the growth inhibition assay to assess the sensitivity of a fungal strain to a compound, as described in Example 19. It is not intended that the present invention be limited to use of this one protocol, as it is contemplated that other fungal growth assays, and variations thereof, also find use with the present invention.

Briefly, serial dilutions of a candidate anti-fungal compound are made in 100 µl of 1×RPMI medium (Life Technologies) and an additional 100 µl 1×RPMI medium containing $2 \times 10^4$ conidia/ml of a test fungal strain is added to each well of 96-well microtiter plates C. albicans or A. fumigatus are equally suitable for use in this assay. Plates are incubated for 48 hours with gentle shaking at 37° C. The amount of growth in each well is estimated either by eye, by microscope examination, or by using an automated 96-well microplate reader capable of measuring turbidity or light absorbance. Such methods may be easily adapted to allow high throughput screening of large numbers of compounds, and may incorporate robotic automation.

3) Identification of Compounds Which Inhibit or Eliminate Fungal Infection in an In Vivo Mouse Model System.

Lastly, compounds which demonstrate an ability to inhibit histidine kinase protein activity in vitro and have antifungal properties in culture are tested in an in vivo mouse model of candidosis/candidemia, as described in Example 13.

This fungal infection model is known in the art (Hanson et al., Antimicrob. Agents Chemother., 35:1334–1337 [1991]). In this assay, five-week-old female CD-1 mice (Charles River Laboratories) are infected intravenously with a wild-type C. albicans strain. The fungal inoculum is prepared by overnight incubation of the fungal strain in modified synthetic amino acid medium-fungal broth (Hanson and Stevens, Antimicrob. Agents Chemother., 36:486–488 [1992]) at 37° C. with shaking at 140 rpm. Cells are harvested and washed twice with sterile saline followed by centrifugation. The cell pellets are resuspended in sterile saline and the number of cells determined by hemacytometer count. Cells are further diluted in sterile saline to obtain the desired inoculum concentration, where $6 \times 10^4$ C. albicans cells are delivered intravenously in a volume of 0.25 ml. Concurrent with the inoculum, the mice are coinjected with a test compound, at an approximate concentration of, but not limited to, 10–100 mg/kg body weight. Mouse mortality is scored through 30 days post infection. Alternatively, mice are injected with the test compound after a fixed interval of time following the original inoculation with C. albicans.

By comparing the mortality of mice injected with the pathogenic fungal strain with the mortality of mice also receiving coinjection of a candidate antifungal drug, compounds which show potential use as antifungal agents can be identified.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated nucleotide sequence selected from the group consisting of the nucleotide sequence encoding the polypeptide comprising the amino acid sequence set forth in SEQ ID NO:35, and its fully complementary sequence.

2. A composition comprising the nucleotide sequence of claim 1.

3. An isolated nucleotide sequence selected from the group consisting of SEQ ID NO:34, SEQ ID NO:36, and their fully complementary sequences.

4. A composition comprising the nucleotide sequence of claim 3.

5. A vector comprising the nucleotide sequence encoding the polypeptide comprising the amino acid sequence set forth in SEQ ID NO:35.

6. The vector of claim 5, wherein said vector is an expression vector.

7. A host cell containing the vector of claim 5, where said host cell is selected from the group consisting of prokaryotic cells and eukaryotic cells.

8. An isolated nucleotide sequence selected from the group consisting of a nucleotide sequence which hybridizes to the complement of the sequence set forth in SEQ ID NO:36 under stringent conditions in 0.5 M $NaH_2PO_4$, pH 7.2, containing 5% SDS at 65° C. overnight, followed by washing once in 40 mM $Na_2HPO_4$, containing 5% SDS, and once in 40 mM $Na_2HPO_4$ containing 1% SDS, wherein said nucleotide sequence encodes a protein having histidine kinase activity, and the complement of said nucleotide sequence.

* * * * *

SEQUENCE LISTING

<160> NUMBER OF SEQ ID NOS: 73

<210> SEQ ID NO 1
<211> LENGTH: 6545
<212> TYPE: DNA
<213> ORGANISM: Neurospora crassa

<400> SEQUENCE: 1

| | | | | | |
|---|---|---|---|---|---|
| agatcttggt | catgaacgtg | gacggctcga | tgtgagaagt | gaaacccaag atataatgct | 60 |
| caaagggttc | catacatacg | cagtactgcg | tagtgtacat | caagtcatac gcgcagagca | 120 |
| cagaccaccc | atacaatatc | aaccctcagg | tcccaagggg | ccaagcacgg cagcaccaca | 180 |
| agcaagagga | agcaaccaag | aagcccgagt | tcagttcatt | gcctgccttg ccgtgcagga | 240 |
| agcgcagcca | gcgctgatcc | ctcccttact | cggcgcactc | ggccggcaaa caccccacc | 300 |
| agcccacccc | catcccgttt | ctgcggcctc | tcgtctctct | tcctgcgcgg ctgtgaagca | 360 |
| tggaaatcaa | ctggagagcc | aaaggggaag | acctgaagac | gggagattac cttagcaagc | 420 |
| actggagagg | cttcgttctt | ctctgacttc | ctttgacccct | gcctggtgtt tgacctcgcc | 480 |
| cagtaacaac | aacaacaaca | acaacaacaa | caacagacca | ctccgggcaa caagtctcag | 540 |
| accttggatc | cgccctccac | cctcgtcgtc | cgcgcgccgc | cattatcctt gttggccatc | 600 |
| gtcggccctg | tccctttctc | atcccatccg | ttttcccttt | cagaatttcc ccatccacgt | 660 |
| gccatccatc | ttctcgacga | agcccttttc | cgcacttgat | ttacctgaac gctccgtcca | 720 |
| cagtacactg | tacaagagtt | cccccgtcaa | cctcaacctc | cctaggtagc aacttggaaa | 780 |
| agaggatgaa | gagagagtcg | actgatggga | taggcaaaac | agttgggagc gaaaaagaaa | 840 |
| agaaacaaaa | accaaagcga | cgctaggaag | aatcgagtgc | agtggtcaac ggcaccaaaa | 900 |
| ccatacccga | ttcattcagc | cattcaacgc | tcggcgggcg | ccctgttcc ccgtcgcacg | 960 |
| gcactaacag | aactagcact | gtgctcctcc | tcctcctcct | cctcctcctc tagcgctccg | 1020 |
| acggactctg | cacctggagt | ttacagactg | acactgcacg | cagtgccctg ctgcggcccg | 1080 |
| gagggtctgt | ctttggtctc | cagtcccgtt | ccagtcccgt | ccatccagga gccagtgatc | 1140 |
| tgatcccatc | caacccagtc | gacccagtcc | acgcccgctg | ccagccagtc gagtccaggc | 1200 |
| accgctcgat | aactctcctc | tttctccgcc | tcactctccc | aaccacagtc cacccaccga | 1260 |
| ccgggccacc | accactcacc | accaccacca | cggcccggac | ttcttcaacc gcagcagcag | 1320 |
| cgcaaggagc | caggcccagc | aacagatcag | ccagctctca | gcagcagcag cagcagcaac | 1380 |
| agcagcagca | gtgccagccc | agtccagtcc | agtccagtcc | gcagtccgcc cgcagtcgtc | 1440 |
| aacgactgac | tgactgactg | aacctgagga | cgagactaga | ctcgctacct acctctacct | 1500 |
| acctacctac | ctacctacct | acctacccac | ccaccgctgt | cgctgtcccc agtcaatcct | 1560 |
| actacctgac | ctaccttagc | cacggagaaa | aaggcgacca | aaacaggcaa acaaaatctc | 1620 |
| ctactgcctc | ctcgcaccga | ggcgcacgtc | gagtctccga | gcctgaagcc tccgtccagc | 1680 |
| tccagctccc | gctctccttt | cgcgatacaa | tcctttttg | aaaaacacaa ttcccaccca | 1740 |
| tcgcggcggg | atatctagta | caaacagtga | gcccactccc | caccagcact gttctttcgt | 1800 |
| ctgaaactgt | caattatacg | cacgcgcttg | cttctcttcac | acctttgctg acgatcccct | 1860 |
| gcttcaagac | caccacaaac | ccgacgctct | gcattgcaat | ttcgcaacat aaccacatca | 1920 |
| agctacccaa | ccagcaacac | agcccagaga | ccagagatcg | attacaacgc cgctccctat | 1980 |
| tctctcgagt | ccatctccca | tctcgattca | attgaaacca | acttcttaga cccgcaaacg | 2040 |

```
cccatgaagt cgcaagagtc gattgttacc cactagcttc cgcgccttgc ccgactgcgt    2100
ttcctgctct attccgtccc caaggctcac ggcgccaacg gccgtagccc acaatcatga    2160
ctgacggacc aactctcgca gctattgctg ctctcgtcaa atccctggct gtcgacccgg    2220
ccactaccca gacctctgga cttcgcccaa gcacccatgt caggcttccc ggtccgtata    2280
cccgtgagaa gggtgatctg gagcgtgagc tctcggctct tgttgtccgc atagagcagc    2340
tggagactgc cgccatcgct gcctctcctc cagccatgcc cgatacacca aatgcgccaa    2400
ccgatgcgct gttttcaaac ggcacccttt cgccatcctc ggaaacgcct gatgcccgct    2460
accccgctcc gctaccgcgg aatggcttca tcgacgaggc ccttgagggt ctccgcgagc    2520
atgtcgacga ccagtccaag ctgcttgaca gccagcgtca ggagcttgct ggggtcaacg    2580
cccagctgat tgagcaaaag caacttcagg aaaaggctct ggctattatc gaacaggaac    2640
gggttgctac ccttgagcgg gaactctgga agcatcaaaa ggccaacgag gccttccaaa    2700
aggctctccg agaaatcggt gagattgtca ctgccgtcgc cagggggtgat ttgtccaaaa    2760 aggtccggat gaactcggtg gaaatggacc cggaaatcac caccttcaag cgtacgataa    2820
acacaatgat ggaccagttg caagtcttct ccagcgaagt ctcgcgtgtc gctcgtgaag    2880
tcggaaccga gggtattctc ggtggccaag ctcagatcga aggcgttgac ggcacctgga    2940
aggaactcac agacaacggt atgtttgatc ccatcttgac agccgcagcc gtagtggcct    3000
atgtgtactg atcatatcat ctagtcaacg tcatggccca gaatcttacc gaccaagtgc    3060
gagagattgc ttccgtaacg actgctgtcg ctcatggcga tcttaccaag aaaatcgagc    3120
gtcccgccaa gggagaaata cttcaacttc aacaaaccat caacacaatg gtggatcagc    3180
tacggacttt cgcctctgaa gttacacgtg tcgccagaga tgtcggtacc gagggtatcc    3240
tcggtggtca agccgacgtt gaaggagtcc agggcatgtg gaacgaactt acggttaatg    3300
tgaacgccat ggccaacaat ctaacaaccc aagtcagaga tatcatcaag gttactaccg    3360
ctgtcgccaa gggtgacctt actcaaaaag tacaagctga atgccgcggt gagattttcg    3420
aactgaagaa gactatcaac tctatggtgg accaactaca acaatttgct cgggaagtca    3480
caaagatcgc cagggaagtc ggaaccgaag gaaggctcgg tgggcaggcc actgttcacg    3540
atgttcaggg tacttggagg gacctcaccg aaaacgtcaa cggcatggcc atgaacttga    3600
ccacacaggt gcgagaaatc gcaaaggtta ctacagccgt cgccaagggt gatttgacca    3660
agaagattgg ggtcgaggtt cagggtgaga tcctggattt gaagaacacc atcaacacca    3720
tggttgaccg tcttggtact ttcgctttcg aggtcagcaa ggtcgccagg gaagtcggca    3780
ccgatggtac cttgggtggt caggcacagg ttgataatgt ggagggcaag tggaaggatc    3840
tcacagagaa cgtcaacacc atggccagca accttacatc tcaggtaagc tgctcctaga    3900
tgatcctttg cggcatgcac tgtttgctaa ctttttcacag gtccgtggga tctctaccgt    3960
cacacaagcc attgccaatg gtgatatgag ccgcaagatt gaagttgaag ccaagggaga    4020
gatactcata ctcaaggaga ctatcaacaa catggttgac cgactctcca tttctctgtaa    4080 tgaggtgcag agagtcgcca aggatgtcgg tgtcgatggt atcatgggag acaagccga    4140 tgttgctggc ctgaagggca ggtggaagga aattccacc gatgtcaaca caatggcgaa    4200
taacttggta tgtctcgccg ccgccagcac ccttgaacag caccccttt tgctaatgcc    4260 ttttacagac ggctcaagtg agagcgttcg gcgacatcac aaatgcagca acagacgggg    4320
actttacaaa actcgtcgag gtagaagcct cgggcgagat ggacgaactc aaaaagaaga    4380
```

-continued

```
tcaatcagat ggtctacaat ttgagggaca gtattcaacg taatacccag gccagggaag       4440
ccgccgaact ggccaataag accaagtccg agttttttggc gaacatgtcc cacgaaatac      4500
gcacacccat gaacggcatt atcggcatga cacaacttac tctcgatact gacctgacac      4560
agtatcagag agaaatgctc aacattgtca actccctggc caacagctta ctgaccatca      4620
tcgacgacat tttggatctg tccaagatcg aagctaggcg tatggtcatc gaagagattc      4680
cttatacgtt gcgtggcacc gtcttcaacg cgctcaagac tcttgccgtc aaggcaaacg      4740
agaagtttct ggatcttacc tatcgtgtcg accattctgt acccgaccac gtcgtcggag      4800
actccttcag gttgcgccag attattctta accttgttgg caacgctatc aagttcaccg      4860
agcatggtga agtcagtctt accatccaga aggcctcttc agtacagtgc agcaccgaag      4920
agtacgctat cgagtttgtc gtttccgaca ctggtatcgg tattccggcg acaagctgg       4980 atctcatctt cgacactttc cagcaggccg atggttcaat gactcgcaag tttggcggta      5040
ctggtctcgg tctctccatt tccaagcgtc ttgtcaacct catgggtggt gacgtgtggg      5100
tgaagagtga gtatggtaag ggtagcaagt tcttcttcac ctgcgtggtc cgcttggcca      5160
acgacgatat ttcgttgatc gccaagcagc tcaaccctta caagagtcac caggtcctgt      5220
tcatcgacaa gggccgcacc ggacatggac cggagatcgc caagatgctc cacggcttgg      5280
gcctcgttcc catcgtcgtc gactcggaga ggaatcctgc gctcgagaag gccagagctg      5340
ccggccaggc gccctacgac gtcatcattg tggactcgat cgaggatgca aggcgcttgc      5400
ggtctgttga cgactttaag taccttccca tcgtattgct agcaccagtc gttcacgtct      5460
cgctaaagtc ttgccttgac ttgggtatca cgtcgtacat gacgacgcct tgtcaactca      5520
ttgacctcgg taacggcatg gtccctgctc tcgaaaatag ggctacgccg tcgctggcgg      5580
acaacaccaa atcttttgag atcctgcttg ccgaagacaa cacggtcaac cagaggctcg      5640
cggtcaagat cctggagaag tatcaccacg tcgtcaccgt tgttggaaac ggtgaagagg      5700
ctgttgaggc cgtcaagagg aaaaagttcg atgtcattct tatggacgtc cagatgccta      5760
ttatggtgag tcaaagctgt ttttcaaacc aagaagccga tgctaacaat tttcataggg      5820
cggtttcgaa gctacggcca agattcgcga gtacgagcgc agcctcggca gccagcgcac      5880
acccatcatc gccctcacgg cgcatgccat gatgggtgac agggaaaagt gtatccaggc      5940
acagatggac gagtatctct ccaagccgct gcagcagaac catctaatcc agaccatact      6000
caagtgtgcg acgctcggcg ggcaactact cgagaagaac cggagcgcg agctgacccg      6060 tgctgccgat gccgtcacag gcggccgccg cgacaacggc atgtactctg ccagccaagc      6120
cgcgcagcac gctgcgctcc gcccacccct cgccaccagg ggcctcactg ccgccgacag      6180
cctcgtctcc ggcttggaga gcccatccat cgtgacggcg ataaggagg atcctctgag       6240 cagggcacgt gcaagcctct ccgaacccaa catccataaa gcaagctaac cgtgtggatg      6300
ggtcaattct gactttatt ggaggaattt agctggtcat acgagcacat actactcttt        6360
gatcaacatc gcgtgcgata caccaagcaa ccaacggcca cgccaactta agtggaaga       6420 agtttttatg agatgggatg gaaggaaaaa gaaacgaaga gagaaaggga agaagaaagg      6480
atggaaagtg gatggagtcc gtgttgtctt tatcgtgttg tgtgtttctc tgtccggtac      6540
ccggg                                                                  6545
```

<210> SEQ ID NO 2
<211> LENGTH: 1298
<212> TYPE: PRT
<213> ORGANISM: Neurospora crassa -continued

```
<400> SEQUENCE: 2

Met Thr Asp Gly Pro Thr Leu Ala Ala Ile Ala Ala Leu Val Lys Ser
  1               5                  10                  15

Leu Ala Val Asp Pro Ala Thr Thr Gln Thr Ser Gly Leu Arg Pro Ser
                 20                  25                  30

Thr His Val Arg Leu Pro Gly Pro Tyr Thr Arg Glu Lys Gly Asp Leu
             35                  40                  45

Glu Arg Glu Leu Ser Ala Leu Val Val Arg Ile Glu Gln Leu Glu Thr
         50                  55                  60

Ala Ala Ile Ala Ala Ser Pro Pro Ala Met Pro Asp Thr Pro Asn Ala
 65                  70                  75                  80

Pro Thr Asp Ala Leu Phe Ser Asn Gly Thr Leu Ser Pro Ser Ser Glu
                 85                  90                  95

Thr Pro Asp Ala Arg Tyr Pro Ala Pro Leu Pro Arg Asn Gly Phe Ile
            100                 105                 110

Asp Glu Ala Leu Glu Gly Leu Arg Glu His Val Asp Asp Gln Ser Lys
            115                 120                 125

Leu Leu Asp Ser Gln Arg Gln Glu Leu Ala Gly Val Asn Ala Gln Leu
130                 135                 140

Ile Glu Gln Lys Gln Leu Gln Glu Lys Ala Leu Ala Ile Ile Glu Gln
145                 150                 155                 160

Glu Arg Val Ala Thr Leu Glu Arg Glu Leu Trp Lys His Gln Lys Ala
                165                 170                 175

Asn Glu Ala Phe Gln Lys Ala Leu Arg Glu Ile Gly Glu Ile Val Thr
            180                 185                 190

Ala Val Ala Arg Gly Asp Leu Ser Lys Lys Val Arg Met Asn Ser Val
            195                 200                 205

Glu Met Asp Pro Glu Ile Thr Thr Phe Lys Arg Thr Ile Asn Thr Met
    210                 215                 220

Met Asp Gln Leu Gln Val Phe Ser Ser Glu Val Ser Arg Val Ala Arg
225                 230                 235                 240

Glu Val Gly Thr Glu Gly Ile Leu Gly Gly Gln Ala Gln Ile Glu Gly
                245                 250                 255

Val Asp Gly Thr Trp Lys Glu Leu Thr Asp Asn Val Asn Val Met Ala
            260                 265                 270

Gln Asn Leu Thr Asp Gln Val Arg Glu Ile Ala Ser Val Thr Thr Ala
            275                 280                 285

Val Ala His Gly Asp Leu Thr Lys Lys Ile Glu Arg Pro Ala Lys Gly
            290                 295                 300

Glu Ile Leu Gln Leu Gln Gln Thr Ile Asn Thr Met Val Asp Gln Leu
305                 310                 315                 320

Arg Thr Phe Ala Ser Glu Val Thr Arg Val Ala Arg Asp Val Gly Thr
                325                 330                 335

Glu Gly Ile Leu Gly Gly Gln Ala Asp Val Glu Gly Val Gln Gly Met
            340                 345                 350

Trp Asn Glu Leu Thr Val Asn Val Asn Ala Met Ala Asn Asn Leu Thr
            355                 360                 365

Thr Gln Val Arg Asp Ile Ile Lys Val Thr Thr Ala Val Ala Lys Gly
        370                 375                 380

Asp Leu Thr Gln Lys Val Gln Ala Glu Cys Arg Gly Glu Ile Phe Glu
385                 390                 395                 400

Leu Lys Lys Thr Ile Asn Ser Met Val Asp Gln Leu Gln Gln Phe Ala
```

-continued

```
                    405                 410                 415
Arg Glu Val Thr Lys Ile Ala Arg Glu Val Gly Thr Glu Gly Arg Leu
                420                 425                 430
Gly Gly Gln Ala Thr Val His Asp Val Gln Gly Thr Trp Arg Asp Leu
                435                 440                 445
Thr Glu Asn Val Asn Gly Met Ala Met Asn Leu Thr Thr Gln Val Arg
            450                 455                 460
Glu Ile Ala Lys Val Thr Thr Ala Val Ala Lys Gly Asp Leu Thr Lys
465                 470                 475                 480
Lys Ile Gly Val Glu Val Gln Gly Glu Ile Leu Asp Leu Lys Asn Thr
                485                 490                 495
Ile Asn Thr Met Val Asp Arg Leu Gly Thr Phe Ala Phe Glu Val Ser
            500                 505                 510
Lys Val Ala Arg Glu Val Gly Thr Asp Gly Thr Leu Gly Gly Gln Ala
            515                 520                 525
Gln Val Asp Asn Val Glu Gly Lys Trp Lys Asp Leu Thr Glu Asn Val
        530                 535                 540
Asn Thr Met Ala Ser Asn Leu Thr Ser Gln Val Arg Gly Ile Ser Thr
545                 550                 555                 560
Val Thr Gln Ala Ile Ala Asn Gly Asp Met Ser Arg Lys Ile Glu Val
                565                 570                 575
Glu Ala Lys Gly Glu Ile Leu Ile Leu Lys Glu Thr Ile Asn Asn Met
            580                 585                 590
Val Asp Arg Leu Ser Ile Phe Cys Asn Glu Val Gln Arg Val Ala Lys
        595                 600                 605
Asp Val Gly Val Asp Gly Ile Met Gly Gly Gln Ala Asp Val Ala Gly
        610                 615                 620
Leu Lys Gly Arg Trp Lys Glu Ile Thr Thr Asp Val Asn Thr Met Ala
625                 630                 635                 640
Asn Asn Leu Thr Ala Gln Val Arg Ala Phe Gly Asp Ile Thr Asn Ala
                645                 650                 655
Ala Thr Asp Gly Asp Phe Thr Lys Leu Val Glu Val Glu Ala Ser Gly
            660                 665                 670
Glu Met Asp Glu Leu Lys Lys Lys Ile Asn Gln Met Val Tyr Asn Leu
            675                 680                 685
Arg Asp Ser Ile Gln Arg Asn Thr Gln Ala Arg Glu Ala Ala Glu Leu
        690                 695                 700
Ala Asn Lys Thr Lys Ser Glu Phe Leu Ala Asn Met Ser His Glu Ile
705                 710                 715                 720
Arg Thr Pro Met Asn Gly Ile Ile Gly Met Thr Gln Leu Thr Leu Asp
                725                 730                 735
Thr Asp Leu Thr Gln Tyr Gln Arg Glu Met Leu Asn Ile Val Asn Ser
            740                 745                 750
Leu Ala Asn Ser Leu Leu Thr Ile Ile Asp Asp Ile Leu Asp Leu Ser
            755                 760                 765
Lys Ile Glu Ala Arg Arg Met Val Ile Glu Glu Ile Pro Tyr Thr Leu
        770                 775                 780
Arg Gly Thr Val Phe Asn Ala Leu Lys Thr Leu Ala Val Lys Ala Asn
785                 790                 795                 800
Glu Lys Phe Leu Asp Leu Thr Tyr Arg Val Asp His Ser Val Pro Asp
                805                 810                 815
His Val Val Gly Asp Ser Phe Arg Leu Arg Gln Ile Ile Leu Asn Leu
            820                 825                 830
```

-continued

Val Gly Asn Ala Ile Lys Phe Thr Glu His Gly Val Ser Leu Thr
    835                 840                 845

Ile Gln Lys Ala Ser Ser Val Gln Cys Ser Thr Glu Tyr Ala Ile
    850                 855                 860

Glu Phe Val Val Ser Asp Thr Gly Ile Gly Ile Pro Ala Asp Lys Leu
865                 870                 875                 880

Asp Leu Ile Phe Asp Thr Phe Gln Gln Ala Asp Gly Ser Met Thr Arg
                885                 890                 895

Lys Phe Gly Gly Thr Gly Leu Gly Leu Ser Ile Ser Lys Arg Leu Val
            900                 905                 910

Asn Leu Met Gly Gly Asp Val Trp Val Lys Ser Glu Tyr Gly Lys Gly
    915                 920                 925

Ser Lys Phe Phe Phe Thr Cys Val Val Arg Leu Ala Asn Asp Asp Ile
    930                 935                 940

Ser Leu Ile Ala Lys Gln Leu Asn Pro Tyr Lys Ser His Gln Val Leu
945                 950                 955                 960

Phe Ile Asp Lys Gly Arg Thr Gly His Gly Pro Glu Ile Ala Lys Met
                965                 970                 975

Leu His Gly Leu Gly Leu Val Pro Ile Val Asp Ser Glu Arg Asn
            980                 985                 990

Pro Ala Leu Glu Lys Ala Arg Ala Ala Gly Gln Ala Pro Tyr Asp Val
    995                 1000                1005

Ile Ile Val Asp Ser Ile Glu Asp Ala Arg Arg Leu Arg Ser Val Asp
    1010                1015                1020

Asp Phe Lys Tyr Leu Pro Ile Val Leu Leu Ala Pro Val Val His Val
1025                1030                1035                1040

Ser Leu Lys Ser Cys Leu Asp Leu Gly Ile Thr Ser Tyr Met Thr Thr
                1045                1050                1055

Pro Cys Gln Leu Ile Asp Leu Gly Asn Gly Met Val Pro Ala Leu Glu
            1060                1065                1070

Asn Arg Ala Thr Pro Ser Leu Ala Asp Asn Thr Lys Ser Phe Glu Ile
            1075                1080                1085

Leu Leu Ala Glu Asp Asn Thr Val Asn Gln Arg Leu Ala Val Lys Ile
            1090                1095                1100

Leu Glu Lys Tyr His His Val Val Thr Val Val Gly Asn Gly Glu Glu
1105                1110                1115                1120

Ala Val Glu Ala Val Lys Arg Lys Lys Phe Asp Val Ile Leu Met Asp
                1125                1130                1135

Val Gln Met Pro Ile Met Gly Gly Phe Glu Ala Thr Ala Lys Ile Arg
            1140                1145                1150

Glu Tyr Glu Arg Ser Leu Gly Ser Gln Arg Thr Pro Ile Ile Ala Leu
        1155                1160                1165

Thr Ala His Ala Met Met Gly Asp Arg Glu Lys Cys Ile Gln Ala Gln
    1170                1175                1180

Met Asp Glu Tyr Leu Ser Lys Pro Leu Gln Gln Asn His Leu Ile Gln
1185                1190                1195                1200

Thr Ile Leu Lys Cys Ala Thr Leu Gly Gly Gln Leu Leu Glu Lys Asn
                1205                1210                1215

Arg Glu Arg Glu Leu Thr Arg Ala Ala Asp Ala Val Thr Gly Gly Arg
            1220                1225                1230

Arg Asp Asn Gly Met Tyr Ser Ala Ser Gln Ala Ala Gln His Ala Ala
            1235                1240                1245

```
Leu Arg Pro Pro Leu Ala Thr Arg Gly Leu Thr Ala Ala Asp Ser Leu
    1250                1255                1260

Val Ser Gly Leu Glu Ser Pro Ser Ile Val Thr Ala Asp Lys Glu Asp
1265            1270                1275                1280

Pro Leu Ser Arg Ala Arg Ala Ser Leu Ser Glu Pro Asn Ile His Lys
                1285                1290                1295

Ala Ser

<210> SEQ ID NO 3
<211> LENGTH: 5175
<212> TYPE: DNA
<213> ORGANISM: Neurospora crassa

<400> SEQUENCE: 3
gtccaggcac cgctcgataa ctctcctctt tctccgcctc actctcccaa ccacagtcca      60
cccaccgacc gggccaccac cactcaccac caccaccacg gcccggactt cttcaaccgc     120
agcagcagcg caaggagcca ggcccagcaa cagatcagcc agctctcagc agcagcagca     180
gcagcaacag cagcagcagt gccagcccag tccagtccag tccagtccgc agtccgcccg     240
cagtcgtcaa cgactgactg actgactgaa cctgaggacg agactagact cgctacctac     300
ctctacctac ctacctacct acctacctac ctacccaccc accggtggcg gtgtccccag     360
tacaaatcct actacctgac ctaccttagc cacggagaaa aaggggaaca aaaacgggca     420
aaacaaaatc tcctactgcc tcctgcgcac cgaggcgcac gtcgagtctc cgagcctgaa     480
gcctccgtcc agctccacgt cccgctctcc tttcgcgata caatcctttt ttgaaaaaca     540
caattcccac ccatcgcggc gggatatcta gtacaaacaa ccaccacaaa cccgacgctc     600
tgcatgtgca atttcgcaac ataaccacat caagctaccc aaccagcaac acagcccaga     660
gaccagagat cgattacaac gccgctccct attctctcga gtccatctcc catctcgatt     720
caattgaaac caacttctta gacccgcaaa cgcccatgaa gtcgcaagag tcgattgtta     780
cccactagct tccgcgcctt gcccgactgc gtttcctgct ctattccgtc cccaaggctc     840
acggcgccaa cggccgtagc ccacaatcat gactgacgga ccaactctcg cagctattgc     900
tgctctcgtc aaatccctgg ctgtcgaccc ggccactacc cagacctctg gacttcgccc     960
aagcacccat gtcaggcttc ccggtccgta tacccgtgag aagggtgatc tggagcgtga    1020
gctctcggct cttgttgtcc gcatagagca gctggagact gccgccatcg ctgcctctcc    1080
tccagccatg cccgatacac caaatgcgcc aaccgatgcg ctgttttcaa acggcaccct    1140
ttcgccatcc tcggaaacgc ctgatgcccg ctaccccgct ccgctaccgc gaaatggctt    1200
catcgacgag gcccttgagg gtctccgcga gcatgtcgac gaccagtcca agctgcttga    1260
cagccagcgt caggagcttg ctggggtcaa cgcccagctg attgagcaaa agcaacttca    1320
ggaaaaggct ctggctatta tcgaacagga acgggttgct acccttgagc gggaactctg    1380
gaagcatcaa aaggccaacg aggccttcca aaaggctctc cgagaaatcg gtgagattgt    1440
cactgccgtc gccaggggtg atttgtccaa aaaggtccgg atgaactcgg tggaaatgga    1500
cccggaaatc accaccttca gcgtacgat aaacacaatg atggaccagt gcaagtctt     1560
ctccagcgaa gtctcgcgtg tcgctcgtga agtcggaacc gagggtattc tcggtggcca    1620
agctcagatc gaaggcgttg acggcacctg gaaggaactc acagacaacg tcaacgtcat    1680
ggcccagaat cttaccgacc aagtgcgaga gattgcttcc gtaacgactg ctgtcgctca    1740
tggcgatctt accaagaaaa tcgagcgtcc cgccaaggga gaaatacttc aacttcaaca    1800
```

-continued

```
aaccatcaac acaatggtgg atcagctacg gactttcgcc tctgaagtta cacgtgtcgc   1860
cagagatgtc ggtaccgagg gtatcctcgg tggtcaagcc gacgttgaag gagtccaggg   1920
catgtggaac gaacttacgg ttaatgtgaa cgccatggcc aacaatctaa caacccaagt   1980
cagagatatc atcaaggtta ctaccgctgt cgccaagggt gaccttactc aaaaagtaca   2040
agctgaatgc cgcggtgaga ttttcgaact gaagaagact atcaactcta tggtggacca   2100
actacaacaa tttgctcggg aagtcacaaa gatcgccagg gaagtcggaa ccgaaggaag   2160
gctcggtggg caggccactg ttcacgatgt tcagggtact tggagggacc tcaccgaaaa   2220
cgtcaacggc atggccatga acttgaccac acaggtgcga gaaatcgcaa aggttactac   2280
agccgtcgcc aagggtgatt tgaccaagaa gattggggtc gaggttcagg gtgagatcct   2340
ggatttgaag aacaccatca acaccatggt tgaccgtctt ggtactttcg ctttcgaggt   2400
cagcaaggtc gccagggaag tcggcaccga tggtaccttg ggtggtcagg cacaggttga   2460
taatgtggag ggcaagtgga aggatctcac agagaacgtc aacaccatgg ccagcaacct   2520
tacatctcag gtccgtggga tctctaccgt cacacaagcc attgccaatg gtgatatgag   2580
ccgcaagatt gaagttgaag ccaagggaga gatactcata ctcaaggaga ctatcaacaa   2640
catggttgac cgactctcca ttttctgtaa tgaggtgcag agagtcgcca aggatgtcgg   2700
tgtcgatggt atcatgggag acaagccga tgttgctggc ctgaagggca ggtggaagga   2760
aattaccacc gatgtcaaca caatggcgaa taacttgacg gctcaagtga gagcgttcgg   2820
cgacatcaca aatgcagcaa cagacgggga ctttacaaaa ctcgtcgagg tagaagcctc   2880
gggcgagatg gacgaactca aaaagaagat caatcagatg gtctacaatt tgagggacag   2940
tattcaacgt aatacccagg ccagggaagc cgccgaactg gccaataaga ccaagtccga   3000
gtttttggcg aacatgtccc acgaaatacg cacacccatg aacggcatta tcggcatgac   3060
acaacttact ctcgatactg acctgacaca gtatcagaga gaaatgctca acattgtcaa   3120
ctccctggcc aacagcttac tgaccatcat cgacgacatt ttggatctgt ccaagatcga   3180
agctaggcgt atggtcatcg aagagattcc ttatacgttg cgtggcaccg tcttcaacgc   3240
gctcaagact cttgccgtca aggaaaccga gaagtttctg gatcttacct atcgtgtcga   3300
ccattctgta cccgaccacg tcgtcggaga ctccttcagg ttgcgccaga ttattcttaa   3360
ccttgttggc aacgctatca agttcaccga gcatggtgaa gtcagtctta ccatccagaa   3420
ggcctcttca gtacagtgca gcaccgaaga gtacgctatc gagtttgtcg tttccgacac   3480
tggtatcggt attccggcgg acaagctgga tctcatcttc gacactttcc agcaggccga   3540
tggttcaatg actcgcaagt ttggcggtac tggtctcggt ctctccattt ccaagcgtct   3600
tgtcaacctc atgggtggtg acgtttgggt gaagagtgag tatggtaagg gtagcaagtt   3660
cttcttcacc tgcgtggtcc gcttggccaa cgacgatatt tcgttgatcg ccaagcagct   3720
caacccttac aagagtcacc aggtcctgtt catcgacaag ggccgcaccg gacatggacc   3780
ggagatcgcc aagatgctcc acggcttggg cctcgttccc atcgtcgtcg actcggagag   3840
gaatcctgcg ctcgagaagg ccagagctgc cggccaggcg ccctacgacg tcatcattgt   3900
ggactcgatc gaggatgcaa ggcgcttgcg gtctgttgac gactttaagt accttcccat   3960
cgtattgcta gcaccagtcg ttcacgtctc gctaaagtct tgccttgact tgggtatcac   4020
gtcgtacatg acgacgcctt gtcaactcat tgacctcggt aacggcatgg tccctgctct   4080
cgaaaatagg gctacgccgt cgctggcgga caacaccaaa tcttttgaga tcctgcttgc   4140
cgaagacaac acggtcaacc agaggctcgc ggtcaagatc ctggagaagt atcaccacgt   4200
```

-continued

| | | | | |
|---|---|---|---|---|
| cgtcaccgtt | gttggaaacg | gtgaagaggc | tgttgaggcc | gtcaagagga aaaagttcga | 4260 |
| tgtcattctt | atggacgtcc | agatgcctat | tatgggcggt | ttcgaagcta cggccaagat | 4320 |
| tcgcgagtac | gagcgcagcc | tcggcagcca | gcgcacaccc | atcatcgccc tcacggcgca | 4380 |
| tgccatgatg | ggtgacaggg | aaaagtgtat | ccaggcacag | atggacgagt atctctccaa | 4440 |
| gccgctgcag | cagaaccatc | taatccagac | catactcaag | tgtgcgacgc tcggcgggca | 4500 |
| actactcgag | aagaaccggg | agcgcgagct | gacccgtgct | gccgatgccg ttacaggcgg | 4560 |
| ccgccgcgac | aacggcatgt | actctgccag | ccaagccgcg | cagcacgctg cgctccgccc | 4620 |
| acccctcgcc | accaggggcc | tcactgccgc | cgacagcctc | gtctccggct tggagagccc | 4680 |
| atccatcgtg | acggcggata | aggaggatcc | tctgagcagg | gcacgtgcaa gcctctccga | 4740 |
| acccaacatc | cataaagcaa | gctaaccgtg | tggatgggtc | aattctgact tttattggag | 4800 |
| gaatttagct | ggtcatacga | gcacatacta | ctctttgatc | aacatcgcgt gcgatacacc | 4860 |
| aagcaaccaa | cggccacgcc | aacttaaagt | ggaagaaggt | ttttatgaga tgggatggaa | 4920 |
| ggaaaaagaa | acgaggagag | aaagggagga | agaaaggatg | gaaagtggat ggagtccgtg | 4980 |
| ttgtctttat | cgtgttgtgt | gttttctctg | tccggtaccc | gggttcaaaa tcaggttttt | 5040 |
| aaggtccaaa | ggcggtttct | gttatcaaca | aggcattgaa | attattactt gcggctggtt | 5100 |
| tgctagtttt | caattttgga | tgtcttgttc | ctctgtctcg | tgtctctctc gtatttactg | 5160 |
| gttcggactg | ttgga | | | | 5175 |

<210> SEQ ID NO 4
<211> LENGTH: 5697
<212> TYPE: DNA
<213> ORGANISM: Neurospora crassa

<400> SEQUENCE: 4

| | | | | |
|---|---|---|---|---|
| ggatccgccc | tccaccctcg | tcgtccgcgc | gccgccatta | tccttgttgg ccatcgtcgg | 60 |
| ccctgtccct | ttctcatccc | atccgttttc | cctttcagaa | tttccccatc cacgtgccat | 120 |
| ccatcttctc | gacgaagccc | ttttccgcac | ttgatttacc | tgaacgctcc gtccacagta | 180 |
| cactgtacaa | gagttccccc | gtcaacctca | acctccctag | gtagcaactt ggaaaagagg | 240 |
| atgaagagag | agtcgactga | tgggataggc | aaaacagttg | ggagcgaaaa agaaaagaaa | 300 |
| caaaaaccaa | agcgacgcta | ggaagaatcg | agtgcagtgg | tcaacggcac caaaaccata | 360 |
| cccgattcat | tcagccattc | aacgctcggc | gggcgcccct | gttccccgtc gcacggcact | 420 |
| aacagaacta | gcactgtgct | cctcctcctc | ctcctcctcc | tcctctagcg ctccgacgga | 480 |
| ctctgcacct | ggagtttaca | gactgacact | gcacgcagtg | ccctgctgcg gccccgacga | 540 |
| gtctgtcttt | ggtctccagt | cccgttccag | tcccgtccat | ccaggagcca gtgatctgat | 600 |
| cccatccaac | ccagtcgacc | cagtccacgc | ccgctgccag | ccagtcgagt ccaggcaccg | 660 |
| ctcgataact | ctcctctttc | tccgcctcac | tctcccaacc | acagtccacc caccgaccgg | 720 |
| gccaccacca | ctcaccacca | ccaccacggc | ccggacttct | tcaaccgcag cagcagcgca | 780 |
| aggagccagg | cccagcaaca | gatcagccag | ctctcagcag | cagcagcagc agcaacagca | 840 |
| gcagcagtgc | cagcccagtc | cagtccagtc | cagtccgcag | tccgcccgca gtcgtcaacg | 900 |
| actgactgac | tgactgaacc | tgaggacgag | actagactcg | ctacctacct ctacctacct | 960 |
| acctacctac | ctacctacct | acccacccac | cggtggcggt | gtcccagta caaatcctac | 1020 |
| tacctgacct | accttagcca | cggagaaaaa | ggggaacaaa | acgggcaaa acaaaatctc | 1080 |

-continued

```
ctactgcctc ctgcgcaccg aggcgcacgt cgagtctccg agcctgaagc ctccgtccag      1140
ctccacgtcc cgctctcctt tcgcgataca atcctttttt gaaaaacaca attcccaccc      1200
atcgcggcgg gatatctagt acaaacagtg agcccactcc ccaccagcac tgttctttcg      1260
tctgaaactg tcaattatac gcacgcgctt gctttcttca cacctttgct gacgatcccc      1320
tgcttcaaga ccaccacaaa cccgacgctc tgcatgtgca atttcgcaac ataaccacat      1380
caagctaccc aaccagcaac acagcccaga gaccagagat cgattacaac gccgctccct      1440
attctctcga gtccatctcc catctcgatt caattgaaac caacttctta gacccgcaaa      1500
cgcccatgaa gtcgcaagag tcgattgtta cccactagct tccgcgcctt gcccgactgc      1560
gtttcctgct ctattccgtc cccaaggctc acggcgccaa cggccgtagc ccacaatcat      1620
gactgacgga ccaactctcg cagctattgc tgctctcgtc aaatccctgg ctgtcgaccc      1680
ggccactacc cagacctctg gacttcgccc aagcacccat gtcaggcttc ccggtccgta      1740
tacccgtgag aagggtgatc tggagcgtga gctctcggct cttgttgtcc gcatagagca      1800
gctggagact gccgccatcg ctgcctctcc tccagccatg cccgatacac caaatgcgcc      1860
aaccgatgcg ctgttttcaa acggcaccct ttcgccatcc tcggaaacgc ctgatgcccg      1920
ctaccccgct ccgctaccgc gaaatggctt catcgacgag gcccttgagg gtctccgcga      1980
gcatgtcgac gaccagtcca agctgcttga cagccagcgt caggagcttg ctggggtcaa      2040
cgcccagctg attgagcaaa agcaacttca ggaaaaggct ctggctatta tcgaacagga      2100
acgggttgct acccttgagc gggaactctg gaagcatcaa aaggccaacg aggccttcca      2160
aaaggctctc cgagaaatcg gtgagattgt cactgccgtc gccagggggtg atttgtccaa      2220 aaaggtccgg atgaactcgg tggaaatgga cccggaaatc accaccttca agcgtacgat      2280
aaacacaatg atggaccagt tgcaagtctt ctccagcgaa gtctcgcgtg tcgctcgtga      2340
agtcggaacc gagggtattc tcggtggcca agctcagatc gaaggcgttg acggcacctg      2400
gaaggaactc acagacaacg gtatgtttga tcccatcttg acagccgcag gccgtagtgg      2460
cctatgtgta ctgatcatat catctagtca acgtcatggc ccagaatctt accgaccaag      2520
tgcgagagat tgcttccgta acgactgctg tcgctcatgg cgatcttacc aagaaaatcg      2580
agcgtcccgc caagggagaa atacttcaac ttcaacaaac catcaacaca atggtggatc      2640
agctacggac tttcgcctct gaagttacac gtgtcgccag agatgtcggt accgagggta      2700
tcctcggtgg tcaagccgac gttgaaggag tccagggcat gtggaacgaa cttacggtta      2760
atgtgaacgc catggccaac aatctaacaa cccaagtcag agatatcatc aaggttacta      2820
ccgctgtcgc caagggtgac cttactcaaa agtacaagc tgaatgccgc ggtgagattt      2880
tcgaactgaa gaagactatc aactctatgg tggaccaact acaacaattt gctcgggaag      2940
tcacaaagat cgccagggaa gtcggaaccg aaggaaggct cggtgggcag gccactgttc      3000
acgatgttca gggtacttgg agggacctca ccgaaaacgt caacggcatg gccatgaact      3060
tgaccacaca ggtgcgagaa atcgcaaagg ttactacagc cgtcgccaag ggtgatttga      3120
ccaagaagat tggggtcgag gttcaggtg agatcctgga tttgaagaac accatcaaca      3180
ccatggttga ccgtcttggt actttcgctt tcgaggtcag caaggtcgcc agggaagtcg      3240
gcaccgatgg taccttgggt ggtcaggcac aggttgataa tgtggagggc aagtggaagg      3300
atctcacaga gaacgtcaac accatggcca gcaaccttac atctcaggta agctgctcct      3360
agatgatcct ttgcggcatg cactgtttgc taacttttca caggtccgtg ggatctctac      3420
cgtcacacaa gccattgcca atggtgatat gagccgcaag attgaagttg aagccaaggg      3480
```

```
agagatactc atactcaagg agactatcaa caacatggtt gaccgactct ccattttctg    3540
taatgaggtg cagagagtcg ccaaggatgt cggtgtcgat ggtatcatgg gaggacaagc    3600
cgatgttgct ggcctgaagg gcaggtggaa ggaaattacc accgatgtca acacaatggc    3660
gaataacttg gtatgtctcg ccgccgccag caccccttgaa cagcacccct ttttgctaat    3720
gccttttaca gacggctcaa gtgagagcgt tcggcgacat cacaaatgca gcaacagacg    3780
gggactttac aaaactcgtc gaggtagaag cctcgggcga gatggacgaa ctcaaaaaga    3840
agatcaatca gatggtctac aatttgaggg acagtattca acgtaatacc caggccaggg    3900
aagccgccga actggccaat aagaccaagt ccgagttttt ggcgaacatg tcccacgaaa    3960
tacgcacacc catgaacggc attatcggca tgacacaact tactctcgat actgacctga    4020
cacagtatca gagagaaatg ctcaacattg tcaactccct ggccaacagc ttactgacca    4080
tcatcgacga cattttggat ctgtccaaga tcgaagctag gcgtatggtc atcgaagaga    4140
ttccttatac gttgcgtggc accgtcttca acgcgctcaa gactcttgcc gtcaaggaaa    4200
ccgagaagtt tctggatctt acctatcgtg tcgaccattc tgtacccgac cacgtcgtcg    4260
gagactcctt caggttgcgc cagattattc ttaaccttgt tggcaacgct atcaagttca    4320
ccgagcatgt tgaagtcagt cttaccatcc agaaggcctc ttcagtacag tgcagcaccg    4380
aagagtacgc tatcgagttt gtcgtttccg acactggtat cggtattccg gcggacaagc    4440
tggatctcat cttcgacact ttccagcagg ccgatggttc aatgactcgc aagtttggcg    4500
gtactggtct cggtctctcc atttccaagc gtcttgtcaa cctcatgggt ggtgacgttt    4560
gggtgaagag tgagtatggt aagggtagca agttcttctt cacctgcgtg gtccgcttgg    4620
ccaacgacga tatttcgttg atcgccaagc agctcaaccc ttacaagagt caccaggtcc    4680
tgttcatcga caagggccgc accggacatg gaccggagat cgccaagatg ctccacggct    4740
tgggcctcgt tcccatcgtc gtcgactcgg agaggaatcc tgcgctcgag aaggccagag    4800
ctgccggcca ggcgccctac gacgtcatca ttgtggactc gatcgaggat gcaaggcgct    4860
tgcggtctgt tgacgacttt aagtaccttc ccatcgtatt gctagcacca gtcgttcacg    4920
tctcgctaaa gtcttgcctt gacttgggta tcacgtcgta catgacgacg ccttgtcaac    4980
tcattgacct cggtaacggc atggtccctg ctctcgaaaa tagggctacg ccgtcgctgg    5040
cggacaacac caaatctttt gagatcctgc ttgccgaaga caacacggtc aaccagaggc    5100
tcgcggtcaa gatcctggag aagtatcacc acgtcgtcac cgttgttgga aacggtgaag    5160
aggctgttga ggccgtcaag aggaaaaagt tcgatgtcat tcttatggac gtccagatgc    5220
ctattatggt gagtcaaagc tgttttttcaa accaagaagc cgatgctaac aattttcata    5280
gggcggtttc gaagctacgg ccaagattcg cgagtacgag cgcagcctcg gcagccagcg    5340
cacacccatc atcgccctca cggcgcatgc catgatgggt gacagggaaa agtgtatcca    5400
ggcacagatg gacgagtatc tctccaagcc gctgcagcag aaccatctaa tccagaccat    5460
actcaagtgt gcgacgctcg gcgggcaact actcgagaag aaccgggagc gcgagctgac    5520
ccgtgctgcc gatgccgtta caggcggccg ccgcgacaac ggcatgtact ctgccagcca    5580
agccgcgcag cacgctgcgc tccgcccacc cctgccacc aggggcctca ctgccgccga    5640
cagcctcgtc tccggcttgg agagcccatc catcgtgacg gcggataagg aggatcc    5697
```

<210> SEQ ID NO 5
<211> LENGTH: 1281
<212> TYPE: PRT

-continued

<213> ORGANISM: Neurospora crassa

<400> SEQUENCE: 5

```
Met Thr Asp Gly Pro Thr Leu Ala Ala Ile Ala Ala Leu Val Lys Ser
  1               5                  10                  15

Leu Ala Val Asp Pro Ala Thr Thr Gln Thr Ser Gly Leu Arg Pro Ser
             20                  25                  30

Thr His Val Arg Leu Pro Gly Pro Tyr Thr Arg Glu Lys Gly Asp Leu
         35                  40                  45

Glu Arg Glu Leu Ser Ala Leu Val Val Arg Ile Glu Gln Leu Glu Thr
     50                  55                  60

Ala Ala Ile Ala Ala Ser Pro Pro Ala Met Pro Asp Thr Pro Asn Ala
 65                  70                  75                  80

Pro Thr Asp Ala Leu Phe Ser Asn Gly Thr Leu Ser Pro Ser Ser Glu
                 85                  90                  95

Thr Pro Asp Ala Arg Tyr Pro Ala Pro Leu Pro Arg Asn Gly Phe Ile
            100                 105                 110

Asp Glu Ala Leu Glu Gly Leu Arg Glu His Val Asp Asp Gln Ser Lys
        115                 120                 125

Leu Leu Asp Ser Gln Arg Gln Glu Leu Ala Gly Val Asn Ala Gln Leu
130                 135                 140

Ile Glu Gln Lys Gln Leu Gln Glu Lys Ala Leu Ala Ile Ile Glu Gln
145                 150                 155                 160

Glu Arg Val Ala Thr Leu Glu Arg Glu Leu Trp Lys His Gln Lys Ala
                165                 170                 175

Asn Glu Ala Phe Gln Lys Ala Leu Arg Glu Ile Gly Glu Ile Val Thr
            180                 185                 190

Ala Val Ala Arg Gly Asp Leu Ser Lys Lys Val Arg Met Asn Ser Val
        195                 200                 205

Glu Met Asp Pro Glu Ile Thr Thr Phe Lys Arg Thr Ile Asn Thr Met
210                 215                 220

Met Asp Gln Leu Gln Val Phe Ser Ser Glu Val Ser Arg Val Ala Arg
225                 230                 235                 240

Glu Val Gly Thr Glu Gly Ile Leu Gly Gly Gln Ala Gln Ile Glu Gly
                245                 250                 255

Val Asp Gly Thr Trp Lys Glu Leu Thr Asp Asn Val Asn Val Met Ala
            260                 265                 270

Gln Asn Leu Thr Asp Gln Val Arg Glu Ile Ala Ser Val Thr Thr Ala
        275                 280                 285

Val Ala His Gly Asp Leu Thr Lys Lys Ile Glu Arg Pro Ala Lys Gly
    290                 295                 300

Glu Ile Leu Gln Leu Gln Gln Thr Ile Asn Thr Met Val Asp Gln Leu
305                 310                 315                 320

Arg Thr Phe Ala Ser Glu Val Thr Arg Val Ala Arg Asp Val Gly Thr
                325                 330                 335

Glu Gly Ile Leu Gly Gly Gln Ala Asp Val Glu Gly Val Gln Gly Met
            340                 345                 350

Trp Asn Glu Leu Thr Val Asn Val Asn Ala Met Ala Asn Asn Leu Thr
        355                 360                 365

Thr Gln Val Arg Asp Ile Ile Lys Val Thr Thr Ala Val Ala Lys Gly
    370                 375                 380

Asp Leu Thr Gln Lys Val Gln Ala Glu Cys Arg Gly Glu Ile Phe Glu
385                 390                 395                 400
```

-continued

```
Leu Lys Lys Thr Ile Asn Ser Met Val Asp Gln Leu Gln Gln Phe Ala
            405                 410                 415
Arg Glu Val Thr Lys Ile Ala Arg Glu Val Gly Thr Glu Gly Arg Leu
        420                 425                 430
Gly Gly Gln Ala Thr Val His Asp Val Gln Gly Thr Trp Arg Asp Leu
        435                 440                 445
Thr Glu Asn Val Asn Gly Met Ala Met Asn Leu Thr Thr Gln Val Arg
    450                 455                 460
Glu Ile Ala Lys Val Thr Thr Ala Val Ala Lys Gly Asp Leu Thr Lys
465                 470                 475                 480
Lys Ile Gly Val Glu Val Gln Gly Glu Ile Leu Asp Leu Lys Asn Thr
                485                 490                 495
Ile Asn Thr Met Val Asp Arg Leu Gly Thr Phe Ala Phe Glu Val Ser
            500                 505                 510
Lys Val Ala Arg Glu Val Gly Thr Asp Gly Thr Leu Gly Gly Gln Ala
        515                 520                 525
Gln Val Asp Asn Val Glu Gly Lys Trp Lys Asp Leu Thr Glu Asn Val
    530                 535                 540
Asn Thr Met Ala Ser Asn Leu Thr Ser Gln Val Arg Gly Ile Ser Thr
545                 550                 555                 560
Val Thr Gln Ala Ile Ala Asn Gly Asp Met Ser Arg Lys Ile Glu Val
                565                 570                 575
Glu Ala Lys Gly Glu Ile Leu Ile Leu Lys Glu Thr Ile Asn Asn Met
            580                 585                 590
Val Asp Arg Leu Ser Ile Phe Cys Asn Glu Val Gln Arg Val Ala Lys
        595                 600                 605
Asp Val Gly Val Asp Gly Ile Met Gly Gly Gln Ala Asp Val Ala Gly
    610                 615                 620
Leu Lys Gly Arg Trp Lys Glu Ile Thr Thr Asp Val Asn Thr Met Ala
625                 630                 635                 640
Asn Asn Leu Thr Ala Gln Val Arg Ala Phe Gly Asp Ile Thr Asn Ala
                645                 650                 655
Ala Thr Asp Gly Asp Phe Thr Lys Leu Val Glu Val Glu Ala Ser Gly
            660                 665                 670
Glu Met Asp Glu Leu Lys Lys Lys Ile Asn Gln Met Val Tyr Asn Leu
        675                 680                 685
Arg Asp Ser Ile Gln Arg Asn Thr Gln Ala Arg Glu Ala Ala Glu Leu
    690                 695                 700
Ala Asn Lys Thr Lys Ser Glu Phe Leu Ala Asn Met Ser His Glu Ile
705                 710                 715                 720
Arg Thr Pro Met Asn Gly Ile Ile Gly Met Thr Gln Leu Thr Leu Asp
                725                 730                 735
Thr Asp Leu Thr Gln Tyr Gln Arg Glu Met Leu Asn Ile Val Asn Ser
            740                 745                 750
Leu Ala Asn Ser Leu Leu Thr Ile Ile Asp Asp Ile Leu Asp Leu Ser
        755                 760                 765
Lys Ile Glu Ala Arg Arg Met Val Ile Glu Glu Ile Pro Tyr Thr Leu
    770                 775                 780
Arg Gly Thr Val Phe Asn Ala Leu Lys Thr Leu Ala Val Lys Glu Thr
785                 790                 795                 800
Glu Lys Phe Leu Asp Leu Thr Tyr Arg Val Asp His Ser Val Pro Asp
                805                 810                 815
His Val Val Gly Asp Ser Phe Arg Leu Arg Gln Ile Ile Leu Asn Leu
```

-continued

```
                    820                 825                 830
Val Gly Asn Ala Ile Lys Phe Thr Glu His Gly Glu Val Ser Leu Thr
                835                 840                 845
Ile Gln Lys Ala Ser Ser Val Gln Cys Ser Thr Glu Tyr Ala Ile
    850                 855                 860
Glu Phe Val Val Ser Asp Thr Gly Ile Gly Ile Pro Ala Asp Lys Leu
865                 870                 875                 880
Asp Leu Ile Phe Asp Thr Phe Gln Gln Ala Asp Gly Ser Met Thr Arg
                885                 890                 895
Lys Phe Gly Gly Thr Gly Leu Gly Leu Ser Ile Ser Lys Arg Leu Val
                900                 905                 910
Asn Leu Met Gly Gly Asp Val Trp Val Lys Ser Glu Tyr Gly Lys Gly
                915                 920                 925
Ser Lys Phe Phe Phe Thr Cys Val Val Arg Leu Ala Asn Asp Asp Ile
                930                 935                 940
Ser Leu Ile Ala Lys Gln Leu Asn Pro Tyr Lys Ser His Gln Val Leu
945                 950                 955                 960
Phe Ile Asp Lys Gly Arg Thr Gly His Gly Pro Glu Ile Ala Lys Met
                965                 970                 975
Leu His Gly Leu Gly Leu Val Pro Ile Val Asp Ser Glu Arg Asn
                980                 985                 990
Pro Ala Leu Glu Lys Ala Arg Ala Ala Gly Gln Ala Pro Tyr Asp Val
                995                 1000                1005
Ile Ile Val Asp Ser Ile Glu Asp Ala Arg Arg Leu Arg Ser Val Asp
    1010                1015                1020
Asp Phe Lys Tyr Leu Pro Ile Val Leu Ala Pro Val Val His Val
1025                1030                1035                1040
Ser Leu Lys Ser Cys Leu Asp Leu Gly Ile Thr Ser Tyr Met Thr Thr
                1045                1050                1055
Pro Cys Gln Leu Ile Asp Leu Gly Asn Gly Met Val Pro Ala Leu Glu
                1060                1065                1070
Asn Arg Ala Thr Pro Ser Leu Ala Asp Asn Thr Lys Ser Phe Glu Ile
                1075                1080                1085
Leu Leu Ala Glu Asp Asn Thr Val Asn Gln Arg Leu Ala Val Lys Ile
                1090                1095                1100
Leu Glu Lys Tyr His His Val Thr Val Val Gly Asn Gly Glu Glu
1105                1110                1115                1120
Ala Val Glu Ala Val Lys Arg Lys Phe Asp Val Ile Leu Met Asp
                1125                1130                1135
Val Gln Met Pro Ile Met Gly Gly Phe Glu Ala Thr Ala Lys Ile Arg
                1140                1145                1150
Glu Tyr Glu Arg Ser Leu Gly Ser Gln Arg Thr Pro Ile Ile Ala Leu
                1155                1160                1165
Thr Ala His Ala Met Met Gly Asp Arg Glu Lys Cys Ile Gln Ala Gln
                1170                1175                1180
Met Asp Glu Tyr Leu Ser Lys Pro Leu Gln Gln Asn His Leu Ile Gln
1185                1190                1195                1200
Thr Ile Leu Lys Cys Ala Thr Leu Gly Gly Gln Leu Leu Glu Lys Asn
                1205                1210                1215
Arg Glu Arg Glu Leu Thr Arg Ala Ala Asp Ala Val Thr Gly Gly Arg
                1220                1225                1230
Arg Asp Asn Gly Met Tyr Ser Ala Ser Gln Ala Ala Gln His Ala Ala
                1235                1240                1245
```

```
Leu Arg Pro Pro Leu Ala Thr Arg Gly Leu Thr Ala Ala Asp Ser Leu
    1250                1255                1260

Val Ser Gly Leu Glu Ser Pro Ser Ile Val Thr Ala Asp Lys Glu Asp
1265                1270                1275                1280

Pro

<210> SEQ ID NO 6
<211> LENGTH: 19
<212> TYPE: DNA
<213> ORGANISM: Artificial Sequence
<220> FEATURE:
<221> NAME/KEY: modified_base
<222> LOCATION: (6)
<223> OTHER INFORMATION: i
<221> NAME/KEY: modified_base
<222> LOCATION: (9)
<223> OTHER INFORMATION: i
<221> NAME/KEY: modified_base
<222> LOCATION: (12)
<223> OTHER INFORMATION: i
<221> NAME/KEY: modified_base
<222> LOCATION: (15)
<223> OTHER INFORMATION: i
<221> NAME/KEY: modified_base
<222> LOCATION: (17)
<223> OTHER INFORMATION: i
<223> OTHER INFORMATION: Description of Artificial Sequence:  Synthetic

<400> SEQUENCE: 6
cayganhtnm gnacncncc                                              19

<210> SEQ ID NO 7
<211> LENGTH: 17
<212> TYPE: DNA
<213> ORGANISM: Artificial Sequence
<220> FEATURE:
<221> NAME/KEY: modified_base
<222> LOCATION: (9)
<223> OTHER INFORMATION: i
<221> NAME/KEY: modified_base
<222> LOCATION: (11)..(12)
<223> OTHER INFORMATION: i
<223> OTHER INFORMATION: Description of Artificial Sequence:  Synthetic

<400> SEQUENCE: 7
gtraayttna nngcrtt                                                17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:  Synthetic
<221> NAME/KEY: modified_base
<222> LOCATION: (6)
<223> OTHER INFORMATION: i
<221> NAME/KEY: modified_base
<222> LOCATION: (9)
<223> OTHER INFORMATION: i
<221> NAME/KEY: modified_base
<222> LOCATION: (12)
<223> OTHER INFORMATION: i

<400> SEQUENCE: 8
gcrttncyna cnarrtt                                                17

<210> SEQ ID NO 9
<211> LENGTH: 20
<212> TYPE: DNA
```

```
<213> ORGANISM: Artificial Sequence
<220> FEATURE:
<223> OTHER INFORMATION: Description of Artificial Sequence:  Synthetic

<400> SEQUENCE: 9
gagagctggc tgatctgttg                                                   20

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:  Synthetic
<221> NAME/KEY: SITE
<222> LOCATION: ()..)
<223> OTHER INFORMATION: The amino acid at this position can be either
      Glutamic Acid or Aspartic Acid.
<221> NAME/KEY: SITE
<222> LOCATION: (3)
<223> OTHER INFORMATION: The amino acid at this position can be either
      Methionine, Isoleucine, Leucine or Phenylalanine.

<400> SEQUENCE: 10

His Xaa Xaa Arg Thr Pro
 1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:  Synthetic
<221> NAME/KEY: SITE
<222> LOCATION: (4)
<223> OTHER INFORMATION: The amino acid at this position can be either
      Serine or Glycine.
<221> NAME/KEY: SITE
<222> LOCATION: (7)
<223> OTHER INFORMATION: The amino acid at this position can be either
      Isoleucine or Valine.

<400> SEQUENCE: 11

Asn Leu Val Xaa Asn Ala Xaa Lys Phe Thr
 1               5                  10

<210> SEQ ID NO 12
<211> LENGTH: 48
<212> TYPE: DNA
<213> ORGANISM: Neurospora crassa

<400> SEQUENCE: 12
agtcagtcag tcagtcagtc agtcgatcga tcgatcgatc gatcgatc                    48

<210> SEQ ID NO 13
<211> LENGTH: 15
<212> TYPE: DNA
<213> ORGANISM: Neurospora crassa

<400> SEQUENCE: 13
gcccacaatc atgac                                                        15

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:  Synthetic

<400> SEQUENCE: 14
```

```
gtcctccaag taccctg                                               17
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 15

```
gatcagctac ggactttc                                              18
```

<210> SEQ ID NO 16
<211> LENGTH: 4453
<212> TYPE: DNA
<213> ORGANISM: Candida albicans

<400> SEQUENCE: 16

```
gtggaggtga tgggtggttg atgaagagga agaggagtta tgaaagttgt gggcacacgc    60
gtttttttttt ttttttgct tcttccttttt tttaggtcgc gcaccaatta ctaattagat   120
tattttttgct attactgggc aaattggatg tggcagatat ctgcaacaca gtatccggat   180
attagtcatg gggcatgtca gatactagta gggtatggca gttggatgcg tgtagggta    240
ctgggcaggg cccggtaaag gaaactaaac atgttagcca gggagtgagg tcctacgggg   300
gggagcatag tacaccagta gtaggacctc ctttgttggt cgtgtgtggt ggcaatatac   360
aaagcccccc cttacatcaa caaaaatttt ttcctctctg ttgtttatct cgagtttctc   420
cctctctctc caatgaaccc cactaaaaaa ccacggttat caccaatgca gccctctgtt   480
tttgaaatac tcaacgaccc tgagctttat agtcagcact gtcatagcct tagggaaaca   540
cttcttgatc atttcaacca tcaagctaca cttatcgaca cttatgaaca tgaactagaa   600
aaatccaaaa atgccaacaa agcgttccaa caagcactta gtgaaatagg tacagttgtt   660
atatctgttg ccatgggaga cttgtccaaa aaagttgaga ttcacacagt agaaaatgac   720
cctgagattt taaaagtcaa aatcaccatc aacaccatga tggatcaatt acagacattt   780
gctaatgagg ttacaaaagt cgccaccgaa gtcgcaaatg gtgaactagg tggacaagcg   840
aaaaatgatg gatctgttgg tatttggaga tcacttacag acaatgttaa tattatggct   900
cttaatttaa ctaaccaagt gcgagaaatt gctgatgtca cacgtgctgt tgccaagggg   960
gacttgtcac gtaaaattaa tgtacacgcc cagggtgaaa tccttcaact tcaacgtaca  1020
ataaacacca tggtggatca gttacgaacg tttgcattcg aagtatctaa agttgctaga  1080
gatgttggtg tgcttggtat attaggagga caagcgttga ttgaaaatgt tgaaggtatt  1140
tgggaagagt tgactgataa tgtcaatgct atggctctta atttgactac acaagtgaga  1200
aatattgcca atgtcaccac tgccgttgcc aaggggggatt tgtcgaaaaa agtcactgct  1260
gattgtaagg gagaaattct tgatttgaaa cttactatta atcaaatggt ggaccgatta  1320
cagaattttg ctcttgcggt gacgacattg tcgagagagg ttggtacttt gggtattttg  1380
ggtggacaag ctaacgtaca ggatgttgaa ggtgcttgga acaggttac agaaaatgtc  1440
aacctaatgg ctactaattt aactaaccaa gtgagatcta ttgctacagt tactactgca  1500
gttgcgcatg gtgatttgtc gcaaaagatt gatgttcatg cccagggaga gattttacaa  1560
ttgaaaaata caatcaacaa gatggtggac tctttgcagt tgtttgcatc agaagtgtcg  1620
aaagtggcac aagatgttgg tattaatgga aaattaggta ttcaagcaca agttagtgat  1680
```

-continued

| | | | | |
|---|---|---|---|---|
| gttgatggat | tatggaagga | aattacgtct | aatgtaaata | ccatggcttc | aaatttaact | 1740 |
| tcgcaagtga | gagcttttgc | acagattact | gctgctgcta | ctgatgggga | tttcactaga | 1800 |
| tttattactg | ttgaagcact | gggagagatg | gatgcgttga | aaacaaagat | taatcaaatg | 1860 |
| gtgtttaact | taagggaatc | gcttcaaagg | aatactgcgg | ctagagaagc | tgctgagttg | 1920 |
| gccaatagtg | cgaaatccga | gttttttagca | aacatgtcgc | atgagattag | aacaccattg | 1980 |
| aatgggatta | ttggtatgac | tcagttgtcg | cttgatacag | agttgacaca | gtaccaacga | 2040 |
| gagatgttgt | cgattgtgca | taacttggca | aattccttgt | tgaccattat | agacgatata | 2100 |
| ttggatattt | ctaagattga | ggcgaataga | atgacggtgg | aacagattga | ttttttcatta | 2160 |
| agagggacag | tgtttggtgc | attgaaaacg | ttagccgtca | aagctattga | aaaaaaccta | 2220 |
| gacttgacct | atcaatgtga | ttcatcgttt | ccagataatc | ttattggaga | tagtttttaga | 2280 |
| ttacgacaag | ttattcttaa | cttggctggt | aatgctatta | agtttactaa | agaggggaaa | 2340 |
| gttagtgtta | gtgtgaaaaa | gtctgataaa | atggtgttag | atagtaagtt | gttgttagag | 2400 |
| gtttgtgtta | gcgacacggg | aataggtata | gagaaagaca | aattgggatt | gattttcgat | 2460 |
| accttctgtc | aagctgatgg | ttctactaca | agaaagtttg | gtggtacagg | tttaggggttg | 2520 |
| tcaatttcca | aacagttgat | acatttaatg | ggtggagaga | tatgggttac | ctcggagtat | 2580 |
| ggatccgggt | caaacttttta | ttttacggtg | tgcgtgtcgc | catctaatat | tagatatact | 2640 |
| cgacaaaccg | aacaattgtt | accatttagt | tcccattatg | tgttatttgt | atcgactgag | 2700 |
| catactcaag | aagaacttga | tgtgttgaga | gatggaatta | tagaacttgg | attgataacct | 2760 |
| ataattgtga | gaaatattga | agatgcaaca | ttgactgagc | cggtgaaata | tgatataatt | 2820 |
| atgattgatt | cgatagagat | tgccaaaaag | ttgaggttgt | tatcagaggt | taaatatatt | 2880 |
| ccgttggttt | tggtccatca | ttctattcca | cagttgaata | tgagagtatg | tattgatttg | 2940 |
| gggatatctt | cctatgcaaa | tacgccatgt | tcgatcacgg | acttggccag | tgcgattata | 3000 |
| ccagcgttgg | agtcgagatc | tatatcacag | aactcagacg | agtcggtgag | gtacaaaata | 3060 |
| ttactagcag | aggacaacct | cgtcaatcag | aaacttgcag | ttaggatatt | agaaaagcaa | 3120 |
| gggcatctgg | tggaagtagt | tgagaacgga | ctcgaggcgt | acgaagcgat | taagaggaat | 3180 |
| aaatatgatg | tggtgttgat | ggatgtgcaa | atgcctgtaa | tgggtgggtt | tgaagctacg | 3240 |
| gagaagattc | gacaatggga | gaaaagtct | aacccaattg | actcgttgac | gtttaggact | 3300 |
| ccaattattg | ccctcactgc | acacgccatg | ttaggtgata | gagaaaagtc | attggccaag | 3360 |
| gggatggacg | attatgtgag | taagccattg | aagccgaaat | tgttaatgca | gacgataaac | 3420 |
| aagtgtattc | ataatattaa | ccagttgaaa | gaattgtcga | gaaatagtag | aggtagcgat | 3480 |
| tttgcaaaga | agatgacccg | aaacacacct | ggaagcacga | cccgtcaggg | gagtgatgag | 3540 |
| gggagtgtag | aggacatgat | tggggacact | ccccgtcaag | ggagtgttga | gggaggggt | 3600 |
| acaagtagta | gaccagtaca | gagaaggtct | gccacagagg | ggtcgatcac | tacaattagt | 3660 |
| gaacaaatcg | accgttagct | aacgactcaa | gcgtcagctt | gagtcaaagc | tacaaatatt | 3720 |
| tagccaattg | tatacttaga | taaataaaat | acaagtaaac | cattgttgtg | tttagatcaa | 3780 |
| taattgaaaa | ataaacaaga | ttactaaaaa | tatcaagcca | aattgttgtg | taggaactgg | 3840 |
| ggttttttt | ttgggtaaa | cttttttacc | aaaaaatgga | taaaaaggg | gatgtggtcc | 3900 |
| cagtagtaac | tttagtgact | gtttaggtta | cttgagctat | ccaagtagaa | tgtcagcccc | 3960 |
| cgcagtaagt | ttggtcttat | tgtttacgga | aaaataagaa | ccttagccct | gaactagccc | 4020 |
| ctacctagtt | ttgatgtgaa | aaattttttt | tttttttta | ttgacgttct | cccccctag | 4080 |

-continued

```
accaatcgaa agccgtggta ttattccggg ctttgaagaa aagtctttct ttttttcttt    4140
ttttttgtat gggcgccaca gtttatgcaa catcacgtga ccttctctca gcaaaaaaaa    4200
accatttata tattccttct catcctcgca gatgagagac aaaaaacaaa caaaaaaaaa    4260
aaaatctttt ttttcgcca cgcacactac catgtcgcaa caaccacatt tacgtctcgg    4320
atctaccgca cctgatttca aagctgatac aactaacggg cctattctgt ttcacgaaat    4380
acattggtga tagctgggct atcttgttct cacatcccgc cgctcgaacc atgtgtgtac    4440
accgaccttt ctg                                                       4453
```

<210> SEQ ID NO 17
<211> LENGTH: 1081
<212> TYPE: PRT
<213> ORGANISM: Candida albicans

<400> SEQUENCE: 17

```
Met Asn Pro Thr Lys Lys Pro Arg Leu Ser Pro Met Gln Pro Ser Val
  1               5                  10                  15

Phe Glu Ile Leu Asn Asp Pro Glu Leu Tyr Ser Gln His Cys His Ser
                 20                  25                  30

Leu Arg Glu Thr Leu Leu Asp His Phe Asn His Gln Ala Thr Leu Ile
             35                  40                  45

Asp Thr Tyr Glu His Glu Leu Glu Lys Ser Lys Asn Ala Asn Lys Ala
         50                  55                  60

Phe Gln Gln Ala Leu Ser Glu Ile Gly Thr Val Val Ile Ser Val Ala
     65                  70                  75                  80

Met Gly Asp Leu Ser Lys Lys Val Glu Ile His Thr Val Glu Asn Asp
                 85                  90                  95

Pro Glu Ile Leu Lys Val Lys Ile Thr Ile Asn Thr Met Met Asp Gln
                100                 105                 110

Leu Gln Thr Phe Ala Asn Glu Val Thr Lys Val Ala Thr Glu Val Ala
            115                 120                 125

Asn Gly Glu Leu Gly Gly Gln Ala Lys Asn Asp Gly Ser Val Gly Ile
        130                 135                 140

Trp Arg Ser Leu Thr Asp Asn Val Asn Ile Met Ala Leu Asn Leu Thr
145                 150                 155                 160

Asn Gln Val Arg Glu Ile Ala Asp Val Thr Arg Ala Val Ala Lys Gly
                165                 170                 175

Asp Leu Ser Arg Lys Ile Asn Val His Ala Gln Gly Glu Ile Leu Gln
            180                 185                 190

Leu Gln Arg Thr Ile Asn Thr Met Val Asp Gln Leu Arg Thr Phe Ala
        195                 200                 205

Phe Glu Val Ser Lys Val Ala Arg Asp Val Gly Val Leu Gly Ile Leu
    210                 215                 220

Gly Gly Gln Ala Leu Ile Glu Asn Val Glu Gly Ile Trp Glu Glu Leu
225                 230                 235                 240

Thr Asp Asn Val Asn Ala Met Ala Leu Asn Leu Thr Thr Gln Val Arg
                245                 250                 255

Asn Ile Ala Asn Val Thr Thr Ala Val Ala Lys Gly Asp Leu Ser Lys
            260                 265                 270

Lys Val Thr Ala Asp Cys Lys Gly Glu Ile Leu Asp Leu Lys Leu Thr
        275                 280                 285

Ile Asn Gln Met Val Asp Arg Leu Gln Asn Phe Ala Leu Ala Val Thr
    290                 295                 300
```

```
Thr Leu Ser Arg Glu Val Gly Thr Leu Gly Ile Leu Gly Gly Gln Ala
305                 310                 315                 320

Asn Val Gln Asp Val Glu Gly Ala Trp Lys Gln Val Thr Glu Asn Val
            325                 330                 335

Asn Leu Met Ala Thr Asn Leu Thr Asn Gln Val Arg Ser Ile Ala Thr
            340                 345                 350

Val Thr Thr Ala Val Ala His Gly Asp Leu Ser Gln Lys Ile Asp Val
            355                 360                 365

His Ala Gln Gly Glu Ile Leu Gln Leu Lys Asn Thr Ile Asn Lys Met
370                 375                 380

Val Asp Ser Leu Gln Leu Phe Ala Ser Glu Val Ser Lys Val Ala Gln
385                 390                 395                 400

Asp Val Gly Ile Asn Gly Lys Leu Gly Ile Gln Ala Gln Val Ser Asp
            405                 410                 415

Val Asp Gly Leu Trp Lys Glu Ile Thr Ser Asn Val Asn Thr Met Ala
            420                 425                 430

Ser Asn Leu Thr Ser Gln Val Arg Ala Phe Ala Gln Ile Thr Ala Ala
            435                 440                 445

Ala Thr Asp Gly Asp Phe Thr Arg Phe Ile Thr Val Glu Ala Leu Gly
450                 455                 460

Glu Met Asp Ala Leu Lys Thr Lys Ile Asn Gln Met Val Phe Asn Leu
465                 470                 475                 480

Arg Glu Ser Leu Gln Arg Asn Thr Ala Ala Arg Glu Ala Ala Glu Leu
            485                 490                 495

Ala Asn Ser Ala Lys Ser Glu Phe Leu Ala Asn Met Ser His Glu Ile
            500                 505                 510

Arg Thr Pro Leu Asn Gly Ile Ile Gly Met Thr Gln Leu Ser Leu Asp
            515                 520                 525

Thr Glu Leu Thr Gln Tyr Gln Arg Glu Met Leu Ser Ile Val His Asn
            530                 535                 540

Leu Ala Asn Ser Leu Leu Thr Ile Ile Asp Asp Ile Leu Asp Ile Ser
545                 550                 555                 560

Lys Ile Glu Ala Asn Arg Met Thr Val Glu Gln Ile Asp Phe Ser Leu
            565                 570                 575

Arg Gly Thr Val Phe Gly Ala Leu Lys Thr Leu Ala Val Lys Ala Ile
            580                 585                 590

Glu Lys Asn Leu Asp Leu Thr Tyr Gln Cys Asp Ser Ser Phe Pro Asp
            595                 600                 605

Asn Leu Ile Gly Asp Ser Phe Arg Leu Arg Gln Val Ile Leu Asn Leu
            610                 615                 620

Ala Gly Asn Ala Ile Lys Phe Thr Lys Glu Gly Lys Val Ser Val Ser
625                 630                 635                 640

Val Lys Lys Ser Asp Lys Met Val Leu Asp Ser Lys Leu Leu Leu Glu
            645                 650                 655

Val Cys Val Ser Asp Thr Gly Ile Gly Ile Glu Lys Asp Lys Leu Gly
            660                 665                 670

Leu Ile Phe Asp Thr Phe Cys Gln Ala Asp Gly Ser Thr Thr Arg Lys
            675                 680                 685

Phe Gly Gly Thr Gly Leu Gly Leu Ser Ile Ser Lys Gln Leu Ile His
            690                 695                 700

Leu Met Gly Gly Glu Ile Trp Val Thr Ser Glu Tyr Gly Ser Gly Ser
705                 710                 715                 720
```

| | | | | | | | | | | | |
|---|---|---|---|---|---|---|---|---|---|---|---|
|Asn|Phe|Tyr|Phe|Thr|Val|Cys|Val|Ser|Pro|Ser|Asn|Ile|Arg|Tyr|Thr|
| | | | |725| | | | |730| | | | |735| |

Asn Phe Tyr Phe Thr Val Cys Val Ser Pro Ser Asn Ile Arg Tyr Thr
                725                 730                 735

Arg Gln Thr Glu Gln Leu Leu Pro Phe Ser Ser His Tyr Val Leu Phe
                740                 745                 750

Val Ser Thr Glu His Thr Gln Glu Glu Leu Asp Val Leu Arg Asp Gly
                755                 760                 765

Ile Ile Glu Leu Gly Leu Ile Pro Ile Ile Val Arg Asn Ile Glu Asp
                770                 775                 780

Ala Thr Leu Thr Glu Pro Val Lys Tyr Asp Ile Ile Met Ile Asp Ser
785                 790                 795                 800

Ile Glu Ile Ala Lys Lys Leu Arg Leu Leu Ser Glu Val Lys Tyr Ile
                805                 810                 815

Pro Leu Val Leu Val His His Ser Ile Pro Gln Leu Asn Met Arg Val
                820                 825                 830

Cys Ile Asp Leu Gly Ile Ser Ser Tyr Ala Asn Thr Pro Cys Ser Ile
                835                 840                 845

Thr Asp Leu Ala Ser Ala Ile Ile Pro Ala Leu Glu Ser Arg Ser Ile
850                 855                 860

Ser Gln Asn Ser Asp Glu Ser Val Arg Tyr Lys Ile Leu Leu Ala Glu
865                 870                 875                 880

Asp Asn Leu Val Asn Gln Lys Leu Ala Val Arg Ile Leu Glu Lys Gln
                885                 890                 895

Gly His Leu Val Glu Val Val Glu Asn Gly Leu Glu Ala Tyr Glu Ala
                900                 905                 910

Ile Lys Arg Asn Lys Tyr Asp Val Val Leu Met Asp Val Gln Met Pro
                915                 920                 925

Val Met Gly Gly Phe Glu Ala Thr Glu Lys Ile Arg Gln Trp Glu Lys
                930                 935                 940

Lys Ser Asn Pro Ile Asp Ser Leu Thr Phe Arg Thr Pro Ile Ile Ala
945                 950                 955                 960

Leu Thr Ala His Ala Met Leu Gly Asp Arg Glu Lys Ser Leu Ala Lys
                965                 970                 975

Gly Met Asp Asp Tyr Val Ser Lys Pro Leu Lys Pro Lys Leu Leu Met
                980                 985                 990

Gln Thr Ile Asn Lys Cys Ile His Asn Ile Asn Gln Leu Lys Glu Leu
                995                 1000                1005

Ser Arg Asn Ser Arg Gly Ser Asp Phe Ala Lys Lys Met Thr Arg Asn
            1010                1015                1020

Thr Pro Gly Ser Thr Thr Arg Gln Gly Ser Asp Glu Gly Ser Val Glu
1025                1030                1035                1040

Asp Met Ile Gly Asp Thr Pro Arg Gln Gly Ser Val Glu Gly Gly Gly
                    1045                1050                1055

Thr Ser Ser Arg Pro Val Gln Arg Ser Ala Thr Glu Gly Ser Ile
            1060                1065                1070

Thr Thr Ile Ser Glu Gln Ile Asp Arg
        1075                1080

<210> SEQ ID NO 18
<211> LENGTH: 368
<212> TYPE: DNA
<213> ORGANISM: Candida albicans

<400> SEQUENCE: 18
cacgagatga ggacgccatt gaatgggatt attggtatga ctcagttgtc gcttgataca    60

```
gagttgacac agtaccaacg agagatgttg tcgattgtgc ataacttggc aaattccttg      120
ttgaccatta tagacgatat attggatatt tctaagattg aggcgaatag aatgacggtg      180
gaacagattg atttttcatt aagagggaca gtgtttggtg cattgaaaac gttagccgtc      240
aaagctattg aaaaaaacct agacttgacc tatcaatgtg attcatcgtt tccagataat      300
cttattggag atagttttag attacgacaa gttattctta acttggctgg taatgccctc      360
aagttcac                                                               368

<210> SEQ ID NO 19
<211> LENGTH: 122
<212> TYPE: PRT
<213> ORGANISM: Candida albicans

<400> SEQUENCE: 19

His Glu Met Arg Thr Pro Leu Asn Gly Ile Ile Gly Met Thr Gln Leu
  1               5                  10                  15

Ser Leu Asp Thr Glu Leu Thr Gln Tyr Gln Arg Glu Met Leu Ser Ile
             20                  25                  30

Val His Asn Leu Ala Asn Ser Leu Leu Thr Ile Ile Asp Asp Ile Leu
         35                  40                  45

Asp Ile Ser Lys Ile Glu Ala Asn Arg Met Thr Val Glu Gln Ile Asp
     50                  55                  60

Phe Ser Leu Arg Gly Thr Val Phe Gly Ala Leu Lys Thr Leu Ala Val
 65                  70                  75                  80

Lys Ala Ile Glu Lys Asn Leu Asp Leu Thr Tyr Gln Cys Asp Ser Ser
                 85                  90                  95

Phe Pro Asp Asn Leu Ile Gly Asp Ser Phe Arg Leu Arg Gln Val Ile
            100                 105                 110

Leu Asn Leu Ala Gly Asn Ala Leu Lys Phe
        115                 120

<210> SEQ ID NO 20
<211> LENGTH: 144
<212> TYPE: DNA
<213> ORGANISM: Artificial Sequence
<220> FEATURE:
<223> OTHER INFORMATION: Description of Artificial Sequence: Synthetic

<400> SEQUENCE: 20
atgaccatga ttacgccact agtccgaggc ctcgagatct atcgatgcat gccatggtac      60
ccgggagctc gaattcgaag cttctgcaga cgcgtcgacg tcatatggat ccgatatcgc     120
cgtggcggcc gctctagaac tagt                                            144

<210> SEQ ID NO 21
<211> LENGTH: 15
<212> TYPE: PRT
<213> ORGANISM: Saccharomyces cerevisiae

<400> SEQUENCE: 21

Arg Tyr Asp Leu Val Leu Met Asp Ile Val Met Pro Asn Leu Asp
  1               5                  10                  15

<210> SEQ ID NO 22
<211> LENGTH: 15
<212> TYPE: PRT
<213> ORGANISM: Neurospora crassa

<400> SEQUENCE: 22
```

```
Lys Phe Asp Val Ile Leu Met Asp Val Gln Met Pro Ile Met Gly
 1               5                  10                  15
```

<210> SEQ ID NO 23
<211> LENGTH: 15
<212> TYPE: PRT
<213> ORGANISM: Saccharomyces cerevisiae

<400> SEQUENCE: 23

```
Asn Tyr Asn Met Phe Ile Met Asp Val Gln Met Pro Lys Val Asp
 1               5                  10                  15
```

<210> SEQ ID NO 24
<211> LENGTH: 15
<212> TYPE: PRT
<213> ORGANISM: Escherichia coli

<400> SEQUENCE: 24

```
Pro Phe Asp Leu Ile Leu Met Asp Ile Gln Met Pro Asp Met Asp
 1               5                  10                  15
```

<210> SEQ ID NO 25
<211> LENGTH: 732
<212> TYPE: PRT
<213> ORGANISM: Neurospora crassa

<400> SEQUENCE: 25

```
Met Thr Asp Gly Pro Thr Leu Ala Ala Ile Ala Ala Leu Val Lys Ser
 1               5                  10                  15

Leu Ala Val Asp Pro Ala Thr Thr Gln Thr Ser Gly Leu Arg Pro Ser
            20                  25                  30

Thr His Val Arg Leu Pro Gly Pro Tyr Thr Arg Glu Lys Gly Asp Val
        35                  40                  45

Val Arg Ile Glu Gln Leu Glu Thr Ala Ile Ala Ala Ser Pro Pro
 50                  55                  60

Ala Met Pro Asp Thr Pro Asn Ala Pro Thr Asp Ala Leu Phe Ser Asn
 65              70                  75                  80

Gly Thr Leu Ser Pro Ser Ser Glu Thr Pro Asp Ala Arg Tyr Phe Ile
                85                  90                  95

Asp Glu Ala Leu Glu Gly Leu Arg Glu His Val Asp Asp Gln Ser Lys
               100                 105                 110

Leu Leu Asp Ser Gln Arg Gln Glu Leu Ala Gly Val Asn Ala Gln Leu
           115                 120                 125

Ile Glu Gln Lys Gln Leu Gln Glu Lys Ala Leu Ala Ile Leu Glu Arg
       130                 135                 140

Glu Leu Trp Lys His Gln Lys Ala Asn Glu Ala Phe Gln Lys Ala Leu
145                 150                 155                 160

Arg Glu Ile Gly Glu Ile Val Thr Ala Val Ala Arg Gly Asp Leu Ser
                165                 170                 175

Lys Lys Val Arg Met Asn Ser Val Glu Met Asp Pro Ile Asn Thr Met
            180                 185                 190

Met Asp Gln Leu Gln Val Phe Ser Ser Glu Val Ser Arg Val Ala Arg
        195                 200                 205

Glu Val Gly Thr Glu Gly Ile Leu Gly Gly Gln Ala Gln Ile Glu Gly
    210                 215                 220

Val Asp Gly Thr Trp Lys Glu Leu Thr Asp Asn Thr Asp Gln Val Arg
225                 230                 235                 240

Glu Ile Ala Ser Val Thr Thr Ala Val Ala His Gly Asp Leu Thr Lys
```

-continued

```
                245                 250                 255
Lys Ile Glu Arg Pro Ala Lys Gly Glu Ile Leu Gln Leu Gln Gln Thr
                    260                 265                 270
Ile Asn Thr Met Val Asp Gln Leu Arg Thr Ala Arg Asp Val Gly Thr
                275                 280                 285
Glu Gly Ile Leu Gly Gly Gln Ala Asp Val Glu Gly Val Gln Gly Met
            290                 295                 300
Trp Asn Glu Leu Thr Val Asn Val Asn Ala Met Ala Asn Asn Leu Thr
305                 310                 315                 320
Thr Gln Val Arg Asp Ile Ile Lys Val Leu Thr Gln Lys Val Gln Ala
                325                 330                 335
Glu Cys Arg Gly Glu Ile Phe Glu Leu Lys Lys Thr Ile Asn Ser Met
                340                 345                 350
Val Asp Gln Leu Gln Gln Phe Ala Arg Glu Val Thr Lys Ile Ala Arg
                355                 360                 365
Glu Val Gly Thr Glu Gly Arg Leu Val Gln Gly Thr Trp Arg Asp Leu
            370                 375                 380
Thr Glu Asn Val Asn Gly Met Ala Met Asn Leu Thr Thr Gln Val Arg
385                 390                 395                 400
Glu Ile Ala Lys Val Thr Thr Ala Val Ala Lys Gly Asp Leu Thr Lys
                405                 410                 415
Lys Ile Gly Val Glu Val Gln Ile Glu Ala Arg Arg Met Val Ile Glu
                420                 425                 430
Glu Ile Pro Tyr Thr Leu Arg Gly Thr Val Phe Asn Ala Leu Lys Thr
                435                 440                 445
Leu Ala Val Lys Ala Asn Glu Lys Phe Leu Asp Leu Thr Tyr Arg Val
                450                 455                 460
Asp His Ser Val Phe Arg Leu Arg Gln Ile Ile Leu Asn Leu Val Gly
465                 470                 475                 480
Asn Ala Ile Lys Phe Thr Glu His Gly Glu Val Ser Leu Thr Ile Gln
                485                 490                 495
Lys Ala Ser Ser Val Gln Cys Ser Thr Glu Glu Tyr Ala Ile Glu Phe
                500                 505                 510
Val Val Ser Asp Thr Gly Ile Gly Ile Pro Ala Asp Lys Leu Asp Leu
                515                 520                 525
Ile Phe Asp Thr Phe Gln Gln Ala Asp Gly Ser Met Thr Arg Lys Phe
                530                 535                 540
Gly Gly Thr Gly Leu Gly Leu Leu Met Gly Gly Asp Val Trp Val Lys
545                 550                 555                 560
Ser Glu Tyr Gly Lys Gly Ser Lys Phe Phe Thr Cys Val Val Arg
                565                 570                 575
Leu Ala Asn Asp Asp Ile Ser Leu Ile Ala Lys Gln Leu Asn Pro Tyr
                580                 585                 590
Lys Ser His Gln Val Leu His Gly Pro Glu Ile Ala Lys Met Leu His
                595                 600                 605
Gly Leu Gly Leu Val Pro Ile Val Asp Ser Glu Arg Asn Pro Ala
            610                 615                 620
Leu Glu Lys Ala Arg Ala Ala Gly Gln Ala Pro Tyr Asp Val Ile Ile
625                 630                 635                 640
Val Asp Ser Ile Ser Val Asp Asp Phe Lys Tyr Leu Pro Ile Val Leu
                645                 650                 655
Leu Ala Pro Val Val His Val Ser Leu Lys Ser Cys Leu Asp Leu Gly
                660                 665                 670
```

```
Ile Thr Ser Tyr Met Thr Thr Pro Cys Gln Leu Ile Asp Leu Gly Asn
            675                 680                 685

Gly Met Thr Pro Ser Leu Ala Asp Asn Thr Lys Ser Phe Glu Ile Leu
        690                 695                 700

Leu Ala Glu Asp Asn Thr Val Asn Gln Arg Leu Ala Val Lys Ile Leu
705                 710                 715                 720

Glu Lys Tyr His His Val Val Thr Val Val Gly Asn
                725                 730

<210> SEQ ID NO 26
<211> LENGTH: 335
<212> TYPE: PRT
<213> ORGANISM: Escherichia coli

<400> SEQUENCE: 26

Met Thr Asn Tyr Ser Leu Arg Ala Arg Met Met Ile Leu Ile Leu Ala
  1               5                  10                  15

Pro Thr Val Leu Ile Gly Leu Leu Ser Ile Phe Phe Val Leu Glu
                 20                  25                  30

Ala Gly Lys Leu Ile Leu Glu Ser Ile Pro Phe Pro Leu Arg Ser Thr
             35                  40                  45

Leu Asp Glu Val Val Thr Leu Leu Ala His Ser His Asp Lys Gly
 50                  55                  60

Leu Glu Leu Thr Leu Asn Ile Lys Ser Asp Val Leu Arg Leu Gln Gln
 65                  70                  75                  80

Ile Ile Thr Asn Leu Val Gly Asn Ala Ile Lys Phe Thr Glu Asn Gly
                 85                  90                  95

Asn Ile Asp Ile Leu Val Glu Lys Arg Ala Leu Ser Asn Thr Lys Val
                100                 105                 110

Gln Ile Glu Val Gln Ile Arg Asp Thr Gly Ile Gly Ile Pro Glu Arg
            115                 120                 125

Asp Gln Ser Arg Leu Phe Gln Ala Phe Arg Gln Ala Asp Ala Ser Ile
130                 135                 140

Ser Arg Arg His Gly Gly Thr Gly Leu Gly Leu Glu Met Gly Gly Asp
145                 150                 155                 160

Ile Ser Phe His Ser Gln Pro Asn Arg Gly Ser Thr Phe Trp Phe His
                165                 170                 175

Ile Asn Leu Asp Leu Asn Pro Asn Ile Ile Glu Gly Pro Ser Thr
                180                 185                 190

Gln Cys Leu Ala Gly Lys Arg Leu Ala Ala Gln Cys Thr Leu Asp Ile
            195                 200                 205

Leu Ser Glu Thr Pro Leu Glu Val Val Tyr Ser Pro Thr Phe Ser Ala
210                 215                 220

Leu Pro Pro Ala His Tyr Asp Met Met Leu Leu Gly Ile Ala Val Thr
225                 230                 235                 240

Phe Arg Glu Pro Leu Lys Ala Val Ser Met Thr Asp Phe Leu Met Leu
                245                 250                 255

Ala Leu Pro Cys His Ala Gln Val Asn Ala Glu Lys Leu Lys Gln Asp
            260                 265                 270

Gly Ile Gly Ala Cys Leu Leu Lys Pro Leu Thr Pro Thr Arg Leu Leu
        275                 280                 285

Pro Ala Leu Thr Leu Leu Pro Val Thr Asp Glu Ser Lys Leu Ala Met
290                 295                 300

Thr Val Met Ala Val Asp Asp Asn Pro Ala Asn Leu Lys Leu Ile Gly
```

```
                305                  310                 315                  320
Ala Leu Leu Glu Asp Met Val Gln His Val Glu Leu Cys Asp Ser
                    325                 330                 335
```

<210> SEQ ID NO 27
<211> LENGTH: 354
<212> TYPE: PRT
<213> ORGANISM: Pseudomonas viridiflava

<400> SEQUENCE: 27

```
Asn Arg Arg Thr Asp Thr Gly Cys Trp Arg Lys Ser Val Leu Asn Lys
 1               5                  10                  15

Leu Gly Ile Lys Gly Arg Val Leu Leu Thr Ile Leu Pro Ala Ser
                20                  25                  30

Leu Met Ala Ala Val Leu Gly Gly Tyr Phe Ile Glu Ala Gly Lys Leu
                35                  40                  45

Val Leu Asp Asn Ile Pro Phe Asn Leu Arg Asp Leu Gln Asp Thr
        50                  55                  60

Leu Thr Ile Leu Ala Pro Ala His Ala Lys Gln Leu Glu Leu Val
 65                 70                  75                  80

Ser Leu Val Tyr Arg Asp Thr Leu Arg Leu Arg Gln Ile Leu Thr Asn
                85                  90                  95

Leu Val Ser Asn Ala Ile Lys Phe Thr Arg Gln Gly Thr Ile Val Ala
                100                 105                 110

Arg Ala Met Leu Glu Asp Glu Thr Glu Glu His Ala Gln Leu Arg Ile
                115                 120                 125

Ser Val Gln Asp Thr Gly Ile Gly Leu Ser Ser Gln Asp Val Arg Ala
                130                 135                 140

Leu Phe Gln Ala Phe Ser Gln Ala Asp Asn Ser Ile Ser Arg Gln Pro
145                 150                 155                 160

Gly Gly Thr Gly Leu Gly Leu Gln Met Gly Glu Ile Gly Val Asp
                165                 170                 175

Ser Thr Pro Gly Glu Gly Ser Glu Phe Trp Ile Ser Leu Asn Leu Pro
                180                 185                 190

Lys Ala Arg Glu Asp Arg Glu Glu Thr Ala Asn Gln Ala Leu Glu Gly
                195                 200                 205

Leu Arg Ala Ala Val Leu Ala Leu Glu His Gln Leu Glu Asp Cys Gly
210                 215                 220

Leu Gln Thr Val Val Phe Thr Asn Leu Glu Asn Leu Asn Gly Val
225                 230                 235                 240

Thr Ala Ala His Glu Thr Pro Gln Ala Ile Asp Leu Val Val Leu Gly
                245                 250                 255

Val Thr Ala Leu His Ile Trp Asp Leu Glu Asn Leu Asn Cys Lys Val
                260                 265                 270

Met Val Leu Cys Pro Thr Thr Glu His Ala Leu Phe Gln Met Ser Val
                275                 280                 285

His Asp Val Tyr Thr Gln Leu Gln Ala Lys Pro Ala Cys Asn Arg Lys
                290                 295                 300

Leu Gln Lys Arg Ala Val Arg Thr Asp Val Ala Leu Pro Leu Ser Ser
305                 310                 315                 320

Arg Ala Pro Arg Val Leu Cys Val Asp Asp Asn Pro Ala Asn Leu Leu
                325                 330                 335

Leu Val Gln Thr Leu Leu Glu Asp Met Gly Ala Glu Val Val Ala Val
                340                 345                 350
```

Asp Gly

<210> SEQ ID NO 28
<211> LENGTH: 351
<212> TYPE: PRT
<213> ORGANISM: Pseudomonas fluorescens

<400> SEQUENCE: 28

```
Met Leu Lys Lys Leu Gly Ile Lys Gly Arg Val Leu Leu Thr Leu
 1               5                  10                  15

Leu Pro Thr Ser Leu Met Ala Leu Val Leu Gly Gly Tyr Phe Ile Glu
                20                  25                  30

Ala Gly Lys Leu Val Leu Asp Ser Ile Pro Phe Asn Leu Arg Asp Leu
            35                  40                  45

Leu Gln Asp Thr Leu Thr Ile Leu Ala Pro Ala Ala His Ala Lys Gln
        50                  55                  60

Leu Glu Leu Val Ser Leu Val Tyr Arg Asp Thr Pro Leu Ser Leu Val
 65                  70                  75                  80

Gly Asp Pro Leu Arg Leu Lys Gln Ile Leu Thr Asn Leu Val Ser Asn
                85                  90                  95

Ala Ile Lys Phe Thr Arg Glu Gly Thr Ile Val Ala Arg Ala Met Leu
            100                 105                 110

Glu Glu Glu His Glu Asp Ser Val Gln Leu Arg Ile Ser Ile Gln Asp
        115                 120                 125

Thr Gly Ile Gly Leu Ser Asn Gln Asp Val Arg Ala Leu Phe Gln Ala
    130                 135                 140

Phe Ser Gln Ala Asp Asn Ser Leu Ser Arg Gln Pro Gly Gly Thr Gly
145                 150                 155                 160

Leu Gly Leu Gln Met Gly Gly Glu Ile Gly Val Asp Ser Thr Pro Gly
                165                 170                 175

Glu Gly Ser Glu Phe Trp Ile Ser Leu Asn Leu Pro Lys Thr Arg Asp
            180                 185                 190

Asp Ala Glu Asp Leu Pro Gly Pro Leu Leu Gly Arg Arg Val Ala
        195                 200                 205

Val Leu Ala Leu Gln His Gln Leu Glu Asp Cys Gly Leu Glu Val Thr
    210                 215                 220

Pro Phe Asn Thr Leu Glu Ala Leu Thr Asn Gly Ile Thr Gly Val His
225                 230                 235                 240

Gln Ser Glu Gln Ala Ile Asp Leu Ala Val Leu Gly Ile Thr Thr Asn
                245                 250                 255

Asp His Ile Trp Asp Leu Glu His Leu Gly Cys Lys Val Leu Val Leu
            260                 265                 270

Cys Pro Thr Thr Glu Gln Thr Leu Phe His Leu Ser Val Pro Asn Pro
        275                 280                 285

His Ser Gln Leu Gln Ala Lys Pro Ala Cys Thr Arg Lys Leu Arg Arg
    290                 295                 300

Arg Arg Ala Arg Ser Glu Pro Glu Glu Thr Leu Ser Ser Arg Ala Pro
305                 310                 315                 320

Arg Val Leu Cys Val Asp Asp Asn Pro Ala Asn Leu Leu Leu Ile Gln
                325                 330                 335

Thr Leu Leu Glu Asp Met Gly Ala Lys Val Leu Ala Val Asp Asn
            340                 345                 350
```

<210> SEQ ID NO 29
<211> LENGTH: 751

```
<212> TYPE: PRT
<213> ORGANISM: Saccharomyces cerevisiae

<400> SEQUENCE: 29

Met Arg Phe Gly Leu Pro Ser Lys Leu Glu Leu Thr Pro Pro Phe Arg
 1               5                  10                  15

Ile Gly Ile Arg Thr Gln Leu Thr Ala Leu Val Ser Ile Val Ala Leu
            20                  25                  30

Gly Ser Leu Ile Ile Leu Ala Val Thr Thr Gly Val Tyr Phe Thr Asp
         35                  40                  45

Arg Leu Tyr Ile Ala Ala Gln Leu Lys Ser Ser Gln Ile Asp Gln Thr
     50                  55                  60

Leu Asn Tyr Leu Tyr Tyr Gln Ala Tyr Leu Ala Ser Arg Asp Ala
 65                  70                  75                  80

Leu Gln Ser Ser Leu Thr Ser Tyr Val Ala Gly Asn Lys Ser Ser Val
                 85                  90                  95

Ile Gln Lys Phe Leu Ser Ser Asn Leu Phe Tyr Val Ala Lys Val
            100                 105                 110

Tyr Asp Ser Ser Phe Asn Ala Val Leu Asn Ala Thr Asn Asn Gly Thr
        115                 120                 125

Gly Asp Leu Ile Pro Glu Asp Val Leu Asp Ser Leu Phe Pro Ser Ser
130                 135                 140

Leu Glu Thr Ile Gly Ile Leu Thr Asp Pro Val Leu Asn Ser Thr Asp
145                 150                 155                 160

Tyr Leu Met Ser Met Ser Leu Pro Ile Phe Ala Asn Pro Ser Ile Ile
                165                 170                 175

Leu Thr Asp Ser Arg Val Tyr Gly Tyr Ile Thr Ile Ser Val Phe Asn
            180                 185                 190

Asp Thr Thr Ala Leu Glu His Ser Thr Ile Ala Ile Ser Ala Val
        195                 200                 205

Tyr Asn Ser Gln Gly Lys Ala Ser Gly Tyr His Phe Val Phe Pro Pro
    210                 215                 220

Tyr Gly Ser Arg Ser Asp Leu Pro Gln Lys Val Ile Ser Ser Ala Phe
225                 230                 235                 240

Arg Asn Gly Lys Gly Gly Ser Leu Lys Gln Thr Asn Ile Leu Ser Thr
                245                 250                 255

Arg Asn Thr Ala Leu Gly Tyr Ser Pro Cys Ser Phe Asn Leu Val Asn
            260                 265                 270

Trp Val Ala Ile Val Ser Gln Pro Glu Ser Leu Ala Lys Ile Ile Thr
        275                 280                 285

Gly Thr Val Ile Ala Ile Gly Val Phe Val Ile Leu Leu Thr Leu Pro
    290                 295                 300

Leu Ala His Trp Ala Val Gln Pro Ile Val Arg Leu Gln Lys Ala Thr
305                 310                 315                 320

Glu Leu Ile Thr Glu Gly Arg Gly Leu Ser Arg Ala Ser Ser Phe Lys
                325                 330                 335

Arg Gly Phe Ser Ser Gly Phe Ala Val Pro Ser Ser Leu Leu Gln Phe
            340                 345                 350

Asn Thr Ala Glu Ala Gly Ser Thr Thr Ser Val Ser Gly His Gly Gly
        355                 360                 365

Ser Gly His Gly Ser Gly Ala Ala Asn Val Leu Gln Arg Thr Lys Leu
    370                 375                 380

Glu Lys Arg Asp Phe Cys Ile Thr Asp Val Ala Leu Gln Ile Lys Ser
385                 390                 395                 400
```

```
Ile Phe Gly Lys Val Ala Lys Asp Gln Arg Val Arg Leu Ser Ile Ser
                405                 410                 415
Leu Phe Pro Asn Leu Ile Arg Asn Arg Ile Ile Gln Ile Val Met Asn
            420                 425                 430
Leu Val Ser Asn Ala Leu Lys Phe Thr Pro Val Asp Gly Thr Val Asp
        435                 440                 445
Val Arg Met Lys Leu Leu Gly Glu Tyr Asp Lys Glu Leu Ser Glu Lys
    450                 455                 460
Lys Gln Tyr Lys Glu Val Thr Glu Asn Leu Glu Thr Thr Asp Lys Tyr
465                 470                 475                 480
Asp Leu Pro Thr Leu Ser Asn His Arg Lys Ser Val Asp Leu Glu Ser
                485                 490                 495
Ser Ala Thr Ser Leu Gly Ser Asn Arg Asp Thr Ser Thr Ile Gln Glu
            500                 505                 510
Glu Ile Thr Lys Arg Tyr Lys Lys Val Asn Asp Arg Glu Lys Ala Ser
        515                 520                 525
Asn Asp Asp Val Ser Ser Ile Val Ser Thr Thr Thr Ser Ser Tyr Asp
530                 535                 540
Asn Ala Ile Phe Asn Ser Gln Phe Asn Lys Ala Pro Gly Ser Asp Asp
545                 550                 555                 560
Glu Glu Gly Pro Lys Thr Trp Val Ile Ser Ile Glu Val Glu Asp Thr
                565                 570                 575
Gly Pro Gly Ile Asp Pro Ser Leu Gln Glu Ser Val Phe His Pro Phe
            580                 585                 590
Val Gln Gly Asp Gln Thr Leu Ser Arg Gln Tyr Gly Gly Thr Gly Leu
        595                 600                 605
Gly Leu Ser Met Met His Gly Thr Met Lys Leu Glu Ser Lys Val Gly
    610                 615                 620
Val Gly Ser Lys Phe Thr Phe Thr Leu Pro Leu Asn Gln Thr Lys Glu
625                 630                 635                 640
Ile Ser Phe Ala Asp Met Glu Phe Pro Phe Glu Asp Glu Phe Asn Pro
                645                 650                 655
Glu Ser Ser Val Ala Lys Ser Ile Lys Ser Arg Gln Ser Thr Ser Ser
            660                 665                 670
Val Ala Thr Pro Ala Thr Asn Arg Ser Ser Leu Thr Asn Asp Val Leu
        675                 680                 685
Pro Glu Val Arg Ser Lys Gly Lys His Glu Thr Lys Asp Val Gly Asn
    690                 695                 700
Asp Asn Gly Gly Leu Glu Gln Leu Gln Glu Lys Asn Ile Lys Pro Ser
705                 710                 715                 720
Ile Cys Leu Thr Gly Ala Glu Val Asn Glu Gln Asn Ser Leu Ser Ser
                725                 730                 735
Lys His Arg Ser Arg His Glu Gly Leu Gly Ser Val Asn Leu Asp
            740                 745                 750

<210> SEQ ID NO 30
<211> LENGTH: 1117
<212> TYPE: PRT
<213> ORGANISM: Candida albicans

<400> SEQUENCE: 30

Asp Leu Leu Cys Trp Ser Cys Val Val Ala Ile Tyr Lys Ala Pro Pro
 1               5                  10                  15

Tyr Ile Asn Lys Lys Phe Phe Leu Ser Val Val Tyr Leu Glu Phe Leu
```

-continued

```
                20                  25                  30
Pro Leu Ser Pro Met Asn Pro Thr Lys Lys Pro Arg Leu Ser Pro Met
             35                  40                  45
Gln Pro Ser Val Phe Glu Ile Leu Asn Asp Pro Glu Leu Tyr Ser Gln
 50                  55                  60
His Cys His Ser Leu Arg Glu Thr Leu Leu Asp His Phe Asn His Gln
 65                  70                  75                  80
Ala Thr Leu Ile Asp Thr Tyr Glu His Glu Leu Gly Lys Ser Lys Asn
                 85                  90                  95
Ala Asn Lys Ala Phe Gln Gln Ala Leu Ser Glu Ile Gly Thr Val Val
            100                 105                 110
Ile Ser Val Ala Met Gly Asp Leu Ser Lys Lys Val Glu Ile His Thr
            115                 120                 125
Val Glu Asn Asp Pro Glu Ile Leu Lys Val Lys Ile Thr Ile Asn Thr
130                 135                 140
Met Met Asp Gln Leu Gln Thr Phe Ala Asn Glu Val Thr Lys Val Ala
145                 150                 155                 160
Thr Glu Val Ala Asn Gly Glu Leu Gly Gly Gln Ala Lys Asn Asp Gly
                165                 170                 175
Ser Val Gly Ile Trp Arg Ser Leu Thr Asp Asn Val Asn Ile Met Ala
            180                 185                 190
Leu Asn Leu Thr Asn Gln Val Arg Glu Ile Ala Asp Val Thr Arg Ala
            195                 200                 205
Val Ala Lys Gly Asp Leu Ser Arg Lys Ile Asn Val His Ala Gln Gly
            210                 215                 220
Glu Ile Leu Gln Leu Gln Arg Thr Ile Asn Thr Met Val Asp Gln Leu
225                 230                 235                 240
Arg Thr Phe Ala Phe Glu Val Ser Lys Val Ala Arg Asp Val Gly Val
                245                 250                 255
Leu Gly Ile Leu Gly Gly Gln Ala Leu Ile Glu Asn Val Glu Gly Ile
            260                 265                 270
Trp Glu Glu Leu Thr Asp Asn Val Asn Ala Met Ala Leu Asn Leu Thr
            275                 280                 285
Thr Gln Val Arg Asn Ile Ala Asn Val Thr Thr Ala Val Ala Lys Gly
            290                 295                 300
Asp Leu Ser Lys Lys Val Thr Ala Asp Cys Lys Gly Glu Ile Leu Asp
305                 310                 315                 320
Leu Lys Leu Thr Ile Asn Gln Met Val Asp Arg Leu Gln Asn Phe Ala
                325                 330                 335
Leu Ala Val Thr Thr Leu Ser Arg Glu Val Gly Thr Leu Gly Ile Leu
            340                 345                 350
Gly Gly Gln Ala Asn Val Gln Asp Val Glu Gly Ala Trp Lys Gln Val
            355                 360                 365
Thr Glu Asn Val Asn Leu Met Ala Thr Asn Leu Thr Asn Gln Val Arg
            370                 375                 380
Ser Ile Ala Thr Val Thr Thr Ala Val Ala His Gly Asp Leu Ser Gln
385                 390                 395                 400
Lys Ile Asp Val His Ala Gln Gly Glu Ile Leu Gln Leu Lys Asn Thr
                405                 410                 415
Ile Asn Lys Met Val Asp Ser Leu Gln Leu Phe Ala Ser Glu Val Ser
            420                 425                 430
Lys Val Ala Gln Asp Val Gly Ile Asn Gly Lys Leu Gly Ile Gln Ala
            435                 440                 445
```

-continued

```
Gln Val Ser Asp Val Asp Gly Leu Trp Lys Glu Ile Thr Ser Asn Val
    450                 455                 460
Asn Thr Met Ala Ser Asn Leu Thr Ser Gln Val Arg Ala Phe Ala Gln
465                 470                 475                 480
Ile Thr Ala Ala Thr Asp Gly Asp Phe Thr Arg Phe Ile Thr Val
                485                 490                 495
Glu Ala Leu Gly Glu Met Asp Ala Leu Lys Thr Lys Ile Asn Gln Met
                500                 505                 510
Val Phe Asn Leu Arg Glu Ser Leu Gln Arg Asn Thr Ala Ala Arg Glu
            515                 520                 525
Ala Ala Glu Leu Ala Asn Ser Ala Lys Ser Glu Phe Leu Ala Asn Met
        530                 535                 540
Ser His Glu Ile Arg Thr Pro Leu Asn Gly Ile Ile Gly Met Thr Gln
545                 550                 555                 560
Leu Ser Leu Asp Thr Glu Leu Thr Gln Tyr Gln Arg Glu Met Leu Ser
                565                 570                 575
Ile Val His Asn Leu Ala Asn Ser Leu Leu Thr Ile Ile Asp Asp Ile
            580                 585                 590
Leu Asp Ile Ser Lys Ile Glu Ala Asn Arg Met Thr Val Glu Gln Ile
        595                 600                 605
Asp Phe Ser Leu Arg Gly Thr Val Phe Gly Ala Leu Lys Thr Leu Ala
610                 615                 620
Val Lys Ala Ile Glu Lys Asn Leu Asp Leu Thr Tyr Gln Cys Asp Ser
625                 630                 635                 640
Ser Phe Pro Asp Asn Leu Ile Gly Asp Ser Phe Arg Leu Arg Gln Val
                645                 650                 655
Ile Leu Asn Leu Ala Gly Asn Ala Ile Lys Phe Thr Lys Glu Gly Lys
            660                 665                 670
Val Ser Val Ser Val Lys Lys Ser Asp Lys Met Val Leu Asp Ser Lys
        675                 680                 685
Leu Leu Leu Glu Val Cys Val Ser Asp Thr Gly Ile Gly Ile Glu Lys
690                 695                 700
Asp Lys Leu Gly Leu Ile Phe Asp Thr Phe Cys Gln Ala Asp Gly Ser
705                 710                 715                 720
Thr Thr Arg Lys Phe Gly Gly Thr Gly Leu Gly Leu Ser Ile Ser Lys
                725                 730                 735
Gln Leu Ile His Leu Met Gly Gly Glu Ile Trp Val Thr Ser Glu Tyr
            740                 745                 750
Gly Ser Gly Ser Asn Phe Tyr Phe Thr Val Cys Val Ser Pro Ser Asn
        755                 760                 765
Ile Arg Tyr Thr Arg Gln Thr Glu Gln Leu Leu Pro Phe Ser Ser His
770                 775                 780
Tyr Val Leu Phe Val Ser Thr Glu His Thr Gln Glu Leu Asp Val
785                 790                 795                 800
Leu Arg Asp Gly Ile Ile Glu Leu Gly Leu Pro Ile Ile Val Arg
                805                 810                 815
Asn Ile Glu Asp Ala Thr Leu Thr Glu Pro Val Lys Tyr Asp Ile Ile
            820                 825                 830
Met Ile Asp Ser Ile Glu Ile Ala Lys Lys Leu Arg Leu Leu Ser Glu
        835                 840                 845
Val Lys Tyr Ile Pro Leu Val Leu Val His His Ser Ile Pro Gln Leu
850                 855                 860
```

-continued

```
Asn Met Arg Val Cys Ile Asp Leu Gly Ile Ser Ser Tyr Ala Asn Thr
865                 870                 875                 880

Pro Cys Ser Ile Thr Asp Leu Ala Ser Ala Ile Ile Pro Ala Leu Glu
                885                 890                 895

Ser Arg Ser Ile Ser Gln Asn Ser Asp Glu Ser Val Arg Tyr Lys Ile
                900                 905                 910

Leu Leu Ala Glu Asp Asn Leu Val Asn Gln Lys Leu Ala Val Arg Ile
                915                 920                 925

Leu Glu Lys Gln Gly His Leu Val Glu Val Glu Asn Gly Leu Glu
            930                 935                 940

Ala Tyr Glu Ala Ile Lys Arg Asn Lys Tyr Asp Val Val Leu Met Asp
945                 950                 955                 960

Val Gln Met Pro Val Met Gly Gly Phe Glu Ala Thr Glu Lys Ile Arg
                965                 970                 975

Gln Trp Glu Lys Lys Ser Asn Pro Ile Asp Ser Leu Thr Phe Arg Thr
                980                 985                 990

Pro Ile Ile Ala Leu Thr Ala His Ala Met Leu Gly Asp Arg Glu Lys
                995                 1000                1005

Ser Leu Ala Lys Gly Met Asp Asp Tyr Val Ser Lys Pro Leu Lys Pro
    1010                1015                1020

Lys Leu Leu Met Gln Thr Ile Asn Lys Cys Ile His Asn Ile Asn Gln
1025                1030                1035                1040

Leu Lys Glu Leu Ser Arg Asn Ser Arg Gly Ser Asp Phe Ala Lys Lys
                1045                1050                1055

Met Thr Arg Asn Thr Pro Gly Ser Thr Arg Gln Gly Ser Asp Glu
            1060                1065                1070

Gly Ser Val Glu Asp Met Ile Gly Asp Thr Pro Arg Gln Gly Ser Val
    1075                1080                1085

Glu Gly Gly Gly Thr Ser Ser Arg Pro Val Gln Arg Arg Ser Ala Thr
    1090                1095                1100

Glu Gly Ser Ile Thr Thr Ile Ser Glu Gln Ile Asp Arg
1105                1110                1115

<210> SEQ ID NO 31
<211> LENGTH: 918
<212> TYPE: PRT
<213> ORGANISM: Escherichia coli

<400> SEQUENCE: 31

Met Thr Asn Tyr Ser Leu Arg Ala Arg Met Met Ile Leu Ile Leu Ala
  1               5                  10                  15

Pro Thr Val Leu Ile Gly Leu Leu Leu Ser Ile Phe Phe Val Val His
                20                  25                  30

Arg Tyr Asn Asp Leu Gln Arg Gln Leu Glu Asp Ala Gly Ala Ser Ile
            35                  40                  45

Ile Glu Pro Leu Ala Val Ser Thr Glu Tyr Gly Met Ser Leu Gln Asn
 50                  55                  60

Arg Glu Ser Ile Gly Gln Leu Ile Ser Val Leu His Arg His Ser
 65                  70                  75                  80

Asp Ile Val Arg Ala Ile Ser Val Tyr Asp Glu Asn Asn Arg Leu Phe
                85                  90                  95

Val Thr Ser Asn Phe His Leu Asp Pro Ser Ser Met Gln Leu Gly Ser
                100                 105                 110

Asn Val Pro Phe Pro Arg Gln Leu Thr Val Thr Arg Asp Gly Asp Ile
            115                 120                 125
```

```
Met Ile Leu Arg Thr Pro Ile Ile Ser Glu Ser Tyr Ser Pro Asp Glu
    130                 135                 140

Ser Pro Ser Ser Asp Ala Lys Asn Ser Gln Asn Met Leu Gly Tyr Ile
145                 150                 155                 160

Ala Leu Glu Leu Asp Leu Lys Ser Val Arg Leu Gln Gln Tyr Lys Glu
                165                 170                 175

Ile Phe Ile Ser Ser Val Met Met Leu Phe Cys Ile Gly Ile Ala Leu
            180                 185                 190

Ile Phe Gly Trp Arg Leu Met Arg Asp Val Thr Gly Pro Ile Arg Asn
        195                 200                 205

Met Val Asn Thr Val Asp Arg Ile Arg Arg Gly Gln Leu Asp Ser Arg
    210                 215                 220

Val Glu Gly Phe Met Leu Gly Glu Leu Asp Met Leu Lys Asn Gly Ile
225                 230                 235                 240

Asn Ser Met Ala Met Ser Leu Ala Ala Tyr His Glu Glu Met Gln His
                245                 250                 255

Asn Ile Asp Gln Ala Thr Ser Asp Leu Arg Glu Thr Leu Glu Gln Met
            260                 265                 270

Glu Ile Gln Asn Val Glu Leu Asp Leu Ala Lys Lys Arg Ala Gln Glu
        275                 280                 285

Ala Ala Arg Ile Lys Ser Glu Phe Leu Ala Asn Met Ser His Glu Leu
290                 295                 300

Arg Thr Pro Leu Asn Gly Val Ile Gly Phe Thr Arg Leu Thr Leu Lys
305                 310                 315                 320

Thr Glu Leu Thr Pro Thr Gln Arg Asp His Leu Asn Thr Ile Glu Arg
                325                 330                 335

Ser Ala Asn Asn Leu Leu Ala Ile Ile Asn Asp Val Leu Asp Phe Ser
            340                 345                 350

Lys Leu Glu Ala Gly Lys Leu Ile Leu Glu Ser Ile Pro Phe Pro Leu
        355                 360                 365

Arg Ser Thr Leu Asp Glu Val Val Thr Leu Leu Ala His Ser Ser His
370                 375                 380

Asp Lys Gly Leu Glu Leu Thr Leu Asn Ile Lys Ser Asp Val Pro Asp
385                 390                 395                 400

Asn Val Ile Gly Asp Pro Leu Arg Leu Gln Gln Ile Ile Thr Asn Leu
                405                 410                 415

Val Gly Asn Ala Ile Lys Phe Thr Glu Asn Gly Asn Ile Asp Ile Leu
            420                 425                 430

Val Glu Lys Arg Ala Leu Ser Asn Thr Lys Val Gln Ile Glu Val Gln
        435                 440                 445

Ile Arg Asp Thr Gly Ile Gly Ile Pro Glu Arg Asp Gln Ser Arg Leu
450                 455                 460

Phe Gln Ala Phe Arg Gln Ala Asp Ala Ser Ile Ser Arg Arg His Gly
465                 470                 475                 480

Gly Thr Gly Leu Gly Leu Val Ile Thr Gln Lys Leu Val Asn Glu Met
                485                 490                 495

Gly Gly Asp Ile Ser Phe His Ser Gln Pro Asn Arg Gly Ser Thr Phe
            500                 505                 510

Trp Phe His Ile Asn Leu Asp Leu Asn Pro Asn Ile Ile Ile Glu Gly
        515                 520                 525

Pro Ser Thr Gln Cys Leu Ala Gly Lys Arg Leu Ala Tyr Val Glu Pro
530                 535                 540
```

-continued

Asn Ser Ala Ala Ala Gln Cys Thr Leu Asp Ile Leu Ser Glu Thr Pro
545                 550                 555                 560

Leu Glu Val Val Tyr Ser Pro Thr Phe Ser Ala Leu Pro Pro Ala His
            565                 570                 575

Tyr Asp Met Met Leu Leu Gly Ile Ala Val Thr Phe Arg Glu Pro Leu
        580                 585                 590

Thr Met Gln His Glu Arg Leu Ala Lys Ala Val Ser Met Thr Asp Phe
    595                 600                 605

Leu Met Leu Ala Leu Pro Cys His Ala Gln Val Asn Ala Glu Lys Leu
610                 615                 620

Lys Gln Asp Gly Ile Gly Ala Cys Leu Leu Lys Pro Leu Thr Pro Thr
625                 630                 635                 640

Arg Leu Leu Pro Ala Leu Thr Glu Phe Cys His His Lys Gln Asn Thr
                645                 650                 655

Leu Leu Pro Val Thr Asp Glu Ser Lys Leu Ala Met Thr Val Met Ala
            660                 665                 670

Val Asp Asp Asn Pro Ala Asn Leu Lys Leu Ile Gly Ala Leu Leu Glu
        675                 680                 685

Asp Met Val Gln His Val Glu Leu Cys Asp Ser Gly His Gln Ala Val
    690                 695                 700

Glu Arg Ala Lys Gln Met Pro Phe Asp Leu Ile Leu Met Asp Ile Gln
705                 710                 715                 720

Met Pro Asp Met Asp Gly Ile Arg Ala Cys Glu Leu Ile His Gln Leu
                725                 730                 735

Pro His Gln Gln Gln Thr Pro Val Ile Ala Val Thr Ala His Ala Met
            740                 745                 750

Ala Gly Gln Lys Glu Lys Leu Leu Gly Ala Gly Met Ser Asp Tyr Leu
        755                 760                 765

Ala Lys Pro Ile Glu Glu Arg Leu His Asn Leu Leu Arg Tyr
    770                 775                 780

Lys Pro Gly Ser Gly Ile Ser Ser Arg Val Val Thr Pro Glu Val Asn
785                 790                 795                 800

Glu Ile Val Val Asn Pro Asn Ala Thr Leu Asp Trp Gln Leu Ala Leu
                805                 810                 815

Arg Gln Ala Ala Gly Lys Thr Asp Leu Ala Arg Asp Met Leu Gln Met
            820                 825                 830

Leu Leu Asp Phe Leu Pro Glu Val Arg Asn Lys Val Glu Glu Gln Leu
        835                 840                 845

Val Gly Glu Asn Pro Glu Gly Leu Val Asp Leu Ile His Lys Leu His
    850                 855                 860

Gly Ser Cys Gly Tyr Ser Gly Val Pro Arg Met Lys Asn Leu Cys Gln
865                 870                 875                 880

Leu Ile Glu Gln Gln Leu Arg Ser Gly Thr Lys Glu Glu Asp Leu Glu
                885                 890                 895

Pro Glu Leu Leu Glu Leu Leu Asp Glu Met Asp Asn Val Ala Arg Glu
            900                 905                 910

Ala Ser Lys Ile Leu Gly
        915

<210> SEQ ID NO 32
<211> LENGTH: 1220
<212> TYPE: PRT
<213> ORGANISM: Saccharomyces cerevisiae

<400> SEQUENCE: 32

```
Met Arg Phe Gly Leu Pro Ser Lys Leu Glu Leu Thr Pro Pro Phe Arg
 1               5                  10                  15
Ile Gly Ile Arg Thr Gln Leu Thr Ala Leu Val Ser Ile Val Ala Leu
            20                  25                  30
Gly Ser Leu Ile Ile Leu Ala Val Thr Thr Gly Val Tyr Phe Thr Ser
        35                  40                  45
Asn Tyr Lys Asn Leu Arg Ser Asp Arg Leu Tyr Ile Ala Ala Gln Leu
    50                  55                  60
Lys Ser Ser Gln Ile Asp Gln Thr Leu Asn Tyr Leu Tyr Tyr Gln Ala
65                  70                  75                  80
Tyr Tyr Leu Ala Ser Arg Asp Ala Leu Gln Ser Ser Leu Thr Ser Tyr
            85                  90                  95
Val Ala Gly Asn Lys Ser Ala Asp Asn Trp Val Asp Ser Leu Ser Val
                100                 105                 110
Ile Gln Lys Phe Leu Ser Ser Asn Leu Phe Tyr Val Ala Lys Val
            115                 120                 125
Tyr Asp Ser Ser Phe Asn Ala Val Leu Asn Ala Thr Asn Asn Gly Thr
    130                 135                 140
Gly Asp Leu Ile Pro Glu Asp Val Leu Asp Ser Leu Phe Pro Leu Ser
145                 150                 155                 160
Thr Asp Thr Pro Leu Pro Ser Ser Leu Glu Thr Ile Gly Ile Leu Thr
                165                 170                 175
Asp Pro Val Leu Asn Ser Thr Asp Tyr Leu Met Ser Met Ser Leu Pro
            180                 185                 190
Ile Phe Ala Asn Pro Ser Ile Ile Leu Thr Asp Ser Arg Val Tyr Gly
        195                 200                 205
Tyr Ile Thr Ile Ile Met Ser Ala Glu Gly Leu Lys Ser Val Phe Asn
    210                 215                 220
Asp Thr Thr Ala Leu Glu His Ser Thr Ile Ala Ile Ser Ala Val
225                 230                 235                 240
Tyr Asn Ser Gln Gly Lys Ala Ser Gly Tyr His Phe Val Phe Pro Pro
                245                 250                 255
Tyr Gly Ser Arg Ser Asp Leu Pro Gln Lys Val Phe Ser Ile Lys Asn
            260                 265                 270
Asp Thr Phe Ile Ser Ser Ala Phe Arg Asn Gly Lys Gly Ser Leu
        275                 280                 285
Lys Gln Thr Asn Ile Leu Ser Thr Arg Asn Thr Ala Leu Gly Tyr Ser
    290                 295                 300
Pro Cys Ser Phe Asn Leu Val Asn Trp Val Ala Ile Val Ser Gln Pro
305                 310                 315                 320
Glu Ser Val Phe Leu Ser Pro Ala Thr Lys Leu Ala Lys Ile Ile Thr
                325                 330                 335
Gly Thr Val Ile Ala Ile Gly Val Phe Val Ile Leu Leu Thr Leu Pro
            340                 345                 350
Leu Ala His Trp Ala Val Gln Pro Ile Val Arg Leu Gln Lys Ala Thr
        355                 360                 365
Glu Leu Ile Thr Glu Gly Arg Gly Leu Arg Pro Ser Thr Pro Arg Thr
    370                 375                 380
Ile Ser Arg Ala Ser Ser Phe Lys Arg Gly Phe Ser Ser Gly Phe Ala
385                 390                 395                 400
Val Pro Ser Ser Leu Leu Gln Phe Asn Thr Ala Glu Ala Gly Ser Thr
                405                 410                 415
```

-continued

```
Thr Ser Val Ser Gly His Gly Gly Ser His Gly Ser Gly Ala Ala
            420                 425             430

Phe Ser Ala Asn Ser Ser Met Lys Ser Ala Ile Asn Leu Gly Asn Glu
        435                 440                 445

Lys Met Ser Pro Pro Glu Glu Glu Asn Lys Ile Pro Asn Asn His Thr
        450                 455                 460

Asp Ala Lys Ile Ser Met Asp Gly Ser Leu Asn His Asp Leu Leu Gly
465                 470                 475                 480

Pro His Ser Leu Arg His Asn Asp Thr Asp Arg Ser Ser Asn Arg Ser
                485                 490                 495

His Ile Leu Thr Thr Ser Ala Asn Leu Thr Glu Ala Arg Leu Pro Asp
                500                 505                 510

Tyr Arg Arg Leu Phe Ser Asp Glu Leu Ser Asp Leu Thr Glu Thr Phe
                515                 520                 525

Asn Thr Met Thr Asp Ala Leu Asp Gln His Tyr Ala Leu Leu Glu Glu
        530                 535                 540

Arg Val Arg Ala Arg Thr Lys Gln Leu Glu Ala Ala Lys Ile Glu Ala
545                 550                 555                 560

Glu Ala Ala Asn Glu Ala Lys Thr Val Phe Ile Ala Asn Ile Ser His
                565                 570                 575

Glu Leu Arg Thr Pro Leu Asn Gly Ile Leu Gly Met Thr Ala Ile Ser
                580                 585                 590

Met Glu Glu Thr Asp Val Asn Lys Ile Arg Asn Ser Leu Lys Leu Ile
        595                 600                 605

Phe Arg Ser Gly Glu Leu Leu Leu His Ile Leu Thr Glu Leu Leu Thr
        610                 615                 620

Phe Ser Lys Asn Val Leu Gln Arg Thr Lys Leu Glu Lys Arg Asp Phe
625                 630                 635                 640

Cys Ile Thr Asp Val Ala Leu Gln Ile Lys Ser Ile Phe Gly Lys Val
                645                 650                 655

Ala Lys Asp Gln Arg Val Arg Leu Ser Ile Ser Leu Phe Pro Asn Leu
                660                 665                 670

Ile Arg Thr Met Val Leu Trp Gly Asp Ser Asn Arg Ile Ile Gln Ile
        675                 680                 685

Val Met Asn Leu Val Ser Asn Ala Leu Lys Phe Thr Pro Val Asp Gly
        690                 695                 700

Thr Val Asp Val Arg Met Lys Leu Leu Gly Glu Tyr Asp Lys Glu Leu
705                 710                 715                 720

Ser Glu Lys Lys Gln Tyr Lys Glu Val Tyr Ile Lys Lys Gly Thr Glu
                725                 730                 735

Val Thr Glu Asn Leu Glu Thr Thr Asp Lys Tyr Asp Leu Pro Thr Leu
                740                 745                 750

Ser Asn His Arg Lys Ser Val Asp Leu Glu Ser Ser Ala Thr Ser Leu
        755                 760                 765

Gly Ser Asn Arg Asp Thr Ser Thr Ile Gln Glu Ile Thr Lys Arg
        770                 775                 780

Asn Thr Val Ala Asn Glu Ser Ile Tyr Lys Lys Val Asn Asp Arg Glu
785                 790                 795                 800

Lys Ala Ser Asn Asp Asp Val Ser Ser Ile Val Ser Thr Thr Thr Ser
                805                 810                 815

Ser Tyr Asp Asn Ala Ile Phe Asn Ser Gln Phe Asn Lys Ala Pro Gly
        820                 825                 830

Ser Asp Asp Glu Glu Gly Gly Asn Leu Gly Arg Pro Ile Glu Asn Pro
```

```
                    835                 840                 845
Lys Thr Trp Val Ile Ser Ile Glu Val Glu Asp Thr Gly Pro Gly Ile
850                 855                 860
Asp Pro Ser Leu Gln Ser Val Phe His Pro Phe Val Gln Gly Asp
865                 870                 875                 880
Gln Thr Leu Ser Arg Gln Tyr Gly Gly Thr Gly Leu Gly Leu Ser Ile
                    885                 890                 895
Cys Arg Gln Leu Ala Asn Met Met His Gly Thr Met Lys Leu Glu Ser
                900                 905                 910
Lys Val Gly Val Gly Ser Lys Phe Thr Phe Thr Leu Pro Leu Asn Gln
            915                 920                 925
Thr Lys Glu Ile Ser Phe Ala Asp Met Glu Phe Pro Phe Glu Asp Glu
        930                 935                 940
Phe Asn Pro Glu Ser Arg Lys Asn Arg Val Lys Phe Ser Val Ala
945                 950                 955                 960
Lys Ser Ile Lys Ser Arg Gln Ser Thr Ser Ser Val Ala Thr Pro Ala
                965                 970                 975
Thr Asn Arg Ser Ser Leu Thr Asn Asp Val Leu Pro Glu Val Arg Ser
            980                 985                 990
Lys Gly Lys His Glu Thr Lys Asp Val Gly Asn Pro Asn Met Gly Arg
        995                 1000                1005
Glu Glu Lys Asn Asp Asn Gly Gly Leu Glu Gln Leu Gln Lys Asn
    1010                1015                1020
Ile Lys Pro Ser Ile Cys Leu Thr Gly Ala Glu Val Asn Glu Gln Asn
1025                1030                1035                1040
Ser Leu Ser Ser Lys His Arg Ser Arg His Glu Gly Leu Gly Ser Val
                1045                1050                1055
Asn Leu Asp Arg Pro Phe Leu Gln Ser Thr Gly Thr Ala Thr Ser Ser
            1060                1065                1070
Arg Asn Ile Pro Thr Val Lys Asp Asp Lys Asn Glu Thr Ser Val
        1075                1080                1085
Lys Ile Leu Val Val Glu Asp Asn His Val Asn Gln Glu Val Ile Lys
    1090                1095                1100
Arg Met Leu Asn Leu Glu Gly Ile Glu Asn Ile Glu Leu Ala Cys Asp
1105                1110                1115                1120
Gly Gln Glu Ala Phe Asp Lys Val Lys Glu Leu Thr Ser Lys Gly Glu
                1125                1130                1135
Asn Tyr Asn Met Ile Phe Met Asp Val Gln Met Pro Lys Val Asp Gly
            1140                1145                1150
Leu Leu Ser Thr Lys Met Ile Arg Arg Asp Leu Gly Tyr Thr Ser Pro
        1155                1160                1165
Ile Val Ala Leu Thr Ala Phe Ala Asp Asp Ser Asn Ile Lys Glu Cys
    1170                1175                1180
Leu Glu Ser Gly Met Asn Gly Phe Leu Ser Lys Pro Ile Lys Arg Pro
1185                1190                1195                1200
Lys Leu Lys Thr Ile Leu Thr Glu Phe Cys Ala Ala Tyr Gln Gly Lys
                1205                1210                1215
Lys Asn Asn Lys
        1220

<210> SEQ ID NO 33
<211> LENGTH: 352
<212> TYPE: DNA
<213> ORGANISM: Aspergillus fumigatus
```

<400> SEQUENCE: 33

```
cacgagttgc ggacgcccat gaaatggaat gcacctggca ttgaccatgt tggggagcac      60
ggagctcgac acccagcagc gtgaatacac ttccattatc gaggattcca tgtcgatttt     120
gcttcaagta atcaacgacg tccttgatta ttctaagtta tcctccggca ccttctctct     180
gaacacagat gtcttgaacg ttgagaatat tgtgggagca gtggtacgga attgcaaggc     240
cttaaaccct gccgtggaga tctcctgttc catgcctccg ggcttcccaa atctgctccg     300
gggtgatccg cttcgctatc ggcaagttga tccagaacct cgtcagcaac gc             352
```

<210> SEQ ID NO 34
<211> LENGTH: 8256
<212> TYPE: DNA
<213> ORGANISM: Aspergillus fumigatus

<400> SEQUENCE: 34

```
gaattccatt ggctgattga tggataaaat catctttgtt gtcttcgcaa agtgaagtct      60
gcatcaaatg aggggactaa agtcaggtga ttgcgctgcc atcgtaaggc tcgagacatt     120
gtgattggtt ctttcgacca agactacagt actcggagta tattgtcaaa gataccagat     180
cgaattgttg agaagattcg tctgtaaaag gcgccggtag ttttttattaa ggaaggtcag     240
atcaatgatt gggctgggtc gccaaaggga tgaaactatt ttggctttca caagtagttt     300
agtgaaactc cacaacccgc aagacggcaa caagacggca tggcattata tgtagcatga     360
ctcgcagagt cagaagaacg tcccattctt tgcagatctt aaactattgg ctctaatttt     420
tagccaaaag tcttcggata aacgccgtct ctagggaggc atgaacatcc cacaggtctg     480
tcggtatggg ccgctagttt cttccatatt ggtcggatca ttaaacctaa ggtgagttga     540
cgtgccttgc aatgctttgg ctgcagatta gtcttcttct agtccactgt actgataata     600
actatcgtcc tcgactagcg ggtagagccg acagtcggac ctgagcgctc tccaattcca     660
acacagatgt caggagccat ttttgcgagg aggtttgtgg ctggaggata taaggaatg      720
agctgcaatg catctgaacg gtgatggggt catagtttgt gtttaaaagg atcaatctcg     780
gatacagcag gtgctgtcag catcgtccaa gatcttcttc cttcgggcgg cttttgttgtg    840
tgatttgtac cctcatcctt tccgttaaga atctagcttt cttgatatttt gtggaagatc    900
tcatcccagt agtcagtgac aaacgattcg agtctcaaat ctcaacagaa gtgccagcaa    960
ggtctcacgc acaaaatggg ggactgcgat aaaaatctcc aaatgcctcc tgtaccgttc   1020
tcacaacgtc caatcatcat tctaggcgca gggatcattg ggtgcgctac agcaagacag   1080
cttctcttaa atggctttcg cgttgtggtt gttgccgagt tcctgccagg cgatcaaaat   1140
attttttacgc atcagcctgg gctggagcaa catggcatgc tgctggcggg atcagttccg   1200
aatatcgata ccttcaagct gttacgcatc ggcatctgtt gaagatggcg caagaaggcc   1260
ccgaatccgg agtttgtctt gtggatgcgc gcgaatatct cgaagaagcg ccatctgaga   1320
actcctcaat ctggggtaag actgtggtca caaatgtagg taatggagcg gtcccactca   1380
tggtgtatgg acatactgat gaggtagttt cgcgaacttt gaacccgggc gaaatatcct   1440
tcctaaactt ccattgcggg tggtcatacc aaacactggt aaacgatcc gacgcgtcac   1500
ttgccctatc tccgagatca gataacggct cttggtggcc agttcattcg aaagcgggtc   1560
gagtccctcc aagagctgta cgccatgttt cccgagtcaa gtgtcttcat caatgccagc   1620
gggctcggaa gcaaaaccct caccgacgtt cgggatgata agtgctttcc tgagcgaggc   1680
```

-continued

```
cagaatgtct tttatcgtac cgacaagtgt cgacagatgt actttcgcaa tggaaaagag     1740
tacacctatg tcatccccccg tcctttatcc gagggggtag tgttagggggg agtcaagcag    1800 ccgaacaacc tgtcagtgac gtttcctgtg catgcatcta tgacgaagct aacattatat     1860
aggtccccag aggttgacat agacgttgct cgagacgaga tcgcgcgcgc tcatcgttcg     1920
caccagagat tgttcccgca gaccccccccg aagagtcatt gagctatatt attggtattc    1980
gaccatcaag gcaaggtggg tttcgcttgc attctgagca attgggccag cggacagtct     2040
tatcagctta tggattcgga ggcggcggct atgcgttttc gtatggtata gcggaagcgt     2100
tgttgacgat gctggagaag tgcgagagag aaaatgtcat catataatat ctctatgtta     2160
acctggagca cccctttagga agaatcccag agcaatatag gcttgttgtt gctactgctt    2220
ccaccctatg catgtaagcc tatgaagtgt gcctcaggct ggccaagaag cctgaaatgg     2280
caaggcatac cacattaaat tgacgacctg ctccatcctt ccatgccaga taaagttacc     2340
gagtccacac agcaacagcg acaatgacaa tgacaagtca gctacctaag gttagtacag     2400
ctatggactc gcaggaactt aaactttcag ctaagttcga cccggctgg ccacgttgaa       2460 ttacgttgcc aatgcaattc ctcgtgaatc tttggcgtca gcgggtcctc ccgatcgcag     2520
atccctgaca cattttcagg ctccaaataa taaaatttac tccaacttga gtcagactcg     2580
tcttgatcca gcgcttccaa gctttggctt gtttcgttca ggagcctgga tccattccat     2640
cacgcactca gccaccccag ccaggcgcgc ggatgggggta cacagacgtt cttctacagt    2700
tactacccgt tgttaactta tcaaaattcg aggcgaccag cagtgctctc aaggagtaag    2760
gtttcggccg agtcctttct tagtatggaa ggaatgccac actcgatatg tcatcatgtc     2820
atcggctctc acgatcggct gagctatgag catccgtgtg ccagcttccc ggagatcgct    2880
ggtaaatatc gcatcttgct ttgaagcgat taagaaacca ccatacaaag gcggactatg     2940
gaaaggaaaa gcaccaatgt cggattcgat tgtcgaaccc agcgagttca tgattcatgt     3000
cagatgcaag ggatctgtgc ggctaggttg cttgatcggg tttagtggaa ttgtcatgta     3060
tactctctgc acggagcaga atttcaaagc cgacgagttg agccagatgt gatcgtattc     3120
aagtgattaa agtgcaaggg acacagtaag tagtgctaga gatctaggat ttactcgcct     3180
ctccacagag gtacacaaac aatcttcagc taaagaggta ctccgtacag tgggcgaaga     3240
aacaactatt tctgattgac tcttcccatc aaagtactgt tatgtgggtc tgcaacttaa     3300
ctctggtagg ccattcacga ttcacacaga atgacaaaaa caggttcatg taccgccatt     3360
ccttccccgc agcccactgg aacttctttc caaccagtgg ctgcacagca aaatcgcaaa     3420
catggtgcaa gtgtgtaaga tgagtagggt ctctctcggt gcgctctgcg atgacgtggg    3480
tggtagtagt ctactgtggt tatgcgactg aatggaatat tatccttatg ggcctactgg     3540
cccgcaggcc tgcaactggt tcttttgaat ggtctttaa cgaatttcca atacacaaca      3600
aatacgggtc aaaattacaa tccttatttg cctcttgagt gtcggaactg aataagttaa     3660
gagtattaac tagttagtta attactaggt actaaactgc atgattactt ttatgtgggg    3720
ccggcgagaa tcgtcatctg caactgtgtt tctactcggc gtatttctca gtgataccctt    3780 tccacattcc atgtgcatct actgatcatc catctgtcgt cttctgggtg agtgagtgga     3840
ctagtccaga atcctgcttg caattctcat ctgtcgccca ctcggccggt tctcggcttc     3900
ggacgtcctt ggttgcgcca caggggaaga caggcaaaag gcagagagcc acagcacaga    3960
cttgggaaac tgataaaaca accactctcc tcatgcgtat tttgaagtag cgagttctcg     4020
gttggcttct tttctgctgt tatctcgcta ccttttgttgt gggggattca gctagcctaa    4080
```

-continued

```
atggccctcg acaaggagct tcttcacctt catctcgggg atggccagca gcgaccctac    4140
aagctttcca cggtcgctac tcctcccgat gaagagcagc tcaatcttca acgcagtgat    4200
aaggatacag ctgaaccgtc tcaaactccc cgctgtgaca ctccgcgaga ggcccacaca    4260
gagatcgtac agaacgatac ttcctcgctg aatcgaattt ccgcttcac tcctgtgccg     4320
accctcatcc tcgactcgtc cttgcgcgtg attgaggtct cggagagcca ccttgctttc    4380
tgcggaaagt ctcgagactt tgtgctgggt gcctccatct acgagcttcc cctcgccact    4440
ataccgtcgc cagacattgc gactctgaac ggtgctttgc acgtggcgat tacgactcgg    4500
gctgtccagg ttgtcgaaac tatccacctt cccagaataa gctcttattt ttcactgaaa    4560
atcaccccca ttttccaggg atccactctg ctgaacctag ttctggaagc gcacaacgtc    4620
acaaggaccc ataccgagtc actgcataat gcctacatca atgagactta caagatcctg    4680
gttgacacga tccgagatta cgctatcttt atgctggacg cgcgcggcaa cattgtaacg    4740
tggaattcgg gcgctgcgat tatcaaggga tataaggcgg atgagattat cggtcggcat    4800
ttctcggtct tctacggacc cgaggatcgg ctggcagaca agcctgggaa ggagctcgaa    4860
ttgtgcctac gggacggaaa agtcgaggat gaaggctggc ggtatcgtca ggatggttta    4920
cggttttggg ccaacgtaat gattacgcct atcttctcat tcggtcggca cgttggtttc    4980
gtcaaaatca ctcgcgactt gaccgagcgc aaagcggctg aagcgcggat ggtggcagct    5040
tttgaggaat catccaagat gaagagtgac ttcctggcca acatgagcca cgagattcgg    5100
actcccatga atggaatgca cctggcattg accatgttgg ggagcacgga gctcgacacc    5160
cagcagcgtg aatacacttc cattatcgag gattccatgt cgattttgct tcaagtaatc    5220
aacgacgtcc ttgattattc taagttatcc tccggcacct tctctctgaa cacagatgtc    5280
ttgagcgttg agaatattgt gggagcagtg gtacggaatt gcaaggcctt aaaccctgcc    5340
gtggagatct cctgttccat gcctccgggc ttcccaaaac tgctccgggg tgatccgctt    5400
cgctatcggc aagtgatcca gaacctcgtg ggaaatgcga tgaagtttac cgagaaaggc    5460
catgtcaagg tcacccatcg ctttgcagta gaggagcacg atgccaatag gtacataatc    5520
acgacagaag tcactgatac tggcatcggg gtgcccgaag atgctataaa cactctttt    5580
accccattta cgcgctttgc ggattcagcc accaagcgct atcagggtac aggacttggc    5640
ttgtccatct gcaagagctt ggcagagctg atggatggca gtgttggtta taaacccaac    5700
ccagaaggaa agggtagctg cttttggctc aacgtgagaa tgcaagctgt cgacattcca    5760
gcgcctagta aagacactcc cgctgctacc gccgaaaata cgtacgaacc catcgaagag    5820
gtcaaggaga ttgcgcctca catgcacata ttgctggtgg aagataatat ggtgaaccaa    5880
atcgttatgc tgaagcttct caaaagcctc ggtttcgaac gtgtcgacac ggcctgggac    5940
ggcgcagacg cagtccgaca ggtgaaacaa acacctctct cttacaatgt tattcttatg    6000
gacatcaaca tgccggttat gaatggactc gaagcaacga ccaagatccg tgaagtgaac    6060
agcgaggtac ccatcatagc actcaccggg aatgcgctca agggagacgc ggagacatac    6120
cttgccagag gcatgaacga ttacgtcgcc aaaccagttc atcgcaagcg gcttgtgcag    6180
ttgttgtgga agtggctcgg ttcgtgagca actgttcctc tggcctcgct ggccggtggc    6240
tcctccgttg ggacaagacc tgattgtcct gttataactt aaagtgggct tggatgcacc    6300
tttgcccgca cccctatcta ccatagctct cgccctcagt tgagcggtgt ctcgctcata    6360
ctaaacgagg cgctatcttt ggtcggcttt gaactatccg gctatgcatc tttcatagcc    6420
```

-continued

```
tcatcaatcg ccaaaagaaa tggccttgat ggctatcagc ttctcgacag attttcacgt      6480
ccgcgtacgt tggccattca cagtacatat ttttcgcgga ccctgcatac tccacccttt      6540
cattatttgc ctcttcgatc acggttcgcc atcaatcatc ccatcataat aaagcgaacc      6600
gtctccgaaa tggattcagt tgcctggctc gggttgtccg gttgggtaac acaggagttt      6660
ggccaagttt gcggatggtc atggagacct atggaacgag gctatacatt catgagagaa      6720
atgtacggct agcgagcaat tgttctagac caggatagca ctaagcatcc tgtccgatca      6780
tgtcacgata ctattgagtc gtttgtctat caggccgcta cccaagccgg gtgtattcat      6840
gtaacacgaa ttgattgcat ttaatggtgg catgaattaa tgagtgtcct tctacatcta      6900
gttcatccgt tgtacctctt ctgtcctttt agtgtatttg tcgagtgtca cacgaccgtg      6960
caactgtagc gccatgtact tgctcggctc aacatttgc acctgttgag ggtagcctgt       7020
tcaacaattc tcaccacaac ggcgacagcg tcccgatgaa gtacgatcct cctccatcct      7080
acatcctact ccttcaaatc agcgcgtcca tccctgcagt gcttcaaccg tcactcatca      7140
agttgatctt tacctatttg cccgtaaatt cgggctagat cggcggtggg gttgggcctt      7200
agctcaatgc gagaaggtag aacctcctga actactgagt tgctcgcaaa acttgtttac      7260
gctttgcgca tgcttcttca aggcttatcc tggcggcggc tgtataccga ggctatgctt      7320
acgaaacggt caatgccgca tatcccttca gtcggacaa ccttgtttac agacagtgtc       7380
ctaccttgtg tctgtgcgtg agaggtgaac cgtgaacctg atcgcctgtc ttttggcggt      7440
tgatgatatg aagatcgtgg ttgtggattc tcacgtgtgc ttgggcaagt cttcccgagg      7500
catggaaaca gctccgctgg taacgactga ctgcatgcat ctttaatcac agccgtgcct      7560
gttgtctcaa agaatgaaag gacgggctat gataagcttc agctagcctc ctatggtcta     7620
tcagaacaca aagataaaaa ggtgcctaga acttccattt ctagtatagt agaagtgata     7680
gtgcatattt cctccatccc ccgctgtggt acaacgccat gaacgaggag aaccgcggtg     7740
ccacacaacc gatccgggta ggacgcaatc cgtaattgat gtcgatcgac atgatagcag     7800
gggctgatcc tccatcttag catgtgcacg attctaatag ctccgctctg tactagtgct     7860
aagccccact gcaacgttcc atcataatag tcaacatcag ggtctaatgc atgatgggta     7920
tgatatgcga gtcgtgcggg ggtcgttgat gtcgatcagg agagatgggt ccaaacattt     7980
atatgaagcg gttccccagg ccgtcttgct aggtacacac aagctattct tgcgctgaat     8040
aatgcgactt tcacacgtac tcctagaact gcagctgcag ctggcgttct ggctatccca     8100
cccgaacgac tatgtcgtgc atgaacgtcg tgctgtcctc ctcgctcctg gacggggag      8160 aaaagacttg ataaggcctc tatcctgcct atgaggattg gtctcactca gtctaaccta     8220
aattgcgtca tgacttgttg atgagatgtt gtactt                               8256
```

<210> SEQ ID NO 35
<211> LENGTH: 708
<212> TYPE: PRT
<213> ORGANISM: Aspergillus fumigatus

<400> SEQUENCE: 35

```
Met Ala Leu Asp Lys Glu Leu Leu His Leu His Leu Gly Asp Gly Gln
 1               5                  10                  15

Gln Arg Pro Tyr Lys Leu Ser Thr Val Ala Thr Pro Pro Asp Glu Glu
            20                  25                  30

Gln Leu Asn Leu Gln Arg Ser Asp Lys Asp Thr Ala Glu Pro Ser Gln
        35                  40                  45
```

```
Thr Pro Arg Cys Asp Thr Pro Arg Glu Ala His Thr Glu Ile Val Gln
         50                  55                  60

Asn Asp Thr Ser Ser Leu Asn Arg Ile Phe Arg Phe Thr Pro Val Pro
 65                  70                  75                  80

Thr Leu Ile Leu Asp Ser Ser Leu Arg Val Ile Glu Val Ser Glu Ser
                 85                  90                  95

His Leu Ala Phe Cys Gly Lys Ser Arg Asp Phe Val Leu Gly Ala Ser
                100                 105                 110

Ile Tyr Glu Leu Pro Leu Ala Thr Ile Pro Ala Pro Asp Ile Ala Thr
        115                 120                 125

Leu Asn Gly Ala Leu His Val Ala Ile Thr Thr Arg Ala Val Gln Val
130                 135                 140

Val Glu Thr Ile His Leu Pro Arg Ile Ser Ser Tyr Phe Ser Leu Lys
145                 150                 155                 160

Ile Thr Pro Ile Phe Gln Gly Ser Thr Leu Leu Asn Leu Val Leu Glu
                165                 170                 175

Ala His Asn Val Thr Arg Thr His Thr Glu Ser Leu His Asn Ala Tyr
                180                 185                 190

Ile Asn Glu Thr Tyr Lys Ile Leu Val Asp Thr Ile Arg Asp Tyr Ala
        195                 200                 205

Ile Phe Met Leu Asp Ala Arg Gly Asn Ile Val Thr Trp Asn Ser Gly
210                 215                 220

Ala Ala Ile Ile Lys Gly Tyr Lys Ala Asp Glu Ile Gly Arg His
225                 230                 235                 240

Phe Ser Val Phe Tyr Gly Pro Glu Asp Arg Leu Ala Asp Lys Pro Gly
                245                 250                 255

Lys Glu Leu Glu Leu Cys Leu Arg Asp Gly Lys Val Glu Asp Glu Gly
                260                 265                 270

Trp Arg Tyr Arg Gln Asp Gly Leu Arg Phe Trp Ala Asn Val Met Ile
        275                 280                 285

Thr Pro Ile Phe Ser Phe Gly Arg His Val Gly Phe Val Lys Ile Thr
290                 295                 300

Arg Asp Leu Thr Glu Arg Lys Ala Ala Glu Ala Arg Met Val Ala Ala
305                 310                 315                 320

Phe Glu Glu Ser Ser Lys Met Lys Ser Asp Phe Leu Ala Asn Met Ser
                325                 330                 335

His Glu Ile Arg Thr Pro Met Asn Gly Met His Leu Ala Leu Thr Met
        340                 345                 350

Leu Gly Ser Thr Glu Leu Asp Thr Gln Gln Arg Glu Tyr Thr Ser Ile
        355                 360                 365

Ile Glu Asp Ser Met Ser Ile Leu Leu Gln Val Ile Asn Asp Val Leu
370                 375                 380

Asp Tyr Ser Lys Leu Ser Ser Gly Thr Phe Ser Leu Asn Thr Asp Val
385                 390                 395                 400

Leu Ser Val Glu Asn Ile Val Gly Ala Val Arg Asn Cys Lys Ala
                405                 410                 415

Leu Asn Pro Ala Val Glu Ile Ser Cys Ser Met Pro Gly Phe Pro
                420                 425                 430

Lys Leu Leu Arg Gly Asp Pro Leu Arg Tyr Arg Gln Val Ile Gln Asn
        435                 440                 445

Leu Val Gly Asn Ala Met Lys Phe Thr Glu Lys Gly His Val Lys Val
450                 455                 460

Thr His Arg Phe Ala Val Glu Glu His Asp Ala Asn Arg Tyr Ile Ile
```

```
                       465                 470                 475                 480
Thr Thr Glu Val Thr Asp Thr Gly Ile Gly Val Pro Glu Asp Ala Ile
                485                 490                 495
Asn Thr Leu Phe Thr Pro Phe Thr Arg Phe Ala Asp Ser Ala Thr Lys
            500                 505                 510
Arg Tyr Gln Gly Thr Gly Leu Gly Leu Ser Ile Cys Lys Ser Leu Ala
        515                 520                 525
Glu Leu Met Asp Gly Ser Val Gly Tyr Lys Pro Asn Pro Glu Gly Lys
    530                 535                 540
Gly Ser Cys Phe Trp Leu Asn Val Arg Met Gln Ala Val Asp Ile Pro
545                 550                 555                 560
Ala Pro Ser Lys Asp Thr Pro Ala Ala Thr Ala Glu Asn Thr Tyr Glu
                565                 570                 575
Pro Ile Glu Glu Val Lys Glu Ile Ala Pro His Met His Ile Leu Leu
            580                 585                 590
Val Glu Asp Asn Met Val Asn Gln Ile Val Met Leu Lys Leu Leu Lys
        595                 600                 605
Ser Leu Gly Phe Glu Arg Val Asp Thr Ala Trp Asp Gly Ala Asp Ala
    610                 615                 620
Val Arg Gln Val Lys Gln Thr Pro Leu Ser Tyr Asn Val Ile Leu Met
625                 630                 635                 640
Asp Ile Asn Met Pro Val Met Asn Gly Leu Glu Ala Thr Thr Lys Ile
                645                 650                 655
Arg Glu Val Asn Ser Glu Val Pro Ile Ile Ala Leu Thr Gly Asn Ala
                660                 665                 670
Leu Lys Gly Asp Ala Glu Thr Tyr Leu Ala Arg Gly Met Asn Asp Tyr
            675                 680                 685
Val Ala Lys Pro Val His Arg Lys Arg Leu Val Gln Leu Leu Trp Lys
        690                 695                 700
Trp Leu Gly Ser
705
```

<210> SEQ ID NO 36
<211> LENGTH: 3168
<212> TYPE: DNA
<213> ORGANISM: Aspergillus fumigatus

<400> SEQUENCE: 36

```
atgcgactga atggaatatt atccttatgg gcctactggc ccgcaggcct gcaactggtt      60
cttttgaatg gtcttttaac gaatttccaa tacacaacaa atacgggtca aaattacaat    120
ccttatttgc ctcttgagtg tcggaactga ataagttaag agtattaact agttagttaa    180
ttactaggta ctaaactgca tgattacttt tatgtggggc cggcgagaat cgtcatctgc    240
aactgtgttt ctactcggcg tatttctcag tgataccttt ccacattcca tgtgcatcta    300
ctgatcatcc atctgtcgtc ttctgggtga gtgagtggac tagtccagaa tcctgcttgc    360
aattctcatc tgtcgcccac tcggccggtt ctcggcttcg acgtccttg gttgcgccac     420
agggaagac aggcaaaagg cagagagcca agcacagac ttgggaaact gataaaacaa      480
ccactctcct catgcgtatt ttgaagtagc gagttctcgg ttggcttctt ttctgctgtt    540
atctcgctac ctttgttgtg ggggattcag ctagcctaaa tggccctcga caaggagctt    600
cttcaccttc atctcgggga tggccagcag cgacccctaca agctttccac ggtcgctact   660
cctcccgatg aagagcagct caatcttcaa cgcagtgata aggatacagc tgaaccgtct    720
```

-continued

| | |
|---|---|
| caaactcccc gctgtgacac tccgcgagag gcccacacag agatcgtaca gaacgatact | 780 |
| tcctcgctga atcgaatttt ccgcttcact cctgtgccga ccctcatcct cgactcgtcc | 840 |
| ttgcgcgtga ttgaggtctc ggagagccac cttgctttct gcggaaagtc tcgagacttt | 900 |
| gtgctgggtg cctccatcta cgagcttccc ctcgccacta tacctgcgcc agacattgcg | 960 |
| actctgaacg gtgctttgca cgtggcgatt acgactcggg ctgtccaggt tgtcgaaact | 1020 |
| atccaccttc ccagaataag ctcttatttt tcactgaaaa tcaccccat tttccaggga | 1080 |
| tccactctgc tgaacctagt tctggaagcg cacaacgtca caaggaccca taccgagtca | 1140 |
| ctgcataatg cctacatcaa tgagacttac aagatcctgg ttgacacgat ccgagattac | 1200 |
| gctatcttta tgctggacgc gcgcggcaac attgtaacgt ggaattcggg cgctgcgatt | 1260 |
| atcaagggat ataaggcgga tgagattatc ggtcggcatt tctcggtctt ctacggaccc | 1320 |
| gaggatcggc tggcagacaa gcctgggaag gagctcgaat tgtgcctacg ggacggaaaa | 1380 |
| gtcgaggatg aaggctggcg gtatcgtcag gatggtttac ggttttgggc caacgtaatg | 1440 |
| attacgccta tcttctcatt cggtcggcac gttggtttcg tcaaaatcac tcgcgacttg | 1500 |
| accgagcgca agcggctga agcgcggatg gtggcagctt ttgaggaatc atccaagatg | 1560 |
| aagagtgact tcctggccaa catgagccac gagattcgga ctcccatgaa tggaatgcac | 1620 |
| ctggcattga ccatgttggg gagcacggag ctcgacaccc agcagcgtga atacacttcc | 1680 |
| attatcgagg attccatgtc gattttgctt caagtaatca cgacgtcct tgattattct | 1740 |
| aagttatcct ccggcacctt ctctctgaac acagatgtct tgagcgttga gaatattgtg | 1800 |
| ggagcagtgg tacggaattg caaggcctta accctgccg tggagatctc ctgttccatg | 1860 |
| cctccgggct tcccaaaact gctccggggt gatccgcttc gctatcggca agtgatccag | 1920 |
| aacctcgtgg gaaatgcgat gaagtttacc gagaaaggcc atgtcaaggt cacccatcgc | 1980 |
| tttgcagtag aggagcacga tgccaatagg tacataatca cgacagaagt cactgatact | 2040 |
| ggcatcgggg tgcccgaaga tgctataaac actctttta ccccatttac gcgctttgcg | 2100 |
| gattcagcca ccaagcgcta tcagggtaca ggacttggct tgtccatctg caagagcttg | 2160 |
| gcagagctga tggatggcag tgttggttat aaacccaacc cagaaggaaa gggtagctgc | 2220 |
| ttttggctca acgtgagaat gcaagctgtc gacattccag cgcctagtaa agacactccc | 2280 |
| gctgctaccg ccgaaaatac gtacgaaccc atcgaagagg tcaaggagat tgcgcctcac | 2340 |
| atgcacatat tgctggtgga agataatatg gtgaaccaaa tcgttatgct gaagcttctc | 2400 |
| aaaagcctcg gtttcgaacg tgtcgacacg gcctgggacg gcgcagacgc agtccgacag | 2460 |
| gtgaaacaaa cacctctctc ttacaatgtt attcttatgg acatcaacat gccggttatg | 2520 |
| aatggactcg aagcaacgac caagatccgt gaagtgaaca gcgaggtacc catcatagca | 2580 |
| ctcaccggga atgcgctcaa gggagacgcg gagacatacc ttgccagagg catgaacgat | 2640 |
| tacgtcgcca aaccagttca tcgcaagcgg cttgtgcagt tgttgtggaa gtggctcggt | 2700 |
| tcgtgagcaa ctgttcctct ggcctcgctg gccggtggct cctccgttgg gacaagacct | 2760 |
| gattgtcctg ttataactta aagtgggctt ggatgctcca tcctttgccc gcacccctat | 2820 |
| ctaccatagc tctcgccctc agttgagcgg tgtctcgctc atactaaacg aggcgctatc | 2880 |
| tttggtcggc tttgaactat ccggctatgc atctttcata gcctcatcaa tcgccaaaag | 2940 |
| aaatggcctt gatggctatc agcttctcga cagattttca cgtccgcgta cgttggccat | 3000 |
| tcacagtaca tattttcgc ggaccctgca tactccaccc tttcattatt tgcctcttcg | 3060 |
| atcacggttc gccatcaatc atcccatcat aataaagcga accgtctccg aaatggattc | 3120 |

```
agttgcctgg ctcgggttgt ccggttgggt aacacaggag tttggcca          3168
```

<210> SEQ ID NO 37
<211> LENGTH: 241
<212> TYPE: DNA
<213> ORGANISM: Aspergillus fumigatus
<220> FEATURE:
<221> NAME/KEY: modified_base
<222> LOCATION: (12)
<223> OTHER INFORMATION: The N at this position can be a, c, t, or g.
<221> NAME/KEY: modified_base
<222> LOCATION: (31)
<223> OTHER INFORMATION: The N at this position can be a, c, t, or g.
<221> NAME/KEY: modified_base
<222> LOCATION: (149)
<223> OTHER INFORMATION: The N at this position can be a, c, t, or g.

<400> SEQUENCE: 37

```
ttgaacgcat gngggatttg aatcccgttt naagaaccga ttacgcctat cttaaaattc    60
cgtcggcacg ttggtttcgt caaaatcact cgcgacttga ccgattttaa agcggctgaa   120
gcgcggatgg tggcaggttt tgaggaatna tccaagatga agagtgattt tctggccaac   180
atgagccacg agattcggac ttcaatgaat ggaatgcaca tggcatttga ccataaaatc   240
c                                                                  241
```

<210> SEQ ID NO 38
<211> LENGTH: 196
<212> TYPE: DNA
<213> ORGANISM: Aspergillus fumigatus
<220> FEATURE:
<221> NAME/KEY: modified_base
<222> LOCATION: (32)
<223> OTHER INFORMATION: The N at this position can be a, c, g, or t.
<221> NAME/KEY: modified_base
<222> LOCATION: (67)
<223> OTHER INFORMATION: The N at this position can be a, c, g, or t.
<221> NAME/KEY: modified_base
<222> LOCATION: (172)
<223> OTHER INFORMATION: The N at this position can be a, c, g, or t.

<400> SEQUENCE: 38

```
tggaaccccc ttcaaagctt cccaagaagc tnatggatgg cagtgttagg ttataaaccc    60
aacccanaag gaagggtca ctgcttttgg ctcaacgtga gaatgcaagc tgtcggcatt    120
ccagcgccta gcttaaagac actcccgctg ttacccgccg aaaatcttac cnaacccatt   180
caatataggt taaggc                                                  196
```

<210> SEQ ID NO 39
<211> LENGTH: 80
<212> TYPE: PRT
<213> ORGANISM: Aspergillus fumigatus
<220> FEATURE:
<221> NAME/KEY: SITE
<222> LOCATION: (4)
<223> OTHER INFORMATION: The Xaa at this position can be any amino acid.
<221> NAME/KEY: SITE
<222> LOCATION: (7)
<223> OTHER INFORMATION: The Xaa at this position can be any amino acid.
<221> NAME/KEY: SITE
<222> LOCATION: (50)
<223> OTHER INFORMATION: The Xaa at this position can be any amino acid.

<400> SEQUENCE: 39

```
Leu Asn Ala Xaa Gly Ile Xaa Ile Pro Phe Glu Glu Pro Ile Thr Pro
 1               5                  10                  15

Ile Phe Ser Phe Gly Arg His Val Gly Phe Val Lys Ile Thr Arg Asp
            20                  25                  30
```

```
Leu Thr Glu Arg Lys Ala Ala Glu Ala Arg Met Val Ala Gly Phe Glu
        35                  40                  45

Glu Xaa Ser Lys Met Lys Ser Asp Phe Leu Ala Asn Met Ser His Glu
    50                  55                  60

Ile Arg Thr Ser Met Asn Gly Met His Met Ala Phe Asp His Lys Ile
65                  70                  75                  80

<210> SEQ ID NO 40
<211> LENGTH: 65
<212> TYPE: PRT
<213> ORGANISM: Aspergillus fumigatus
<220> FEATURE:
<221> NAME/KEY: SITE
<222> LOCATION: (11)
<223> OTHER INFORMATION: The Xaa at this position can be any amino acid.
<221> NAME/KEY: SITE
<222> LOCATION: (23)
<223> OTHER INFORMATION: The Xaa at this position can be any amino acid.
<221> NAME/KEY: SITE
<222> LOCATION: (58)
<223> OTHER INFORMATION: The Xaa at this position can be any amino acid.

<400> SEQUENCE: 40

Trp Lys Pro Leu Gln Ser Phe Pro Arg Ser Xaa Trp Met Ala Val Leu
1               5                   10                  15

Gly Tyr Lys Pro Asn Pro Xaa Gly Lys Gly His Cys Phe Trp Leu Asn
            20                  25                  30

Val Arg Met Gln Ala Val Gly Ile Pro Ala Pro Ser Leu Lys Thr Leu
        35                  40                  45

Pro Leu Leu Pro Ala Glu Asn Leu Thr Xaa Pro Ile Gln Tyr Arg Leu
    50                  55                  60

Arg
 65

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence:  Synthetic
<221> NAME/KEY: SITE
<222> LOCATION: (3)
<223> OTHER INFORMATION: The amino acid at this position can be aspartic
      acid or glutamic acid.
<221> NAME/KEY: SITE
<222> LOCATION: (16)
<223> OTHER INFORMATION: The amino acid at this position can be
      methionine or leucine.
<221> NAME/KEY: SITE
<222> LOCATION: (19)
<223> OTHER INFORMATION: The amino acid at this position can be
      methionine or isoleucine.

<400> SEQUENCE: 41

Lys Ser Xaa Phe Leu Ala Asn Met Ser His Glu Ile Arg Thr Pro Xaa
1               5                   10                  15

Asn Gly Xaa

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence:  Synthetic
<221> NAME/KEY: SITE
<222> LOCATION: (2)
```

```
<223> OTHER INFORMATION: The amino acid at this position can be
      isoleucine or valine.
<221> NAME/KEY: SITE
<222> LOCATION: (6)
<223> OTHER INFORMATION: The amino acid at this position can be
      isoleucine or valine.
<221> NAME/KEY: SITE
<222> LOCATION: (7)
<223> OTHER INFORMATION: The amino acid at this position can be
      asparagine or glutamine.

<400> SEQUENCE: 42

Val Xaa Leu Met Asp Xaa Xaa Met Pro Val Met
 1               5                  10

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 43
tggtacaggt ttagggttgt c                                           21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 44
aacatggcgt atttgcatag g                                           21

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 45
tggatccagt actaatagga attgatttgg                                  30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 46
tggatcctct agaaggacca cctttgattg                                  30

<210> SEQ ID NO 47
<211> LENGTH: 147
<212> TYPE: DNA
<213> ORGANISM: Aspergillus fumigatus

<400> SEQUENCE: 47
atgcgactga atggaatatt atccttatgg gcctactggc ccgcaggcct gcaactggtt    60
cttttgaatg gtcttttaac gaatttccaa tacacaacaa atacgggtca aaattacaat   120
ccttatttgc ctcttgagtg tcggaac                                      147
```

```
<210> SEQ ID NO 48
<211> LENGTH: 49
<212> TYPE: PRT
<213> ORGANISM: Aspergillus fumigatus

<400> SEQUENCE: 48

Met Arg Leu Asn Gly Ile Leu Ser Leu Trp Ala Tyr Trp Pro Ala Gly
 1               5                  10                  15

Leu Gln Leu Val Leu Leu Asn Gly Leu Leu Thr Asn Phe Gln Tyr Thr
            20                  25                  30

Thr Asn Thr Gly Gln Asn Tyr Asn Pro Tyr Leu Pro Leu Glu Cys Arg
        35                  40                  45

Asn

<210> SEQ ID NO 49
<211> LENGTH: 630
<212> TYPE: DNA
<213> ORGANISM: Aspergillus fumigatus

<400> SEQUENCE: 49
ccttgcgcgt gattgaggtc tcggagagcc accttgcttt ctgcggaaag tctcgagact      60
ttgtgctggg tgcctccatc tacgagcttc ccctcgccac tatacctgcg ccagacattg    120
cgactctgaa cggtgctttg cacgtggcga ttacgactcg ggctgtccag gttgtcgaaa    180
ctatccacct tcccagaata agctcttatt tttcactgaa aatcaccccc attttccagg    240
gatccactct gctgaaccta gttctggaag cgcacaacgt cacaaggacc cataccgagt    300
cactgcataa tgcctacatc aatgagactt acaagatcct ggttgacacg atccgagatt    360
acgctatctt tatgctggac gcgcgcggca acattgtaac gtggaattcg ggcgctgcga    420
ttatcaaggg atataaggcg gatgagatta tcggtcggca tttctcggtc ttctacggac    480
ccgaggatcg gctggcagac aagcctggga aggagctcga attgtgccta cgggacggaa    540
aagtcgagga tgaaggctgg cggtatcgtc aggatggttt acggttttgg gccaacgtaa    600
tgattacgcc tatcttctca ttcggtcggc                                      630

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 50
ccttgcgcgt gattgaggtc tcgg                                              24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 51
gccgaccgaa tgagaagata ggcg                                              24

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
```

<400> SEQUENCE: 52
agcgcggatg gtggcagctt t                                          21

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 53
ttgattactt gaagcaaaat cg                                       22

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 54
gacgtctgtc gagaagtttc tgatcg                                26

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 55
gtattgggaa tccccgaaca tcgcctc                             27

<210> SEQ ID NO 56
<211> LENGTH: 658
<212> TYPE: DNA
<213> ORGANISM: Artificial Sequence
<220> FEATURE:
<223> OTHER INFORMATION: Description of Artificial Sequence: Synthetic

<400> SEQUENCE: 56
gacgtctgtc gagaagtttc tgatcgaaaa gttcgacagc gtctccgacc tgatgcagct    60
ctcggagggc gaagaatctc gtgctttcag cttcgatgta ggagggcgtg gatatgtcct   120
gcgggtaaat agctgcgccg atggtttcta caaagatcgt tatgtttatc ggcactttgc   180
atcggccgcg ctcccgattc cggaagtgct tgacattggg gaattcagcg agagcctgac   240
ctattgcatc tcccgccgtg cacagggtgt cacgttgcaa gacctgcctg aaaccgaact   300
gcccgctgtt ctgcagccgg tcgcggaggc catggatgcg atcgctgcgg ccgatcttag   360
ccagacgagc gggttcggcc cattcggacc gcaaggaatc ggtcaataca ctacatggcg   420
tgatttcata tgcgcgattg ctgatcccca tgtgtatcac tggcaaactg tgatggacga   480
caccgtcagt gcgtccgtcg cgcaggctct cgatgagctg atgctttggg ccgaggactg   540
ccccgaagtc cggcacctcg tgcacgcgga tttcggctcc aacaatgtcc tgacggacaa   600
tggccgcata acagcggtca ttgactggag cgaggcgatg ttcggggatt cccaatac    658

<210> SEQ ID NO 57
<211> LENGTH: 26
<212> TYPE: DNA
<213> ORGANISM: Artificial Sequence
<220> FEATURE:

<223> OTHER INFORMATION: Description of Artificial Sequence: Synthetic

<400> SEQUENCE: 57
gacgtctgtc gagaagtttc tgatcg 26

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 58
gtattgggaa tccccgaaca tcgcctc 27

<210> SEQ ID NO 59
<211> LENGTH: 2124
<212> TYPE: DNA
<213> ORGANISM: Aspergillus fumigatus

<400> SEQUENCE: 59

| | |
|---|---|
| atggccctcg acaaggagct tcttcacctt catctcgggg atggccagca gcgaccctac | 60 |
| aagcttttcca cggtcgctac tcctcccgat gaagagcagc tcaatcttca acgcagtgat | 120 |
| aaggatacag ctgaaccgtc tcaaactccc cgctgtgaca ctccgcgaga ggcccacaca | 180 |
| gagatcgtac agaacgatac ttcctcgctg aatcgaattt ccgcttcac tcctgtgccg | 240 |
| accctcatcc tcgactcgtc cttgcgcgtg attgaggtct cggagagcca ccttgctttc | 300 |
| tgcggaaagt ctcgagactt tgtgctgggt gcctccatct acgagcttcc cctcgccact | 360 |
| atacctgcgc cagacattgc gactctgaac ggtgctttgc acgtggcgat tacgactcgg | 420 |
| gctgtccagg ttgtcgaaac tatccaccct cccagaataa gctcttattt ttcactgaaa | 480 |
| atcaccccca ttttccaggg atccactctg ctgaacctag ttctggaagc gcacaacgtc | 540 |
| acaaggaccc ataccgagtc actgcataat gcctacatca atgagactta caagatcctg | 600 |
| gttgacacga tccgagatta cgctatcttt atgctggacg cgcgcggcaa cattgtaacg | 660 |
| tggaattcgg gcgctgcgat tatcaaggga tataaggcgg atgagattat cggtcggcat | 720 |
| ttctcggtct tctacggacc cgaggatcgg ctggcagaca agcctgggaa ggagctcgaa | 780 |
| ttgtgcctac gggacggaaa agtcgaggat gaaggctggc ggtatcgtca ggatggtttta | 840 |
| cggttttggg ccaacgtaat gattacgcct atcttctcat tcggtcggca cgttggttc | 900 |
| gtcaaaatca ctcgcgactt gaccgagcgc aaagcggctg aagcgcggat ggtggcagct | 960 |
| tttgaggaat catccaagat gaagagtgac ttcctggcca acatgagcca cgagattcgg | 1020 |
| actcccatga atggaatgca cctggcattg accatgttgg ggagcacgga gctcgacacc | 1080 |
| cagcagcgtg aatacacttc cattatcgag gattccatgt cgattttgct tcaagtaatc | 1140 |
| aacgacgtcc ttgattattc taagttatcc tccggcacct tctctctgaa cacagatgtc | 1200 |
| ttgagcgttg agaatattgt gggagcagtg gtacggaatt gcaaggcctt aaaccctgcc | 1260 |
| gtggagatct cctgttccat gcctccgggc ttcccaaaac tgctccgggg tgatccgctt | 1320 |
| cgctatcggc aagtgatcca gaacctcgtg ggaaatgcga tgaagtttac cgagaaaggc | 1380 |
| catgtcaagg tcacccatcg ctttgcagta gaggagcacg atgccaatag gtacataatc | 1440 |
| acgacagaag tcactgatac tggcatcggg gtgcccgaag atgctataaa cactcttttt | 1500 |
| accccatttta cgcgctttgc ggattcagcc accaagcgct atcagggtac aggacttggc | 1560 |
| ttgtccatct gcaagagctt ggcagagctg atggatggca gtgttggtta taaacccaac | 1620 |

```
ccagaaggaa agggtagctg cttttggctc aacgtgagaa tgcaagctgt cgacattcca      1680
gcgcctagta aagacactcc cgctgctacc gccgaaaata cgtacgaacc catcgaagag      1740
gtcaaggaga ttgcgcctca catgcacata ttgctggtgg aagataatat ggtgaaccaa      1800
atcgttatgc tgaagcttct caaaagcctc ggtttcgaac gtgtcgacac ggcctgggac      1860
ggcgcagacg cagtccgaca ggtgaaacaa acacctctct cttacaatgt tattcttatg      1920
gacatcaaca tgccggttat gaatggactc gaagcaacga ccaagatccg tgaagtgaac      1980
agcgaggtac ccatcatagc actcaccggg aatgcgctca agggagacgc ggagacatac      2040
cttgccagag gcatgaacga ttacgtcgcc aaaccagttc atcgcaagcg cttgtgcag      2100 ttgttgtgga agtggctcgg ttcg                                            2124

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 60
atgcgactga atggaatatt atccttatgg                                        30

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 61
agatgcacat ggaatgtgga aagg                                              24

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 62
atgattactt ttatgtgggg                                                   20

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 63
atcactgcgt tgaagattga gctgctcttc                                        30

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 64
tgatcatcca tctgtcgtct tctggg                                            26
```

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 65
gcgcttccag aactaggttc agc                                              23

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 66
gaggcccaca cagagatcgt                                                  20

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 67
ttgattactt gaagcaaaat c                                                21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 68
agcgcggatg gtggcagctt t                                                21

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 69
gccaagtcct gtaccc                                                      16

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 70
gagatctcct gttccatgcc t                                                21

<210> SEQ ID NO 71
<211> LENGTH: 27
<212> TYPE: DNA
<213> ORGANISM: Artificial Sequence
<220> FEATURE:

```
<223> OTHER INFORMATION: Description of Artificial Sequence: Synthetic

<400> SEQUENCE: 71
tttcacctgt cggactgcgt ctgcgcc                                        27

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 72
cccgctgcta ccgccgaaaa tac                                            23

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 73
ctcgttccat aggtctccat gacc                                           24
```